(12) United States Patent
Stadler et al.

(10) Patent No.: US 11,596,150 B2
(45) Date of Patent: *Mar. 7, 2023

(54) LONG CHAIN GLYCOLIPIDS USEFUL TO AVOID PERISHING OR MICROBIAL CONTAMINATION OF MATERIALS

(71) Applicant: IMD NATURAL SOLUTIONS GMBH, Dortmund (DE)

(72) Inventors: Marc Stadler, Niederkirchen (DE); Jens Bitzer, Dortmund (DE); Bärbel Köpcke, Dortmund (DE); Kathrin Reinhardt, Dortmund (DE); Jana Moldenhauer, Dortmund (DE)

(73) Assignee: IMD NATURAL SOLUTIONS GMB, Dortmund (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/778,101

(22) Filed: Jan. 31, 2020

(65) Prior Publication Data

US 2020/0154708 A1 May 21, 2020

Related U.S. Application Data

(62) Division of application No. 14/124,429, filed as application No. PCT/EP2012/002399 on Jun. 6, 2012, now abandoned.

(30) Foreign Application Priority Data

Jun. 10, 2011 (EP) .................................... 11004776

(51) Int. Cl.

| | | |
|---|---|---|
| A01N 43/16 | (2006.01) | |
| C07H 15/04 | (2006.01) | |
| A23B 4/20 | (2006.01) | |
| A23B 9/26 | (2006.01) | |
| A23B 5/14 | (2006.01) | |
| A61K 8/37 | (2006.01) | |
| C12P 19/44 | (2006.01) | |
| A61K 8/365 | (2006.01) | |
| A61Q 17/00 | (2006.01) | |
| A23B 7/154 | (2006.01) | |
| A01N 63/30 | (2020.01) | |
| A61K 8/9728 | (2017.01) | |
| A23L 2/44 | (2006.01) | |

(Continued)

(52) U.S. Cl.
CPC ............. *A01N 43/16* (2013.01); *A01N 63/30* (2020.01); *A23B 4/20* (2013.01); *A23B 5/14* (2013.01); *A23B 7/154* (2013.01); *A23B 9/26* (2013.01); *A23L 2/44* (2013.01); *A61K 8/33* (2013.01); *A61K 8/365* (2013.01); *A61K 8/37* (2013.01); *A61K 8/9728* (2017.08); *A61Q 5/02* (2013.01); *A61Q 17/005* (2013.01); *C07H 15/04* (2013.01); *C12P 19/44* (2013.01)

(58) Field of Classification Search
CPC . C07H 15/04; A61K 8/99; A61K 8/33; A61K 8/365; A61K 8/37; A01N 43/16; A01N 63/04; A23B 4/20; A23B 5/14; A23B 7/154; A23B 9/26; A23L 2/44; A61Q 5/02; A61Q 17/005; C12P 19/04
See application file for complete search history.

(56) References Cited

U.S. PATENT DOCUMENTS

| | | |
|---|---|---|
| 2,974,044 A | 3/1961 | Farrow et al. |
| 5,616,358 A | 4/1997 | Taylor et al. |

(Continued)

FOREIGN PATENT DOCUMENTS

| | | |
|---|---|---|
| CN | 1729293 A | 2/2006 |
| EP | 0750903 A1 | 1/1997 |

(Continued)

OTHER PUBLICATIONS

Nishida et al., "Structure Elucidation of Glycosidic Antibiotics Glykenins", The Journal of Antibiotics, vol. 44, No. 5, (1991) pp. 541-545.

(Continued)

*Primary Examiner* — Matthew P Coughlin
*Assistant Examiner* — Thurman Wheeler
(74) *Attorney, Agent, or Firm* — Norris McLaughlin, P.A.

(57) ABSTRACT

The invention relates to the use of, and methods of use employing, certain glycolipid compounds as defined in detail below and having preservative or antimicrobial properties, novel compounds of the glycolipid class, and related invention embodiments.
The compounds have the formula I

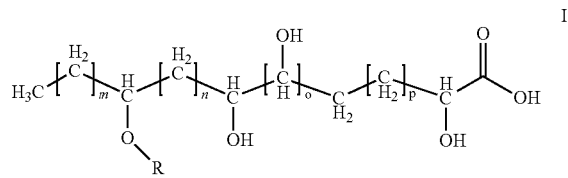

wherein m is 3 to 5, n is 2 to 5, o is 0 or 1 and p is 3 to 17, with the proviso that the sum m+n+o+p is not less than 14; and
R is a carbohydrate moiety bound via one of its carbon atoms to the binding oxygen,
and/or a physiologically, especially pharmaceutically or nutraceutically or cosmetically, acceptable salt thereof, or an ester thereof,
as such or in the form of a composition,
where the compound may be present in open chain form and/or in the form of a lactone (FIG. 1).

8 Claims, 4 Drawing Sheets

Specification includes a Sequence Listing.

(51) Int. Cl.
*A61K 8/33* (2006.01)
*A61Q 5/02* (2006.01)

(56) References Cited

U.S. PATENT DOCUMENTS

| | | | |
|---|---|---|---|
| 6,051,212 | A | 4/2000 | Kado |
| 6,506,738 | B1 | 1/2003 | Yu et al. |
| 7,714,185 | B2 | 5/2010 | Napier et al. |
| 10,638,757 | B2 * | 5/2020 | Henkel ................. A23L 3/3517 |
| 2006/0246556 | A1 | 11/2006 | Napier et al. |
| 2009/0067121 | A1 | 3/2009 | O'Sullivan et al. |
| 2010/0151104 | A1 | 6/2010 | Smith |
| 2012/0152149 | A1 | 6/2012 | Mijolovic et al. |

FOREIGN PATENT DOCUMENTS

| | | |
|---|---|---|
| EP | 1 151 677 A1 | 11/2001 |
| EP | 2 025 250 A1 | 2/2009 |
| JP | 2002 212079 A | 7/2002 |
| JP | 2006 176438 A | 7/2006 |
| JP | 2006 188475 A | 7/2006 |
| JP | 2006-223757 | 8/2006 |
| JP | 2009 531310 A | 9/2009 |
| KR | 2003 0012821 A | 2/2003 |
| WO | 96 38057 A1 | 12/1996 |
| WO | 03/034994 A2 | 5/2003 |
| WO | 2007 130738 A1 | 11/2007 |
| WO | 2009 000097 A2 | 12/2008 |
| WO | 2010 062548 A1 | 6/2010 |
| WO | 2011 023582 A2 | 3/2011 |
| WO | 2011 042088 A2 | 4/2011 |

OTHER PUBLICATIONS

Nishida et al., "Glykenin", Jissai (1996), pp. 252-272.
Nishida et al., "Structural elucidation of glycosidic antibiotics produced by Basidiomycetes", Tennen Yuki Kagobutsu FTronkai KKoen Yoshishu (1987), 29, pp. 729-736.
Nishida et al., "Structure Elucidation of Glycosidic Antibiotics, Glykenins, from *Basidiomycetes* sp. II. Absolute Structures of Unusual Polyhydroxylated C26-Fatty Acids, Aglycones of Glykenins", Chem. Pharm. Bull. 38 (9), (1990); pp. 2381-2389.
Nishida et al., "Structural elucidation of glycosidic antibiotics produced by Basidiomycetes", Symposium on the Chemistry of Natural Products (1987), pp. 253-259.
Nishida et al., "Structure Elucidation of Glykenin Glycosidic Antibiotics from *Basidiomycetes* sp. V. High-Performance Liquid Chromatographic Separation of Components of Glykenin"; Journal of Chromatography A, 664, (1994) pp. 195-202.
Nishida et al., "Structure Elucidation of Glykenin Glycosidic Antibiotics from *Basidiomycetes* sp. VI. Structure Characterization of the GK Components Using Frit-FAB LC/MS"; J. Mass Spectron. Soc. Jpn., vol. 43, No. 1, 1995, pp. 27-35.
Nishida et al., "Structure Elucidation of Glykenin Glycosidic Antibiotics from *Basidiomycetes* sp. VII. Structure Elucidation of the GK Components Using Tandem Mass Spectrometry"; J. Mass Spectron. Soc. Jpn., vol. 43, No. 1, 1995, pp. 37-44.
Nishikawa Carbohydrates esters Chern. Pharm. Bull. p. 387, 1975.

* cited by examiner

LONG CHAIN GLYCOLIPIDS USEFUL TO AVOID PERISHING OR MICROBIAL CONTAMINATION OF MATERIALS

PRIORITY CLAIM

This application is a division of U.S. patent application Ser. No. 14/124,429, filed Dec. 6, 2013, which is, in turn, a 371 of International Patent Application No. PCT/EP2012/002399, filed Jun. 6, 2012, which claims foreign priority benefit under 35 U.S.C. § 119 of the European Patent Application No. 11004776.8, filed Jun. 10, 2011, the disclosures of which patent applications are incorporated herein by reference.

SUMMARY OF THE INVENTION

The invention relates to the use of, and methods of use employing, certain glycolipid compounds as defined in detail below and having preservative or antimicrobial properties, novel compounds of the glycolipid class, and related invention embodiments.

These and related invention embodiments are described below and in the claims which are incorporated into the specification by reference.

BACKGROUND OF THE INVENTION

Bacteria and other microbial organisms cause food and beverage products, cosmetic and home care products as well as other products to go bad, thereby reducing the shelf life or useful life of such products or goods. Thus, numerous efforts have been made to reduce the deleterious effects of microbial contaminants in food and beverage products, cosmetics, dressing material and other materials, e.g. medical devices such as implants.

Other food preservatives such as salt, sugar and vinegar have been used for generations and while relatively safe to use, their preservative effect is limited in both duration of effect and the types of food and beverages for which they can be used. In addition, at higher levels, preservatives such as salt and vinegar can affect the taste of the product.

Commonly used preservatives for cosmetics include antimicrobial agents such as quaternary ammonium compounds, alcohols, chlorinated phenols, parabens and paraben salts, imidazolidinyl urea, phenoxyethanol, p-hydroxybenzoate, small carboxylic acids like benzoic acid, sorbic acid, salicylic acid, formic acid, proponic acid or corresponding salts. Formaldehyde-releasers and isothiazolinones may also be used.

However, these materials often may not be tolerated or, e.g. in the case of formaldehyde, may even be toxic and even carcinogenic, or they may cause allergies or food intolerance.

Another preservative e.g. used in food and especially beverages is sulfuric acid, while in meat products, e.g. sausages, preserved meat and meat, stabilizers which decrease water activity such as potassium and/or sodium nitrites and nitrates are often added. Also smoke is often used for preserving meat products, with the undesirable side effect of formation of polycyclic aromatic hydrocarbons which have carcinogenic properties.

Food and beverages have varying degrees of sensitivity to microbiological spoilage depending on intrinsic factors of the food or beverage such as pH, nutrient content (e.g., juice, vitamin, or micronutrient content), carbonation level, Brix (an indicator of sugar content), water quality (e.g., alkalinity and/or hardness), and preservatives.

Spoilage events occur when microorganisms are able to overcome the product's intrinsic protection factors and grow. The microorganisms' ability to overcome these hurdles can be influenced by, among other things, initial contamination level, temperature, water content, e.g. water activity, and package integrity. Of special importance are also recurrent contaminations of cosmetics, e.g. by hand contact during normal use.

A number of organisms are responsible for spoiling a variety of beverages materials, including cold-filled beverages. Yeasts such as *Saccharomyces, Zygosaccharomyces, Candida*, and *Dekkera* spp. are most common. Also, acidophilic bacteria such as *Lactobacillus, Leuconostoc, Gluconobacter*, and *Zymomonas* spp., and molds like *Penicillium, Aspergillus* and *Mucor* spp. can spoil various water containing materials.

Other materials and also other types of beverages are susceptible to spoilage by microorganisms. Spores of acidophilic, thermophilic bacteria, such as *Alicyclobacillus* spp., and heat resistant mold spores of Byssochlamys, its anamorphic (asexual) stages *Paecilomyces*, and *Neosartorya* spp. can survive pasteurization and may spoil non-carbonated, hot-filled products such as sport drinks and teas. Also, packaged waters are susceptible to contamination by molds.

In cosmetic, personal care and home care products spoilage occurs by a variety of micro-organisms, ranging from Gram-positive bacteria (e.g. *Staphylococcus* spp.), Gram-negative bacteria (e.g. *Escherichia coli, Pseudomonas* spp.) to yeasts (e.g. *Candida albicans*) and common molds (e.g. *Aspergillus niger*). Microbial growth in or on these products depends on several intrinsic factors such as water activity of the formulation (minimum water activity requirements for growth or proliferation range from 0.99 for *Acinetobacter* species down to 0.61 for some fungal species), formulation composition, pH value (e.g., optimum pH for the growth of most yeasts and molds is between 4.0 and 6.0), and processing conditions such as temperature. While high temperatures, e.g. 80° C. for 20 minutes, may reduce microbial contaminations during processing, it is important to prevent inactivation or degradation of the preservatives in the formulation. Furthermore, product packaging, solubility of the preservative and its antimicrobial susceptibility profile will influence preserving efficacy and, consequently, the shelf life of the products.

Protection against microbiological spoilage of sensitive products can be achieved using chemical preservatives and/or processing techniques such as hot filling, tunnel pasteurization, ultra-high temperature (UHT), or pasteurization followed by aseptic packaging, and/or pasteurization followed by chilling the beverage. Generally, beverages with a pH<4.6 can be chemically preserved, heat processed, and filled into packages such that the product is not re-contaminated. For example, process techniques such as cold-filling, followed by chemical preservatives or pasteurization with cold filling, may be used to preserve a cold-filled beverage. In a similar manner, this same beverage may be processed using non-preserved techniques such as hot filling, tunnel pasteurization, pasteurization followed by aseptic filling, or requiring the beverage to be chilled, i.e., under refrigeration following the pasteurization step. Beverages having a pH 2-4.6 must be processed such that spores are destroyed using ultra-high temperatures followed by aseptic filling into packages or by using a retort.

Current preservation systems for acidic, shelf-stable, carbonated and non-carbonated food or beverages, e.g. soft drinks, generally rely on weak acid preservatives (e.g., benzoic and/or sorbic acid). Benzoic and sorbic acids (and salts thereof) effectively inhibit yeasts, bacteria, and molds with some exceptions. Weak acids in beverages exist in equilibrium between their dissociated and undissociated forms, which is dependent upon the dissociation constant of the acid (pKa) and the beverage's pH. The pKa for benzoic acid is 4.19 and the pKa of sorbic acid is 4.76. A beverage pH below the pKa of the involved acid pushes the equilibrium towards the undissociated form. The undissociated form is more efficacious against microorganisms; therefore, weak acid preservatives are most effective in the low pH range.

The preservation properties of weak acids may be enhanced by the addition of preservative enhancers, such as chelating compounds, to the material to be preserved, e.g. a food, beverage or cosmetic preparation. For example, common chelating compounds added include calcium disodium ethylenediaminetetraacetic acid (EDTA) or one or more of the polyphosphates such as sodium hexametaphosphate (SHMP).

In high nutrient, non-carbonated products, such as those beverages containing juice, vitamins, and/or minerals, the weak acids are more likely to exert inhibition if used in conjunction with preservative enhancers. Also weak acid preservation systems, however, have limitations:

Genetic adaptation and subsequent resistance by microorganisms is one of the biggest concerns (see Piper. et al., Microbiol. (2001) 147: 2635-2642). Certain yeasts such as *Z. bailii, Z. bisporus, Candida krusei*, and *S. cerevisiae* have specific genes that enable them to resist the weak acid preservatives and grow. This happens despite the presence of preservatives and regardless of the co-presence of EDTA or SHMP. Some bacteria such as *Gluconobacter* spp. are also thought to be preservative resistant. The levels of weak acids necessary to overcome this resistance have been shown to be far beyond regulatory limits on use levels. Most often, spoilage of preserved teas, juice-containing beverages, and carbonated beverages is due to preservative resistant microorganisms.

Medium chain saturated fatty acids and their esters with oligohydroxylated compounds have been found to possess inhibitory effects against several bacteria and fungi. The minimum inhibitory concentration values reach a maximum with a chain length of about 8 to 12 carbon atoms (Varvaresou, Int. J. Cosmetic Sci (2009) 31: 163-75).

In addition, the other process techniques for low acid beverages (i.e., pH≥4.6) have limitations. Such low acid beverages should be thermally-treated sufficiently to destroy spores of *Clostridium botulinum* and *Bacillus* species (*B. cereus, B. subtilis* and others). Examples of such processes include UHT and retort. Even after such processing, the beverage products should be handled in a way to prevent post-processing contamination. Research, however, suggests that there may still be various strains of microorganisms that can survive those different processing techniques. To that end, those processing techniques may not eliminate the potential for spoilage.

Other chemical preservatives can likewise cause adverse side effects when consumed. Thus, many existing preservatives must be regulated and have legally imposed upper limits on usage. In addition, many preservatives, such as sodium benzoate, proprionates, aromatic benzenes, organic acids, propylene glycol and glycerol, for example, when used at levels sufficient for antimicrobial effects, impart an unpleasant taste on the beverage or food, masking or altering to some degree the taste expected by the consumer. Weak acids can impart throat or mouth burn when used at high levels. Although there are certain shelf-stable beverages where this attribute may be acceptable, this sensory perception is often considered negative. Similarly, polyphosphates used in weak acid preservation systems can have some limitations. For example, polyphosphates can impart off-flavors to a beverage.

Certain emollient solvents exhibit synergistic action when combined with essential oils or ingredients against microorganisms as noted in WO 03/034994, which is incorporated by reference in its entirety. The emollient solvents used as preservatives in cosmetics do not usually produce skin reactions, and in addition, render the skin smooth and silky.

In a series of publications Nishida et al. reported on compounds of an unidentified strain of "*Basidiomycetes* sp." to produce glycolipids which are assumed to exhibit inhibitory activity against Gram-positive bacteria (Nishida, Tetrahedron Lett 1988, 29(41): 5287-90; Chem Pharm Bull 1990, 38(9): 2381-9; J Antibiot 1991, 44(5): 541-5; Chem Pharm Bull 1991, 39(11): 3044-7; Proc "Symposium on the chemistry of natural organic compounds" 1987, 29: 729-36; ibid 1990, 32: 253-9) and against infection by polio and herpes virus (J Chrom 1994, 664(2): 195-202; J Mass Spectrom Soc Jpn 1995, 43(1): 27-36; ibid 37-44). Much effort was done in the structure elucidation and the results were presented in detail in the above cited publications; nevertheless the authors did not present any data of the suggested antimicrobial activity. Later on, one of the compounds isolated by Nishida et al. (Glykenin IVA) was reported as antifungal agent from a *Dacrymyces* sp. (Wunder, A., Diss. 1995, Univ. Kaiserslautern, Germany). Mierau (Z Naturforsch 2003; 58c: 541-6) made reference to this work. In neither of the cited publications, details on the biological data and the identity of the producer organisms were reported.

JP 2006-176438 A and J. Antibiot. 2007, 60, 633-639 disclose F-19848 A, a glyocolipid obtained from the fermentation broth of the fungus strain *Dacrymyces* sp. SANK 20204, as inhibitor of hyaluronic acid binding receptor CD44 and as being useful for treating or preventing degenerative arthritis or a disease caused by the degenerative arthritis.

Biosurfactants are produced extracellularly or as a part of the cellular membrane by various organisms such as bacteria and fungi. Their structures usually contain a hydrophobic non-polar moiety that consists of unsaturated, saturated, and/or oxidized lipids or fatty acids, and a hydrophilic component, which may be composed of amino acids, carbohydrates, phosphates or cyclic peptides. They are generally classified into glycolipids, lipopeptides, phospholipids, fatty acids and polymeric compounds according to their chemical structures. Biosurfactants are produced by a wide range of microorganisms and therefore differ in their chemical structure. Some biosurfactants have antimicrobial activity against bacteria, yeasts, molds or viruses. Moreover, they can prevent microbial colonization of surfaces such as those of implanted medical devices through their ability to disrupt biofilms on these surfaces.

Sophorolipids, rhamnolipids and mannosyl-erythritol lipids are the most widely used glycolipid biosurfactants in cosmetics.

Rhamnolipids are known for their efficiency in remove of nosocomial microbes in biofilms. A biofilm is characterized by a strong adherence activity of the engaged microorganisms. Known biosurfactants with anti-adhesive or biofilm disrupting activity are produced by *Lactobacillus acidophilus, L. fermentum, Lactococcus lactis, Streptococcus thermophilus, Bacillus subtilis, B. licheniformis, Brevibacterium aureum, Pseudomonas aeruginosa*, and *P. putida*.

The genus *Lactobacillus* produces the lipopeptide surlactin, the genus *Bacillus* produces lipopeptides belonging to the fengycin-like and surfactin-like families of secondary metabolites. Another lipopeptide has been isolated from *Brevibacterium aureum*. *Streptococcus thermophilus* is a producer of yet unidentified glycolipids, which contain sizeable amounts of nitrogen (Rodrigues, Colloids & Surfaces B: Biointerfaces (2006) 53: 105-112). Further known producers of biosurfactants exhibiting activity against microorganisms involved in biofilms are *Pseudomonas aeruginosa* which produces rhamnolipids, and *P. putida*, which produces lipopeptides. The nitrogen containing biosurfactants produced by *Streptococcus mitis* were not yet identified. *Lactococcus lactis* produces a low molecular weight [467 Da] biosurfactant consisting of methyl-2-O-methyl-beta-d-xylopyranoside with octadecanoic acid. (Saravanakumari & Mani, Bioresour Technol (2010) 101: 8851-8854).

A good overview of different classes of known biosurfactants is given by Rahman et al. (Biotechnology (2008): 360-70) presenting great advantages of theses compounds against synthetic compounds such as a lower toxicity, higher biodegradability, a better environmental compatibility and their ability to tolerate extreme temperature, pH and salinity. Nevertheless the reported difficulties in the production teach the limitation of industrial usage as being relative low yields, high fermentation costs and difficult isolation procedures within industrial processes. Acceptable economic production of biosurfactants in large scale is suggested by the use of industrial wastes as process media.

As commonly understood in the art, the definitions of the terms "preserve", "preservative," and "preservation" do not provide a standard time period for how long the matter to be preserved is kept from spoilage, decomposition, or discoloration. The time period for "preservation" can vary greatly, depending on the subject matter. Without a stated time period, it can be difficult or impossible to infer the time period required for a composition to act as a "preservative".

In summary, many preservatives and preservation methods have undesirable side effects, such as toxicity, allergenicity, carcinogenicity, occasionally formation of resistance, and/or often are not accepted by the consumers in a time where natural preservation is preferred over preservation with synthetic or other products having a negative health image.

Accordingly, a great need exists for effective, relatively inexpensive, non-toxic, naturally derived preservative compositions that avoid disadvantages as mentioned and are capable of reducing microbial contamination and concomitant spoilage in a wide range of perishable food, beverages, cosmetics, and other consumer goods, but without appreciably altering the taste, color, odor, or function of the product.

General Description of the Invention

Surprisingly, new compounds were found and isolated from strains of Dacryopinax spathularia and other fungal strains belonging to the Dacrymycetaceae family, and for them as well as for compounds of the same class it has been found that they have novel and useful properties. The compounds are described in more detail below.

The class of compounds of the formula I, both insofar as they are not novel as well as they are novel, is not known in the art for any spoilage/perishing preventing activity.

Very surprisingly therefore, it has been found that these compounds exhibit a strong inhibition activity against microorganisms which are responsible for spoiling or deterioration of orally consumable products (such as food products and beverages) or cosmetic compositions. For example, an extract of Dacryopinax according to the present invention can show a broader activity spectrum than the corresponding single components of the produced glycolipid complex (glycolipid mixture) that have been isolated to purity. Such multi-component mixtures exhibit a remarkable long term activity against numerous important spoilage microbes, including e.g. *Zygosaccharomyces* and *Bacillus* species.

Further surprisingly, the microorganisms used in the present invention allow producing large amounts of the compounds of formula I in a cost effective production process.

They are, for example, able to reduce growth of microbial contaminants such as bacteria, yeasts, molds and other microorganisms and their spores, especially those which are temperature resistant e.g. thermophilic or heat resistant, or acidophilic e.g. microorganisms which tolerate a lower pH value that cause spoilage of food, beverages, cosmetics and other materials.

The glycolipids do not exhibit a distinctive taste or unpleasant mouth feeling and therefore this application relates to the use of glycolipids in materials which get in contact with the oral cavity of a human. This application also relates to synergistic combinations of antimicrobial ingredients that can be used in orally consumable compositions, such as food and beverages, without imparting off-flavors.

Yet surprisingly it was found that the use of a simple medium only using dextrose or glucose as carbon source and a small amount of yeast extract can be superior against typical complex media known from the literature. However, also the use of other media or growth substrates is included. Furthermore it was found that this culture medium supported particularly high production rates at relatively low biomass production, which facilitated downstream processing of the crude glycolipid products, allowing their easy recovery from the culture fluid by precipitation.

The glycolipids of the present invention can be shown to demonstrate a broad antimicrobial spectrum and can be incorporated as additives into various materials as a preservative or an agent with preserving activity, especially as cosmetic additive and/or food additive and/or beverage additive based on this antimicrobial activity.

Although the mechanism of action for the glycolipids is unknown, these compounds can, without that this is intended to mean a comprehensive and concluding definition of their properties, be considered as biosurfactants and, additionally, might influence the cell membranes of microorganisms. Other known biosurfactants are rhamnolipids, sophorolipids, lipopeptides like chlamydocin, surfactin, lichenysin G, etc. as cited by Mukherjee (in "Biosurfactins", R Sen ed., Springer, 2010, chapter 4, "Microbial Surfactants and Their Potential Applications"). The cited biosurfactants differ from the compounds of formula I of the present invention. Although Mukherjee listed compounds named as glycolipids, the structures of these compounds differ significantly from those of the present invention:

The compounds useful according to the invention are in general characterized
    by a long chain fatty acid with at least 20 carbon atoms;
    by a carbohydrate moiety which is not attached to the acid group:
    by an alpha hydroxyl group;
    and by at least one further hydroxyl group, in the "center" of the fatty acid carbon chain, clearly separated from both the alpha position and the glycosyl substituent.

Especially compounds of the formula I represented below which are esterified in their carbohydrate moiety by other acids than acetic acid, in particular esterified by isovaleric acid, are not known in the art and thus novel.

DETAILED DESCRIPTION OF THE INVENTION

In a first embodiment, the invention relates to the use of a compound of the formula I, or a mixture of two or more such compounds of the formula I,

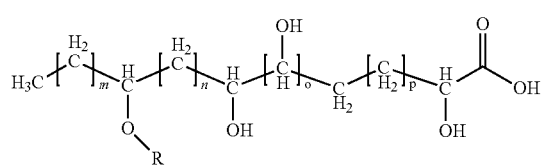

wherein m is 3 to 5, n is 2 to 5, o is 0 or 1 and p is 3 to 17, with the proviso that the sum m+n+o+p is not less than 14; and R is a carbohydrate moiety bound via one of its carbon atoms to the binding oxygen, and/or a physiologically, especially pharmaceutically or nutraceutically or cosmetically, acceptable salt thereof, or an ester thereof, as such or in the form of a composition, where the compound may be present in open chain form and/or in the form of a lactone, as agent with preservative or antimicrobial properties, comprising adding the agent to a material, where said material is preferably selected from the group consisting of a cosmetic, a food, a beverage, a pharmaceutical, a medical device, a home care, and an active packaging material.

Preferred is the use, where in the compound of the formula I, m is 3 to 5, n is 2 to 5, o is 0 or 1, p is 5 to 15 and R is a moiety of the subformula

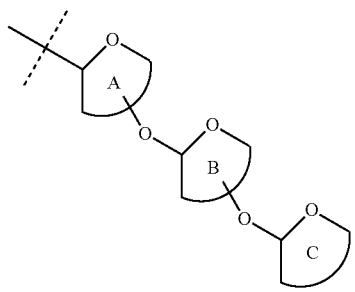

wherein the rings A, B and C are monosaccharide moieties each independently from the others with 5 or 6 ring members, wherein one or more of the hydroxyl groups may be acylated.

In other terms: A compound for use according to the invention is especially a linear carboxylic acid with at least 20 carbon atoms, preferably 22 to 28, 24 to 26, in particular 26, substituted at position 2, that means the alpha position, with a hydroxyl group; substituted with a second hydroxyl group at the omega-5, omega-6 or omega-7 position which is itself substituted by a carbohydrate, e.g. as defined below, and one additional (a third) hydroxyl group between the omega and the alpha substituents which is separated from the second one by two to five methylene groups, where optionally this third hydroxyl group has a vicinal hydroxyl group, in the direction of the acidic end.

In another embodiment of the invention, the compound or compounds of the formula I, a physiologically acceptable salt thereof, and/or an ester thereof, is added in the form of an extract from a natural source or obtained from such an extract. Preferably, the source of the extract is a fungus belonging to family Dacrymycetaceae, a species of the genera Dacryopinax, Ditiola, Guepiniopsis and/or Femsjonia, more especially Dacryopinax spathularia, *Dacrymyces* sp., *Dacrymyces stillatus*, *Dacrymyces chrysocomus*, *Guepiniopsis buccina* and/or *Femsjonia luteo-alba* (=*Ditiola pezizaeformis*). Especially preferred are Dacryopinax spathularia strain MUCL 53181, *Dacryopinax spathularia* strain MUCL 53182, *Ditiola radicata* strain MUCL 53180, *Ditiola nuda* strain MUCL 53179, *Dacrymyces chrysocomus* strain CBS280.84 and Femsjonia luteo-alba (=*Ditiola pezizaeformis*) strain MUCL 53500.

In our investigations we found *Dacryopinax spathularia* strain MUCL 53181 to be the best strain for identified so far for producing the compounds of formula I and mixtures of two or more compounds of formula I, in particular those described in detail hereinafter, particularly the compounds of formula I exhibiting the strongest antimicrobial activity against yeasts and molds. Thus, in a further aspect the present invention also relates to *Dacryopinax spathularia* strain MUCL 53181 as such.

Another embodiment relates to the use as described above or below of one or more compounds of the formula I, where the material to which such compound(s) are applied is subjected to a heat treatment before, during or after addition of the compound(s) of the formula I, a physiologically acceptable salt thereof and/or an ester thereof.

In another embodiment, the invention relates to a novel compound of the formula I, or a mixture of two or more compounds of the formula I including a novel compound of the formula I, where the compound or compounds may be present in open chain form and/or in the form of a lactone, and/or a pharmaceutically or nutraceutically or cosmetically acceptable salt thereof, as such.

Another embodiment of the invention relates to a compound or a mixture of compounds of the formula I shown above or as defined above or below, where the moiety R carries at least one hydroxyl group esterified with an acid with 3 or more carbon atoms, a physiologically acceptable salt, and/or an ester thereof, especially wherein the acid is a $C_5$-$C_{10}$-alkanoic acid, especially isovaleric acid; a physiologically acceptable salt, and/or an ester thereof, more especially a compound selected from the group of compounds represented by the following formulae:

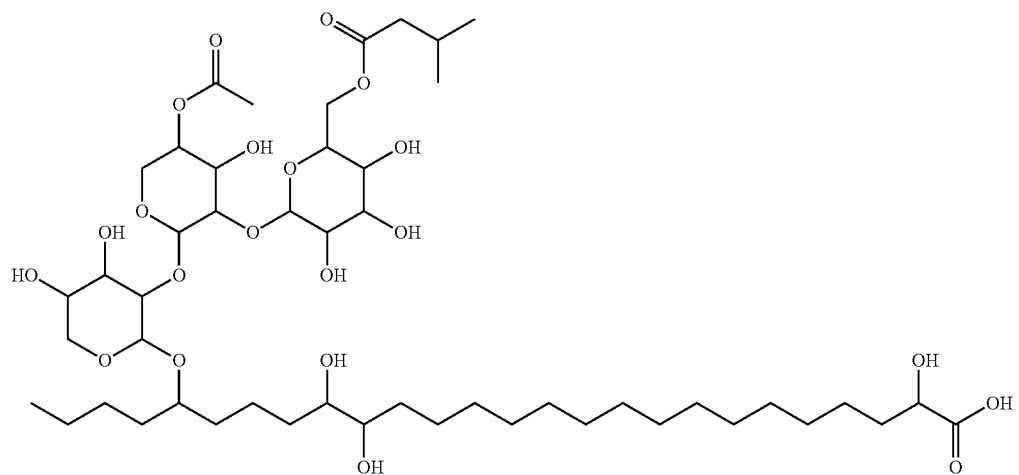
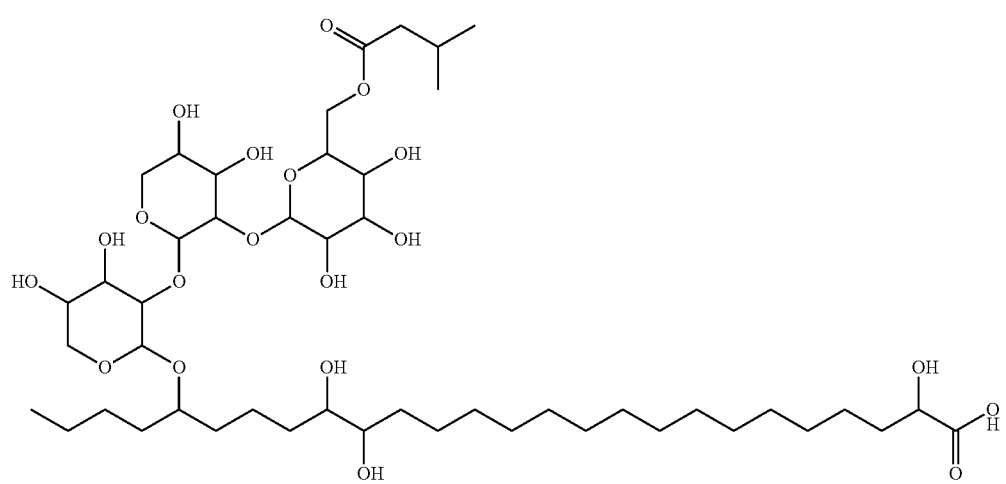
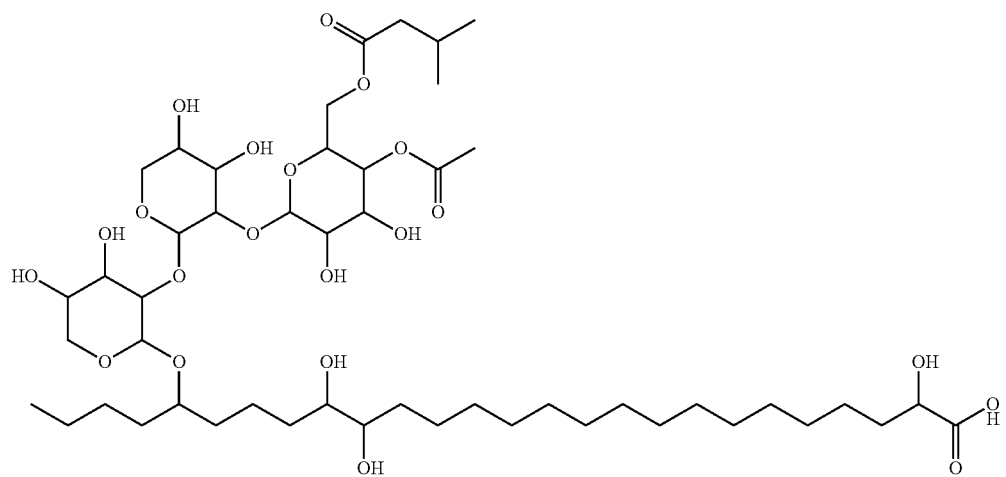

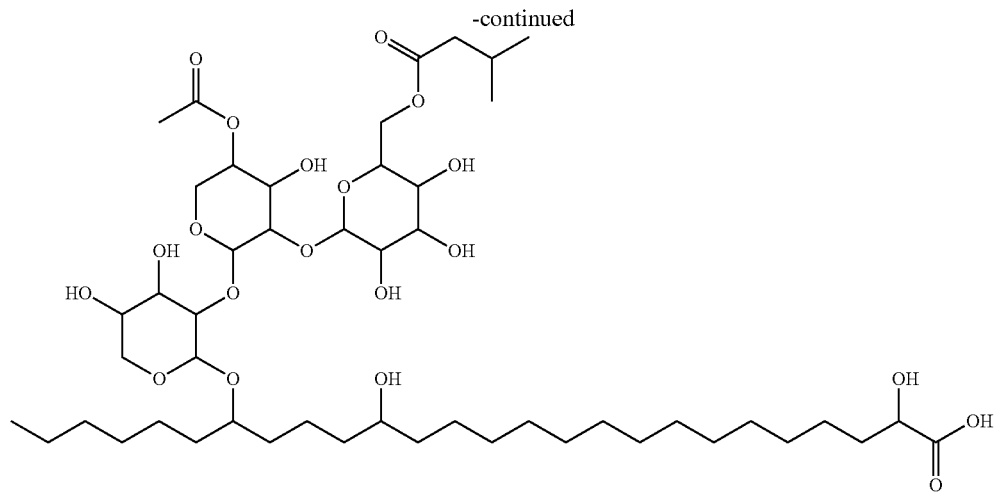
-continued and/or a physiologically acceptable salt, and/or an ester of the acid group thereof.

In yet another embodiment, the present invention relates to a preservative or antimicrobial composition, comprising as active agent a compound or a mixture of compounds of the formula I, a physiologically acceptable salt thereof, and/or an ester thereof, as described herein, alone or with another additive, such as a carrier material, where the preservative composition is especially for use in a cosmetic, a food, a beverage, a pharmaceutical, a medical device, or an active packaging material, especially in the form of a powder or a liquid, e.g. a composition which is a coating or film. The composition, in a more specific embodiment of the invention, may be a precursor of a beverage, especially a concentrate, a syrup or a powder.

In another embodiment, the composition defined in the preceding paragraph is an antimicrobial composition for enhancing the stability against microorganisms, especially where at least one microorganism is selected from the group consisting of mold, yeast and bacteria.

In another embodiment, the composition according to any one of the two preceding paragraphs is a preservative or antimicrobial composition for a pharmaceutical, a medical device, a food container, a beverage container, or especially a food, a beverage, a cosmetic, or a home care product.

In another embodiment, the composition according to any one of the two preceding paragraphs is a biofilm inhibiting agent and used as such by administering, or in methods comprising administering, one or more compounds of the formula I, or a composition comprising it, to surfaces or materials coming into contact with surfaces. This way biofilms on various materials including medical devices, teeth, containers, home care products, pipes or mains or other liquid conducting or containing devices and the like can be avoided.

In yet another embodiment of the invention, the composition according to any one of the preceding four paragraphs comprises an additional preservative.

The invention, in yet another embodiment, also relates to an extract comprising one or more compounds of the formula I, a physiologically acceptable salt thereof, and/or an ester thereof, as shown or defined above or below.

A further invention embodiment relates to a method of enhancing microbial stability of a material, comprising adding to said material one or more compounds of the formula I, a physiologically acceptable salt thereof, and/or an ester thereof, as shown or defined above or below, preferably a material selected from the group consisting of a cosmetic, a food, a beverage, a pharmaceutical, a home care, a medical device, and an active packaging material, especially a beverage, or a food, or a cosmetic.

Another embodiment of the invention relates to a material comprising, as or within a coating and/or as admixture, an additive in the form of a compound or a mixture of compounds of the formula I, a physiologically acceptable salt thereof and/or an ester thereof, as defined above or below. This material must be other than the fungus from which the compound or compounds of the formula I are extracted. In another embodiment of the invention, the material is a cosmetic, a food, a beverage, a pharmaceutical, a home care, a medical device, or an active packaging material, especially a beverage, a beverage precursor, especially a concentrate, syrup or powder, a food or a cosmetic. In another embodiment, such material comprises an additional preservative.

Another invention embodiment relates to a material according to the preceding paragraph, which is obtained after heat treatment.

The invention also relates to a method of extracting and/or isolating one or more compounds of the formula I, especially as described below and/or in the Examples.

The invention also relates to the embodiments in the claims and especially the dependent claims which are herewith incorporated by reference into the description.

The compounds of the present invention or useful according to the present invention of the formula I, according to present knowledge, are produced only by fungi of the family Dacrymycetaceae, particularly by fungi of the genera *Dacryopinax* (e.g. *D. spathularia*), *Dacrymyces*, *Ditiola* (e.g. *Ditiola radicata* or *Ditiola nuda*), *Guepiniopsis* and *Femsjonia* (e.g. *F. luteo-alba*). All these fungi have in common that they belong to family Dacrymycetaceae. All species of Dacrymycetaceae hitherto known are wood-inhabiting saprotrophs, which may either cause brown rot or white rot (Seifert, Mycologia 75 (1983): 1011-1018). Even though they can be isolated easily from spores of basidiocarps growing in the field and readily grow in culture, relatively few strains of Dacrymycetes are deposited in public collections.

The fungal genus *Dacryopinax* G. W. Martin was erected by Martin (Lloydia 11 (1948): 111-122) and currently comprises 23 accepted taxa, including 22 species and one variety (fide Mycobank; http://www.mycobank.org). According to the latter database, the genus is presently classified in the Basidiomycota, class Dacrymycetes, order Dacrymycetales, family Dacrymycetaceae. Members of the Dacrymycetes (previously often referred to as order Dacrymycetales before it was elevated to class rank), are characterized by their unique basidial morphology with two equidiametrous epibasidia, thus shaping the basidium like a tuning fork. In addition, they have dolipores with continuous parenthesomes.

These common morphological and ultrastructural features were supported very well in various molecular phylogenetic studies, as reflected by Hibbett (Mycologia 98, 917-925, 2006) and references cited therein. Most species of the Dacrymycetes still belong to order Dacrymycetales, family Dacrymycetaceae. The latter family comprises eight genera, which have been traditionally separated on the basis of macroscopical (primarily relating to the basidiocarp habit) and microscopical (e.g., the wall thickness of marginal hyphae in the sterile parts of basidiocarps) morphological characters of the fruiting bodies (i.e., basidiocarps). However, this classification is not unequivocal and therefore gave rise to various alternative taxonomic concepts over the past decades. For instance, McNabb (N.Z.J. Bot 3, 59-72, 1965), gave the first comprehensive treatment of *Dacryopinax* and circumscribed its basidiocarp habit as follows; "Fructifications extremely variable in shape, stipitate with a spathulate, petaloid, flabellate, cupulate, obliquely cupulate, inversely cupulate, foliose, or occasionally lobed and somewhat morchelloid pileus" This circumscription, which is still valid until today, suggests that *Dacryopinax* is a complex genus. In addition, recent molecular phylogentic studies by Shirouzu et al (Mycoscience 48:388-394, 2007 and Persoonia 23, 16-34, 2009) suggested that convergent evolutionary developments in the Dacrymycetales and Dacrymycetaceae might have given rise to development of similar morphological features, hence the basidiocarps that are characteristic of *Dacryopinax* and other genera of Dacrymycetaceae might have evolved independently more than once.

The currently accepted type species of *Dacryopinax* is *Dacryopinax elegans*. However, by far the most cited species in the literature is *Dacryopinax spathularia* (Schwein Fr.) G. W. Martin. This species was first described from South Carolina, USA, and had been treated under different names (i.e., *Merulius spathularius, Guepinia spathularia*) before Martin proposed the genus *Dacryopinax*. Under *Guepinia spathularia* (which is an invalid, later synonym of a plant genus name and therefore had to be abandoned), this fungus was already reported to occur in various tropical and subtropical regions of the world, including Northern Australia, New Zealand, Asia and America by Saccardo, P. A., Sylloge Fungorum 6, p 808 (1888) and has since then been reported from numerous other countries of the world. *Dacryopinax spathularia* possesses an unusual geographical distribution. According to McNabb (N.Z.J. Bot 3 (1965): 59-72) it is widely distributed throughout both hemispheres, but has never been found in Europe, though it occurs in North Africa and eastern Russia. The species is characterised by having variable, albeit typically spathulate basidiocarps of up to 2.5 mm height, uniseptate spores, and thick-walled, cylindrical abhymenial hairs.

*Dacryopinax spathularia* is one of the species in the family and order which is capable of producing comparably large basidiocarps. It was reported to be used as "edible mushroom" by the indigenous population of Cameroon (Van Dyck et al., Ambio 32 (2003): 19-23). The entire fungal family Dacrymycetaceae does not contain any poisonous species, even though the basidiocarps of most species are rather inconspicuous and/or have a tough, rubbery consistence that prevents their culinary use. Interestingly, the cultures of certain *Dacrymyces* species, which can be regarded as closely related to *Dacryopinax*, have been patented for their utility in production of carotene pigments (U.S. Pat. No. 2,974,044). Carotenoids are also apparently the only secondary metabolites that were so far reported from a species of *Dacryopinax*, and their production in the cultures of *D. spathularia* have been studied in detail by Vail & Lilly (Mycologia 60 (1968): 902-907).

The fungal strains that produce the compounds of the present invention were characterised by morphological methodology, using phase contrast microscopy of cultures grown on solid YMG medium, and by molecular phylogenetic methods. Since the LSU or 28S/5.8S nuc-rDNA had recently been reported to be informative for the phylogenetic assessments of the Dacrymycetes by Shirouzu et al (Persoonia 23, 16-34, 2009), and the authors of the latter paper published numerous reliable reference sequence data, this region of the DNA was chosen for comparison upon characterisation of the strains of Dacrymycetes that are the subject of the present invention.

DNA for PCR was isolated from YMG cultures. The 28S/5.8S nuc-rDNA regions were then amplified using primers LR7 and 5.8SR (Vilgalys Lab, Duke University, Durham, USA, http://www.biology.duke.edu/fungi/mycolab/primers.htm), using the PCR Taq PCR Core Kit (Qiagen, Hilden), and applying a standard thermal profile with an annealing temperature of 53° C. Amplification products were purified using SigmaSpin Post-Reaction Clean-Up columns (Sigma-Aldrich), using the protocol supplied by the manufacturer. Nucleotide sequences were obtained by cycle sequencing using a DNA Cycle Sequencing Kit (Jena Bioscience, Jena, Germany) and 5' IRD700-labelled primer LROR (Vilgalys Lab). Labelled primers were custom synthesized by Eurofins MWG Operon, Ebersberg, Germany). The cycle sequencing products were then analysed using a LI-COR 4200 (Li-Cor Bioscience, Lincoln, NB) genetic analyser. In the following the characteristics of five strains that were identified of producers of the glycolipids that are subject of the current invention are briefly summarised.

Strain FU50088 was isolated from the sporocarp of an unidentified basidiomycete growing on wood in French Guiana by Sergej Buchet in 2002, provided to Bayer Healthcare AG, and selected for fermentation in order to provide extracts that are suitable for natural products screening. On YMG agar at 23° C., the culture attained about 10 mm diameter after 10 days of incubation. The mycelium at first appeared velvety and white, but soon attained a strong yellowish color. The occasional presence of clamp connections revealed that the fungus belongs to the Basidiomycota. After 5 days of incubation, conidiogenous cells appeared in abundance on the vegetative hyphae, showing polyblastic, sympodial conidiogenesis, producing subglobose hyaline conidia, averaging 5-6×2.5-3 µm in size. These characteristics were found to be largely in agreement with the data reported by Shirouzu et al (Persoonia 23, 16-34, 2009). The LSU nucrDNA sequence of this strain FU50088 is included here as sequence <SEQ ID NO: 1>.

The strain was studied in comparison with an authentic strain of *Dacryopinax spathularia*, CBS 197.63, originating from Africa, which was obtained from the Centrallbureau voor Schimmelcultures, Utrecht, The Netherlands. Its morphological characteristics, as well as its secondary metabolite production were largely in accordance with that of strain FU50088. Furthermore, a high degree of homology was observed between the 5.8S/ITS nrDNA and 28S nrDNA sequences of the two aforementioned strains and reference DNA sequence data that had been published on the Internet by specialists in the taxonomy and phylogeny of Basidiomycota, under the name of *Dacryopinax spathularia* or synonyms thereof. Therefore, strain FU50088 was identified to belong to the species *Dacryopinax spathularia* by morphological, molecular phylogenetic and chemotaxonomic methodology and is referred herein as this species.

The reference strain *Dacryopinax spathularia* CBS 197.63, collected from Bangui, Central African Republic, isolated by J. Boidin and deposited with CBS in April 1963, resembled *Dacryopinax spathularia* strain FU50088 in its growth and morphological characteristics. However, its pigmentation was not as intense, and even in aged cultures, the mycelia only turned pale yellow. The conidia were subglobose to ovoid, measuring 3-6.5(–8)×2.5-4 µm. The LSU nucrDNA sequence of this reference strain CBS 197.63 is included here as sequence <SEQ ID NO: 2>.

Three other strains that were not assigned to the genus *Dacryopinax* but are members of family Dacrymycetaceae as well were obtained from public culture collections, studied and found to produce the compounds of the invention. Their history and characteristics are given below:

*Ditiola nuda* strain CBS 173.60 was isolated in Shirokane, Tokyo, Japan, from a petiole of the plant *Shiia sieboldii* according to the information provided in the CBS catalogue and deposited with CBS by K. Tubaki in 1960. The strain showed similar growth characteristics to *Dacryopinax spathularia* FU50088 and like those of the latter strain; its conidia measured 6-5×2.5-3 µm. The LSU nucrDNA sequence of *Ditiola nuda* strain CBS 173.60 is included here as sequence <SEQ ID NO: 3>.

*Ditiola radicata* strain CBS 126.84 was isolated from sporocarps growing on gymnosperm wood collected in August 1982 in Canada, Alberta, Banff National Park, C Level Cirque Trail, by Keith A. Seifert and deposited with CBS in 1984. The strain showed similar growth and morphological characteristics to *Dacryopinax spathularia* FU50088, but had smaller conidia (4-5×1.5-2 µm). The LSU nucrDNA sequence of *Ditiola radicata* strain CBS 126.84 is included here as sequence <SEQ ID NO: 4>.

*Ditiola pezizaeformis* strain ATCC13299 was originally deposited with ATCC as Femsjonia luteo-alba. The strain had been used in an U.S. Pat. No. 2,974,044 and claimed to be a producer of carotenoids. However, according to the current taxonomy, Femsjonia luteo-alba is a synonym of the valid, internationally accepted name, *Ditiola pezizaeformis*, as reported by Reid (A monograph of the British Dacrymycetales.

Transactions of the British Mycological Society 62 (1974): 433-494) and in accordance with current entries in Mycobank and other taxonomic databases and monographs of *Basidiomycetes*. The strain ATCC13299 also showed similar growth and morphological characteristics to strain FU50088, and its conidia were elongate-ellipsoid to subglobose, 5-6.5×1.5-2 µm. The LSU nucrDNA sequence of *Ditiola pezizaeformis* strain ATCC13299 is included here as sequence <SEQ ID NO: 5>.

*Dacryopinax spathularia* strain FU50088 has been deposited under the Budapest Treaty at BCCM/MUCL, Mycothèque de l'Université catholique de Louvain, Place Croix du Sud 3, B-1348 Louvain-la-Neuve, Belgium, under the designation number MUCL 53181 on 11 Oct. 2010.

Other strains which produce the compounds of the invention have also been deposited under the Budapest Treaty at BCCM/MUCL: *Dacryopinax spathularia*, CBS 197.63 under the designation number MUCL 53182 on 11 Oct. 2010, *Ditiola radicata*, CBS 126.84 under the designation number MUCL 53180 on 11 Oct. 2010, *Ditiola nuda*, CBS 173.60 under the designation number MUCL 53179 on 11 Oct. 2010, and *Femsjonia luteo-alba* Fr.1849, ATCC13299 under the designation number MUCL 53500 at 19 May 2011.

Surprisingly the compounds of the invention e.g. compounds of the formula I exhibit a strong, long term inhibitory activity against organisms involved in spoilage of pharmaceutical nutraceutical, nutritional, cosmeceutical, and/or cosmetic preparations or compositions. Said compounds are especially useful against acidophilic spoilage yeasts, which are involved in spoiling or deterioration of beverages. Even more surprisingly these compounds are able to inhibit the growth of thermophilic molds, which are difficult to control with standard sterilizing and/or pasteurizing processes.

APPLICATIONS & DEFINITIONS

Figure 1:
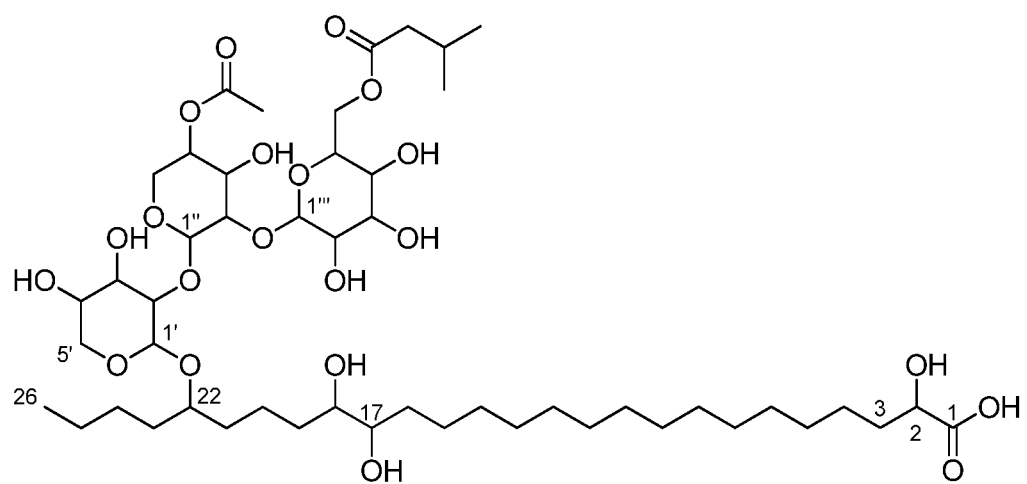
FIG. 1: Atom numbering of the compounds of the invention for signal assignments of analytical processes.

The general expressions, within the present disclosure, preferably have the following meaning, where in each embodiment one, more than one or all more general expressions may, independently of each other, be replaced with the more specific definitions, thus forming special, e.g. preferred, embodiments of the invention, respectively:

Preferably, the compounds of the formula I are natural compounds, that is, compounds that are present in and can be isolated or extracted from natural sources (especially those mentioned in detail above and below) without chemical synthesis steps (though they may also be prepared or modified by chemical synthesis, e.g. acylated or the like), or be modified by certain downstream processing procedures (e.g. permethylated under influence of acidic methanol) and are thus present as extracts or purified components of extracts, and not derivatives only obtainable by chemical synthesis.

They can also be present and used as part of an extract which is obtainable by extracting a fungus or a part from an appropriate fungus of the genus *Dacryopinax*.

"Substantially" means preferably that the corresponding impurities are present only in trace amounts, e.g. in less than 5% by weight, less than 4% by weight, less than 3% by weight, less than 2% by weight, less than 1% by weight, less than 0.5% by weight or less than 0.2% by weight, in relation to the complete weight of the corresponding dry extract or compound of the formula I or mixture of compounds of the formula I.

In the context of the present invention, the terms "essentially consists of" or "essentially consisting of" mean that the total weight share is 90 wt. % or more, preferably 95 wt. % or more, more preferably 98 wt. % or more, most preferably 99 wt. % or more, in each case based on the total amount used. For example, a "mixture essentially consisting of" means that the total amount of the constituents as defined in the respective case is 90 wt. % or more, preferably 95 wt. % or more, more preferably 98 wt. % or more, most preferably 99 wt. % or more, in each case based on the total weight of the mixture The term "Glycolipid" can be replaced with "glycosylated fatty acid" as well, where it is used with regard to the compounds of the formula I.

"A compound of the formula I" or "compound(s) of the formula I" can refer to one or more compounds of the formula I, that is one compound or a mixture of compounds of the formula I, or to the USE of a compound of the formula I, where reference to compound(s) of the formula I always includes the compound(s) as such or in the form of a salt (especially a physiologically, that is, e.g., pharmaceutically, nutraceutically or cosmetically) acceptable salt, a solvate and/or a tautomer thereof, or in the lactone form. In all cases this means that either only one compound (in substantially pure form or as a direct extract or a further enriched extract) or a mixture of two or more compounds of the formula I (which mixture is preferred) can be present, e.g. in an extract or pharmaceutical, nutraceutical or cosmetical formulation according to the invention, or that it or they can be of use according to the invention.

The compounds of the formula I may also be esterified at their free carboxyl group shown in formula I on the right hand side with alcohols, e.g. alcohols with 1 to 10 carbon atoms, such as alkanols, e.g. $C_1$-$C_7$alkanols, such as methanol or ethanol, phenyl-$C_1$-$C_4$alkanols, such as benzyl alcohol, or the like. Preferred are the compounds not esterified at the carboxyl group in formula I on the right hand side.

Preferably, the total weight share of the compound or all compounds of the formula I in an extract or mixture of compounds of the formula I or a purified compound of the formula I that is of use according to the invention in the final extract, mixture or compound (direct or further enriched) is in the range from 0.01% to 100% by weight, more preferably from 1% to 100% or to 99% by weight, in another embodiment from 5% to 100% or to 99% by weight, or from 20% to 100% or to 95% by weight, or e.g. from 50% to 100% or to 90% by weight.

Wherever used in the invention "%" e.g. percent is defined by the weight portion of the part of interest of the total weight, e.g. % is meant as % by weight; except where otherwise explicitly defined.

For the purpose of the invention the term "carbohydrate" is used in conformity with the IUPAC recommendations (Pure and Applied Chemistry, 1995, 67, 1307). The term "carbohydrate having 3 to 30 (preferably 6 to 18) carbon atoms bound via one of its oxygen atoms" especially refers to mono, oligo- or polysaccharidyl moieties bound via one of their oxygen atoms. The carbohydrates forming the basis for such moieties include, but are not limited to, monosaccharides, disaccharides, further oligosaccharides, or polysaccharides.

Monosaccharide for example includes, but is not limited to, aldotrioses such as glyceraldehyde, ketotrioses such as dihydroxyacetone, aldotetroses such as erythrose and threose, ketotetroses such as erythrulose, aldopentoses such as arabinose, lyxose, ribose and xylose, and desoxypentoses such as deoxyribose; ketopentoses such as ribulose and xylulose; hexoses, especially aldohexoses such as allose, altrose, galactose, glucose, gulose, idose, mannose and talose, or ketohexoses such as fructose, psicose, sorbose and tagatose, or desoxyhexoses such as rhamnose, cymarose, fucose, 2-desoxyglucose or 2-deoxygalactose; heptoses such as mannoheptulose, sedoheptulose; octoses such as octolose, 2-keto-3-deoxy-manno-octonate; nonoses such as sialoseallose.

Disaccharides for example include, but are not limited to, trehalose, sucrose, kojibiose, sophorose, nigerose, laminaribiose, maltose, cellobiose, isomaltose, gentiobiose, lactose, melibiose, neohsperidose, rutinose, primeverose, sambubiose, xylobiose, lathyrose and mannobiose.

Oligosaccharides for example include, but are not limited to, raffinose, nystose, panose, cellotriose, maltotriose, maltotetraose, xylobiose, galactotetraose, isopanose, cyclodextrin (alpha-CD) or cyclomaltohexaose, beta-cyclodextrin (beta-CD) or cyclomaltoheptaose and gamma-cyclodextrin (gamma-CD) or cyclomaltooctaose. Polysaccharides for example include, but are not limited to, xylan, mannan, galactan, glucan, arabinan, pustulan, gellan, guaran, xanthan, and hyaluronan. Some examples include, but not limited to, starch, glycogen, cellulose, inulin, chitin, amylose and amylopectin.

In the case of di-, tri- and oligo-saccharides the bonds between the carbohydrate subunits may include various possible types, e.g. preferably in the form of glycosidic connections of the 1→2, 1→3, 1→4 and 1→6 types, in particular the glycosidic connections are of the 1→2 type.

Especially preferred are trisaccharide carbohydrate moieties, especially of the formula

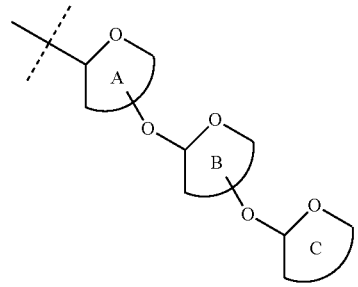

wherein the rings A, B and C are monosaccharide moieties each independently from the others with 5 or 6 ring members, wherein one or more of the hydroxyl groups may be acylated or etherified.

Preferably the carbohydrate moieties without substitutents resulting from acylation or etherification have 15 to 18 carbon atoms and they are especially selected from the hexapyranosyl-pentapyranosyl-pentapyranosid type such as beta-D-glucopyranosyl-(1→2)-beta-D-xylopyranosyl-(1→2)-beta-D-xylopyranosid or the hexapyranosyl-pentapyranosyl-hexapyranosid type such as beta-D-glucopyranosyl-(1→2)-beta-D-xylopyranosyl-(1→2)-beta-D-glucopyranosid.

The carbohydrates may carry one, more or all hydroxyl groups in modified form, e.g. as etherified hydroxyl or especially esterified hydroxyl as defined below, respectively, for example in a form acylated by a $C_2$-$C_{10}$-alkanoic acid, e.g. acetylated, e.g. mono- or di or tri- or tetra-acetylated, form. A particularly preferred modified form is represented by those compounds of the formula I which have one or more hydroxyl groups in the carbohydrate moiety that is or are acylated by an isovaleryl (3-methyl-butanoyl) moiety—these compounds are novel and thus also as such form an invention embodiment.

Individual compounds of formula I with an acyl substituent with more than 2 carbon atoms, such as (and preferably) an isovaleryl substituent (and preferably one single isovaleryl substituent), in the carbohydrate moiety R typically exhibit a stronger antimicrobial activity, particularly against yeasts and molds, especially against yeasts and molds of relevance regarding food, beverage and/or cosmetic spoilage, and/or a broader activity spectrum than the corresponding compounds with an acetyl substituent in the carbohydrate moiety R.

Further esters may be acetates; propionates; butyrates; isobyturates; valerates such as n-pentanoate) or 2-methyl butyrate, or the unsaturated derivatives such as but not limited to 2-methyl-2-butenoate (e.g. angeloate or tiglate), 3-methyl-2-butenoate or 3-methyl-3-butenoate (senecioate), or hydroxylated derivatives such as 2-methyl-3-hydroxy butyrate or 2-hydroxymethyl butyrate; or hexenoates such as n-hexanoate (caproate), isohexanoates such as but not limited to 2-methylvalerate, 3-methylvalerate, 4-methylvalerate, 2,3-dimethyl butyrate, or the unsaturated derivatives e.g. 2-ethyl-2-butyrate, 2-methyl-2-pentenoate, 4-methyl-2-pentenoate; or aminoacyl, e.g. alanyl, cysteinyl, aspartyl, glutamyl, phenylalanyl, glycyl, histidyl, isoleucyl, lysyl, leucyl, methionyl, asparaginyl, pyrrolysinyl, prolyl, glutaminyl, arginyl, seryl, threonyl, selenocysteyl, valyl, tryptophanyl or tyrosinyl. The acylated forms may preferably be natural products, but they can also be products of chemical or enzymatic acylation, e.g. using active forms of the acids and, where required to avoid reaction of other functional groups, introduction and, especially to obtain the final product, removal of protecting groups ("Pg").

The protection of such functional groups by such protecting groups ("Pg"), the protecting groups themselves, and their removal reactions are described for example in standard reference works, such as J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie" (Methods of organic chemistry), Houben Weyl, 4th edition, Volume 15/I, Georg Thieme Verlag, Stuttgart 1974, in H.-D. Jakubke and H. Jescheit, "Aminosauren, Peptide, Proteine" (Amino acids, peptides, proteins), Verlag Chemie, Weinheim, Deerfield Beach, and Basel 1982, and in Jochen Lehmann, "Chemie der Kohlenhydrate: Monosaccharide und Derivate" (Chemistry of carbohydrates: monosaccharides and derivatives), Georg Thieme Verlag, Stuttgart 1974. Especially preferred protecting groups are hydroxyl protecting groups, such as tert-butyldimethylsilyl, methyl, methoxymethyl, or trityl.

The chemical acylation can take place with the corresponding acid as such or preferably in the form of a reactive derivative. Reactive (or active) derivatives used as such include the halogenides, e.g. chlorides, or nitrophenyl esters, e.g. the 2,4-dinitrophenyl esters, or acid anhydrides (symmetric or e.g. with acetic acid) of the carboxy groups of the acids to be reacted.

For in situ formation, customary coupling agents may be applied. Such reagents are known to the person skilled in the art and can be deduced conveniently from many sources, e.g. Aldrich ChemFiles—Peptide Synthesis (Aldrich Chemical Co., Inc., Sigma-Aldrich Corporation, Milwaukee, Wis., USA) Vol. 7 No. 2, 2007 (see http://www.sigmaaldrich.com/etc/medialib/docs/Aldrich/Brochure/al_chemfile_v7_n2.Par.0001.File.tmp/al_chemfile_v7_n2.pdf). Among the possible coupling agents for amide and ester bond synthesis the following may be mentioned:

Triazoles, uronium or hexafluorophosponium derivatives, e.g. 1-hydroxy-benzotriazole (HOBt), Carbodiimides, e.g. dicyclohexylcarbodiimide, active ester forming agents, e.g. 2-mercaptobenzothiazole (2-MBT), azide forming agents, e.g. diphenyl phosphoryl azide, acid anhydrides, such as propane phosphonic acid anhydride, acid halogenation agents, e.g. 1-chloro-N,N,2-trimethyl-1-propenylamine, or the like, or mixtures of two or more such agents.

While the compounds of the formula I are preferably obtained by extraction in the form of extracts from natural sources or in further enriched or purified from such extracts (see below), they can also be obtained by chemical synthesis methods.

For example, the compounds may be synthesized chemically e.g. by a convergent strategies. The glycoside part and the unbranched long-chain α-hydroxy carboxylic acid part of the molecules are build up separately, with the hydroxyl groups and the carboxylic acid moieties being protected by suitable protecting groups. Afterwards, both building blocks are connected via building a glycosidic linkage using methods described in the scientific literature. Finally, removal of the protecting groups will lead to the desired compounds.

The following Reaction schemes provides an Example of a possible synthesis pathway:

Scheme for Synthesis (See Also Next Pages):

(1) Synthesis of Glycoside Unit

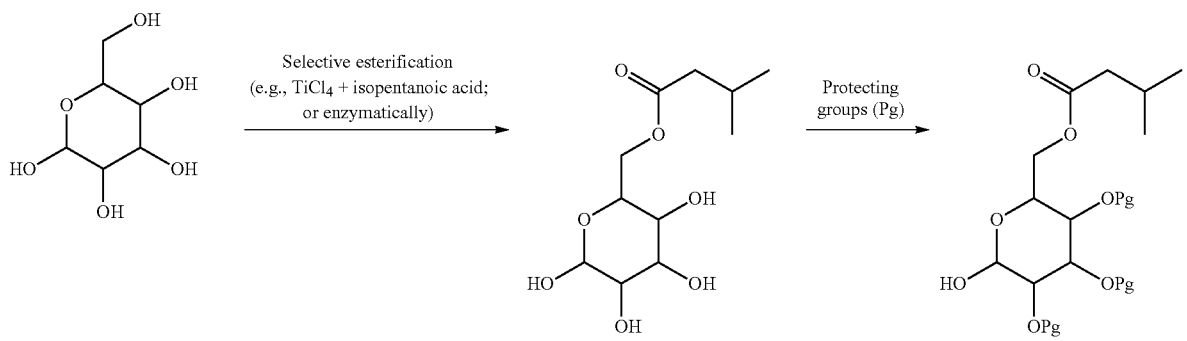

21 22
-continued
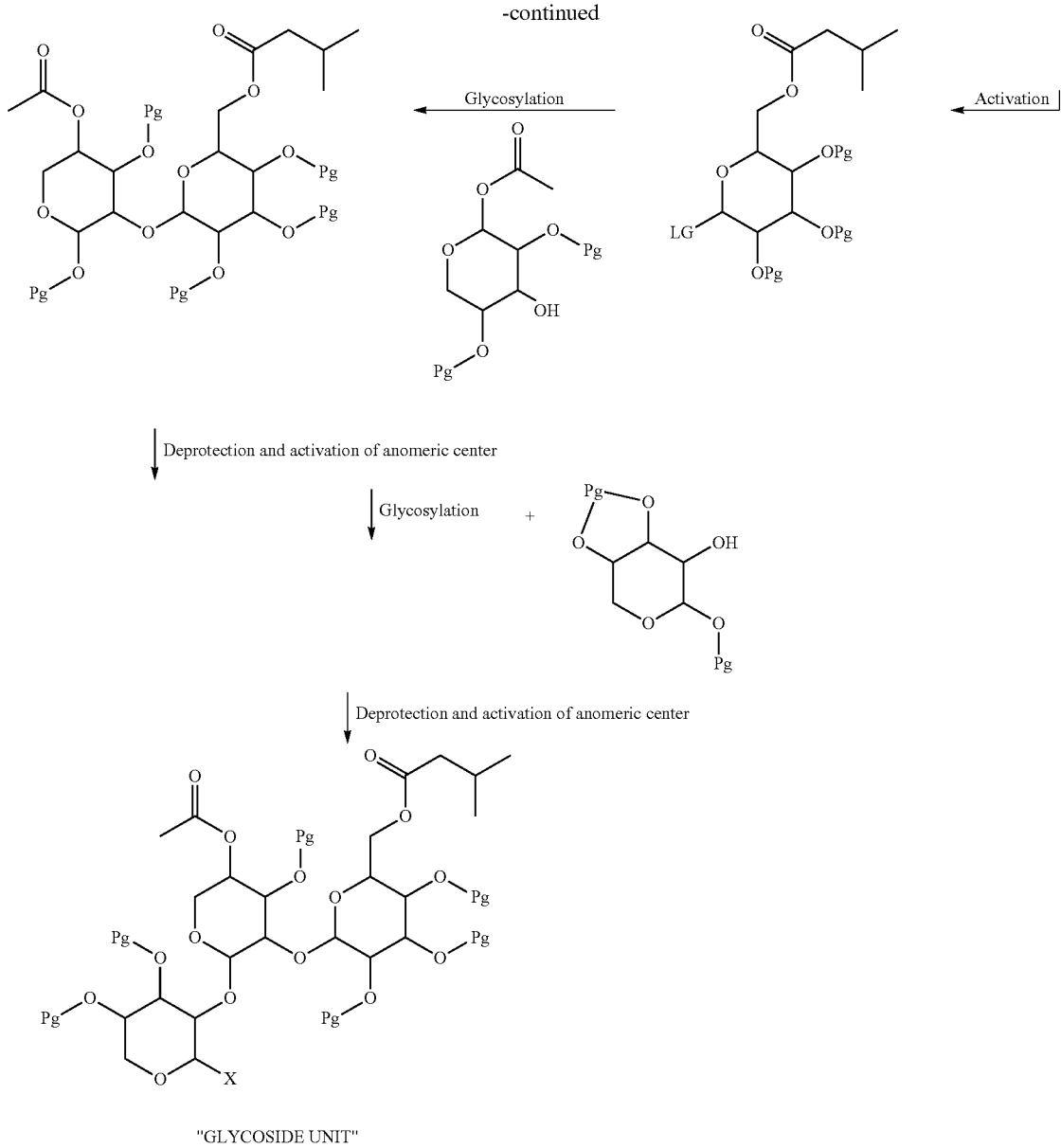
(2) Synthesis of Long-Chain Carboxylic Acid Unit
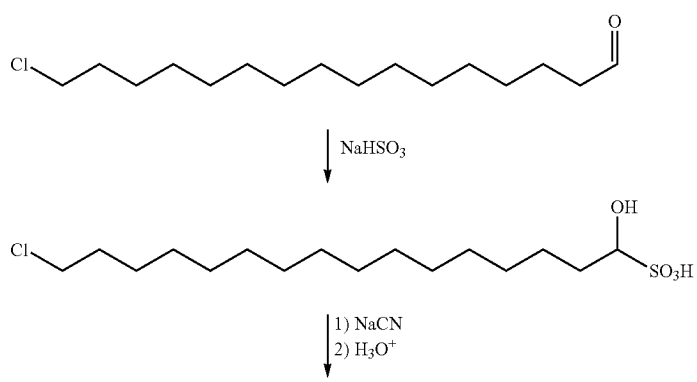

-continued

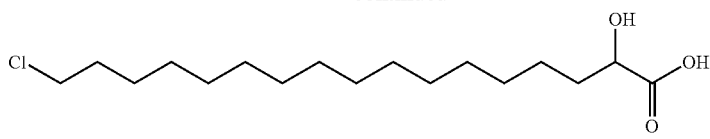

↓ Protection
of COOH and alpha-OH

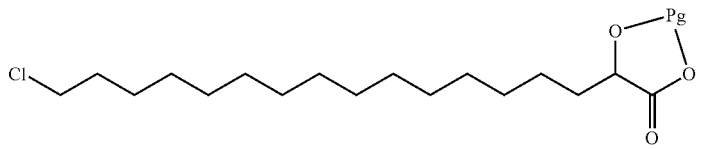

+ 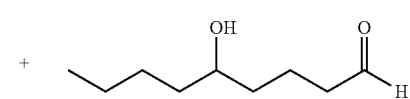

↓ Synthesis of alkenic carboxylic acid
(e.g., by Wittig reaction or variants thereof,
or Horner-Wadsworth-Evans reaction,
or Julia olefination;
or metathesis
or aldol condensation
or knoevenagel condensation, etc.)

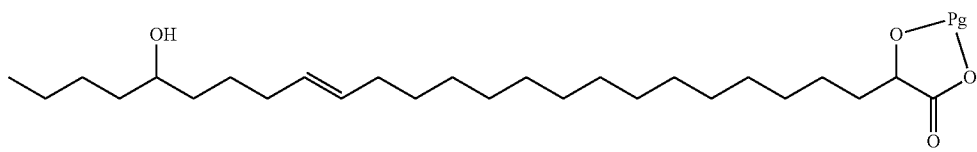

↓ Dihydroxylation
(e.g. Sharpless dihydroxylation,
or Prévost-hydroxylation)

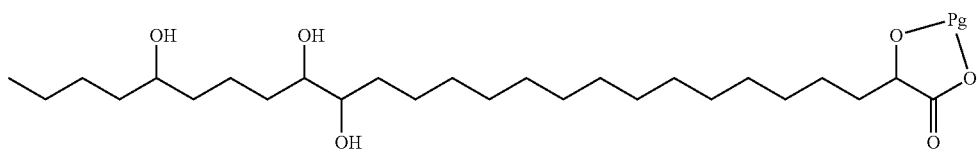

↓ Protection of 1,2-diol
(e.g. generation of acetonide:
acetone, TsOH)

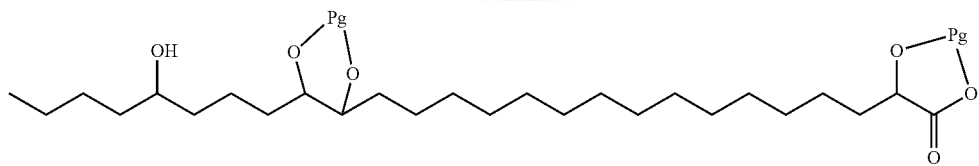

"LONG CHAIN CARBOXYLIC ACID UNIT"

"GLYCOSIDE UNIT"     "LONG CHAIN CARBOXYLIC ACID UNIT"

(3) Coupling of long-chain carboxylic acid unit and glycoside unit
(e.g. Me$_2$S, 2-Cl-pyridine, Tf$_2$O;
or by Koenigs-Knorr reaction;
or by Fischer-Helferich reaction;
or by Trichloroacetimidate methodology;
or by Thioglycoside coupling;
or by Fraser-Reid synthesis;
etc.)

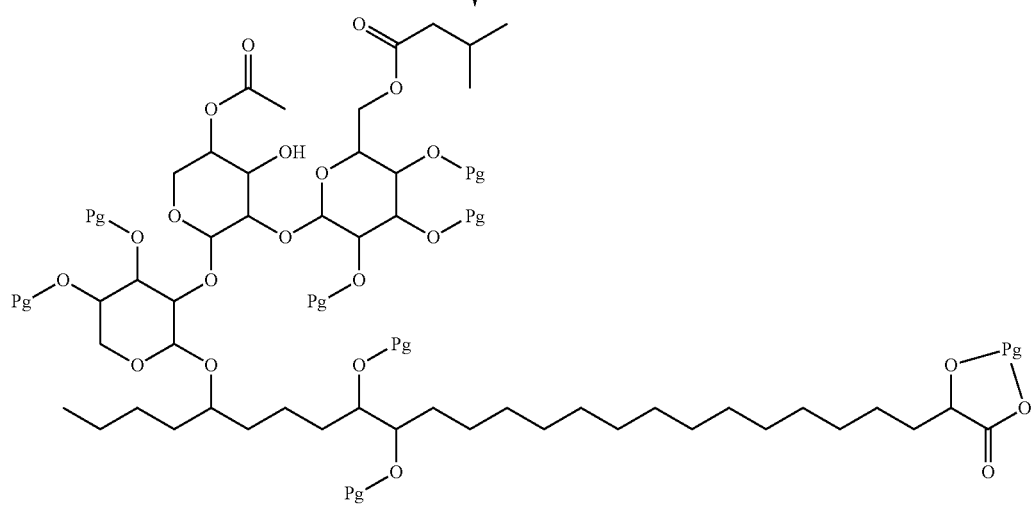

(4) Deprotection of hydroxy groups
and carboxylic acid
(e.g.; H$_2$/Pd; or NaOMe/MeOH)

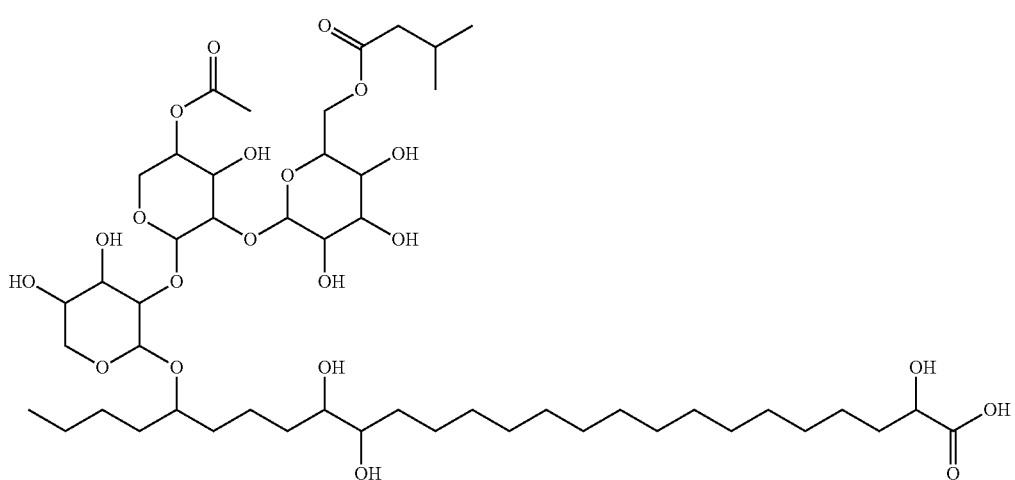

Synthetic methods for qlycosylation reactions—including protection, activation and de-protection strategies—are described, e.g., in the following literature:

J. McMurry; *Organic Chemistry*, 5th ed.; Brooks/Cole; 2000, 1031; D E. Levy, P. Fügedi; *The organic chemistry of sugars*; Taylor & Francis, 2006, 181-197; S. Bufali, P. Seeberger, *Org. React.* 2006, 68, 303; G.-J. Boons, K. J. Hale, *Organic synthesis with carbohydrates*. Blackwell Publishing, 2000; R. R. Schmidt, J. Michel, *Angew. Chem. Int. Ed. Engl.* 1980, 19, 731-732; X. M. Zhu, R. R. Schmidt, *Angew. Chem. Int. Ed.* 2009, 48, 1900-1934; R. R. Kale et al, *Angew. Chem. Int. Ed.* 2008, 47, 1265-1268; N. Miquel, S. Vignando, G. Russo, L. Lay, *Synlett* 2004, 2, 341-343; W. Koenigs, E. Knorr, *Chem. Ber.* 1901, 34, 957-981; Fraser-Reid, B.; Tatsuta, K.; Thiem, J., Hrsg., Glycoscience—Chemistry and Chemical Biology, Springer: Berlin, (2001); Lindhorst, T. K., *Essentials of Carbohydrate Chemistry and Biochemistry*, Wiley-VCH: Weinheim, (2000); Bochov, A. F.; Zaikov, G. E., *Chemistry of the O-Glycosidic Bond: Formation and Cleavage*, Pergamon Press: Oxford, (1979); Fraser-Reid, B.; Wu, Z.; Udodong, U. E.; Ottosson, H., *J. Org. Chem.*, (1990) 55, 6068-6070; Lemieux, R. U.; Morgan, A. R., *Can. J. Chem.*, (1965) 43, 2190-2198; Sinay, P., *Pure Appl. Chem.*, (1991) 63, 519-528 Toshima, K.; Tatsuta, K., *Chem. Rev.*, (1993) 93, 1503-1531; Evans, W. L.; Reynolds, D. D.; Talley, E. A., *Adv. Carbohydr. Chem.*, (1951) 6, 27-81

Synthetic methods for dihydroxylation reactions are described, e.g., in the following literature:

R. Brückner: *Reaktionsmechanismen*, 2. Aufl, Spektrum Verlag, Heidelberg/Berlin 2003, 750-758; M. H. Junttila, O. E. O. Hormi, *J. Org. Chem.*, 2004, 69, 4816-4820; M. H. Junttila, O. O. E. Hormi, *J. Org. Chem.*, 2009, 74, 3038-3047; B. M. Choudary, N. S. Chodari, K. Jyothi, M. L. Kantam, *J. Am. Chem. Soc.*, 2002, 124, 5341-5349; G. M. Mehltretter, S. Bhor, M. Klawonn, C. Döbler, U. Sundermeier, M. Eckert, H.-C. Militzer, M. Beller, *Synthesis*, 2003, 295-301; L. C. Branco, C. A. M. Afonso, *J. Org. Chem.*, 2004, 69, 4381-4389; Krauch, H.; Kunz, H., *Reaktionen der Organischen Chemie*, 6. Aufl.; Hüthig: eidelberg, (1997); S. 434-436; Hudlicky, T.; Fan, R.; Luna, H.; Olivo, H.; Price, J., *Pure Appl.* Chem., (1992) 64, 1109-1113; Jacobsen, E. N., *Acc.* Chem. Res., (2000) 33, 421-431; Kolb, H. C.; Van-Nieuwenhze, M. S.; Sharpless, K. B., *Chem. Rev.*, (1994) 94, 2483-2547.

Synthetic methods for reactions connecting two building blocks via double bond generation are described, e.g., in the following literature:

Ivin, K. J.; Mol, J. C., Olefin Metathesis and Metathesis Polymerization, Academic Press: New York, (1997); Grubbs, R. H., *Handbook of Metathesis*, Wiley-VCH: Weinheim, (2003); Bd. 1-3; Fürstner, A.; Langemann, K., *Synthesis*, (1997), 792-803; Fürstner, A., *Angew. Chem.*, (2000) 112, 3140-3172; Blakemore, P. R., *J. Chem. Soc., Perkin Trans.* 1, (2002), 2563-2585; Staden, L. F., van; Gravestock, D.; Ager, D. J., *Chem. Soc. Rev.*, (2002) 31, 195-200; Wittig, G., Angew. Chem., (1980) 92, 671-675; Schlosser, M.; Christmann, K., Synthesis, (1969), 38-39; Maryanoff, B. E.; Reitz, A. B., *Chem. Rev.*, (1989) 89, 863-927; Murphy, P. J.; Brennan, J., Chem. Soc. Rev., (1988) 17, 1-30; Boutagy, J.; Thomas, R., Chem. Rev., (1974) 74, 87-99; Clayden, J.; Warren, S., *Angew. Chem.*, (1996) 108, 261-291; Bückner, R., Reaktionsmechanismen, 2. Aufl.; Spektrum: Heidelberg, (2003); Ager, D. J., *Synthesis*, (1984), 384-398; Mukaiyama, T.; Asami, M., *Top. Curr. Chem.*, (1985) 127, 133-167.

Further, the present glycolipid compounds of the formula I comprise all stereoisomers, such as those which may exist due to asymmetric carbons on the various substituents, including enantiomeric forms and diastereomeric forms. Individual stereoisomers of the glycolipid derivatives of the present invention may, for example, be substantially free of other isomers, or may be admixed, for example, as racemates or with all other, more than one other, or two to less than all other selected stereoisomers, e.g. diastereomers.

Especially the vicinal dihydroxy group in the fatty acid part is in one embodiment of the invention to be understood as syn and/or anti configurated.

To the extent that compounds the formula I and salts thereof may exist in their tautomeric form, all such tautomeric forms are contemplated herein as part of the present invention embodiments.

As the final carboxyl group of the carboxylic acid chain may also form a lactone with one of the hydroxyl groups present on the rest of a molecule of the formula I, compounds of the formula I may also be present in the lactone form, either purely or in admixture with the open chain form.

The salts of compound(s) of the formula I are especially physiologically acceptable salts, that is, salts that have no disturbing toxical, allergenic and/or mutagenic properties on human or animal cells. Such salts can be selected from those known in the art, e.g. using calcium, sodium, magnesium, or ammonium as counterions of the carboxylic group or the salts mentioned below.

Where salt-forming groups (e.g. acidic groups, such as carboxylic acid groups, or basic groups, such as amino or imino groups) are present within them, the glycolipid compounds of the formula I may be in the free form or in the form of salts. The term "salt(s)", as employed herein, denotes acidic and/or basic salts formed with inorganic and/or organic acids and bases. In addition, when a compound of the formula I contains both a basic moiety and an acidic moiety, "inner salts" may be formed and are included within the term "salt(s)" as used herein. Pharmaceutically or nutraceutically or cosmetically acceptable (i.e., non-toxic, physiologically acceptable) salts are preferred, although other salts are also useful, e.g., in isolation or purification steps which may be employed during preparation. Salts of compounds of the formula I may be formed, for example, by reacting a compound of the formula I with an amount of acid or base, such as an equivalent amount, in a medium such as one in which the salt precipitates or in an aqueous medium followed by lyophilisation or followed by the addition of a water miscible organic solvent. Also ion exchangers can be used to form salts from free forms or free forms from salts of a compound of the formula I. "Free form" refers to "form without salt-forming counterions", e.g. in non-salt form.

Where two active groups with different charge are present, also internal or zwitterionic salts can be formed.

Where the compounds of the formula I (or glycolipids of the formula I or the like) are mentioned in the present disclosure, this also comprises the corresponding (especially physiologically acceptable) salts thereof, also where not explicitly stated, as well as the esters, as well as the lactones, or mixtures of two or more of these forms.

The compounds of the formula I which contain an acidic moiety (e.g. carboxyl (—COOH) groups) may form salts with a variety of organic and inorganic bases. Exemplary basic salts include ammonium salts, non-toxic metal salts derived from metals of groups Ia, Ib, IIa and IIb of the Periodic Table of Elements, e.g. alkali metal salts such as sodium, lithium, or potassium salts, alkaline earth metal salts such as calcium or magnesium salts, or salts with other metals, such as zinc, salts with organic bases (for example, organic amines) such as unsubstituted or hydroxy-substituted mono-, di- or tri-alkylamines, especially mono-, di- or tri-lower alkylamines, or quaternary ammonium compounds, for example with alkyl amines, e.g. t-butyl amine, N-methyl-N-ethylamine, diethylamine, triethylamine, mono-, bis- or tris-(2-hydroxy-lower alkyl)amines, such as mono-, bis- or tris-(2-hydroxyethyl)amine, 2-hydroxy-tert-butylamine or tris(hydroxymethyl)methylamine, N,N-di-lower alkyl-N-(hydroxy-lower alkyl)-amines, such as N,N-dimethyl-N-(2-hydroxyethyl)-amine or tri-(2-hydroxyethyl)-amine, or N-methyl-D-glucamine; or cyclic amines such as piperidine, N-lower alkyl piperidine e.g. N-methyl-piperidine, piperazine, or quaternary ammonium salts formed via common processes out of the above define amines, such as tetrabutylammonium salts, or with benzathines, dicyclohexylamines, N-methyl-D-glucamines, N-methyl-D-glucamides, purines, caffeine, theobromine, hydrabamine, choline, betaine, or salts with amino acids such as arginine, lysine, histidine and the like. Also salts with salt-forming pharmaceutical and/or nutraceutical carrier materials are possible and encompassed by the invention.

Isolation

In order to obtain the compounds of the formula I, as such or comprised in an extract, preferably the desired substances of the formula I are isolated from natural sources, either with subsequent chemical modification (e.g. acylation) or preferably without such chemical modification.

The purpose of the extraction and especially isolation step is to retain the desired substances. Desired substances in the present context are any substances that directly or indirectly contribute to the preservative properties of the composition, with the proviso that one or more compounds of the formula I are also included. The isolation can be performed by isolating or separating the one or more compounds of the formula I according to chemical and/or physical properties. Examples of chemical properties include affinity for one or more compounds and chemical stability. Examples of physical properties include mass or size, charge, solubility, polarity, distribution, absorption to surfaces, melting point, and the like.

Natural compounds of the formula I, or extracts comprising one or more thereof, for USE in or according to the present invention are isolated from one or more cultures, especially liquid cultures, of mushrooms of the genera listed above or below, e.g. with the genetic characteristics provided in detail below.

By the term "extract", either a direct extract (in liquid or preferably dried form), e.g. obtained as described below, or preferably a further enriched extract (obtainable e.g. by one or more further purification steps after extraction, e.g. chromatography, for example as described below) containing one or more, preferably two or more compounds of the formula I is meant.

The compound(s) of the formula I in the form of an extract and extracts according to the invention can be obtained especially preferably by extraction of liquid cultures, especially liquid or solid mycelial cultures, of mushrooms of the genus *Dacryopinax*, e.g. mushrooms or parts thereof of the species *Dacryopinax*, mushrooms of the genus *Ditiola*, e.g. mushrooms or parts thereof, and/or mushrooms of the genus *Femsjonia luteo-alba*, e.g. mushrooms or parts thereof, especially the species and more especially the deposited strains as defined above.

Extracts according to the invention or useful according to the invention may be manufactured according to any suitable process, preferably comprising extraction of one or more compounds of the formula I. The term "extract" wherever used also includes precipitates, e.g. manufactured as described below.

For example, the extraction of one or more compounds and/or mixture of compounds of the formula I from a cultured mushroom (especially from submerged mycelial culture) or mushroom part of the genera mentioned above by means of a lipophilic (preferably non-aqueous) solvent.

Extraction thus may take place with a non polar or weakly polar (meaning less polar than water) solvent or solvent mixture, meaning that the preferred obtainable or obtained extracts according to the invention are lipophilic extracts.

Preferably, the polarity is defined by an $E_T(30)$ value of 56 kcal/mol or lower (at 25° C. and 1 bar), e.g. of 52 kcal/mol or lower (water has an $E_T(30)$ of 63.1). The $E_T(30)$ method is based on a method published by Reichart et al. and makes use of the stabilisation of the ground state of the betaine dye 2,6-diphenyl-4-(2,4,6-triphenyl-1-pyridinio)phenolate, CAS No 10081-39-7, in apolar solvents leading to a higher energy for the transition from the ground state (HOMO) to the first excited state (LUMO) of the molecule (see K. Dimroth, J Lieb Ann d Chemie (1963) 661(1): 1-37, DOI 10.1002/jlac.19636610102).

Examples of appropriate solvents are organic solvents (two or more of which can also be mixed), e.g. a ketone or an ester, such as acetone and/or ethyl acetate, an ether, e.g. a cyclic ether such as dioxane, and/or (also in a specific embodiment) an alcohol e.g. ethanol, and/or a liquid or superfluid gas, especially superfluid $CO_2$.

Alternatively, the extract may be obtained by bringing a culture supernatant to a slightly alkaline pH, e.g. by adding an alkalimetal hydroxide, such as sodium or potassium hydroxide, separating of any solid material, e.g. the mycelia or other solid components, e.g. by microfiltration, acidifying the filtrate by addition of an acid, e.g. an organic or inorganic acid, such as a hydrohalogenide, such as hydrochloride, to an appropriate pH, e.g. lower than the pKa (which may, for compounds of the formula I, be assumed to lie in the range of about 4.0 to 5.0, e.g. 4.2 to 4.5), removing the supernatant from an obtained precipitate (which comprises the compounds of the formula I) and optionally washing the precipitate and/or extracting the compounds of the formula I at an appropriate pH into a less polar solvent, e.g. one as mentioned above. This process (also leading to what is called an "extract" in the present disclosure) is especially preferred as it leads to high yield and helps to avoid the use of solvents, thus being both economically and ecologically advantageous.

The addition according to the use or method of the invention preferably takes place by mixing the resulting extract or isolated compound(s) of the formula I into such a material or by impregnating or coating it with the compound(s) of the formula as such or in an appropriate (e.g. liquid) composition.

For preservative or antimicrobial compositions, further processing steps may precede and/or follow, such as drying (e.g. freeze-drying, spray-drying, fluid bed or spouted bed or evaporation), granulation, agglomeration, concentrating (e.g. to syrups, formed via concentration and/or with the aid of thickeners), pasteurizing, sterilizing, freezing, dissolving, dispersing, filtering, centrifuging, confectioning, and the like.

The compounds of the formula I have surprisingly been found to show especially preservative or antimicrobial purposes (the term "antimicrobial" especially referring to treated materials which are not treated to avoid perishing of themselves but are to be used in a form not contaminated by microbes, e.g. implants or the like, while the term "preservative activity" also includes antimicrobial activity, but also other stabilizing activity, e.g. by emulsification or acidification due to addition of the compound(s) of the formula I to perishable goods).

The preservative and antimicrobial properties can conveniently be shown by methods known in the art, e.g. as described below and in the Examples.

In such tests, antimicrobial and preservative activity can be shown.

The term "enhance the stability against microorganisms" refers to inhibiting the growth or killing microorganisms, thus providing a material equipped according to the invention with one or more compounds of the formula I with protection against microbial damage, films or degradation.

Among the materials to which one or more compounds of the formula I can be added, the following may be mentioned: A material selected from the group consisting of a cosmetic, a home care product, a food, a beverage, a pharmaceutical, a medical device, and an active packaging material. Also semi-finished products or precursors are included, e.g. especially in the case of beverages or foods, ready-to-use powders or concentrates.

Food & Beverages

The term "food" sometimes also named "foodstuff" means articles used for food or (drink) for man or other animals, chewing gum, and articles used for components of any such article. The term "food" especially refers to materials, usually of plant, animal or other organism origin, that comprise body nutrients, such as carbohydrates, fats, proteins, vitamins and/or minerals, and is ingested and assimilated by the human or animal organism to produce energy, stimulate growth and maintain life. Usually, food has a rather solid form, but may also be near liquid, e.g. in the case of yoghurt or the like. "Food" includes a raw, cooked, or processed edible substance, ice, or ingredient used or intended for use or for sale in whole or in part for human or animal consumption, or chewing gum.

"Beverage" means a liquid product for drinking, usually including water, which may be consumed to quench thirst, to provide nutrition, for pleasure or relish purposes and/or for other functional purposes (e.g. to administer medicines or other functional materials).

Among the liquids for human or animal consumption those can be mentioned which are labelled as juice, drink (including soft drink, such as lemonade), non-alcoholic or alcoholic beverage, and/or cocktail.

"Juice" means the aqueous liquid expressed or extracted from one or more fruits or vegetables, purées of the edible portions of one or more fruits or vegetables, or any concentrates of such liquid or puree.

The use as an agent with preservative properties of a compound or compounds of the formula I includes also the use in precursor products of beverages, e.g. concentrates, syrups and/or powders will reconstitute to a beverage in the sense of the invention by the addition of water.

The term "infant formula" means a food which purports to be or is represented for special dietary use solely as a food for infants by reason of its simulation of human milk or its suitability as a complete or partial substitute for human milk.

Beverages can be alcoholic and/or non alcoholic, carbonated and/or non carbonated Beverages include non-dairy milks, and the like.

Beverages may include water, flavoured water, fortified waters, flavoured beverages, carbonated water, e.g. flavoured seltzer or soda waters, juices, cola, lemon-lime, ginger ale, and root beer beverages which are carbonated in the manner of soft drinks, as well as beverages that provide health or wellness benefits from the presence of metabolically active substances, such as vitamins, amino acids, proteins, carbohydrates, lipids, or polymers thereof, where such products may also be formulated to contain milk, coffee, or tea (e.g. green tea) or other botanical solids, syrup, diet beverages, carbonated soft drinks, fruit juices, e.g. orange juice, grapefruit juice, apple juice, red grape juice, white grape juice, pear juice, concord grape juice, pineapple juice, pomegranate juice, cranberry juice, passion fruit juice, lime juice, lemon juice, mango juice, guava juice, banana juice, red and black currant juice, cashew apple juice, cantaloupe melon juice, apricot juice, blackberry juice, lingonberry juice, dewberry juice, gooseberry juice, crabapple juice, prune juice, plum juice, kiwi juice, strawberry juice, blueberry juice, red raspberry juice, black raspberry juice, cherry juice, watermelon juice, peach juice, nectarine juice, loganberry juice, honeydew melon juice, papaya juice, boysenberry juice, youngberry juice, rhubarb juice, guanabana juice, acai juice, goji juice, fig juice, elderberry juice, date juice, carambola juice, acerola juice, quince juice, bilberry juice, tangerine juice, fruit containing beverages, e.g. fruit drinks which provide the flavor of any of the e.g. aforementioned fruit juices and contain greater than 0% fruit juice but less than 100% fruit juice, fruit flavored beverages, vegetable juices, e.g. tomato juice, beet juice, carrot juice, celery juice, vegetable containing beverages, which provide the flavor of any of the aforementioned vegetable juices and contain greater than 0% vegetable juice but less than 100% vegetable juice, isotonic beverages, non-isotonic beverages, soft drinks containing a fruit juice, coffee, tea, tea beverages prepared from tea concentrate, extracts, or powders, drinkable dairy products, e.g. drinkable yogurts (drink yoghurt), kefir or buttermilk, hot chocolate, chocolate powders/mixes, drinkable soy products, non-diary milks, e.g. coconut milk, alcoholic beverages, e.g. malt beverages, wine, beer, distilled liquors, spirits, sparkling wine, champagne or liqueurs, fruit smoothies, horchata (vegetable and/or rice components made into a beverage), sport drinks, energy drinks, health drinks, shakes, protein drinks (e.g. dairy, soy, rice or other), drinkable soy yogurts, low acid beverages as defined in US 21 C.F.R. Part 113. Acidified beverages as defined in US 21 C.F.R. Part 114, nectars, tonics, frozen carbonated beverages, frozen uncarbonated beverages, liquid meal replacements, infant formulations, and combinations or mixtures thereof.

It is also possible to formulate such beverages to contain one or more nutraceuticals. Herein, a nutraceutical is a substance that has been shown to possess, minimally, either a general or specific health benefit or sense of wellness as documented in professional journals or texts. Nutraceuticals, however, do not necessarily act to either cure or prevent specific types of medical conditions.

Apart from one or more compounds of the formula I, the foods or beverages may comprise further customary additives for food and/or beverages.

For the purpose of the invention "additives" in the sense of "sweeteners" are substances used to impart a sweet taste to foods (this term in the present paragraph also including beverages) or in table-top sweeteners; "antioxidants" are substances that hinder the oxidation of components, e.g. avoiding that the material becomes rancid; "colors" are substances which add or restore color in a food, and include natural constituents of foods and natural sources which are normally not consumed as foods as such and not normally used as characteristic ingredients of food. Preparations obtained from foods and other edible natural source materials obtained by physical and/or chemical extraction resulting in a selective extraction of the pigments relative to the nutritive or aromatic constituents are colors within the meaning of this Regulation; "preservatives" are substances which prolong the shelf-life of foods by protecting them against deterioration caused by micro-organisms and/or which protect against growth of pathogenic micro-organisms; "antioxidants" are substances which prolong the shelf-life of foods by protecting them against deterioration caused by oxidation, such as fat rancidity and color changes; "carriers" are substances used to dissolve, dilute, disperse or otherwise physically modify a food additive or a flavouring, food enzyme, nutrient and/or other substance added for nutritional or physiological purposes to a food without altering its function (and without exerting any technological effect themselves) in order to facilitate its handling, application or use; "acids" are substances which increase the acidity of a foodstuff and/or impart a sour taste to it; "acidity regulators" are substances which alter or control the acidity or alkalinity of a foodstuff; "anti-caking agents" are substances which reduce the tendency of individual particles of a foodstuff to adhere to one another; "anti-foaming agents" are substances which prevent or reduce foaming; "bulking agents" are substances which contribute to the volume of a foodstuff without contributing significantly to its available energy value; "emulsifiers" are substances which make it possible to form or maintain a homogenous mixture of two or more immiscible phases such as oil and water in a foodstuff; "emulsifying salts" are substances which convert proteins contained in cheese into a dispersed form and thereby bring about homogenous distribution of fat and other components; "firming agents" are substances which make or keep tissues of fruit or vegetables firm or crisp, or interact with gelling agents to produce or strengthen a gel; "flavor enhancers" are substances which enhance the existing taste and/or odor of a foodstuff; "foaming agents" are substances which make it possible to form a homogenous dispersion of a gaseous phase in a liquid or solid foodstuff; "gelling agents" are substances which give a foodstuff texture through formation of a gel; "glazing agents" (including lubricants) are substances which, when applied to the external surface of a foodstuff, impart a shiny appearance or provide a protective coating; "humectants" are substances which prevent foods from drying out by counteracting the effect of an atmosphere having a low degree of humidity, or promote the dissolution of a powder in an aqueous medium; "modified starches" are substances obtained by one or more chemical treatments of edible starches, which may have undergone a physical or enzymatic treatment, and may be acid or alkali thinned or bleached; "packaging gases" are gases other than air, introduced into a container before, during or after the placing of a foodstuff in that container; "propellants" are gases other than air which expel a foodstuff from a container; "raising agents" are substances or combinations of substances which liberate gas and thereby increase the volume of a dough or a batter; "sequestrants" are substances which form chemical complexes with metallic ions; "stabilizers" are substances which make it possible to maintain the physico-chemical state of a foodstuff; stabilizers include substances which enable the maintenance of a homogenous dispersion of two or more immiscible substances in a foodstuff, substances which stabilize, retain or intensify an existing color of a foodstuff and substances which increase the binding capacity of the food, including the formation of cross-links between proteins enabling the binding of food pieces into re-constituted food; "thickeners" are substances which increase the viscosity of a foodstuff;

"flour treatment agents" are substances, other than emulsifiers, which are added to flour or dough to improve its baking quality.

Among known preservatives for food and beverages (also named additional (chemical) preservatives herein), the following may be mentioned, without excluding others: benzoic acid, benzoic acid sodium salt, benzoic acid potassium salt, benzoic acid calcium salt, propionic acid, salicylic acid, sorbic acid, sorbic acid sodium salt, sorbic acid potassium salt, sorbic acid calcium salt, ethyl para-hydroxybenzoate, sodium ethyl para-hydroxybenzoate, propyl para-hydroxybenzoate, sodium propyl para-hydroxybenzoate, methyl para-hydroxybenzoate, sodium methyl para-hydroxybenzoate, sulphur dioxide, sodium sulphite, sodium hydrogen sulphite, sodium metabisulphite, potassium metabisulphite, calcium sulphite, calcium hydrogen sulphite, biphenyl or diphenyl, orthophenyl phenol, sodium orthophenyl phenol, thiabendazole, nisin, natamycin or pimaracin, formic acid, sodium formate, calcium formate, hexamethylene tetramine or hexamine, formaldehyde, dimethyl dicarbonate, sodium nitrite, potassium nitrite, sodium nitrate, potassium nitrate, acetic acid, sodium acetates, e.g. sodium hydrogen acetate, potassium acetate, calcium acetate, ammonium acetate, lactic acid, propionic acid, sodium propinate, potassium propionate, calcium propionate, oric acid, sodium tetraborate (borax), invertase, lysozyme.

Preferably, however, no such preservatives are added in the embodiments of the present invention.

The consumables of the present invention, e.g., beverages, may have a pH ranging from 1.5 to 10, e.g. from about 1.5 to about 4.6 It is known in the art that the pH of a beverage may be a factor in maintaining a shelf-stable beverage, as the growth of some microorganisms may be hindered under acidic conditions. This, however, is not the case for acidophilic micro-organisms such as *Lactobacillus*, *Saccharomyces* and *Candida* which thrive in such an acidic environment. Utilizing the present invention allows the composition to maintain microbial stability even in view of these acidophilic microorganisms.

For an acidic beverage (pH<4.6), the acidity of the beverage can be adjusted to and maintained within the recited range by known and conventional methods in the art. For example, the pH can be adjusted using one or more acidulant(s), also named acidity regulator(s), e.g. as defined below.

In addition, the use of acidity regulators may assist in microbial inhibition at the same time as maintaining the pH of the beverage. Compositions of the present invention, however, may inherently have a desirable pH without the use of any acidity regulator or other components to modify the pH. Thus, the incorporation of at least one acidity regulator is optional in compositions of the present invention.

Moreover, the amounts of the acidity regulator(s), which may be present in the composition according to the present disclosure, are those conventionally used in beverage compositions. For example, at least one acidulant may be present in an amount ranging from about 0.01% to about 1% by weight relative to the composition.

An aspect of the invention is directed to preserving a broad range of beverage products that possess a pH of less than 7.5, in particular less than about 4.6, such as 2.5 to 4.6 against spoilage by yeast, mold and a range of acid tolerant bacteria. Preservation of product can be accomplished merely through the addition of the chemical agents described herein, but it is also possible to supplement the action of the chemicals with purely physical forms of preservation such as alteration of product temperature, various wavelengths of irradiation, pressure or combinations thereof. In certain exemplary embodiments, the pH of the beverage product comprising the preservative system is e.g., about 4.6 or less, about 2.5 to about 4.4, about 2.6 to about 4.5.

The acidity regulator(s) may be in an undissociated form or in their respective salt form such as potassium, sodium, or hydrochloride salts, or be a mixture, thus forming a kind of buffer for an intended pH. Among acidity regulators (pH regulators), organic and inorganic acids to be used in adjusting the pH of a composition of the present invention such as a beverage may be mentioned, e.g. acetic acid, sodium acetates, e.g. sodium hydrogen acetate, potassium acetate, calcium acetate, ascorbic acid, sodium ascorbate, potassium ascorbate, carbon dioxide, sodium carbonates incl.sodium hydrogen carbonate (bicarbonate of soda) and sodium sesquicarbonate, potassium carbonates, e.g. potassium hydrogen carbonate, ammonium carbonates, e.g. ammonium hydrogen carbonate, magnesium carbonates, e.g. magnesium hydroxide carbonate (syn. magnesium hydrogen carbonate), malic acid, fumaric acid, sodium fumarate, potassium fumarate, calcium fumarate, calcium citrates incl.mono, di or tri calcium salts, triammonium citrate, ammoniumferrocitrate, sodium malates, e.g. sodium hydrogen malate, potassium malate, calcium malates, e.g. calcium hydrogen malate, adipic acid, sodium adipate, potassium adipate, succinic acid, 1,4-heptonolactone, potassium chloride, calcium chloride, ammonium chloride or ammonia solution, magnesium chloride, stannous chloride, sodium sulphates, e.g. sodium hydrogen sulphate, potassium sulphates, e.g. potassium hydrogen sulphate, calcium sulphate, ammonium sulphate, magnesium sulphate or Epsom salts, copper sulphate, aluminium sulphate, aluminium sodium sulphate, aluminium potassium sulphate, aluminium ammonium sulphate, sodium hydroxide, potassium hydroxide, calcium hydroxide, ammonium hydroxide, magnesium hydroxide, calcium oxide, magnesium oxide, sodium ferrocyanide, potassium ferrocyanide, calcium ferrocyanide, dicalcium diphosphate, tartaric acid, sodium tartaric acid, potassium tartaric acid, gluconic acid, glucono-delta-lactone, or mixtures of two or more thereof, may be mentioned. Note that the compounds of the formula I, due to their acid/base properties, can also be used to regulate the pH of a composition comprising them.

Among the emulsifiers, the following may be mentioned:

lecithins; metatartaric acid, calcium tartrate; alginic acid and the sodium, potassium, ammonium and calcium salts, propane-1,2-diol alginate; agar; Carrageenan; processed eucheuma seaweed; locust bean gum; carob gum; guar gum; tragacanth; acacia gum; gum arabic; xanthan gum; Karaya gum; Tara gum; Gellan gum; glycerol; Konjac, konjac gum, konjac glucomannane; soybean emicellulose; *Cassia* gum; polyoxyethylene (8) stearate; polyoxyethylene sorbitan monolaurate, polysorbate 20; polyoxyethylene sorbitan mono-oleate, polysorbate 80; polyoxyethylene sorbitan monopalmitate, polysorbate 40; polyoxyethylene sorbitan monostearate, polysorbate 60; polyoxyethylene sorbitan tristearate, polysorbate 65; pectins and amidated pectin; ammonium phosphatides; sucrose acetate isobutyrate; glycerol esters of wood rosins; diphosphates and salts, disodium, trisodium diphosphate, tetrasodium diphosphate, dipotassium diphosphate, tetrapotassium diphosphate, dicalcium diphosphate, calcium dihydrogen diphosphate; triphosphates and salts, pentasodium, pentapotassium; polyphosphates and salts, sodium, potassium, sodium calcium, calcium, sodium aluminium, aluminium; beta-cyclodextrine; cellulose, podered or microcrystalline and derivatives, methyl-, ethyl-, hydroxypropyl-, hydroxypropyl methyl-, ethyl methyl-, carboxy methyl-, crosslinked sodium carboxy methyl-, enzymatically hydrolysed carboxy methyl-; sodium, potassium and calcium salts of fatty acids; magnesium salts of fatty acids; mono- and diglycerides of fatty acids; acetic acid esters of mono- and diglycerides of fatty acids; lactic acid esters of mono- and diglycerides of fatty acids; citric acid esters of mono- and diglycerides of fatty acids; tartaric acid esters of mono- and diglycerides of fatty acids; mono- and diacetyltartaric acid esters of mono- and diglycerides of fatty acids; mixed acetic and tartaric acid esters of mono- and diglycerides of fatty acids; sucrose esters of fatty acids; sucroglycerides; polyglycerol esters of fatty acids; polyglycerol polyricinoleate; propane-1,2-diol esters of fatty acids; thermally oxidised soya bean oil interacted with mono- and diglycerides of fatty acids; sodium stearoyl-2-lactylate; calcium stearoyl-2-lactylate; stearyl tartrate; sorbitan monostearate; sorbitan tristearate; sorbitan monolaurate; sorbitan monooleate; sorbitan monopalmitate; invertase; silicon dioxide (Silica); magnesium stearate, calcium stearate; oxidized starch; acetylated distarch phosphate; starch sodium octenyl succinate; acetylated oxidised starch, or mixtures of two or more thereof.

As anti-oxidants, among others the following may be mentioned:

ascorbic acid and salts, sodium, calcium; fatty acid esters of ascorbic acid; tocopherols, alpha-tocopherol, gamma-tocopherol, delta-tocopherol; propyl gallate; octyl gallate; dodecyl gallate; erythorbic acid, sodium erythorbate; tertiary-butyl hydroquinone (TBHQ); butylated hydroxyanisole (BHA); butylated hydroxytoluene (BHT); extracts of rosemary; 4-hexylresorcinol, or mixtures of two or more thereof.

Such additives may be present in relative amounts, considering the complete composition of the food or beverage product concerned, in amounts summing up to from 0.01% up to 90% by weight, e.g. from 0.05% to 50% by weight, e.g. from 0.1% to 5% by weight or from 0.2% to 20% by weight.

Cosmetics

The compounds of the formula I, in view of their preservative properties, are also useful in supporting or providing preservation of cosmetics.

The term "cosmetic" is here intended to mean (1) an article, e.g. a mixture or substance or product, intended to be placed in contact with the various external parts of the human body or animal body (epidermis, hair system, nails, lips and external genital organs), e.g. which can be rubbed, poured, sprinkled, or sprayed on, or otherwise applied to the human body or any part thereof, including the oral cavity and the teeth, skin and hair, with a view exclusively or mainly to cleaning them, perfuming them, changing their appearance and/or correcting body odors, and/or protecting them or keeping them in good condition.; and (2) articles intended for use as a component of any such articles; explicitly including soap.

The term cosmetics as used here also includes "personal care products" and "personal hygiene products", such as menstrual care products, handkerchief tissues and the like.

For example, cosmetic products include but are not limited to:

Creams, emulsions, lotions, gels and oils for the skin (hands, face, feet, etc.); face masks (with the exception of peeling products); tinted bases (liquids, pastes, powders); make-up powders, after-bath powders, hygienic powders, etc.; toilet soaps, deodorant soaps, etc.; perfumes, toilet waters and eau de Cologne; bath and shower preparations (salts, foams, oils, gels, etc.); depilatories; deodorants and anti-perspirants; hair care products, (hair tints and bleaches; products for waving, straightening and fixing); setting products; cleansing products (lotions, powders, shampoos, hand washing products, (hand) disinfecting products); conditioning products (lotions, creams, oils); hairdressing products (lotions, lacquers, brilliantines); shaving products (creams, foams, lotions, etc.); products for making up and removing make-up from the face and the eyes; products intended for application to the lips; products for care of the teeth and the mouth (e.g. gargles, mouthwash or toothpastes); products for nail care and make-up; products for external intimate hygiene; sunbathing products; products for tanning without sun; skin-whitening products; anti-wrinkle products, tampons, sanitary towels, wet wipes, diapers or handkerchiefs.

Depending on the field of application, certain above mentioned cosmetic products may also be used in the medical filed, in particular certain washing products are suitable as disinfecting products, such as hand disinfecting products or instrument disinfecting products.

In all cases, the antimicrobial properties of the compounds of the formula I may provide, as additional benefit in the sense of a bonus effect, their antimicrobial efficiency to the cosmetic properties of the formulations, although the purely cosmetic use of the corresponding cosmetics is preferably predominant.

The cosmetics may comprise, in relationship to their intended use, various active and inactive ingredients, named "cosmetic additives" in the following.

Among the cosmetic additives, the following, without limiting the scope of possible additives, may be mentioned:

"Abrasives" are substances which remove materials from various body surfaces or aids mechanical tooth cleaning or improves gloss, "absorbents" are substances which take up water- and/or oil-soluble dissolved or finely dispersed substances, "anti-cakings" are substances which allow free flow of solid particles and thus avoids agglomeration of powdered cosmetics into lumps or hard masses, "anti-corrosives" are substances which prevent corrosion of the packaging, "anti-dandruffs" are substances which help to control dandruff, "anti-foaming" are substances which suppress foam during manufacturing or reduce the tendency of finished products to generate foam, "anti-microbials" are substances which help to control the growth of micro-organisms on the skin, "anti-oxidants" are substances which inhibit reactions promoted by oxygen, thus avoiding oxidation and rancidity, "anti-perspirants" are substances which reduce perspiration, "anti-plaques" are substances which help to protect against plaque, "anti-seborrhoeics" are substances which help to control sebum production, "anti-statics" are substances which reduce static electricity by neutralising electrical charge on a surface, "astringents" are substances which contract the skin, "bindings" are substances which provide cohesion in cosmetics, "bleachings" are substances which lightens the shade of hair or skin, "bufferings" are substances which stabilize the pH of cosmetics, "bulkings" are substances which reduce bulk density of cosmetics, "chelatings" are substances which react and form complexes with metal ions which could affect the stability and/or appearance of cosmetics, "cleansings" are substances which help to keep the body surface clean, "cosmetic colorants" are substances which color cosmetics and/or imparts color to the skin and/or its appendages (e.g. hair or nails) (e.g. dyes or pigments, e.g. lactoflavin, caramel capsanthin, capsorubin, beetroot red, anthocyanins, bromothymol blue, bromocresol green, acid red, aluminium, magnesium, calcium and zinc stearates); "denaturants" are substances which render cosmetics unpalatable, mostly added to cosmetics containing ethyl alcohol; "deodorants" are substances which reduce or mask unpleasant body odors, "depilatories" are substances which remove unwanted body hair; "detanglings" are substances which reduce or eliminate hair intertwining due to hair surface alteration or damage and, thus, helps combing; "emollients" are substances which soften and smooth the skin; "emulsifiers" are substances which promote the formation of intimate mixtures of non-miscible liquids by altering the interfacial tension; "emulsion stabilizers" are substances which help the process of emulsification and improves emulsion stability and shelf-life; "film formings" are substances which produce, upon application, a continuous film on skin, hair or nails; "foamings" trap numerous small bubbles of air or other gas within a small volume of liquid by modifying the surface tension of the liquid; "foam boosters" are substances which improve the quality of the foam produced by a system by increasing one or more of the following properties: volume, texture and/or stability; "gel formers" are substances which give the consistency of a gel (a semi-solid preparation with some elasticity) to a liquid preparation; "hair conditioners" are substances which leave the hair easy to comb, supple, soft and shiny and/or imparts volume, lightness, gloss, etc; "hair dyes" are substances which color hair; "hair fixers" are substances which permit physical control of hairstyle; "hair waving or straighteners" are substances which modify the chemical structure of the hair, allowing it to be set in the style required; "humectants" are substances which hold and retain moisture; "hydrotropers" are substances which enhance the solubility of substance which is only slightly soluble in water; "keratolytics" are substances which help to eliminate the dead cells of the stratum corneum; "masking agents" are substances which reduce or inhibit the basic odor or taste of the product; "moisturing" compounds increase the water content of the skin and helps keep it soft and smooth; "nail conditioners" are substances which improve the cosmetic characteristics of the nail; "opacifiers" are substances which reduce transparency or translucency of cosmetics; "oral care" provides cosmetic effects to the oral cavity, e.g. cleansing, deodorising, protecting; "oxidizers" are substances which change the chemical nature of another substance by adding oxygen or removing hydrogen; "pearlescents" are substances which impart a nacreous appearance to cosmetics; "plasticizers" are substances which soften and make supple another substance that otherwise could not be easily deformed, spread or worked out; "preservatives" (additional preservatives) are substances which inhibit primarily the development of micro-organisms in cosmetics; "propellants" are substances which generate pressure in an aerosol pack, expelling contents when the valve is opened, some liquefied propellants can act as solvents; "reducers" are substances which change the chemical nature of another substance by adding hydrogen or removing oxygen; "refatters" are substances which replenish the lipids of the hair or of the top layers of the skin; "refreshers" are substances which impart a pleasant freshness to the skin; "skin conditioners" are substances which maintain the skin in good condition; "skin protectors" are substances which help to avoid harmful effects to the skin from external factors; "smoothers" are substances which seek to achieve an even skin surface by decreasing roughness or irregularities; "solvents" are substances which dissolve other substances; "soothers" are substances which helps lightening discomfort of the skin or of the scalp; "stabilizers" are substances which improve ingredients or formulation stability and shelf-life; "surfactants" are substances which lower the surface tension of cosmetics as well as aids the even distribution of the product when used; "tanning" is a process which darkens the skin with or without exposure to UV; "tonics" are substances which produce a feeling of well-being on skin and hair; "UV absorbers" are substances which protect the cosmetic product from the effects of UV light; "UV filters" are substances which filter certain UV rays in order to protect the skin or the hair from harmful effects of these rays; "viscosity controllers" are substances which increase or decrease the viscosity of cosmetics.

In one embodiment, the formulations can be or comprise or contain cosmetic additives such as those conventionally used in cosmetic preparations, e.g. sunscreens, preservatives, bactericides, fungicides, virucides, cooling substances, insect repellents (e.g. DEET, IR 3225, Dragorepel), plant extracts, antiinflammatory substances, wound healing accelerators (e.g. chitin or chitosan and its derivatives), film-forming substances (e.g. polyvinylpyrrolidones or chitosan or its derivatives), customary antioxidants, vitamins (e.g. vitamin C and derivatives, tocopherols and derivatives, vitamin A and derivatives), 2-hydroxycarboxylic acids (e.g. citric acid, malic acid, L-, D- or DL-lactic acid), skin colorants (e.g. walnut extracts or dihydroxyacetone), active ingredients for promoting hair growth (e.g. minoxidil, diphencyprone, hormones, caffeine, finasteride, phytosterols such as beta-sitosterol, biotin, or extracts of *Cimicifuga racemosa, Eugenia caryophyllata* or *Hibiscus rosa-sinensis*, barley, hops, or rice or wheat hydrolysates), skin care products (e.g. cholesterol, ceramides, pseudoceramides), softening, moisturizing and/or moisture-retaining substances (e.g. glycerol or urea), fats, oils, saturated fatty acids, monounsaturated or polyunsaturated fatty acids, alpha-hydroxy acids, polyhydroxy fatty acids or their derivatives (e.g. linoleic acid, alpha-linolenic acid, gamma-linolenic acid or arachidonic acid and their respective natural or synthetic esters), waxes or other conventional constituents of a cosmetic or dermatological formulation, such as alcohols, polyols, polymers, foam stabilizers, electrolytes, organic solvents, silicone derivatives or chelating agents (e.g. ethylenediaminetetraacetic acid and derivatives), anti-dandruff substances (e.g. climbazole, ketoconazole, piroctonoleamine, zinc pyrithione), hair care products, perfumes, antifoams, dyestuffs, pigments with a coloring action, thickeners (advantageously silicon dioxide, aluminium silicates such as bentonites, polysaccharides or their derivatives, e.g. hyaluronic acid, guar kernel flour, xanthan gum, hydroxy-propyl methyl cellulose or allulose derivatives, particularly advantageously poly-acrylates such as carbopols, or poly-urethanes), surface-active substances, emulsifiers, plant parts and plant extracts (e.g. *arnica*, aloe, beard lichen, ivy, stinging nettle, *ginseng*, henna, chamomile, marigold, rosemary, sage, horsetail or thyme), animal extracts, e.g. royal jelly or propolis, proteins, protein hydrolysates, yeast extracts, hop and wheat extracts, peptides or thymus extracts.

Among the "preservatives" (additional preservatives) for cosmetic preparations, the following may be mentioned: benzoic acid, formic acid and their sodium salt; propionic acid, salicylic acid, sorbic acid, other weak acids, e.g. free fatty acids, esters and derivatives thereof,undec-10-enoic acid and their salts; formaldehyde incl. para formaldehyde; biphenyl-2-ol and its salts; zinc pyrithione; inorganic sulphites and hydrogen-sulphites; chlorobutanol; 4-hydroxybenzoic acid and its salts and esters; 3-acetyl-6-methylpyran-2,4 (3H)-dione (dehydracetic acid) and its salts; 3,3'-dibromo-4,4'-hexamethylenedioxydibenzamidine (dibromohexamidine) and its salts (including isethionate); thiomersal; phenylmercuric salts (including borate); hexetidine; 5-bromo-5-nitro-1,3-dioxane; bronopol; 2,4-dichlorobenzyl alcohol; triclocarban; 4-chloro-m-cresol; triclosan; 4-chloro-3,5-xylenol; 3,3'-bis (1-hydroxymethyl-2,5-dioxo-imidazolidin-4-yl)-1,1'-methylenediurea (imidazolidinyl urea); poly (1-hexamethylenebiguanide hydrochloride; 2-phenoxyethanol; hexamethylenetetramine (methenamine); methenamine 3-chloroallylochloride; 1-(4-chlorophenoxy)-1-(imidazol-1-yl)-3,3-dimethylbutan-2-one; 1,3-bis (hydroxymethyl)-5,5-dimethylimidazolidine-2,4-dione; benzyl alcohol; 1-hydroxy-4-methyl-6(2,4,4-trimethylpentyl) 2-pyridone and its monoethanolamine salt; 6,6-dibromo-4,4-dichloro-2,2'-methylenediphenol (bromochloro-phen); 4-isopropyl-m-cresol; mixture of 5-chloro-2-methyl-isothiazol-3(2H)-one and 2-methylisothiazol-3(2H)-one with magnesium chloride and magnesium nitrate; 2-benzyl-4-chlorophenol (clorophene); 2-chloroacetamide; chlorhexidine and its digluconate, diacetate and dihydrochloride; 1-phenoxypropan-2-ol; alkyl (C12-C22) trimethyl ammonium, bromide; 4,4-dimethyl-1,3-oxizalidine; N-(hydroxymethyl)-N-(dihydroxymethyl-1,3-dioxo-2, 5-imidazolidinyl-4)-N'-(hydroxymethyl) urea and chloride; 1,6-Di-(4-amidinophenoxy)-n-hexane (Hexamidine) and its salts (including isethionate and p-hydroxybenzoate); glutaraldehyde (pentane-1,5-dial); 5-ethyl-3,7-dioxa-1-azabicyclo [3.3.0] octane; 3-(p-chlorophenoxy)-propane-1,2 diol (chlorphenesin); sodium hydroxymethylamino acetate (sodium hydroxymethylglycinate); silver chloride deposited on titanium dioxide; benzethonium chloride; benzalkonium chloride, bromide and saccharinate; benzylhemiformal; iodopropynyl butylcarbamate (IPBC) 3-iodo-2-propynylbutylcarbamate; methylisothiazolinone, sodium hexametaphosphate, ethylenediaminetetraacetic acid, peptides such as polylysine, lauric arginate, cultured dextrose, neem oil, eugenol, p-cymene, thymol, carvacrol, linalool, hydroxycinnamic acid, cinnamic acid, cinnamic aldehyde, tea tree oil, fingerroot extract, acai powder, 4-hydroxybenzyl isothiocyanate and/or white mustard seed essential oil, ferulic acid, or mixtures of two or more thereof.

Other preserving agents such 1,3-diols which are named in WO 2011/023582 and/or benzaldehydes such as those disclosed in WO 2009/000097, or extracts from *Scutellaria baicalensis* such as those disclosed in KR 20030012821 are also understood as preservatives. Preferred are *Scutellaria baicalensis* extracts comprising dimethoxytetrahydroxyflavone and/or baicaleine (5,6,7-trihydroxyflavone), e.g. as obtainable by extraction with a solvent selected from propylene glycol, glycerine, 1,3-butylene glycol, water, ethanol, and mixtures thereof.

The cosmetics according to the invention preferably comprise only natural preservatives, or no preservatives are added in view of the preservative properties of the compound(s) of the formula I.

The invention also comprises cosmetics, especially their use, comprising beyond one or more of the compounds of the formula I also "other natural antimicrobially active agents", e.g. proteins, corresponding peptides alone or in combination, natural essential oils or derivatives thereof, such as oil from anis, lemon, orange, grapefruit, rosemary, thyme, lavender, tee tree, citron, wheat, lemon grass, cedar, cinnamon, *eucalyptus*, peppermint, basil, fennel, menthol, *Ocmea origanum, Hydastis carradensis, Krameria lappacea, Podophyllum* spp., *Curcuma longa*, or mixtures of two or more such oils.

In certain embodiments of the invention, essential oils are used in combination with emollient solvents and AHAs. Essential oils ("EOs"), as defined herein, are volatile oils obtained from plant or animal sources, or their synthetic equivalents, and are composed of complex mixtures of several constituents as monoterpenes and sesquiterpene hydrocarbons, monoterpene and sesquiterpene; alcohols, esters, ethers, aldehydes, ketones, oxides and the like. Examples of EOs include but are not limited to: bergamot oil, clary sage oil, sage oil, almond oil, ylang-ylang oil, neroli oil, sandalwood oil, frankincense oil, ginger oil, peppermint oil, lavender oil, jasmine absolute, geranium oil bourbon, spearmint oil, elove oil, patchouli oil, rosemary oil, rosewood oil, sandalwood oil, tea tree oil, vanilla oil, lemongrass oil, cedarwood oil, balsam oils, tangerine oil, Hinoki oil, Hiba oil, ginko oil, *eucalyptus* oil, lemon oil, orange oil, thyme oil, savory oil, oregano oil, and sweet orange oil. Botanicals, such as camphor and cinnamon may also be used. Individual constituents ("ICs") of essential oils may be natural or entirely or partially synthetic, and include, but are not limited to, I-citronellol, alpha-amylcinnamaldehyde, lyral, geraniol, farnesol, hydroxycitronellal, isoeugenol, eugenol, eucalyptol, linalool, citral, thymol, limonene and menthol. Additionally, sesquiterpenoids such as nerolidol, farnesol, bisabolol and apritone may also be used in the present invention. Mixtures of one or more EO, one or more IC, and one or more EO as well as one or more IC, are encompassed by the present invention.

Possible UV filters include but are not limited to: phenylen-1,4-bis-(2-benzimidazyl)-3,3'-5,5'-tetrasulfonic acids; 2-phenylbenzimidazol-5-sulfonic acid and corresponding salts; 1,4-di(2-oxo-10-sulfo-3-bornylidenmethyl)-benzene and corresponding salts; 4-(2-oxo-3-bornylidenmethyl)benzenesulfonic acid and its salts; 2-methyl-5-(2-oxo-3-bornylidenmethyl)sulfonic acid and its salts; 2,2'-methylen-bis-(6-(2H-benzotriazol-2-yl)-4-(1,1,3,3-tetramethylbutyl)-phenol); 2-(2H-benzotriazol-2-yl)-4-methyl-6-[2-methyl-3-[1,3,3,3-tetramethyl-1-[(trimethylsilyl)oxy]disiloxanyl]propyl]-phenol; 3-(4-methylbenzyliden)campher; 3-benzylidencampher; 4-(tert-butyl)-4'-methoxydibenzoylmethane; 2-(4'-diethylamino-2'-hydoxybenzoyl)-benzoic acid methyl ester; terephthalidendicamphersulfonic acid; 4-(dimethylamino)-benzoic acid (2-ethylhexyl)ester; 4-(dimethylamino)benzoic acid amylester; 4-ethoxybenzalmalonic acid (2-ethylhexyl)ester; 2-hydroxy-4-methoxybenzophenone; 2-hydroxy-4-methoxy-4'-methylbenzophenone; 2,2'-dihydroxy-4-methoxybenzophenone; 2-ethylhexyl-2-hydroxybenzoate; 3-(4-(2,2-bis ethoxycarbonylvinyl)-phenoxy) propenyl)-methoxysiloxan/dimethylsiloxan-copolymer; dioctylbutylamidotriazone (INCI: Diethylhexyl-Butamidotriazone); 2,4-bis-[5-1 (dimethylpropyl) benzoxazol-2-yl-(4-phenyl)-imino]-6-(2-ethylhexyl)-imino-1,3,5-triazine (CAS RN 288254-16-0); 4,4',4"-(1,3,5-triazin-2,4,6-triyltriimino)-tris-benzoic acid tris(2-ethylhexylester) (also: 2,4,6-tris-[anilino-(p-carbo-2'-ethyl-1'-hexyloxy)]-1,3,5-triazine (INCI: Ethylhexyl Triazone); 2,4-bis-{[4-(2-ethyl-hexyloxy)-2-hydroxy]-phenyl}-6-(4-methoxyphenyl)-1,3,5-triazine (INCI: Bis-Ethylhexyloxyphenol Methoxyphenyl Triazin); 2,4,6-tris-(biphenyl)-1,3,5-triazine; 2,4-bis-(4'-di-neopentylamino-benzalmalonat)-6-(4"-butylaminobenzoat)-s-triazine, 4-dicyanomethylen-2,6-dimethyl-1,4-dihydropyridin-N-(ethyloxysulfate ester salt), titan dioxides, zinc oxides, merocyanine, piperazine derivatives as mentioned in WO 2011/042088 without being limited to these.

Possible solvents include but are not limited to: alcohols such as methanol, ethanol, butanol, pentanol (amyl alcohol), ethylene glycol, propylene glycol, glycerol, butyl acetate, dimethlsulfoxide, acetone, methyl ethyl ketone, hydrocarbons such as hexane, pentane, oils such as *Zea mays* oil, or the like.

The cosmetics may be solid, e.g. of a waxy appearance or the like, or liquid or in the form of pastes or creams, e.g. as emulsions, solutions or suspensions, e.g. oil in water or water in oil (O/W or W/O) mixtures. They can thus form e.g. a solution, an emulsion of the water-in-oil (W/O) type or oil-in-water (O/W) type, or a multiple emulsion, for example of the water-in-oil-in-water (W/O/W) type, a gel, a hydrodispersion, a solid stick or else an aerosol.

The possible surfactants include but are not limited to customary ones, e.g. anionic, non-ionic, amphoteric tensides, such as soaps or sodium dodecylsulfate, or the substances disclosed in WO 2011/023582.

It is to be mentioned here that in view of their molecular structures the compounds of the formula I can also contribute surfactant properties to a composition according to the invention, so that this use is a preferred embodiment of the invention.

The composition comprising one or more compounds of the formula I according to the invention can be applied to the skin or lips or other body surfaces, e.g. hair, nails or teeth, according to the use for which it is intended. It can thus be used in a method for the cosmetic treatment of said body surfaces, e.g. the skin, comprising the application of the composition according to the invention to said body surface, e.g. the skin, for example for the purpose of toning it up, of regenerating it or of smoothing out its e.g. wrinkles in skin and/or for combating ageing, e.g. of the skin, or the damaging effects of UV radiation and/or for strengthening skin tissues, teeth, hair and/or nails against attacks from the surroundings.

In an alternative form, the composition according to the invention can be used for the manufacture of a dermatological preparation.

Home Care Products

As possible home care products to be equipped with one or more of the compounds of the formula I, among others, laundry detergents, dishwashing detergents, fabric softeners, hard surface cleaner or bleach compositions; surface, laundry and/or dish cleaners, laundry soaps, air fresheners and odor eliminators, insect repellents, laundry detergents, fabric softeners, bleaching agents, organic cleaners, degreasers, stain removers, window and glass cleaners, bathroom and toilet bowl cleaners, floor cleaners, carpet cleaners, pet odor removers, cat litter deodorizers, car refresheners, furniture polishes, waterless hand cleaners, disinfectants, spray deodorizers, food processing plant cleaners, coloring matters or other like home care applications may be mentioned.

The home care products have customary compositions. For example, in addition to surfactants, conventional solvents, dyes, preservatives, emulsifying agents, perfumes, antibacterial agents, thickeners, conditioners, antistatic agents, silicone surfactants, and other like ingredients that are typically present in conventional home care formulations may be comprised. Mixtures and/or combinations of the aforementioned additional formulating agents may also be employed in the present invention. The amounts of the additional formulating agents that may be employed in the present invention are within ranges that are well known to those skilled in the art and further formulating is performed using processes that are also well known in the art.

Pharmaceuticals

Pharmaceuticals comprise one or more pharmaceutically active agents and a pharmaceutically acceptable carrier material.

Examples of such pharmaceuticals (pharmaceutical compositions) are e.g. solid (tablet, capsule, powder, medical chewing gum, lozenge, suppository) or liquid formulations (e.g. injection solution, infusion solution, syrup, drinkable solution), a spray, or a pasty material, e.g. a gel or a cream.

Among the possible active ingredients, all drugs known in the art may be added, e.g. (without that this enumeration is intended to be limiting) bronchodilators, antipyretics, analgetics, antiphlogistics, antiarrhythmics, blood-pressure reducing agents, vasodilators, anticholinergics, antiarteriosclerotics, enzymes, antibodies, secretolytics, ulcer preparations, antiproliferative agents, vasoconstrictors, expectorants, antitussiva, mucolytics, or secretomotorics; in particular, free of antiallergics (including those referred to hereinbefore), such as α-sympathicometics (in particular Phenylephrin, Ephedrin, Tetryzolin, Naphazolin, Oxymetozolin, Xylometazolin or Tramazolin), antihistamines, non-steroidal or steroidal anti-inflammatory active substances (in particular Triamcinolone acetonide, glucocorticoids, such as Prednisolone, Triamcinolonacetonide, Clomethasone, Dexamethasone, or Fluticasone), $\beta_2$ sympathomimetics; mast cell stabilizers, aromatase inhibitors; antiestrogens; topoisomerase I inhibitors; topoisomerase II inhibitors; microtubule active compounds; alkylating compounds; histone deacetylase inhibitors; compounds which induce cell differentiation processes; cyclooxygenase inhibitors; MMP inhibitors; mTOR inhibitors; antineoplastic antimetabolites; platin compounds; compounds targeting/decreasing a protein or lipid kinase activity and further anti-angiogenic compounds; compounds which target, decrease or inhibit the activity of a protein or lipid phosphatase; gonadorelin agonists; anti-androgens; methionine aminopeptidase inhibitors; bisphosphonates; biological response modifiers; antiproliferative antibodies; heparanase inhibitors; inhibitors of Ras oncogenic isoforms; telomerase inhibitors; proteasome inhibitors; compounds used in the treatment of hematologic malignancies; compounds which target, decrease or inhibit the activity of Flt-3; Hsp90 inhibitors such as 17-AAG (17-allylamino-geldanamycin, NSC330507), 17-DMAG (17-dimethylaminoethylamino-17-demethoxy-geldanamycin, NSC707545), IPI-504, CNF1010, CNF2024, CNF1010 from Conforma Therapeutics; temozolomide (TEMODAL®); kinesin spindle protein inhibitors, such as SB715992 or SB743921 from GlaxoSmithKline, or pentamidine/chlorpromazine from CombinatoRx; MEK inhibitors such as ARRY142886 from Array PioPharma, AZD6244 from AstraZeneca, PD181461 from Pfizer, leucovorin, EDG binders, antileukemia compounds, ribonucleotide reductase inhibitors, S-adenosylmethionine decarboxylase inhibitors, antiproliferative anti-bodies or other chemotherapeutic compounds; tricyclics, e.g. benzodiazepines including mitochondrial benzodiazepine-ligands MAO inhibitors, SSRI's, SNRI's, NK receptor antagonists, CRF-receptor antagonists, 5HT7 receptor-antagonists, mGlu receptor agonists/antagonist/modulators, GABA-A or GABA-A/B receptor agonist/antagonists or modulators, vasopressin receptor antagonists, herbal medicine such as St. John's Wort, 5-HT1A receptor agonists, vasopressin receptor-antagonists, acetylcholine-esterase inhibitors, such as rivastigmine or donepezil, mixed acetylcholine/butyrylcholine esterase-inhibitors. nicotinic-alpha7-receptor agonists, typical or atypical antipsychotics, such as clozapine or haloperidol, nicotinic-alpha7-receptor agonists, antimanic agents (e.g. lithium, Carbamazepine, Valproate) or any atypical or typical antipsychotic; or the like; pharmaceutically acceptable salts thereof, if salt-forming groups are present; or combinations of two or more of the aforementioned active substances or their pharmaceutically acceptable salts.

Pharmaceutical compositions comprising one or more active ingredients and one or more compounds of the formula I in association with at least one pharmaceutical acceptable carrier or diluent may be manufactured in conventional manner by mixing with a pharmaceutically acceptable carrier or diluent.

The invention relates also to pharmaceutical compositions comprising an antimicrobially effective amount, especially an amount effective in the treatment of one of the abovementioned disorders, of one or more compounds of the formula I, a pharmaceutically acceptable salt thereof, and/or an ester thereof, together with one or more pharmaceutically acceptable carriers that are suitable for topical, enteral, for example oral or rectal, or parenteral administration and that may be inorganic or organic, solid or liquid. There can be used for oral administration especially tablets or gelatin capsules that comprise the active ingredient together with diluents, for example lactose, dextrose, mannitol, and/or glycerol, and/or lubricants and/or polyethylene glycol. Tablets may also comprise binders, for example magnesium aluminum silicate, starches, such as corn, wheat or rice starch, gelatin, methylcellulose, sodium carboxymethylcellulose and/or polyvinylpyrrolidone, and, if desired, disintegrators, for example starches, agar, alginic acid or a salt thereof, such as sodium alginate, and/or effervescent mixtures, or adsorbents, dyes, flavorings and sweeteners. It is also possible to use the pharmacologically active compounds of the present invention in the form of parenterally administrable compositions or in the form of infusion solutions. The pharmaceutical compositions may be sterilized and/or may comprise excipients, for example preservatives, stabilizers, wetting compounds and/or emulsifiers, solubilizers, salts for regulating the osmotic pressure and/or buffers. The present pharmaceutical compositions, which may, if desired, comprise other pharmacologically active substances are prepared in a manner known per se, for example by means of conventional mixing, granulating, confectioning, dissolving or lyophilizing processes, and comprise approximately from 1% to 99% by weight, especially from approximately 1% to approximately 60%, active ingredient(s) and 0.001 to 10, 0.01 to 8, 0.02 to 6 or 0.03 to 5 weight percent of the compound(s) of the formula I, a pharmaceutically acceptable salt thereof and/or an ester thereof. Also the use of their preservative or antimicrobial properties in said pharmaceutical compositions by the addition of one or more compounds of the formula I is included.

Additives, both in the case of foods and of cosmetics, as well as in the case of pharmaceuticals (the term pharmaceuticals also including nutraceuticals), may exhibit more than one property as selected from the above lists or other not cited properties, e.g. preservatives may also act as acidity regulators and vice versa, or e.g. antioxidants may act as preservatives as well as acidity regulators, or other thinkable multi functional uses.

Medical Devices

Medical devices are especially devices intended for use in the diagnosis of disease or other conditions, or in the cure, mitigation, treatment, or prevention of disease, in man or other animals, and mean e.g. any instrument, apparatus, appliance, material or other article, whether used alone or in combination, including the software necessary for its proper application intended by the manufacturer to be used for human beings for the purpose of:

diagnosis, prevention, monitoring, treatment or alleviation of disease, diagnosis, monitoring, treatment, alleviation of or compensation for an injury or handicap, investigation, replacement or modification of the anatomy or of a physiological process, control of conception, and which does not achieve its principal intended action in or on the human body by pharmacological, immunological or metabolic means, but which may be assisted in its function by such means.

Among the medical devices, among others, e.g. implants, prosthesis, plasters (=adhesive tapes), (wound) dressing materials, bandages, cotton wool, gauze bandages, surgical instruments, tooth brushes, syringes, syringe needles, medication containers, infusion bottles, infusion tubes, valves or multiports used in infusion, infusion needles, infusion assemblies, surgical instruments, catheters, artificial or natural tissues or membranes, tooth brushes, and the like may be mentioned.

Possible implants include but are not limited to:

a) Surgical meshes or other 2-dimensionally extended or extendable materials (such as membranes), such as polypropylene meshes (e.g. BARD MESH® from Bard Inc., SURGIPRO® from US Surgical, Inc., TRELEX® from Boston Scientific, PROLENE® or MERSILENE® from Ethicon, Inc.), polyester meshes (e.g. MERSILENE® from Ethicon), expanded polytetrafluoroethylen meshes (e.g. SOFT TISSUE PATCH® from W.L. Gore & Associates, Inc), polyamide materials or the like, e.g. for the repair of hernias; or such meshes or materials 2-dimensionally extended or extendable materials, such as polyglactin (e.g. VICRYL® from Ethicon, Inc.), polyglykolate (e.g. DEXON® from US Surgical, Inc.), polydioxanone (PDS), polyglyconate (e.g. MAXON@, Davis & Geck, Gosport, UK) or collagene materials, e.g. COOK SURGISIS® from Cook Biomedical, Inc.; other possible membrane or mesh materials include FLUORO-TEX® Pericardial and Peritoneum Surgical Membrane or FLUORO-TEX Dura Substitute (each from C.R. Bard) orr PRECLUDE® Pericardial Membrane PRECLUDE® Peritoneal Membrane and PRECLUDE® Dura Substitute Membrane each from W.L. Gore & Associates, silicone elastomers, such as SILASTIC Rx® Medical Grade Sheeting from Dow Corning or mikroporous Polypropylen from Celgard, Inc., for example where the implant is used to seal compartmenting tissues or structures in the body, such as peritoneum, pleura, diaphragma, lung, pericard or the like; b) electrode coatings, e.g. for electrodes of pacemakers or neural or muscular stimulation or the like, e.g. made from tungsten, silicon, platinum-iridium or stainless steel or combinations thereof;

c) degradable or non-degradable bone or cartilage implants;

d) orthopaedic implants, such as hard tissue, bone or joint replacing implants, for example for hip or knee or other joint repair, e.g. implants made from stainless steel, cobalt-chromium alloys, titanium or titanium alloys, pure titanium, tantalum, plastics materials such as polyethylene, polypropylene, polylactate, carbon fibre, ceramics or compounds of two or more such materials;

e) screws, nails, threads, plates or other hard fixation materials for hard tissues, e.g. from the materials mentioned under d);

f) oral, such as dental implants, e.g. from the materials mentioned under d);

g) Bone fillers, such as bone cement composites, hydroxyl apatite composites or polycaprolactone (Blurr plug);

h) implants coming into contact with blood, such as vascular grafts, e.g. from biocompatible plastics materials, such as extended polytetrafluoroethylene or poly[ethylene terephthalate], stents (e.g. from metals or metal alloys, such as (e.g. 316L) stainless steel, cobalt-chromium-nickel-molybdenum-iron alloy, Tantalum, shape memory alloys, e.g. nitinol, or (e.g. shape memory) polymer materials, such as polyethylene or polyurethane), heart or venous valves (e.g. from polymer or metal or natural materials or combinations thereof, e.g. pyrolytic carbon, titanium coated with pyrolytic carbon, and the sewing ring cuff is e.g. teflon, polyester or dacron), stent/valve combinations, or continuous accesses e.g. to veins, or to the peritoneum e.g. for peritoneal dialysis or the like;

i) implants for delivery of signals or chemical substances, e.g. drugs, coming into contact with tissue and/or body fluids, e.g. pumps for delivery of drugs or pacemakers;

j) organs or tissues for transplantation (e.g. to decrease the expression of antigens evoking transplant rejection), especially autografts, allografts, heterografts or xenografts;

k) skin substitutes or wound coating materials, such as natural (e.g. keratinocytes in combination with human fibroblasts in bovine type I collagen or other ECM proteins and cytokines, such as Apligraf® (Organogenisis Inc.), or from synthetics, or combinations with natural materials e.g. synthetic polysiloxanes with bovine type I collagen and chondroitin-6-sulphate (e.g. Integra® (Johnson & Johnson Medica Care Life)) or preferably from synthetics alone or combined with human dermal tissue (e.g. Tanscyte® (Advanced Tissue Sciences Inc.)), allografts, collagen (e.g. in reconstituted form) or the like;

l) suturing materials (especially for internal sutures not accessible from the outside), e.g. from absorbable or non-absorbable synthetics or natural materials (e.g. cat gut).

Especially preferred are artificial implants made from metals, metal alloys, synthetic materials (=polymers) (either degradable or non-degradable), carbon fibres, boranes, ceramics, glass or bone replacement materials, especially of the types a) to i) or k) to l) mentioned above, including composites of two or more such materials.

The implants may be for permanent (e.g. in the case of joint replacement) or transitory (e.g. in the case of fixing devices or skin replacements) insertion or other administration.

Especially here the biofilm inhibiting usefulness of the compound(s) of formula I and of compositions comprising them is of advantage.

Active Packaging Materials

Among the active packaging materials, e.g. food or beverage or pharmaceutical or surgical packaging material having a spoilage preventing/preservative effect e.g. against colonialisation by bacterial or other microorganismic films or against spoiling of materials coming into contact with other perishable products can be mentioned, e.g. cans, wraps, foils, bottles, mugs, cartons, tubs, bags, cartridges, tubes, sachets, ampoules, sacks, or the like.

Both with regard to medical devices and to active packaging materials, as well as with regard to personal care products used having a predetermined shape, the application of compound(s) of the formula I is especially by coating e.g. on surfaces coming into contact with perishable products or a human or an animal, or bulk integration (e.g. by mixing of starting materials and/or impregnation of final products) into the material.

The compound(s) of the formula I to medical devices and active packaging materials can especially be applied (alone or in combination with appropriate carrier materials) on surfaces coming into contact with perishable products or a human or an animal, e.g. in the form of a coating, or applied by bulk integration into the material.

The materials equipped (which form an embodiment of the invention) or to be equipped with one or more compounds of the formula I may comprise the compound(s) of the formula I, a physiologically acceptable salt thereof and/or an ester thereof, either in admixture to the bulk of the material, or (in the case of products with a stable surface) by covalent and/or non-covalent attachment to (parts or the whole of) said surface.

For covalent attachment, the surface must either expose or be chemically modified to expose functional groups which would allow for covalent bonding of the compound of the formula I either directly or via a spacer molecule.

In the case of he covalently bound (at least bivalent) linker molecules, these may allow covalent or non-covalent binding of the compounds of the formula I.

The linker in the covalent attachment method can be any linker.

Covalent binding of the compounds of the formula I with or without linkers can take place directly by reacting their precursors with the surfaces without activation or to activated surfaces on the implants or other products. Examples are 1. epoxy- or activated ester-functionalized surfaces, where reaction with OH— or amino groups in the linker precursors is possible.

2. Where the linker precursors are organic compounds which are furnished terminally with a thiol group, they can be bound e.g. via gold-plated surfaces or maleinimide-layered surfaces.

3.) Linker precursors which, during the process of manufacture, are furnished terminally with a carboxyl or phosphate group, can be activated to active esters or the like, e.g. with EDC, so that an OH-, SH- or amino-reactive on the surface can be bound.

4.) Precursors for homo- or preferably hetero-bifunctional cross-linker which can be bound to reactive groups at the surface, such as carboxyl, epoxy, OH, SH, aldehyde or amino groups; or other known methods.

5.) Other directly functionalized surfaces, e.g. especially polymers with plasma-coated aldehydes.

Other possible activations for both covalent and non-covalent binding include but are not limited to glow-discharged surfaces, electrostically charged surfaces, and/or roughened surfaces. Also coating with materials, e.g. gels, varnishes, paints or the like, comprising the compound(s) of the formula I, is a method for providing their surfaces with these compounds.

In the (preferred) case of the non-covalent attachment, the material can be any substrate. This substrate could be a synthetic polymer (i.e. polyacrylate, polylactide-co-gly-colide, polyethylene, or polypropylene), carbon fibre, glass, boranes, metal (i.e. titanium or stainless steel), natural polymer (i.e. collagen or alginate), or any other surface that is capable of supporting a coating, e.g. in solid or fibre form, respectively. Composites of two or more such materials are also included. The non-covalent can, for example, be via adsorption, integration into a coating matrix or the like.

The compounds of the formula I in the embodiments of the invention, in a further embodiment, can be used also where the materials (products) with which they are associated (e.g. by mixing in) require a heat treatment, e.g. to achieve pasteurization sterilization or the like.

Thus, in one embodiment, the one or more compounds of the formula I is/are heat stable. In one example the compound(s) of the formula I fully or partially retain(s) structure and activity e.g. regarding its preservative properties after heating. Heating of the antimicrobial composition can be performed at 60-130° C., such as in the range of 60-65° C., 65-70° C., 70-75° C., 75-80° C., 80-85° C., 85-90° C., 90-95° C., 95-100° C., 100 –105° C., 105-110° C., 110-115° C., 115-120° C., 120-125° C., 125-130° C.

In one embodiment heating is performed at about 65-75° C., more preferred at about 70° C. In one embodiment heating is performed at about 90-110° C., more preferred at about 100° C.

In yet another embodiment heating is performed at about 120-125° C., more preferred at about 121° C.

According to the present invention, heating can be performed for shorter or longer periods of time, such as from a minute to several hours. Heating can for example be performed for a few minutes such as in the range of about 1-5 minutes, 5-10 minutes, 10-15 minutes, 15-20 minutes, 20-25 minutes, 25-30 minutes, 30 minutes-to 1 hour.

For the purpose of the invention other known preserving agents or known preservatives may be added to the pharmaceutical incl. nutraceutical and cosmeceutical, nutritive or cosmetic product as well as to the composition.

Preferred combinations of the compounds of the invention for use in food and beverages are with weak organic acids, especially preferred are combinations with sorbic acid and/or benzoic acid and their appropriate salts, or with natural preservatives.

Among possible preferred combinations of the compounds of the invention for cosmetic use are combinations with $C_1$-$C_4$ alkyl para-hydroxybenzoate or its salts, e.g. methylparaben, ethylparaben, propylparaben, isopropylparaben, butylparaben, isobutylparaben and their appropriate salts, benzylparaben, benzoic acid or its salts, e.g. sodium benzoate, N-(3-chloroallyl)hexaminium chloride, alcohols or polyols, such as ethanol, propylene glycol, benzyl alcohol or 2-phenoxyethanol, benzalkonium chloride, chloroacet-amide, thimerosal, benzalkonium chloride, cetylpyridinium chloride, N-(3-chloroallyl)hexaminium chloride, formaldehyde donors, such as imidazolidinyl urea, diazolidinyl urea, or DMDM hydantoin, isothiazolinones, such as KATHON® CG, available commercially from Rohm & Haas, Philadelphia, Pa., which contains a chloro-substituted isothiazolinone (methylchloroisothiazolinone), other chlorinated aromatic compounds, such as chlorphenesin, phenoxyethanol, vicinal diols, such as a 1,2-alkane diol or a glyceryl monoether, such as glyceryl laurate, decyl glycoside isothiazolinone compounds, such as methylisothiazolinone, e.g. 2-methyl-3(2H)isothiazolinone, propionic acid and its salts, undec-10-enoic acid and salts, *Scutellaria baicalensis* extracts (such as e.g. available from BMB-FS, or the like), or mixtures of two or more such preservatives.

In all materials, the compound(s) of the formula I can also be used as emulsifiers, in addition to use of their preservative properties.

The compound or compounds of the formula I are preferably comprised, taking the weight or the material to which it is added and the compound(s) of formula I as 100 weight %, in a relative weight share of 0.00001 to 10 weight percent.

In the foods or beverages according to the invention, the compound or compounds of the formula I are preferably added/comprised in a concentration e.g. in the range from 50 to 20000 ppm, e.g. from 100 to 1000 ppm, for example from 10 to 120 ppm, such as from 30 to 60 ppm, or e.g. from 0.1-150 ppm, where ppm refers to weight parts per million.

"Minimal inhibitory concentration" (MIC) is a term for which no standard time period is routinely defined or understood. In the medical fields, MIC is frequently employed to designate the concentration of a substance which prohibits the growth of a single type of microorganism in over-night incubation as compared to a positive control without the substance. However, the rest of the scientific community has adopted the term MIC to mean any of a number of conditions of period of incubation and degree of inhibition.

Even within the medical field, it is recognized that an MIC value developed over a period of 24 hours incubation may not be the same value developed after 48 hours or longer. In other words, a substance may exhibit an observable MIC during the first 24 hours of an experiment, but exhibit no measurable MIC relative to the positive control after 48 hours.

The following table gives some of the compounds of the formula I that are of interest in the various embodiments of the present invention.

TABLE 1

| Name (if known: CAS number): | Cpd. Number |
|---|---|
| 2,17,18-trihydroxy-hexacosanoic acid 22-O-[6-isovaleroyl-hexapyranosyl-(1→2)-5-acetyl-pentapyranosyl-(1→2)-penta-pyranosid]- | [1] |
| | [2] |
| Glykenin-IIC 134528-36-2 | [3] |

TABLE 1-continued

| Name (if known: CAS number): | Cpd. Number |
|---|---|
| | [4] |
| | [5] |
| Glykenin IIIB or Glykenin IIIC 134528-37-3, 134479-71-3 | [6] |
| Glykenin IVC or IVB 134479-72-4, 134528-38-4 | [7] |

TABLE 1-continued

| Name (if known: CAS number): | Cpd. Number |
|---|---|
| | [8] |
| | [9] |
| | [11] |
| | [12] |

TABLE 1-continued

| Name (if known: CAS number): | Cpd. Number |
|---|---|
| | [13] |
| | [14] |
| Glykenin DGC or Glykenin DGB 112965-51-2, 112848-53-0 | [16] |
| | [17] |

TABLE 1-continued

| Name (if known: CAS number): | Cpd. Number |
|---|---|
| Antibiotic F 19848A 895129-04-1 | [10] |
| | [18] |
| | [19] |
| | [20] |

TABLE 1-continued

Name
(if known: CAS Cpd.
number): Number

[21]

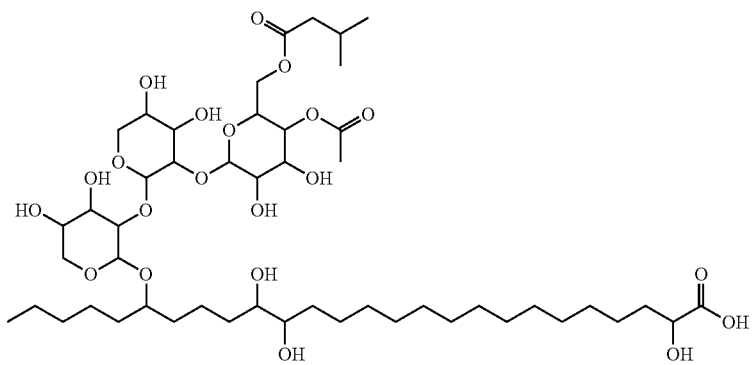 [SMILES: CCCCCC(CCCC(O)C(O)CCCCCCCCCCCCCC(O)C(=O)O)OC1OCC(O)C(O)C1OC1OCC(O)C(O)C1OC1OC(COC(=O)CC(C)C)C(OC(C)=O)C(O)C1O]

The preserving properties of the compounds of the invention e.g. compounds of the formula I can be evaluated according methods cited in the art such as WO 2010/062548. For example, they can be determined for beverages using the method described in Example 3 in WO 2010/062548 which is incorporated herein by reference. For example, a single preparation of base beverage is employed to prepare each of five tests and consists of 4% apple juice, 68 g/l sucrose, 52 g/l glucose, 2 g/l fructose in batch water which is formulated to 90 ppm hardness with calcium chloride and magnesium chloride. A pH of 3.4 is achieved through combinations of malic acid and sodium malate for all preparations regardless of the presence or absence of compounds of the formula I. The total combined quantity of sodium malate and malic acid is near constant, but the ratio of malic acid and malate may vary slightly given the presence of compound of the formula I. It is relevant that the beverage employed for testing does not naturally contain any substance with measurable antimicrobial activity such as in essential oils. Where required, compound of the formula I is supplemented from separately prepared stock solutions. Dimethyl dicarbonate is delivered by means of a hypodermic needle (Hamilton syringe) through septum that seals the test vessel against loss of moisture. Dimethyl dicarbonate stock solution consists of 1 ml dimethyl dicarbonate (1.25 g) in 49 ml of 100% ethanol (25 mg/ml). Hence, a microliter of stock contains 25 microgram of dimethyl dicarbonate. Each of the five tests employs the same bio-indicator organisms; Growth (+) versus no growth (−) is established by visual inspection or spectrophotometrically (see e.g. Examples below). The organism names and their strain numbers, as well as incubation times and details on deviating assay conditions, if any were used, are mentioned in the Examples.

Among the preferred embodiments of the invention, the following are to be mentioned:

A) The first embodiment of the invention is the use of a compound of formula I, or a mixture of two or more such compounds of the formula I, and/or a physiologically, especially pharmaceutically or nutraceutically or cosmetically, acceptable salt thereof, or an ester thereof, where the compound may be present in open chain form and/or in the form of a lactone, as agent with preservative or antimicrobial properties, comprising adding the agent to a material, where said material is preferably selected from the group consisting of a cosmetic, a food, a beverage, a pharmaceutical, a medical device, and an active packaging material, or a method comprising the use mentioned therein.

B) Especially preferred is said use or method, where the material to which the agent is added is a cosmetic, a food or a beverage.

C) Another invention embodiment related to the use or method according to paragraph A) or B), where in the compound of the formula I m is 3 to 5, n is 2 to 5, o is 0 or 1, p is 5 to 15 and R is a moiety of the subformula

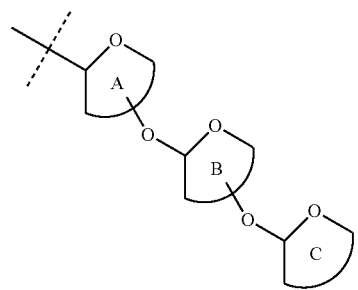

wherein the rings A, B and C are monosaccharide moieties each independently from the others with 5 or 6 ring members, wherein one or more of the hydroxyl groups may be acylated, preferably by a $C_2$-$C_{10}$alkanoic, more preferably a $C_3$-$C_{10}$alkanoic acid.

D) Another invention embodiment relates to the use or method according to paragraph A) above, wherein the compound or mixture of compounds of the formula I comprises, preferably, at least one compound selected from the group of compounds mentioned in table 1, or a physiologically acceptable salt thereof.

E) Another invention embodiment relates to the use or method according to any one of paragraphs A) to D) above, wherein the compound or compounds of the formula I, or a physiologically acceptable salt, or a physiologically acceptable ester thereof, is added to enhance the stability against microorganisms.

F) Another invention embodiment relates to the use or method according to paragraph E) above, where the microorganism is at least one microorganism selected from the group consisting of mold, yeast and bacteria of a beverage or a food or a cosmetic.

G) Another invention embodiment relates to the use or method according to any one of paragraphs A) to F) above, where at least one additional preservative is added.

H) Another invention embodiment relates to the use or method according to any one of paragraphs A) to G) above, where the compound or compounds of the formula I, a physiologically acceptable salt thereof, and/or an ester thereof, is added in the form of an extract (this term including a precipitate) from a natural source or obtained from such an extract.

I) Another invention embodiment relates to the use or method according to paragraph H), where the source of the extract is a *Dacryopinax*, a *Ditiola* and/or a Femsjonia fungus.

J) Another invention embodiment relates to the use or method according to paragraph H), where the source of the extract is *Dacryopinax spathularia, Dacrymyces* sp., *Ditiola radicata, Ditiola nuda* and/or *Femsjonia luteo-alba* (=*Ditiola pezizaeformis*).

K) Another invention embodiment relates to the use or method according to paragraph J) above, where the source of the extract is *Dacryopinax spathularia* strain FU50088, *Ditiola radicata* strain MUCL 53180, *Ditiola nuda* strain CBS 173.60 or *Femsjonia luteo-alba* (=*Ditiola pezizaeformis*) strain MUCL 53500.

L) Another invention embodiment relates to the use or method according to any one of paragraphs A) to K), where the material is subjected to a heat treatment before, during or after addition of the compound(s) of the formula I, a physiologically acceptable salt thereof and/or an ester thereof, as defined in any one of paragraphs A), C), D) or H) to K), especially heating the material to a temperature from 60 to 130° C.

M) Another invention embodiment relates to a compound or a mixture of compounds of the formula I shown in paragraph A) or as defined in any one of paragraphs C), D) or H) to L), where the moiety R carries at least one hydroxyl group esterified with an acid with 3 or more carbon atoms, a physiologically acceptable salt, and/or an ester thereof.

N) Another invention embodiment relates to the compound or compound mixture of paragraph M), wherein the acid is a $C_5$-$C_{10}$-alkanoic acid, especially isovaleric acid; a physiologically acceptable salt, and/or an ester thereof.

O) Another invention embodiment relates to a compound of the formula I described herein, selected from the group of compounds represented in Table 1 with the following compound numbers: [1], [12], [13], [14], [17] and [18], and in a broader aspect from compound [4], a physiologically acceptable salt, and/or an ester thereof.

P) A further embodiment of the invention relates to a preservative or antimicrobial composition, comprising as active agent a compound or a mixture of compounds of the formula I, a physiologically acceptable salt thereof, and/or an ester thereof, as shown or defined in any one of paragraphs A), C), D) and H) to O), alone or with another additive, such as a carrier material, where the preservative composition is especially for use in a cosmetic, a food, a beverage, a pharmaceutical, a medical device, or an active packaging material.

Q) Another invention embodiment relates to the composition according to paragraph P) which is a powder.

R) Another invention embodiment relates to the composition according to paragraph P) which is a liquid.

S) Yet another invention embodiment relates to the composition according to paragraph P) which is a coating or film.

T) Another invention embodiment relates to the composition according to any one of paragraphs P) to S), wherein the preservative or antimicrobial composition is for enhancing the stability against microorganisms.

U) Another invention embodiment relates to the composition according to paragraph T), wherein the microorganisms are at least one microorganism selected from the group consisting of mold, yeast and bacteria.

V) Another invention embodiment relates to the composition according to any one of paragraphs P) to U), being a preservative or antimicrobial composition for a pharmaceutical, a medical device, a food container, a beverage container, or especially a food, a beverage or a cosmetic or a home care product.

W) Another invention embodiment relates to the composition according to any one of paragraphs P) to V), which comprises an additional preservative.

Y) Another invention embodiment relates to the composition according to any one of paragraphs P) to W), which is a precursor of a beverage, especially a concentrate, a syrup or a powder.

Z) Another invention embodiment relates to an extract comprising one or more compounds of the formula I, a physiologically acceptable salt thereof, and/or an ester thereof, as shown or defined in any one of paragraphs A), C), D) or H) to O).

AA) Another invention embodiment relates to a method of enhancing microbial stability of a material, comprising adding one or more compounds of the formula I, a physiologically acceptable salt thereof, and/or an ester thereof, as shown or defined in any one of paragraphs A), C), D) or H) to O) to a material, preferably a material selected from the group consisting of a cosmetic, a food, a beverage, a pharmaceutical, a medical device, and an active packaging material.

BA) Another invention embodiment relates to the method of paragraph AA), wherein the material is a beverage or a food.

CA) Another invention embodiment relates to the method of paragraph AA), wherein the material is a cosmetic.

DA) Another invention embodiment relates to a material comprising, as or within a coating and/or as admixture, an additive in the form of a compound or a mixture of compounds of the formula I, a physiologically acceptable salt thereof and/or an ester thereof, as defined in any one of paragraphs A), C), D) or H) to O).

EA) Another invention embodiment relates to the material of paragraph DA), which is a cosmetic, a food, a beverage, a pharmaceutical, a medical device, or an active packaging material.

FA) Another invention embodiment relates to the material according to paragraph DA) which is a beverage.

GA) Another invention embodiment relates to the material in the form of a compound or a mixture of compounds of the formula I, a physiologically acceptable salt thereof and/or an ester thereof, according to paragraph FA), where the beverage is selected from the group consisting of water, flavoured water, fortified water, a flavoured beverage, carbonated water, a juice, cola, lemon-lime, ginger ale, root beer beverages which are carbonated in the manner of soft drinks, a syrup, a diet beverages, a carbonated soft drink, a fruit juice, other fruit containing beverages which provide the flavor of fruit juices and contain greater than 0% fruit juice but less than 100% fruit juice, fruit flavored beverages, vegetable juices, vegetable containing beverages, which provide the flavor of any of the aforementioned vegetable juices and contain greater than 0% vegetable juice but less than 100% vegetable juice, isotonic beverages, non-isotonic beverages, soft drinks containing a fruit juice, coffee, tea, tea beverages prepared from tea concentrate, extracts, or powders, drinkable dairy products, hot chocolate, chocolate powders/mixes, drinkable soy products, non-diary milks, alcoholic beverages, fruit smoothies, horchata, sport drinks, energy drinks, health drinks, wellness drinks, shakes, protein drinks, drinkable soy yogurts, low acid beverages, acidified beverages, nectars, tonics, frozen carbonated beverages, frozen uncarbonated beverages, liquid meal replacements, infant formulations, and combinations or mixtures thereof.

HA) Another invention embodiment relates to the material according to paragraph DA) which is a beverage precursor, especially a concentrate, syrup or powder.

IA) Another invention embodiment relates to the material according to paragraph DA) which is a food.

JA) Another invention embodiment relates to the material according to paragraph DA) which is a cosmetic.

KA) Another invention embodiment relates to the material in the form of a cosmetic according to paragraph JA) which is cream, emulsion, lotion, gel or oil for the skin; a face masks, a tinted base, a make-up powder, an after-bath powder, a hygienic powder, a toilet soap, a deodorant soap, a perfumes, a toilet water, an eau de Cologne, a bath or shower preparation; a depilatory; a deodorant, an antiperspirant, a hair care product; a setting product; a cleansing product; a conditioning product; a hairdressing product; a shaving products; a product for making up and removing make-up from the face and the eyes, a product intended for application to the lips, a products for care of the teeth and/or the mouth; a product for nail care and/or make-up, a product for external intimate hygiene, a sunbathing product, a product for tanning without sun, a skin-whitening product, an anti-wrinkle product, a tampon, a sanitary towel, a diaper or a handkerchief.

LA) Another invention embodiment relates to the cosmetic material according to any one of paragraphs JA) and LA), which comprises one or more additives selected from the group consisting of abrasives, absorbents, anti-cakings, anti-corrosives, anti-dandruffs, anti-foamings, anti-microbials, anti-oxidants, anti-perspirants, anti-plaques, anti-seborrhoeics, anti-statics, astringents, bindings, bleachings, bufferings, bulkings, chelatings, cleansings, cosmetic colorants, denaturants, deodorants, depilatories, detanglings, emollients, emulsifiers, emulsion stabilizers, film formings, foamings, foam boosters, gel formers, hair conditioners, hair dyes, hair fixers, hair waving or straighteners, humectants, hydrotropers, keratolytics, masking agents, moisturing, nail conditioners, opacifiers, oral care, oxidizers, pearlescents, plasticizers, preservatives, propellants, skin protectors, smoothers, solvents, soothers, stabilizers, surfactants, tanning, tonics, UV absorbers, UV filters, and viscosity controllers.

MA) Another invention embodiment relates to the cosmetic material according to any one of paragraphs JA) and LA), where the formulations can be or comprise or contain cosmetic additives selected from sunscreens, preservatives, bactericides, fungicides, virucides, cooling substances, insect repellents, plant extracts, antiinflammatory substances, wound healing accelerators, film-forming substances, customary antioxidants, vitamins, 2-hydroxycarboxylic acids, skin colorants, active ingredients for promoting hair growth, skin care products, softening, moisturizing and/or moisture-retaining substances, fats, oils, saturated fatty acids, monounsaturated or polyunsaturated fatty acids, alfa-hydroxy acids, polyhydroxy fatty acids or their derivatives, waxes, alcohols, polyols, polymers, foam stabilizers, electrolytes, organic solvents, silicone derivatives or chelating agents, antidandruff substances, hair care products, perfumes, antifoams, dyestuffs, pigments with a coloring action, thickeners, surface-active substances, emulsifiers, plant parts and plant extracts, animal extracts, proteins, protein hydrolysates, yeast extracts, hop and wheat extracts, peptides and thymus extracts.

NA) Another invention embodiment relates to the material according to any one of paragraphs DA) to MA) comprising an additional preservative.

PA) Another invention embodiment relates to the material according to any one of paragraphs DA) to NA) which is obtained after heat treatment, especially at 60 to 130° C.

QA) Another invention embodiment relates to a compound of the formula I or a mixture of such compounds, according to any one of paragraphs A), B) and H) to O) or a composition comprising them, especially according to any one of paragraphs P) to S) mentioned above, as a biofilm inhibiting agent and its corresponding use, e.g. by administering, or in methods comprising administering, one or more compounds of the formula I, or a composition comprising them, to surfaces or materials coming into contact with surfaces.

In a preferred embodiment, the invention relates to (the use of) one or more compounds of the above formula I, one or more physiologically acceptable salts of a compound of the above formula I, or a mixture thereof, as agent with preservative properties against (i) Gram-positive bacteria and/or (ii) fungi, wherein the (i) Gram-positive bacteria are selected from the group consisting of the genera *Bacillus, Brevibacterium, Lactobacillus, Micrococcus, Staphylococcus, Streptococcus, Clostridium, Chlamydia, Enterococcus, Listeria, Corynebacterium, Leuconostoc, Pediococcus, Propionibacterium,* and the fungi preferably are selected from the group consisting of (ii-a) fungi from the families Trichocomaceae, Arthrodermataceae and Mucoraceae, more preferably molds (moulds) of the genera *Aspergillus, Botryotinia, Byssochlamys, Magnaporthe, Paecilomyces, Neosartorya, Mucor, Penicillium, Rhizopus, Talaromyces,* and *Trichophyton,*

(ii-b) yeasts from the order Saccharomycetales, preferably yeasts from the families Saccharomycetaceae or Pichiaceae, more preferably from the group consisting of the genera *Brettanomyces, Candida, Dekkera, Pichia, Saccharomyces,* and *Zygosaccharomyces,* preferably comprising adding the agent to a material, where said material is selected from the group consisting of a cosmetic product, a food product, a beverage, a pharmaceutical product, a medical device, a medical hygiene product, a home care product, and an active packaging material.

In a more preferred embodiment, the invention relates to (the use of) one or more compounds of the above formula I, one or more physiologically acceptable salts of a compound of the above formula I, or a mixture thereof, wherein m is 3 to 5, n is 3, o is 0 or 1 and p is 11 to 14, preferably m is 3 to 5, n is 3, o is 0 or 1 and p is 12 or 13, and R is a trisaccharide carbohydrate moiety of the subformula

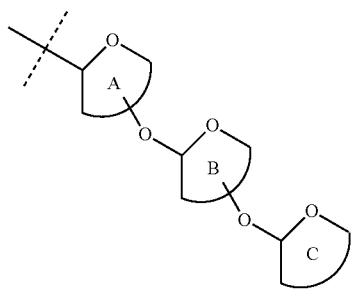

bound via a carbon atom to the binding oxygen (via the bond indicated by the dotted line), wherein ring A is a xylopyranoside moiety, ring B is a xylopyranosyl moiety, and ring C is glucopyranosyl moiety, and wherein one or more of the hydroxyl groups of said rings are esterified with a $C_2$-$C_{10}$-alkanoic acid, preferably a $C_3$-$C_{10}$-alkanoic acid, more preferably a $C_3$-$C_6$-alkanoic acid, as agent with preservative properties against (i) Gram-positive bacteria and/or (ii) fungi, as indicated above, preferably comprising adding the agent to a material, where said material is preferably selected from the group consisting of a cosmetic product, a food product, a beverage, a pharmaceutical product, a medical device, a medical hygiene product, a home care product, and an active packaging material.

As already mentioned, and especially due to their excellent and generally superior antimicrobial properties (in particular regarding yeasts and molds), preferred compounds or mixtures of compounds of the formula I shown above are defined by a trisaccharide carbohydrate moiety R carrying at least one hydroxyl group esterified with an acid with 3 or more carbon atoms, particularly wherein the acid is a $C_3$-$C_{10}$-alkanoic acid, especially wherein the acid is a $C_3$-$C_6$-alkanoic acid, and/or a physiologically acceptable salt thereof.

In a particularly preferred embodiment, the invention relates to (the use of) one or more compounds of the above formula I, one or more physiologically acceptable salts of a compound of the above formula I, or a mixture thereof (preferably as defined in one of the preferred or particularly preferred embodiments herein) as agent with preservative properties against bacteria selected from the group consisting of *Bacillus subtilis, Bacillus cereus, Brevibacterium epidermidis, Brevibacterium linens, Chlamydia trachomatis, Clostridium perfringens, Clostridium botulinum, Clostridium sporogenes, Corynebacterium xerosis, Corynebacterium variabile, Corynebacterium minutissimum, Enterococcus faecalis, Lactobacillus plantarum, Listeria monocytogenes, Listeria welshimeri, Micrococcus luteus, Propionibacterium acnes, Staphylococcus aureus, Staphylococcus epidermidis, Streptococcus mutans*, and *Streptococcus pneumoniae*,
and/or filamentous fungi selected from the group consisting of *Aspergillus brasiliensis, Aspergillus flavus, Aspergillus fumigatus, Aspergillus niger, Botrytis cinerea, Byssochlamys fulva, Magnaporthe grisea (Magnaporthe oryzae, Pyricularia oryzae), Mucor plumbeus, Rhizopus arrhizus, Rhizopus nigricans, Rhizopus stolonifer*, and *Talaromyces luteus*,
and/or yeast selected from the group consisting of *Brettanomyces bruxellensis, Brettanomyces naardenensis, Candida albicans, Candida glabrata, Candida lusitaniae, Candida tropicalis, Dekkera bruxellensis, Dekkera naardenensis, Saccharomyces cerevisiae, Zygosaccharomyces bailii, Zygosaccharomyces bisporus, Zygosaccharomyces florentinus*, and *Zygosaccharomyces rouxii*.

Within the scope of the present text, the terms "for oral consumption", "orally consumable" or "food product" and the like in particular refer to materials which are intended to be swallowed by a human being in an unchanged (i.e. by direct oral consumption, "ready-to-eat", "ready-to-drink") or processed state and then to be digested.

The term "ready-to-use" product refers to a product, the composition of which, in terms of the substances which determine the flavour, is (essentially) complete. The term "ready-to-use" product includes carbonated and non-carbonated liquids and viscous or semisolid products. Examples of "ready-to-use" products include deep-frozen products which, prior to consumption, are be defrosted and heated before consumption. The ready-to-use products may also be "ready-to-eat" or "ready-to-drink", like e.g. carbonated beverages, flavoured milk, (water) ice, yoghurts, and the like, or may have to be diluted with water before oral consumption, which is for example the case for beverage syrups.

Yeasts are able to grow in orally consumable compositions, such as foods and beverages, with a low pH values (generally pH 5.0 or lower), and in the presence of sugars, organic acids or other easily metabolized carbon sources. During their growth, yeasts metabolize some food components and produce metabolic products. This causes the physical, chemical, and sensory properties of an orally consumable composition to change, and the composition is spoiled. The growth of yeast within orally consumable compositions is often seen on their surface, as in cheeses or meats, or by the fermentation of sugars in beverages, such as juices, and semi-liquid products, such as syrups and jams.

Of particular relevance in the context of orally consumable compositions are *Aspergillus niger, Brettanomyces bruxellensis, Brettanomyces naardenensis, Dekkera bruxellensis, Dekkera naardenensis, Saccharomyces cerevisiae, Zygosaccharomyces bailii, Zygosaccharomyces bisporus, Zygosaccharomyces florentinus*, and *Zygosaccharomyces rouxii*.

The yeasts of the *Zygosaccharomyces* genus have had a long history as spoilage yeasts within the food industry. This is due mainly to the fact that these species can grow in the presence of high sucrose, ethanol, acetic acid, sorbic acid, benzoic acid, and sulphur dioxide concentrations (which are some of the commonly used preservatives in orally consumable compositions).

*Clostridium botulinum* is a Gram-positive bacterium that produces several toxins, inter alia neurotoxins that cause the flaccid muscular paralysis seen in botulism. Botulism poisoning can occur due to improperly preserved food or canned food that was not processed using correct preservation times and/or pressure. Mainly slightly acidic or neutral food is at risk which was stored under anaerobic conditions (generally pH >4.6) and storage temperatures above 10° C. The latter is generally given for canned foods, such as meat and fish preserves, mayonnaise, but also slightly acidic fruit or vegetables.

*Bacillus cereus* may be harmful to humans and cause foodborne illness (severe nausea, vomiting and diarrhea), particularly in foods like meat, milk, spices, seasonings, fruits, vegetables, cereal and cereal products, rice products and (ready-to-eat) rice dishes. *Bacillus cereus* is also known to cause chronic skin infections and keratitis.

*Bacillus subtilis* is known to cause disease in severely immunocompromised patients, and it may cause food poisoning. *Bacillus subtilis* spores can survive the extreme heat during cooking. *Bacillus subtilis* strains are responsible for causing ropiness in spoiled bread dough.

*Micrococcus luteus* is found in soil, dust, water and air, and is part of the normal flora of the mammalian skin and mucosae. It is further a food spoiling bacterium and often found on spoiled meat. In immunocompromised patients, *Micrococcus luteus* may cause infections.

*Propionibacterium acnes* is largely commensal and part of the healthy adult human skin flora. It lives primarily on fatty acids in sebum secreted by sebaceous glands in the follicles and is linked to the skin condition acne. *Propionibacterium acnes* can also cause chronic blepharitis and endophthalmitis, the latter particularly following intraocular surgery.

Dental plaque is a biofilm formed by colonizing bacteria trying to attach themselves to a smooth tooth surface. A microorganism significantly contributing dental plaque and tooth decay is *Streptococcus mutans*.

The rice blast fungus *Magnaporthe grisea* (syn.: *Pyricularia oryzae*; conidial stage/anamorph: *Pyricularia grisea*) attacks leaves, grains, and other parts of rice plants.

Athlete's foot (tinea pedis) is a communicable disease caused by parasitic molds in the genus *Trichophyton*, predominantly *Trichophyton rubrum* and/or *Trichophyton mentagrophytes*. These can also cause skin infections on other areas of the body, most often under toenails (onychomycosis) or on the groin (tinea cruris).

*Mucor* species are often involved in the composting of plants and plant residues and are found on foods such as milk, butter, cheese and tomatoes. *Mucor plumbeus* has a worldwide distribution in soil. As spoilage germ, *Mucor plumbeus* is mainly found on fermented foods (such as bread, beer, wine, cheese, yoghurt, kefir, salami), and on grain.

Mucormycosis (sometimes also referred to as Zygomycosis) is the term used to describe fungal infections caused by fungi in the order Mucorales, inter alia by species in the *Mucor* genus. These rare yet serious and potentially life-threatening fungal infections usually affect the face, oropharyngeal (nose/mouth) cavity, gastrointestinal tract or the skin. Individuals with immune disorders (immunocompromised) are more prone to this type of fungal infection.

*Rhizopus* is a genus of fungi found on plants and on various other organic substrates, including mature fruits and vegetables, jellies, syrups, bread, peanuts and tobacco. Some *Rhizopus* species are opportunistic agents of human zygomycosis (fungal infection) and can be fatal. *Rhizopus* infections are also an associated complication of diabetic ketoacidosis.

*Rhizopus arrhizus* is the most common cause of mucormycosis in humans and occasionally infects other animals.

*Rhizopus nigricans* is a fungus commonly known as bread mold and is the most common species of *Rhizopus*. It is found on old food. The spores, dispersed in hot dry weather, contain allergenic proteins, which can produce respiratory and nasal symptoms. Food handling workers are particularly at risk if they are mold allergic.

*Rhizopus stolonifer* (black bread mold) is a widely distributed mold and is most commonly found growing on bread and soft fruits such as bananas and grapes, and causes damage to the surface where it lives. It is capable of causing opportunistic infections of humans.

*Staphylococcus aureus* is the most common species to cause staphylococcal infections. *Staphylococcus aureus* can cause a range of illnesses, from minor skin infections to life-threatening diseases such as pneumonia, meningitis, osteomyelitis, endocarditis, toxic shock syndrome, bacteremia, and sepsis. *Staphylococcus aureus* strains are also responsible for food poisoning through the production of an enterotoxin, particularly in meat, meat products (e.g. luncheon meats, cold meats, sausages), milk, milk products, such as cheese).

*Clostridium perfringens* is widely present in nature and can be found as a normal component of decaying vegetation, but also in the intestinal tract of humans. *Clostridium perfringens* bacteria often cause of foodborne illness, particularly in poorly prepared meat and poultry. Often, meat is well prepared, but too far in advance of consumption. Since *Clostridium perfringens* forms spores that can withstand cooking temperatures, upon standing or storage germination ensues and infective bacterial colonies develop. *Clostridium perfringens* causes a wide range of symptoms: it is a very common cause of food poisoning and the most common bacterial agent for gas gangrene, which is necrosis, putrefaction of tissues, and gas production.

Fungi of the genus *Aspergillus* may cause infections causing a variety of diseases called aspergillosis (common forms are allergic bronchopulmonary aspergillosis, pulmonary aspergilloma and invasive aspergillosis).

*Aspergillus flavus* is a common mold in the environment, and can cause storage problems in stored grains. It can also be a human pathogen, associated with aspergillosis and other infections.

*Aspergillus fumigatus* is one of the most common *Aspergillus* species to cause disease in individuals with an immunodeficiency. In immunocompromised individuals, such patients receiving immunosuppressive therapy for autoimmune or neoplastic disease, organ transplant recipient, and people with AIDS or leukemia, the fungus is more likely to become pathogenic and cause aspergillosis. *Aspergillus fumigatus* primarily causes invasive infection in the lung (e.g. chronic pulmonary infections) and represents a major cause of morbidity and mortality in these individuals.

*Aspergillus niger* causes black mold on certain fruits and vegetables such as grapes, onions, and peanuts, and is a common contaminant of food. For example, *Aspergillus niger* causes a common postharvest disease of onions. *Aspergillus niger* is less likely to cause human disease than some other *Aspergillus* species, but, if large amounts of spores are inhaled, a serious lung disease (aspergillosis can occur). *Aspergillus niger* is one of the most common causes of otomycosis (fungal ear infections).

*Chlamydia* infection is one of the most common sexually transmitted infections in humans, and caused by the bacterium *Chlamydia trachomatis*. *Chlamydia* is a major infectious cause of human genital and eye disease. *Chlamydia* conjunctivitis or trachoma is a common cause of blindness worldwide. Both sexes can display urethritis, proctitis, trachoma, and infertility. If untreated, chlamydial infections can cause serious health problems. *Chlamydia trachomatis* is also an important neonatal pathogen, where it can lead to infections of the eye (trachoma) and pulmonary complications.

*Enterococcus faecalis* inhabits the gastrointestinal tracts of humans and other mammals. It may cause endocarditis and bacteremia, urinary tract infections, meningitis, and other infections in humans (e.g. in root canal-treated teeth). It can even cause life-threatening infections in humans, especially in hospital environment.

*Listeria* may be been found in uncooked meats, uncooked vegetables, fruit, pasteurized or unpasteurized milk, foods made from milk, and processed foods. Pasteurization and sufficient cooking kill *Listeria*; however, contamination may occur after cooking and before packaging. For example, processing plants producing ready-to-eat foods, such as hot dogs, deli meats, fish products, cheeses, milk, and deli salads, follow extensive sanitation policies and procedures to prevent *Listeria* contamination. The major human pathogen in the *Listeria* genus is *Listeria monocytogenes*. It is usually the causative agent of listeriosis, a serious bacterial infection caused by eating food contaminated with *Listeria monocytogenes*.

Yeasts of the *Candida* genus are a group of opportunistic pathogens that causes oral and vaginal infections in humans, known as candidiasis. The pathogenic yeasts of candidiasis are *Candida albicans, Candida tropicalis, Candida stellatoidea, Candida glabrata, Candida krusei, Candida parapsilosis, Candida guilliermondii, Candida viswanathii,* and *Candida lusitaniae*, of these *Candida albicans* being the most important and most relevant.

*Candida glabrata* is the second most common *Candida* pathogen after *Candida albicans*, also causing infections of the urogenital tract, and of the bloodstream (candidemia). *Candida glabrata* has been shown to be a highly opportunistic pathogen and is especially prevalent in immunocompromised individuals and elderly. *Candida glabrata* can also adhere to biotic and abiotic surfaces, thereby forming microbial "biofilms" on e.g. urinary catheters or indwelling intravenous catheters. It may also cause problems with dental devices, such as dentures.

Additionally, in particular *Staphylococcus aureus, Candida albicans, Aspergillus brasiliensis* and *Aspergillus niger* are likely microbiological contaminants of cosmetic formulations.

Species of certain bacteria such as *Staphylococcus epidermidis, Corynebacterium xerosis, Corynebacterium minutissimum* and *Brevibacterium epidermidis* are largely responsible for the formation of underarm and/or foot odor, or body odor in general. *Brevibacterium* linens inter alia causes foot odor.

In another aspect the present invention relates to one or more compounds of formula I and/or the physiologically acceptable salts thereof, particularly one or more compounds selected from the group consisting of [1], [2], [3], [4], [5], [6], [7], [8], [9], [10], [11], [12], [13], [14], [18], [19], [20], [21] and the physiologically acceptable salts thereof, for use in the prophylactic and/or therapeutic treatment of a disorder, disease or condition selected from the group consisting of mycoses (fungal infections), preferably *Aspergillus, Candida* or *Mucor* associated mycoses, particularly *Candida* associated mycoses.

Particularly relevant and preferably treated are mycoses selected from the group consisting of candidiasis [in particular oral (thrush) *Candida* infections, infections of the urogenital (e.g. vaginal) tract by *Candida* bacteria (in particular by *Candida albicans* and/or *Candida glabrata*), diaper candidiasis (*Candida* associated diaper dermatitis, diaper rash)], invasive candidiasis (particularly candidemia (infections of the bloodstream)), aspergillosis and mucormycosis.

The compounds of formula I and/or the physiologically acceptable salts thereof, particularly those selected from the group consisting of [1], [2], [3], [4], [5], [6], [7], [8], [9], [10], [11], [12], [13], [14], [18], [19], [20], [21] and the physiologically acceptable salts thereof, are particularly beneficial for use in the prophylactic treatment of a disorder, disease or condition mentioned above.

As used herein, the term "effective amount" or "effective dose" refers to the (preferably oral) administration of an effective dose of one or more compounds of formula I and/or the physiologically acceptable salts thereof that produces the effects for which it is administered.

As used herein, the term "therapeutical" or "therapeutically" refers to the (in particular oral) administration of a therapeutically effective dose of one or more compounds of formula I and/or the physiologically acceptable salts thereof (preferably in form of a mixture, a composition or a material as defined in the context of the present invention) that produces the effects for which it is administered, i.e. that will elicit the biological or medical response (in vitro or in vivo, preferably in vivo in a mammal, particularly in vivo in human being) that is being sought, in particular the amelioration and/or alleviation of the symptoms of the disorder, disease or condition being treated up to and including complete cure.

As used herein, the term "prophylactic" or "prophylactically" refers to the (in particular oral) administration of a prophylactically effective dose of one or more compounds of formula I (preferably in form of a mixture, a composition or a material as defined in the context of the present invention) that produces the effects for which it is administered, i.e. that will elicit the biological or medical response (in vitro or in vivo, preferably in vivo in a mammal, particularly in vivo in a human being) that is being sought, in particular the prevention of the onset of a disorder, disease or condition in individuals at risk for such disorder, disease or condition as mentioned herein.

The present invention also relates to a method of reducing the activity and/or number of pathogenic Gram-positive bacteria and/or pathogenic fungi in an immunocompromised individual, comprising the following step:

administering (preferably orally or topically) to a mammal, particularly an immunocompromised mammal, particularly an immunosuppressed human being, an effective total amount of one or more compounds of formula I as defined herein, and/or one or more physiologically acceptable salts thereof, particularly one or more compounds selected from the group consisting of [1], [2], [3], [4], [5], [6], [7], [8], [9], [10], [11], [12], [13], [14], [18], [19], [20], [21] and the physiologically acceptable salts thereof, or an extract or material according to the present invention, preferably in a preferred or particularly preferred embodiment according to the present invention.

Preferably, the pathogenic Gram-positive bacteria are selected from the group consisting of the genera *Bacillus, Clostridium, Listeria, Micrococcus* and *Staphylococcus*, more preferably selected from the group consisting of *Bacillus cereus, Clostridium sporogenes, Clostridium perfringens, Listeria monocytogenes, Micrococcus luteus, Staphylococcus aureus, Staphylococcus epidermidis*.

Preferably, the pathogenic fungi are selected from the group consisting of the genera *Aspergillus* and *Candida*, more preferably selected from the group consisting of *Aspergillus flavus, Aspergillus fumigatus, Candida albicans, Candida glabrata, Candida lusitaniae*, and *Candida tropicalis*.

The present invention also relates to a method for the prophylactic and/or therapeutic treatment of a disease, disorder or condition, comprising the following step:

administering (preferably orally or topically) to a mammal, particularly an immunocompromised mammal, particularly an immunosuppressed human being, an effective total amount of one or more compounds of formula I as defined herein, and/or one or more physiologically acceptable salts thereof, particularly one or more compounds selected from the group consisting of [1], [2], [3], [4], [5], [6], [7], [8], [9], [10], [11], [12], [13], [14], [18], [19], [20], [21], and the physiologically acceptable salts thereof, or an extract or material according to the present invention, preferably in a preferred or particularly preferred embodiment according to the present invention.

The compounds of formula I (for use) according to the present invention and/or the physiologically acceptable salts thereof (preferably the preferred or particularly preferred compounds of formula I defined above) show a comparatively weak activity against Gram-negative bacteria, such as *Escherichia coli, Pseudomonas aeruginosa, Pseudomonas putida* or *Salmonella typhimurium*. In our own investigations regarding such Gram-negative bacteria generally MIC values >100 ppm were observed, typically in the range of 200-500 ppm.

Thus, in a preferred embodiment, a material according to the present invention, preferably a cosmetic or a pharmaceutical, comprises (i) one or more compounds of formula I (for use) according to the present invention and/or the physiologically acceptable salts thereof, and (ii) one or more agents exhibiting an antimicrobial activity against Gram-negative bacteria, preferably selected from the group consisting of Triclosan® (2,4,4'-trichloro-2'-hydroxydiphenyl ether), chlorhexidine, chlorhexidine salts (preferably chlorhexidine diacetate, chlorhexidine dichloride, chlorhexidine digluconate), octenidine, octenidine dihydrochloride, 2-bromo-2-nitropropane-1,3-diol, polyaminopropyl biguanide, imidazolidinyl urea, diazolidinyl urea, chlorphenesin, DMDM hydantoin, sodium hydroxymethylglycinate, phenoxyethanol, isothiazolinones (preferably methylisothiazolinone, methylchloroisothiazolinone), benzalkonium chloride (alkyldimethylbenzylammonium chloride, preferably N-octyl-N-benzyl-N,N-dimethylammonium chloride, N-decyl-N-benzyl-N,N-dimethylammonium chloride, N-dodecyl-N-benzyl-N,N-dimethylammonium chloride, N-tridecyl-N-benzyl-N,N-dimethylammonium chloride, N-tetradecyl-N-benzyl-N,N-dimethylammonium chloride, N-hexadecyl-N-benzyl-N,N-dimethylammonium chloride, N-octadecyl-N-benzyl-N,N-dimethylammonium chloride), and lantibiotics (preferably those disclosed in U.S. Pat. No. 7,960,505 B2).

In some cases, a material according to the present invention, preferably a cosmetic or a pharmaceutical, comprises (i) one or more compounds of formula I (for use) according to the present invention and/or the physiologically acceptable salts thereof, and (ii) one or more parabens (parahydroxybenzoic acid esters) and/or the salts thereof, preferably one, two or more parabens selected from the group consisting of methylparaben, ethylparaben, propylparaben, isopropylparaben, butylparaben, isobutylparaben, benzylparaben and the physiologically acceptable salts (preferably the sodium salts) thereof.

Compounds of the formula I, mixtures thereof, and the physiologically acceptable salts thereof are preferred in the context of the present invention, wherein R is a moiety of formula

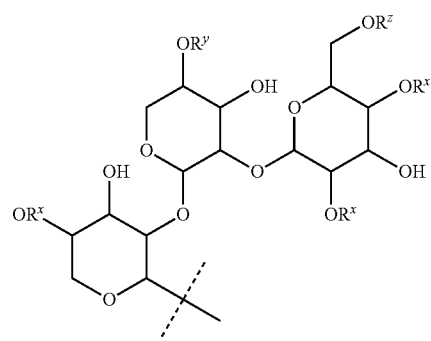

wherein $R^z$ denotes H or $C_2$-$C_6$-alkanoyl, preferably H, acetyl or $C_5$-alkanoyl, more preferably H, acetyl or isovaleryl, most preferably isovaleryl, $R^y$ denotes H or $C_2$-$C_6$-alkanoyl, preferably H or acetyl, and $R^x$, independent of each other, each denote H or $C_2$-$C_6$-alkanoyl, preferably H or acetyl, with the proviso that at least one of $R^x$, $R^y$ and $R^z$ is not hydrogen.

Compounds of the formula I, mixtures thereof, and the physiologically acceptable salts thereof are more preferred in the context of the present invention, wherein R is a moiety of formula

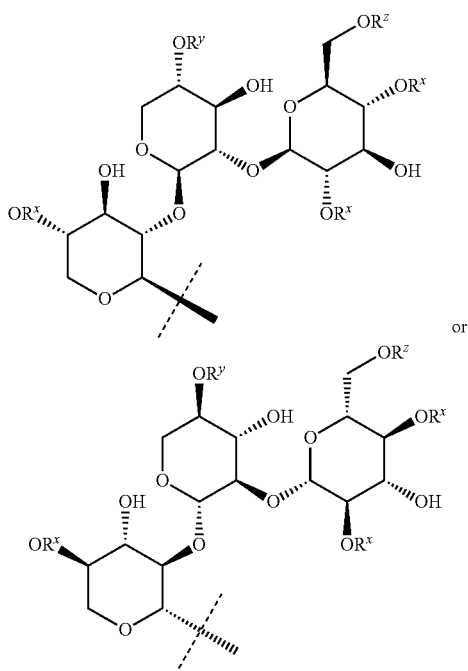

wherein

R$^z$ denotes H, acetyl or isovaleryl, most preferably isovaleryl,

R$^y$ denotes H or C$_2$-C$_6$-alkanoyl, preferably H or acetyl, and R$^x$, independent of each other, each denote H or C$_2$-C$_6$-alkanoyl, preferably H or acetyl, with the proviso that at least one of R$^y$ and R$^z$ is not hydrogen, preferably R$^z$ is not hydrogen.

Individual compounds of formula I with an acyl substituent with more than 2 carbon atoms, such as an isovaleryl substituent, in the trisaccharide carbohydrate moiety R exhibit a stronger antimicrobial activity, particularly against yeasts and molds, especially against yeasts and molds of relevance regarding food, beverage and/or cosmetic spoilage, and/or a broader activity spectrum than the corresponding compounds with an acetyl substituent in the trisaccharide carbohydrate moiety R.

It was also found in own investigations that mixtures comprising (i) two, three, four, five, six or more compounds of the above preferred formula I, (ii) two, three, four, five, six or more physiologically acceptable salts of a compound of the above preferred formula I, or a mixture thereof, or (iii) one, two, three or more compounds of the above preferred formula I and one, two, three or more physiologically acceptable salts of a compound of the above preferred formula I typically showed a broader activity spectrum and/or stronger long term inhibitory activity, particularly against yeasts and molds, especially against yeasts and molds of relevance regarding food, beverage and/or cosmetic spoilage, in comparison to individual compounds of (preferred) formula I or a physiologically acceptable salt thereof.

Said stronger long term inhibitory activity—which typically is bactericidal and/or fungicidal, and not merely bacteriostatic and/or fungistatic) and/or broader long term inhibitory activity spectrum of mixtures according to the present invention against organisms involved in spoilage of preparations or compositions with a high water content (generally 50 wt. % or more, based on the total weight of the preparation or composition) is especially useful against acidophilic spoilage yeasts, which are for example involved in spoiling of beverages. These mixtures according to the present invention are particularly able to inhibit the growth of thermophilic molds, which are difficult to control with standard sterilizing and/or pasteurizing processes.

Especially preferred in the context of the present invention in view of the excellent properties is a mixture of three or more compounds of formula I or the physiologically acceptable salts thereof, said mixture comprising (a) one or more compounds of formula I or a physiologically acceptable salt thereof, wherein one group of R$^x$, R$^y$, and R$^z$ is not hydrogen, (b) one or more compounds of formula I or a physiologically acceptable salt thereof wherein two groups of R$^x$, R$^y$, and R$^z$ are not hydrogen, and (c) one or more compounds of formula I or a physiologically acceptable salt thereof wherein three groups of R$^x$, R$^y$, and R$^z$ are not hydrogen, wherein preferably the total amount of the compounds of group (a) is 2 wt. % or more, preferably 3 wt. % or more, more preferably 5 wt. % or more, in each case based on the total weight of the mixture, and/or said mixture comprises one, two, three or all compounds [5], [8], [12], and [14], and/or the total amount of the compounds of group (b) is 20 wt. % or more, preferably 25 wt. % or more, more preferably 30 wt. % or more, even more preferably 35 wt. % or more, most preferably 40 wt. % or more, in each case based on the total weight of the mixture, and/or said mixture comprises one, two, three, four, five or all compounds [1], [6], [7], [10], [13], and [18], more preferably comprises [1] and/or [7], particularly more preferably [1] and [7], and/or said mixture comprises compound [1], preferably in a total amount of 1 wt. % or more, more preferably 2 wt. % or more, even more preferably 4 wt. % or more, particularly preferably 5 wt. % or more, and/or said mixture comprises compound [7], preferably in a total amount of 5 wt. % or more, more preferably 8 wt. % or more, even more preferably 10 wt. % or more, particularly preferably 12 wt. % or more, and/or the total amount of the compounds of group (c) is 1 wt. % or more, preferably 1.5 wt. % or more, more preferably 2 wt. % or more, in each case based on the total weight of the mixture, and/or said mixture comprises [3] and/or [9], preferably compound [9].

In a preferred mixture according to the present invention, preferably the average degree of acylation is as follows:

1.1 to 2.2 acetyl groups per molecule, preferably 1.3 to 1.9 acetyl groups per molecule, and/or 0.1 to 1.0 isovaleryl groups per molecule, preferably 0.15 to 0.6 isovaleryl groups per molecule, wherein the average degree of acylation preferably is determined via $^1$H-NMR quantification using an average molecular weight for the glycolipids of 985 g/mol. As internal standard preferably 1,3,5-trichlorobenzene may be used. The $^1$H-NMR signal used for said quantification was that of the hydrogen atom bound to the carbon atom in position C-2 (i.e. (C$\underline{H}$)OH, the carbon atom bearing the alpha-hydroxy group relative to the carboxylic acid group at C-1).

A mixture according to the present invention, an extract according to the present invention, a material according to the present invention, and/or a composition according to the present invention preferably comprises less than 25 wt. % of Glykenin IVA ((2S,16R,17S,21R)-2,16,17-trihydroxy-21-[[2-O-[2-O-(6-O-acetyl-β-D-glucopyranosyl)-β-D-xylopyranosyl]-4-O-acetyl-β-D-xylopyranosyl]oxy]hexacosanoic acid), more preferably less than 20 wt. % of Glykenin IVA, particularly preferably less than 15 wt. % of Glykenin IVA, in each case based on the total amount of compounds of formula I and the physiologically acceptable salts thereof.

Preferably, a mixture comprises compounds [1] and [7], and the physiologically acceptable salts thereof, wherein more preferably the total amount of compound [1] and the physiologically acceptable salts thereof is 1 wt. % or more, more preferably 2 wt. % or more, more preferably 3 wt. % or more, and/or compound [7] and the physiologically acceptable salts thereof is 1 wt. % or more, more preferably 2 wt. % or more, more preferably 3 wt. % or more, and/or the compounds [1] and [7], and the physiologically acceptable salts thereof is 5 wt. % or more, more preferably 8 wt. % or more, even more preferably 12 wt. % or more, the weight percentages in each case relating to the total weight of the mixture, More preferably, a mixture according to the present invention comprises a total amount of 1-20 wt. %, preferably 2-15 wt. %, of compound [1] and the physiologically acceptable salts thereof, a total amount of 0-10 wt. %, preferably 0.5-5 wt. %, of compound [5] and the physiologically acceptable salts thereof, a total amount of 0-10 wt. %, preferably 0.5-5 wt. %, of compound [6] and the physiologically acceptable salts thereof, a total amount of 2-75 wt. %, preferably 5-50 wt. %, of compound [7] and the physiologically acceptable salts thereof, a total amount of 0-12 wt. %, preferably 1-8 wt. %, of compound [8] and the physiologically acceptable salts thereof, a total amount of 0-12 wt. %, preferably 1-8 wt. %, of compound [9] and the physiologically acceptable salts thereof, a total amount of 0-12 wt. %, preferably 1-10 wt. %, of compound [10] and the physiologically acceptable salts thereof, a total amount of 0-10 wt. %, preferably 0.5-6 wt. %, of compound [12] and the physiologically acceptable salts thereof, a total amount of 0-8 wt. %, preferably 0.25-4 wt. %, of compound [13] and the physiologically acceptable salts thereof, a total amount of 0-8 wt. %, preferably 0.25-5 wt. %, of compound [18] and the physiologically acceptable salts thereof, and additionally preferably one, several or all of the following further parameters apply:

said mixture comprises a total amount of compounds of formula I and the physiologically acceptable salts thereof of 75 wt. % or more, preferably 80 wt. % or more, more preferably 85 wt. % or more, said mixture comprises less than 8 wt. %, preferably less than 6 wt. %, more preferably less than 4 wt. %, of compounds of formula I without any acyl substituents in the trisaccharide carbohydrate moiety R (particularly less than 2.0 wt. % of compound [16]), said mixture comprises Glykenin IVA in an amount of 25 wt. % or less, preferably of 20 wt. % or less, more preferably of 15 wt. % or less, said mixture comprises proteins in a total amount of 2 wt. % or less, preferably of 1.25 wt. % or less, more preferably of 1.0 wt. % or less, and/or said mixture comprises water in a total amount of 4 wt. % or less, preferably of 3 wt. % or less, more preferably of 2 wt. % or less, the percentages in each case relating to the total weight of the mixture.

Particularly preferably, a mixture according to the present invention comprises a total amount of 3-15 wt. %, of compound [1] and the physiologically acceptable salts thereof, a total amount of 0.5-5 wt. % of compound [5] and the physiologically acceptable salts thereof, a total amount of 0.5-5 wt. % of compound [6] and the physiologically acceptable salts thereof, a total amount of 10-35 wt. % of compound [7] and the physiologically acceptable salts thereof, a total amount of 1-8 wt. % of compound [8] and the physiologically acceptable salts thereof, a total amount of 1-8 wt. % of compound [9] and the physiologically acceptable salts thereof, a total amount of 1-10 wt. % of compound [10] and the physiologically acceptable salts thereof, a total amount of 0.5-6 wt. % compound [12] and the physiologically acceptable salts thereof, a total amount of 0.25-4 wt. % of compound [13] and the physiologically acceptable salts thereof, and a total amount of 0.25-5 wt. % of compound [18] and the physiologically acceptable salts thereof, and additionally preferably one, two, three, four or all of the following further parameters apply:

said mixture comprises a total amount of compounds of formula I and the physiologically acceptable salts thereof of 85 wt. % or more, more preferably of 90 wt. % or more, said mixture comprises less than 5 wt. %, preferably less than 3 wt. %, of compounds of formula I without any acyl substituents in the trisaccharide carbohydrate moiety R (particularly less than 1.0 wt. % of compound [16]), said mixture comprises Glykenin IVA in an amount of 20 wt. % or less, preferably of 15 wt. % or less, said mixture comprises proteins in a total amount of 1.25 wt. % or less, preferably of 0.95 wt. % or less.

and/or said mixture comprises water in a total amount of 3 wt. % or less, preferably of 2 wt. % or less, the percentages in each case relating to the total weight of the mixture.

Such a particularly preferred mixture according to the present invention had the following average degree of acylation:

1.4 to 1.8 acetyl groups per molecule, and 0.2 to 0.5 isovaleryl groups per molecule.

In view of their broad activity spectrum and particularly high efficacy (which was found to be superior to otherwise identical compounds of formula I not carrying a hydroxyl group esterified with isovaleric acid), particularly against yeasts and molds, especially against yeasts and molds of relevance regarding food, beverage and/or cosmetic spoilage, the compounds of formula I, mixtures thereof, and the physiologically acceptable salts thereof are especially preferred in the context of the present invention wherein

77
m is 3, 4 or 5, n is 3, o is 0 or 1 and p is 11 to 14 (preferably p is 12 or 13), and
R is a moiety of formula
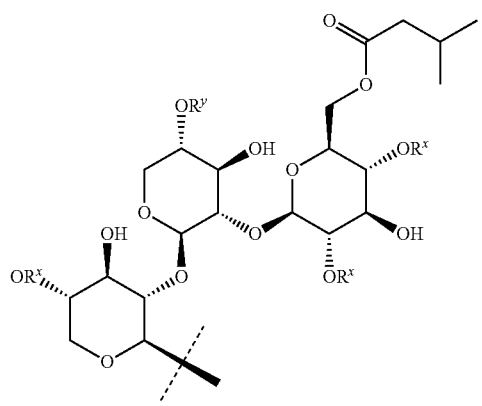
or
78
-continued
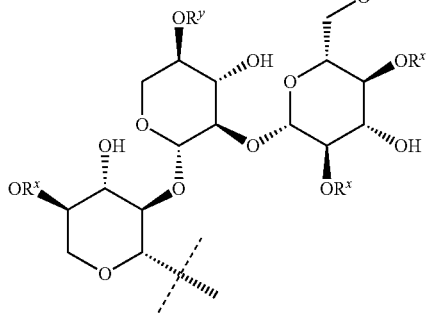
wherein
R$^y$ denotes H or $C_2$-$C_6$-alkanoyl, preferably H or acetyl, and R$^x$, independent of each other, each denote H or $C_2$-$C_6$-alkanoyl, preferably H or acetyl.
Particularly preferred are compounds of formula I of the following formulae
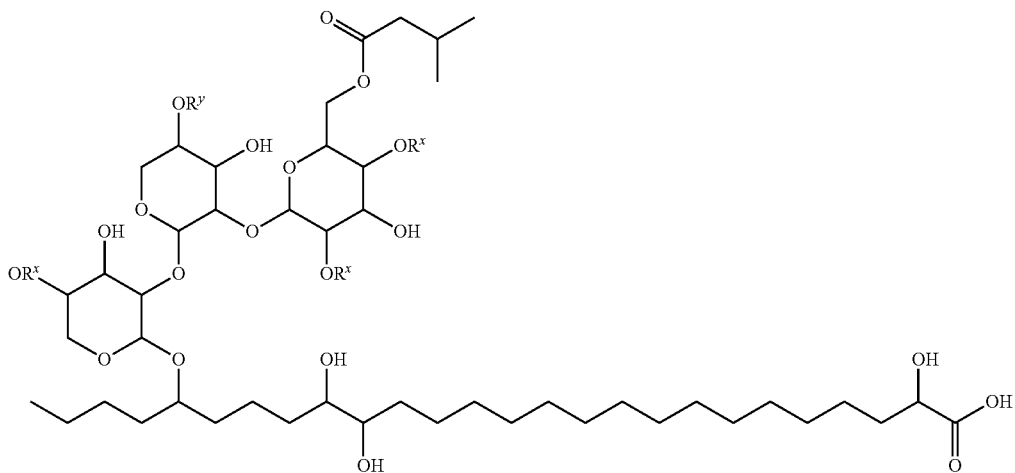
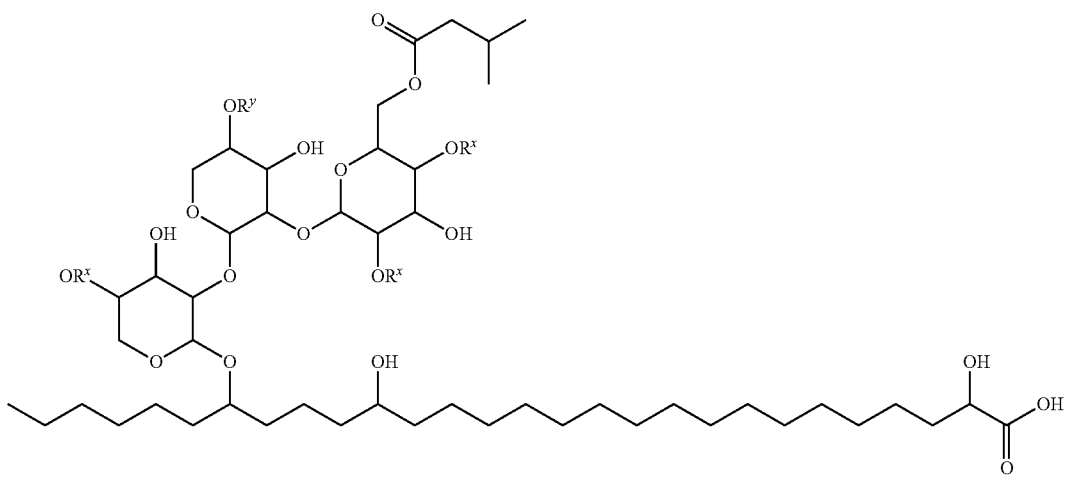

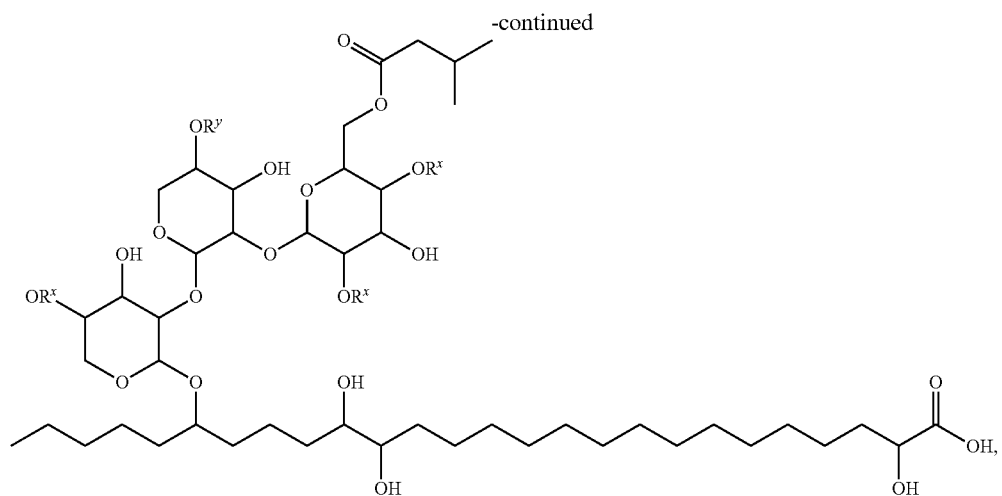
more preferably of the following formulae
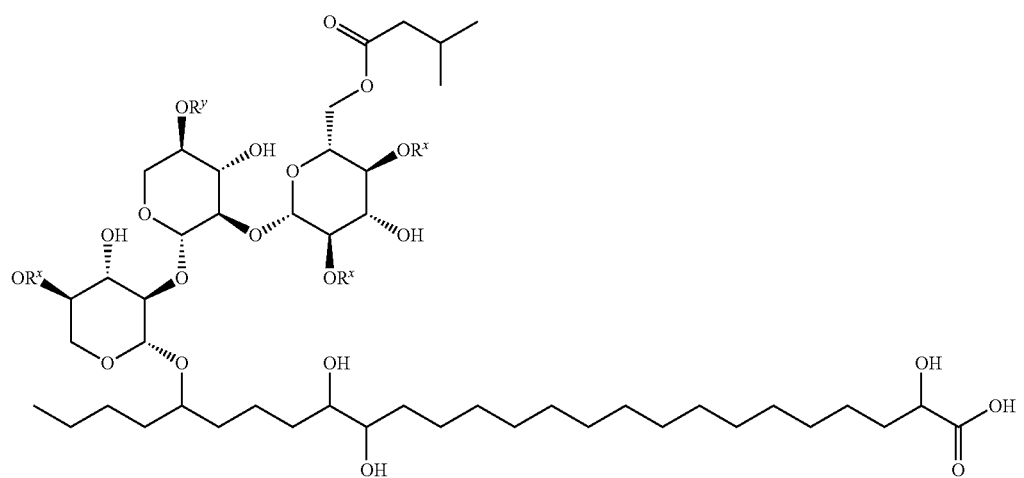
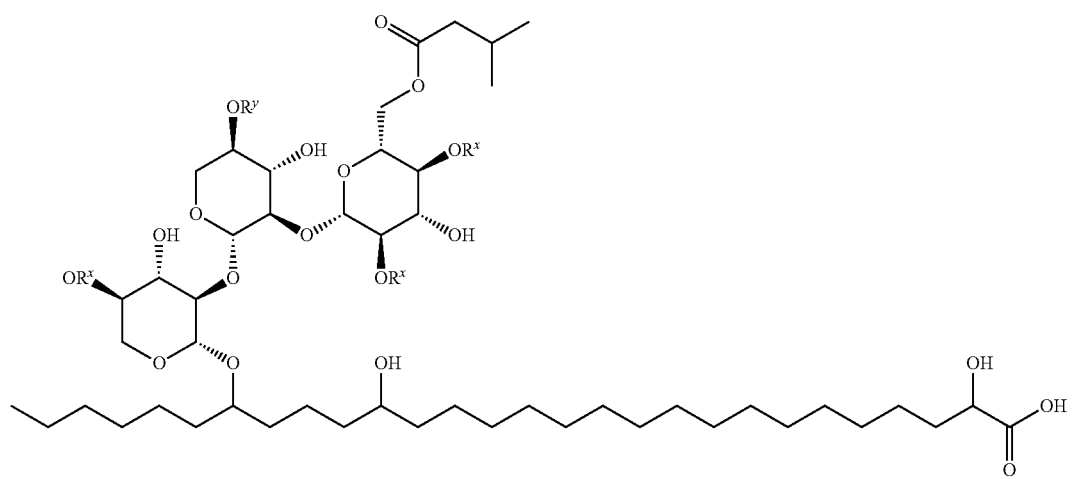

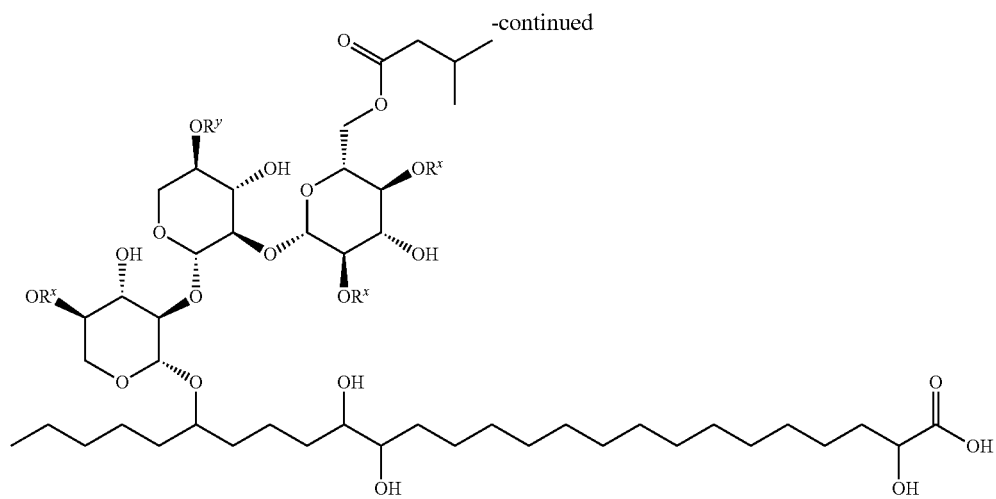
wherein in each of said formulae
$R^y$ denotes H or $C_2$-$C_6$-alkanoyl, preferably H or acetyl, and each $R^x$, independently of the other $R^x$, denotes H or $C_2$-$C_6$-alkanoyl, preferably H or acetyl.
Particularly preferred are the following compounds of formulae [1a], [12a], [13a], [18a], [19a], [20a], and [21a], mixtures thereof, and the physiologically acceptable salts thereof
[1a]
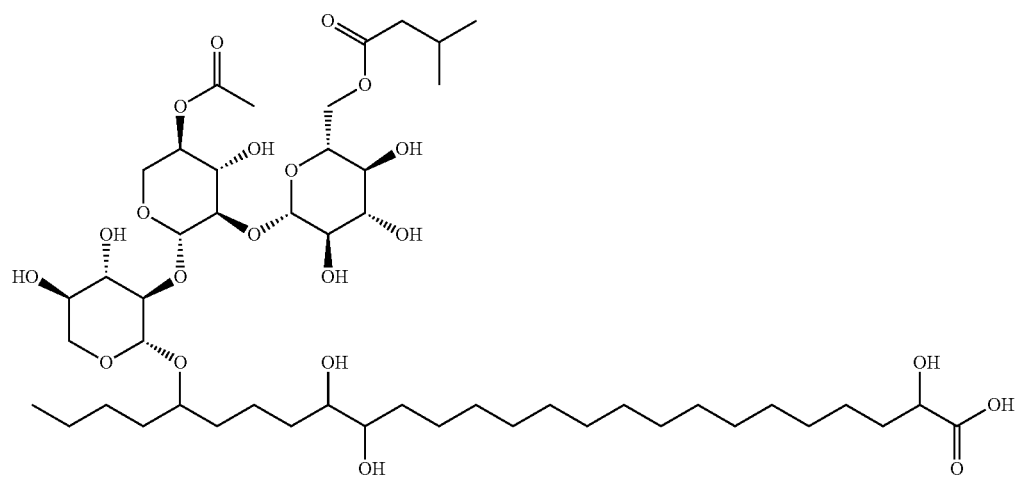
[12a]
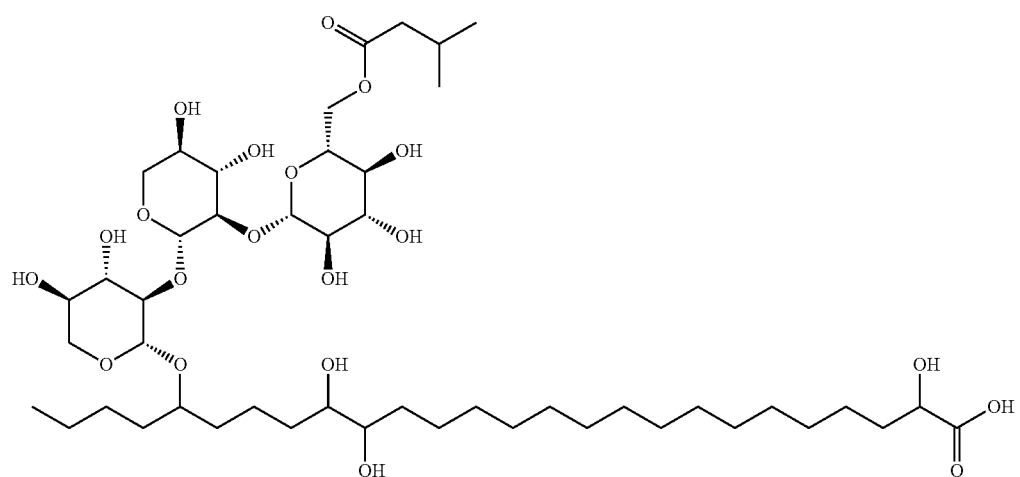

-continued
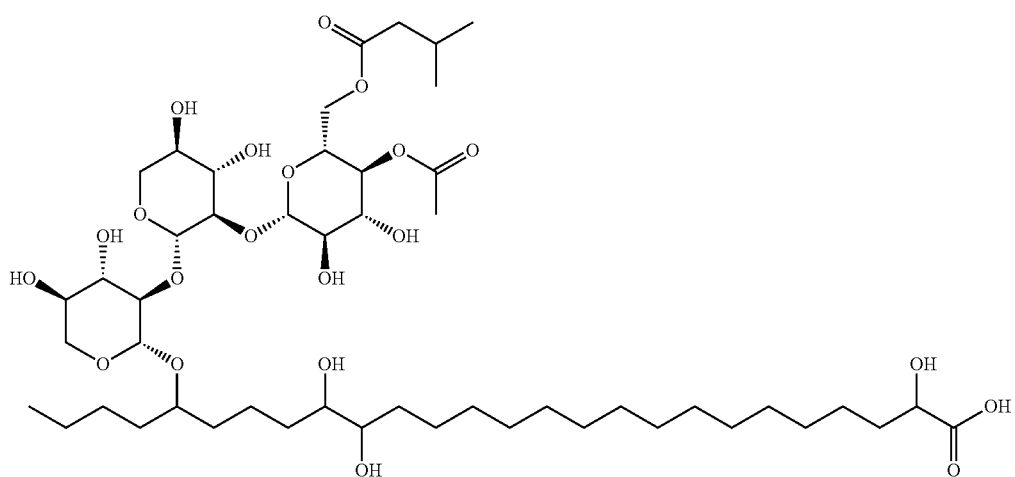
[13a]
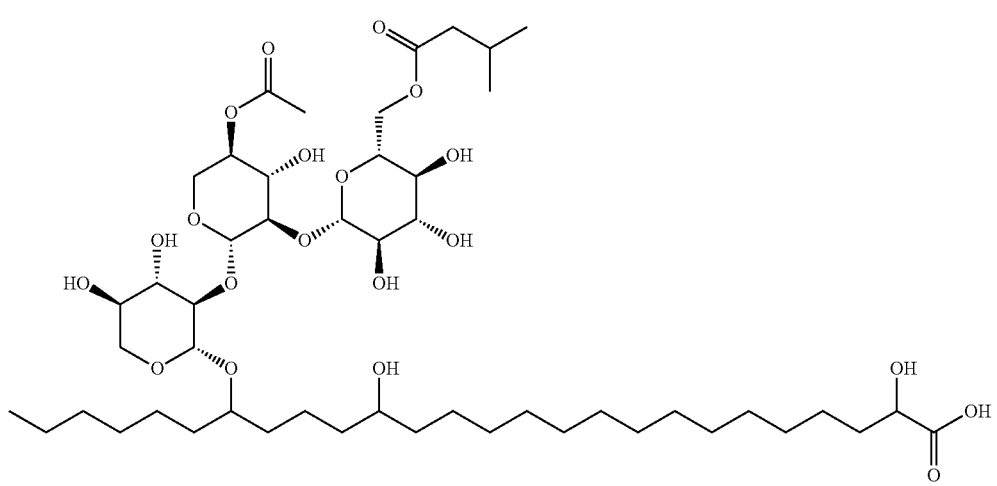
[18a]
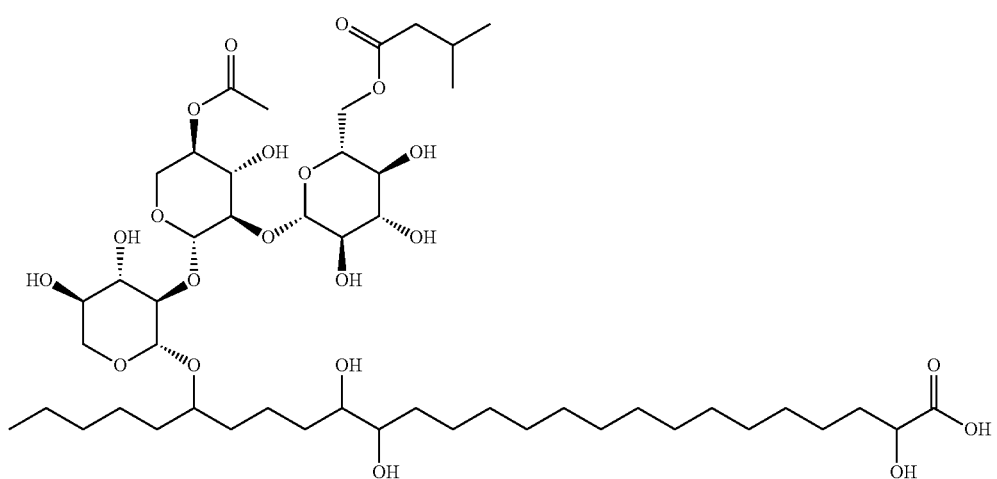
[19a]

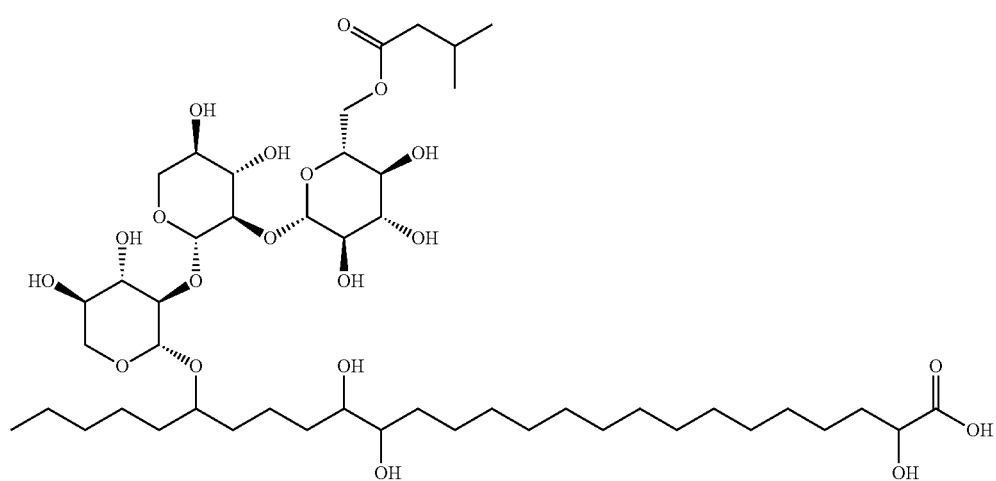
[20a]
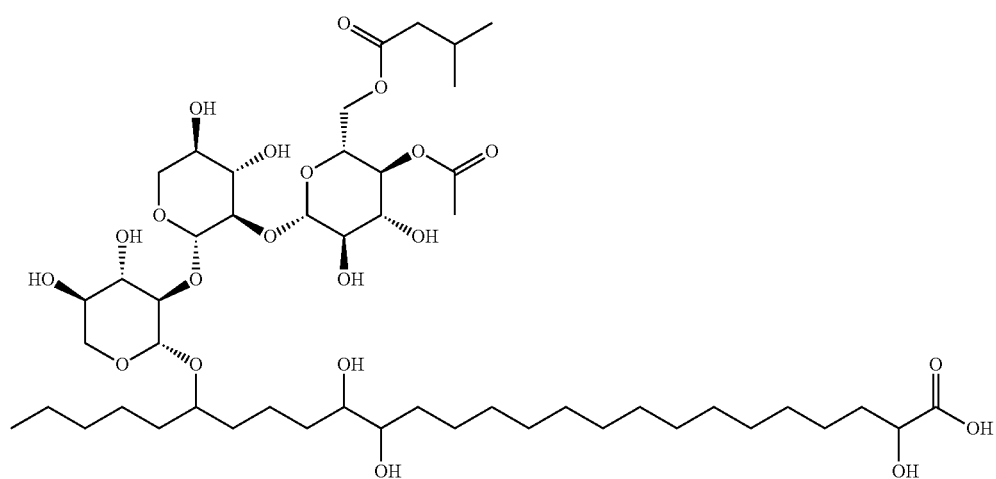
[21a]
Particularly preferred are the following compounds of formulae [1b], [12b], [13b] and [18b], mixtures thereof, and the physiologically acceptable salts thereof
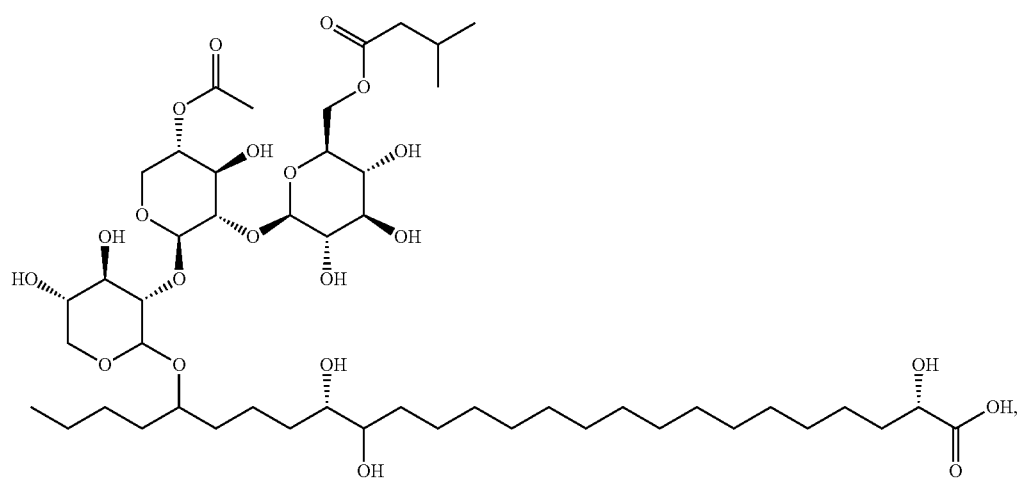
[1b]

more preferably
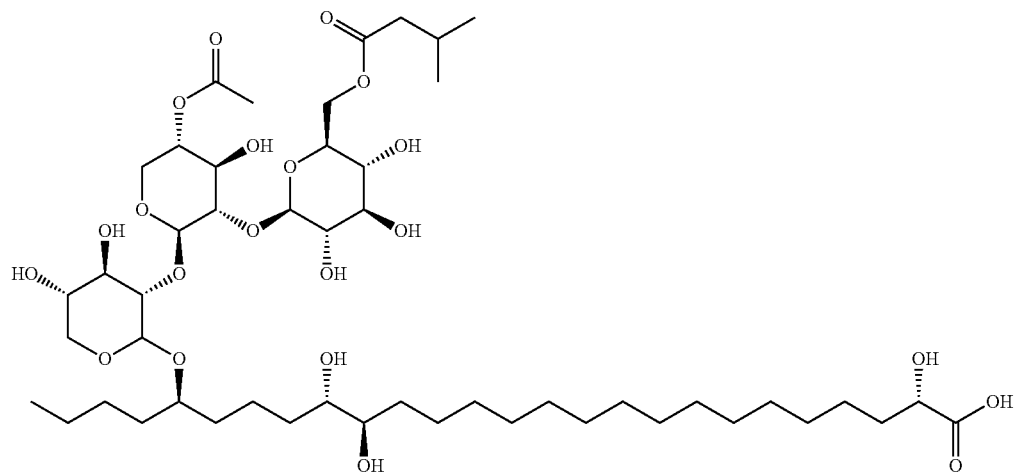
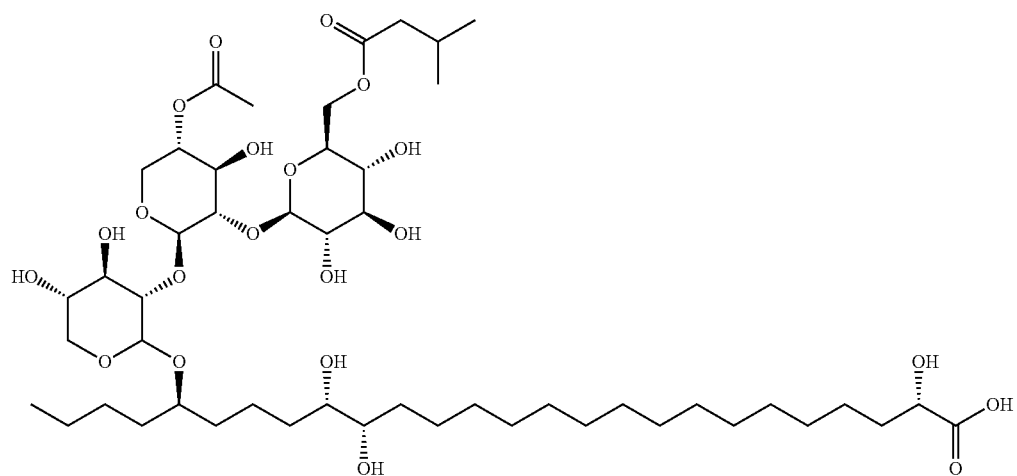 [SMILES: CCCC[C@@H](CCC[C@H](O)[C@@H](O)CCCCCCCCCCCCCC[C@H](O)C(=O)O)OC1OC[C@H](O)[C@@H](O)[C@@H]1O[C@H]1OC[C@H](OC(C)=O)[C@@H](O)[C@@H]1O[C@H]1O[C@@H](COC(=O)CC(C)C)[C@H](O)[C@@H](O)[C@@H]1O]
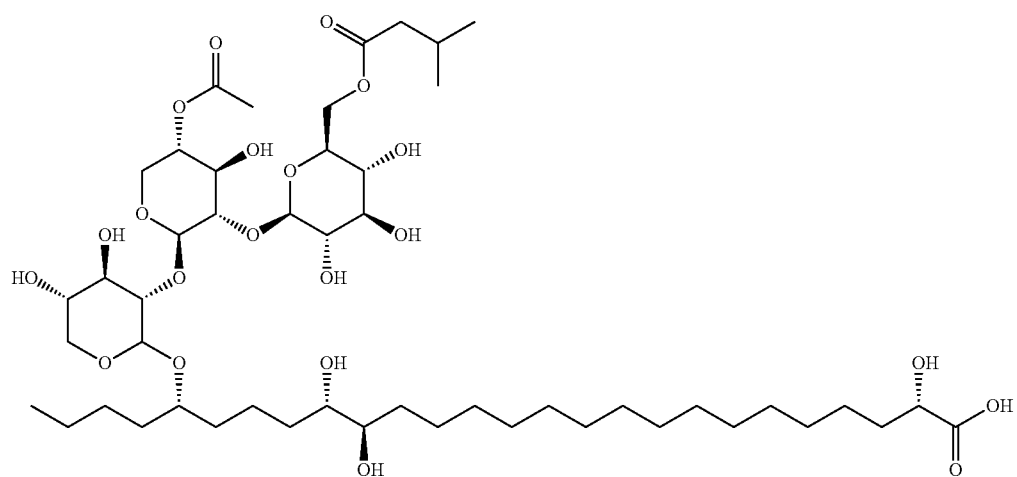

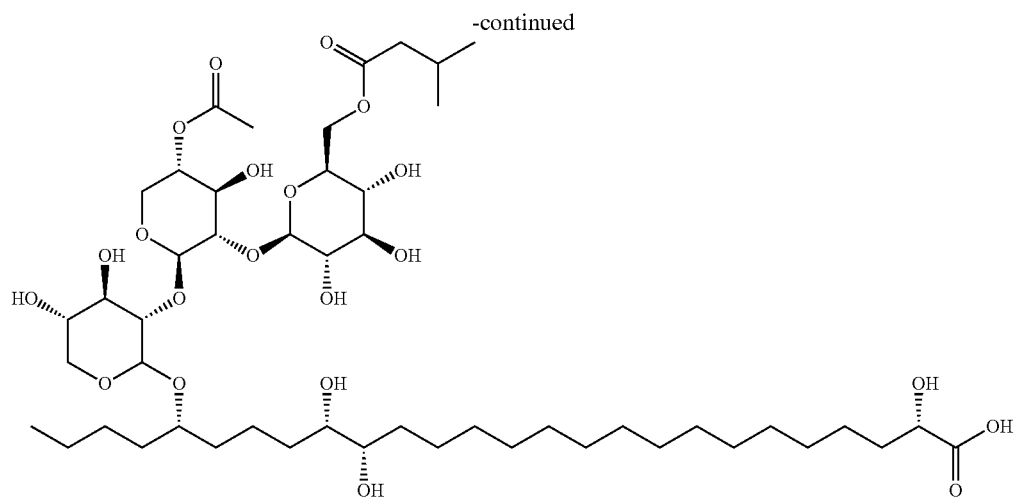
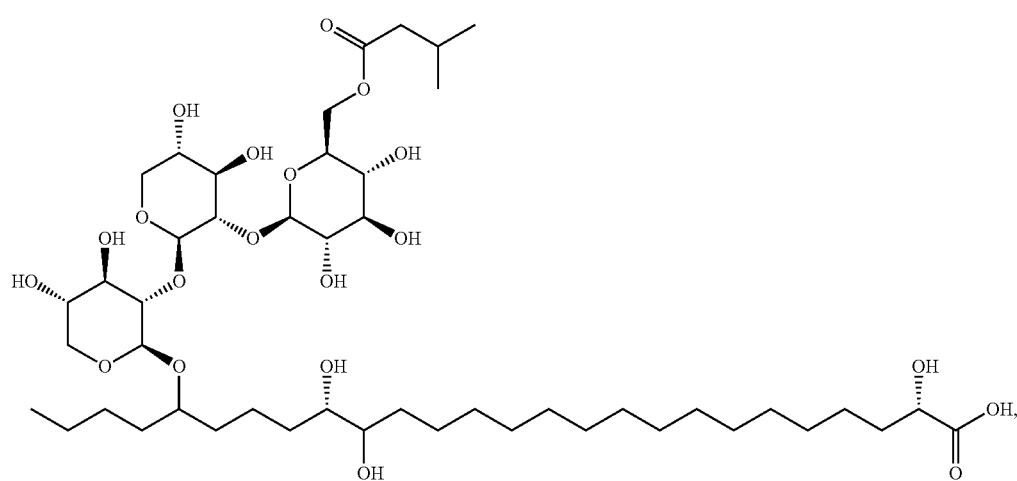
more preferably
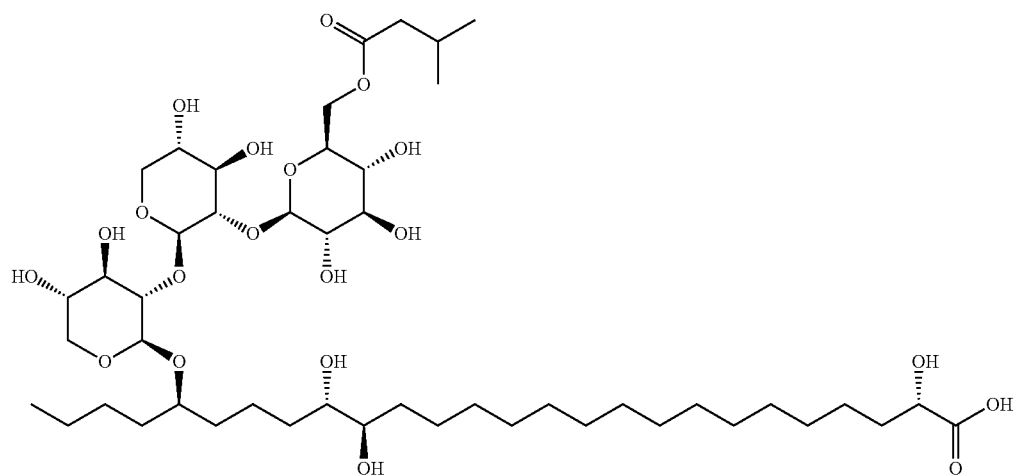

-continued
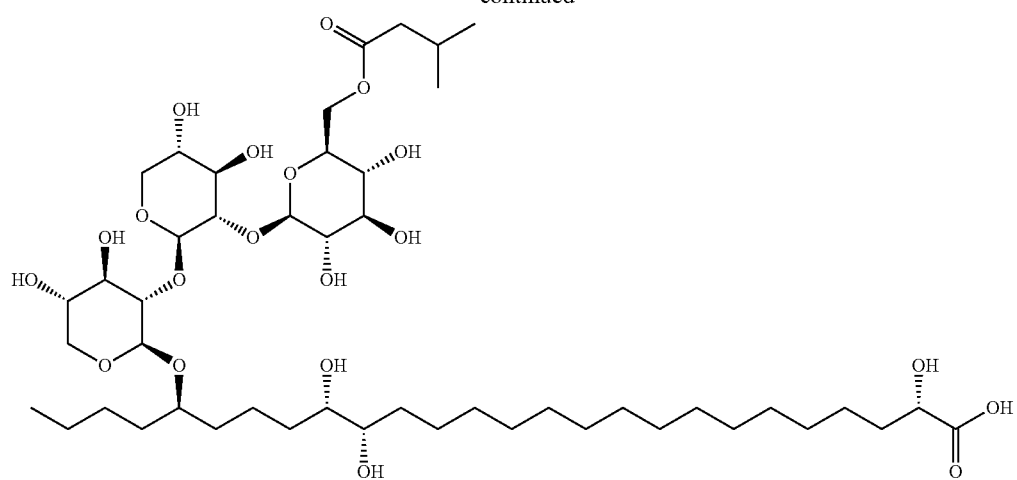
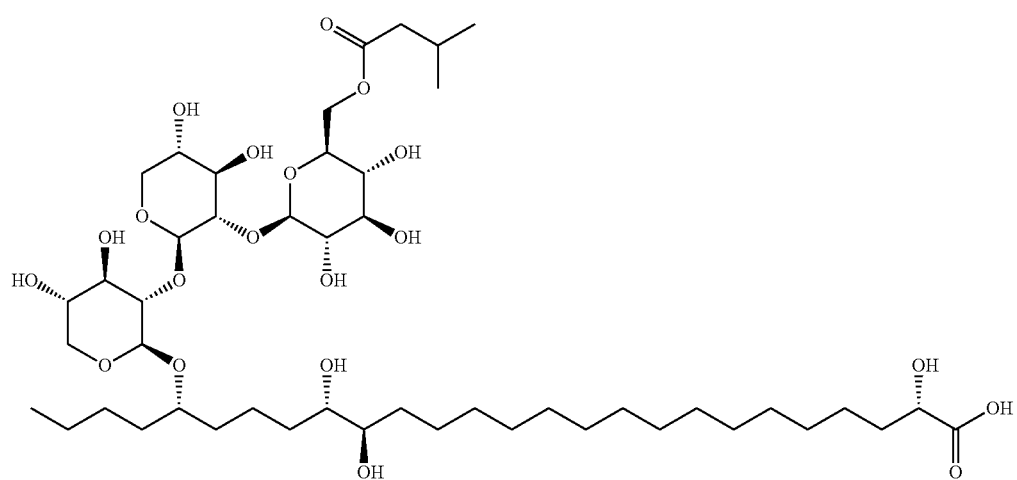
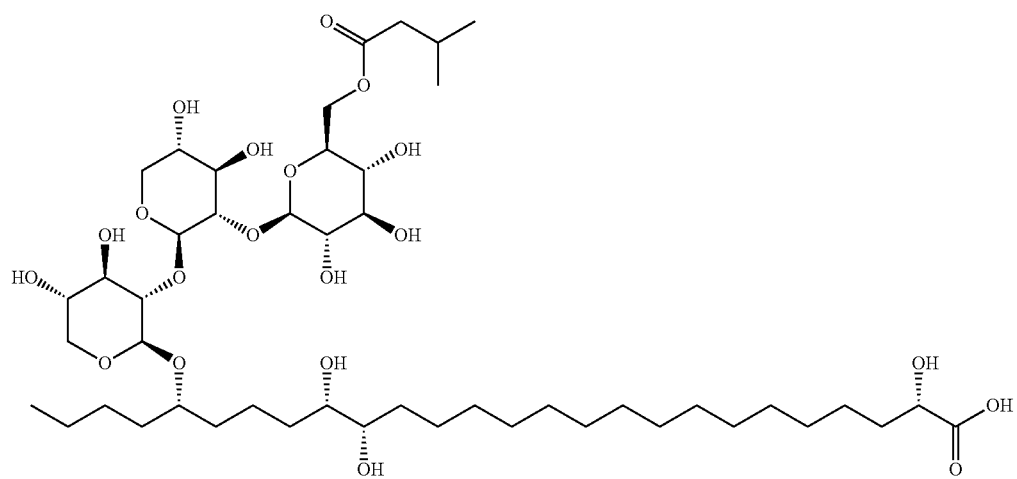 [SMILES: CCCC[C@@H](CCC[C@H](O)[C@@H](O)CCCCCCCCCCCCCC[C@H](O)C(=O)O)O[C@H]1OC[C@H](O)[C@@H](O)[C@@H]1O[C@H]1OC[C@H](O)[C@@H](O)[C@@H]1O[C@H]1O[C@@H](COC(=O)CC(C)C)[C@H](O)[C@@H](O)[C@@H]1O]

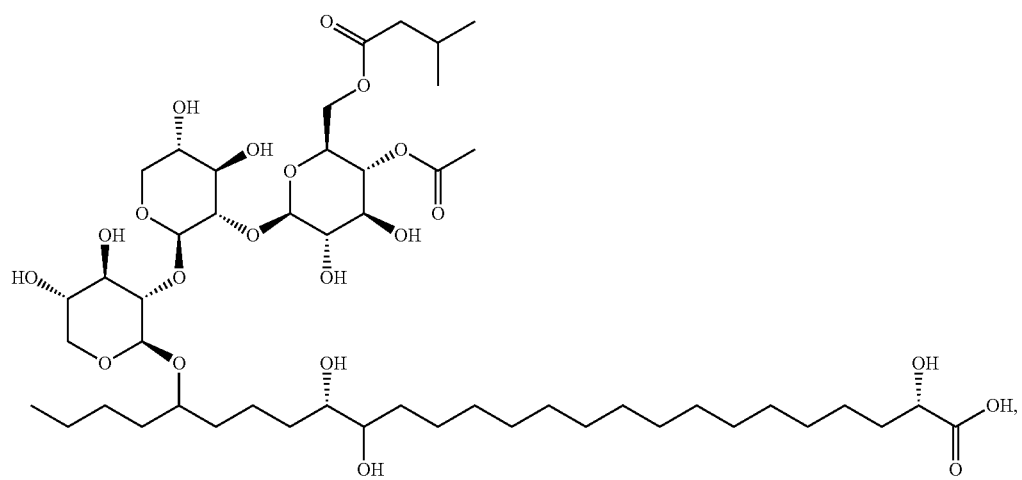
more preferably
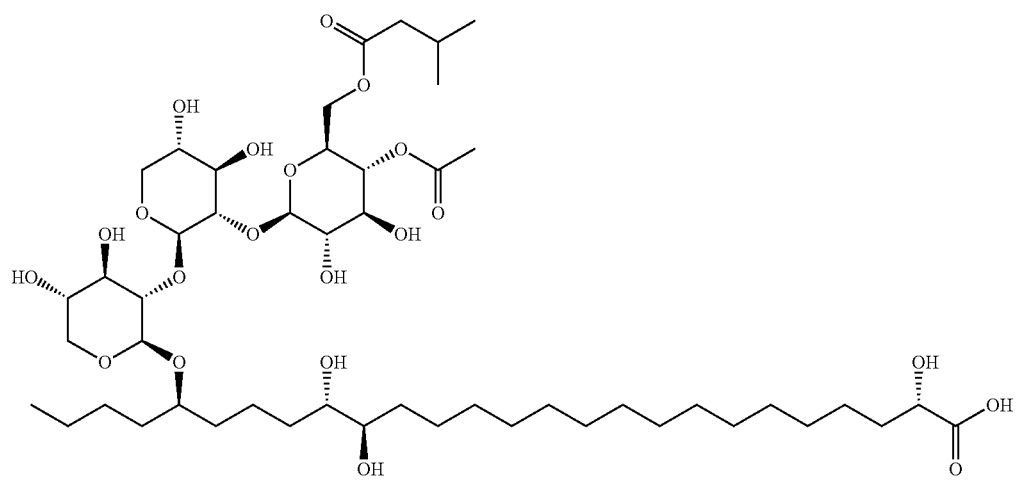
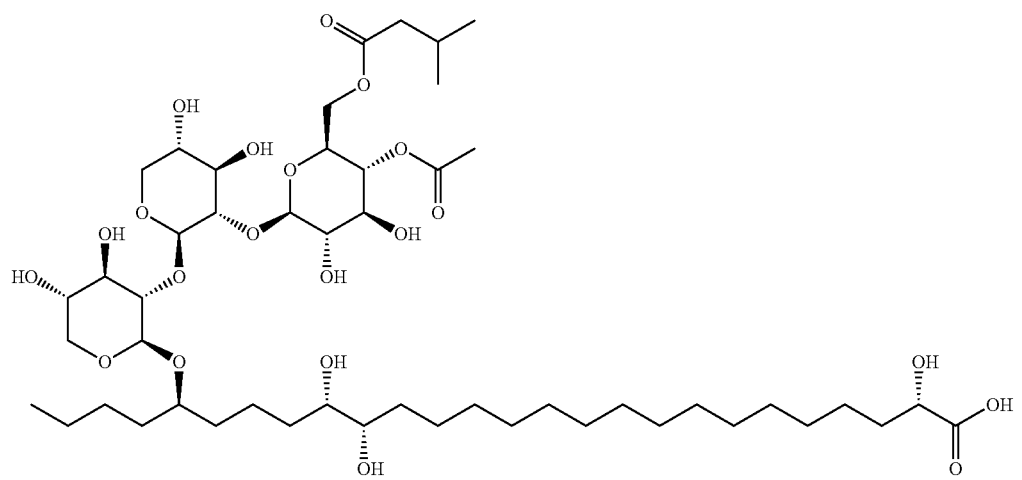
[13b]

-continued
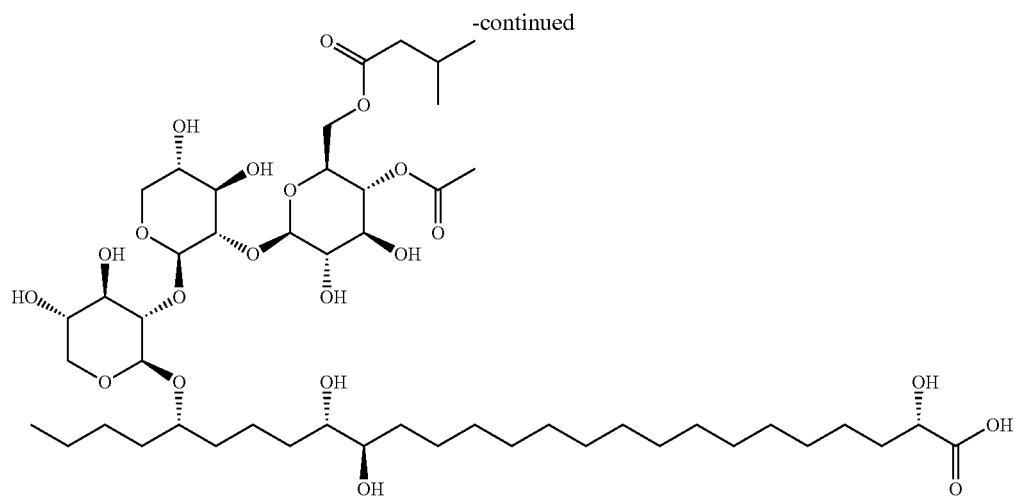
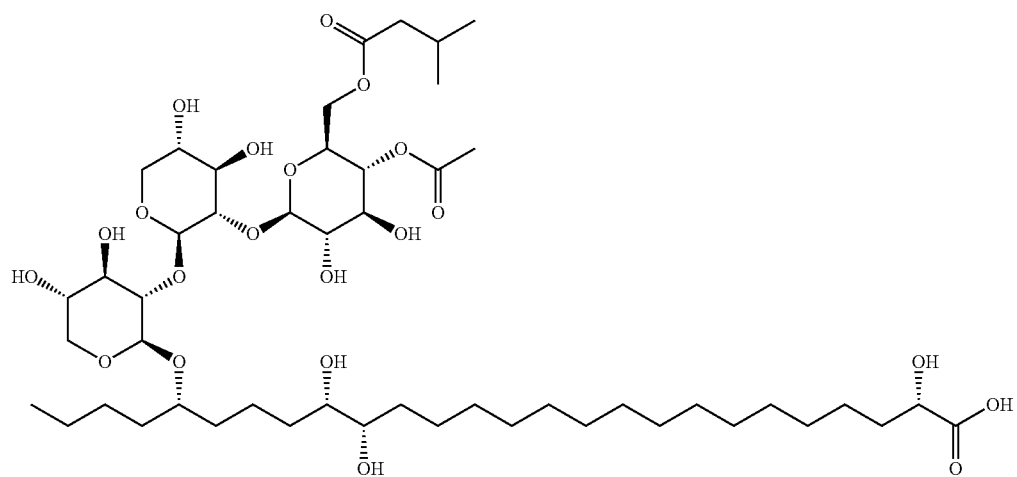 [SMILES: CCCC[C@@H](CCC[C@H](O)[C@@H](O)CCCCCCCCCCCCCC[C@H](O)C(=O)O)O[C@H]1OC[C@H](O)[C@@H](O)[C@@H]1O[C@H]1OC[C@H](O)[C@@H](O)[C@@H]1O[C@H]1O[C@@H](COC(=O)CC(C)C)[C@H](OC(C)=O)[C@@H](O)[C@@H]1O]
[18b]
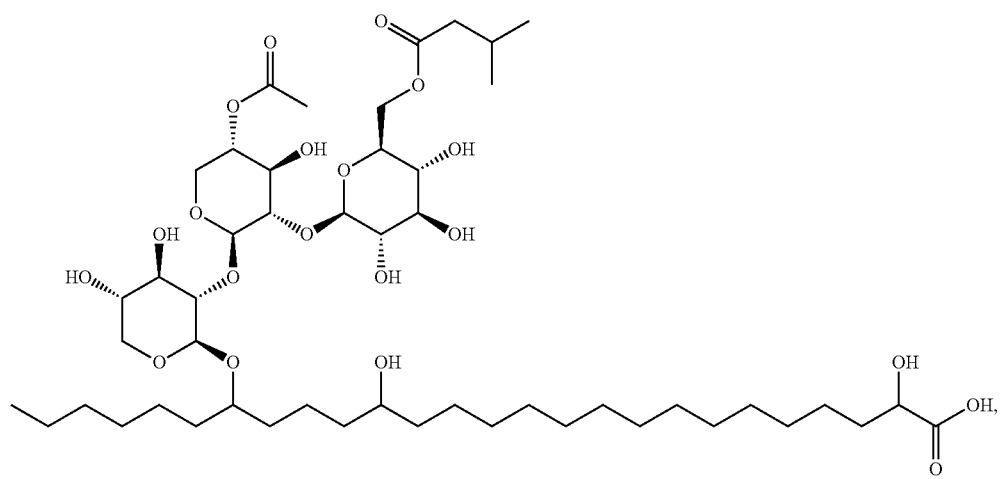

more preferably
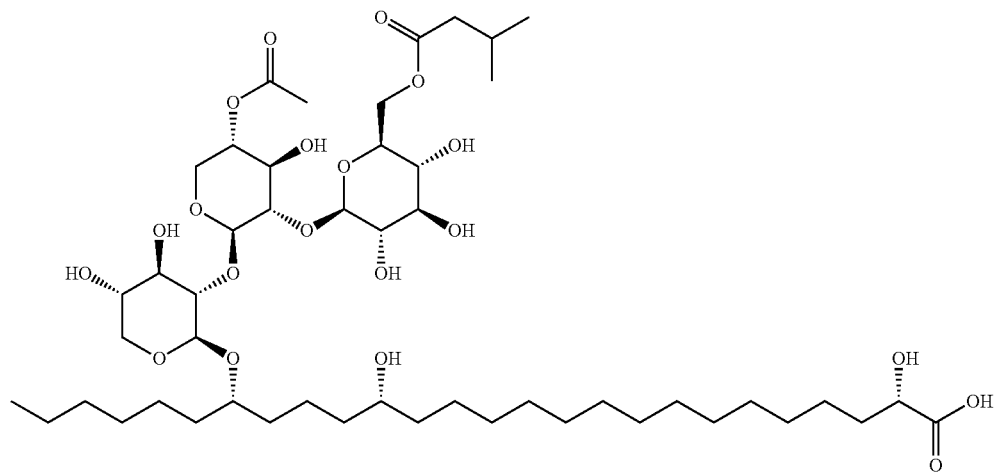
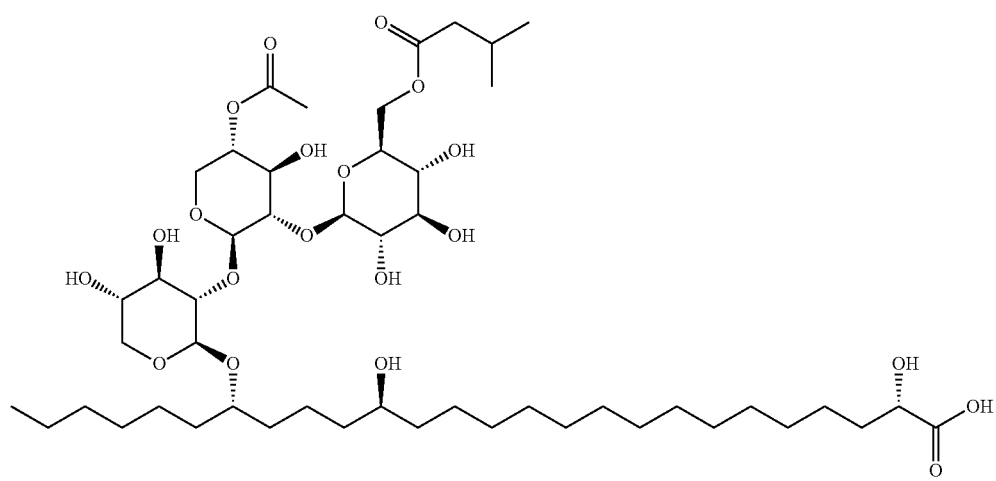
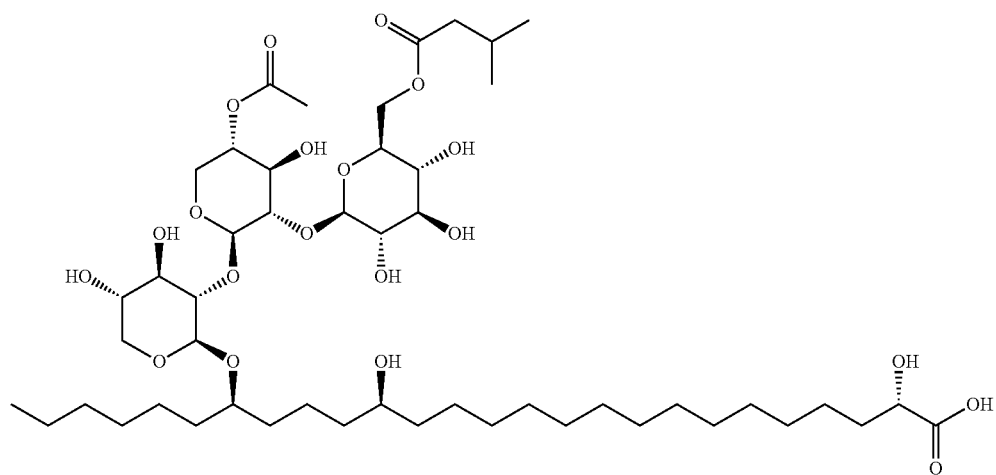

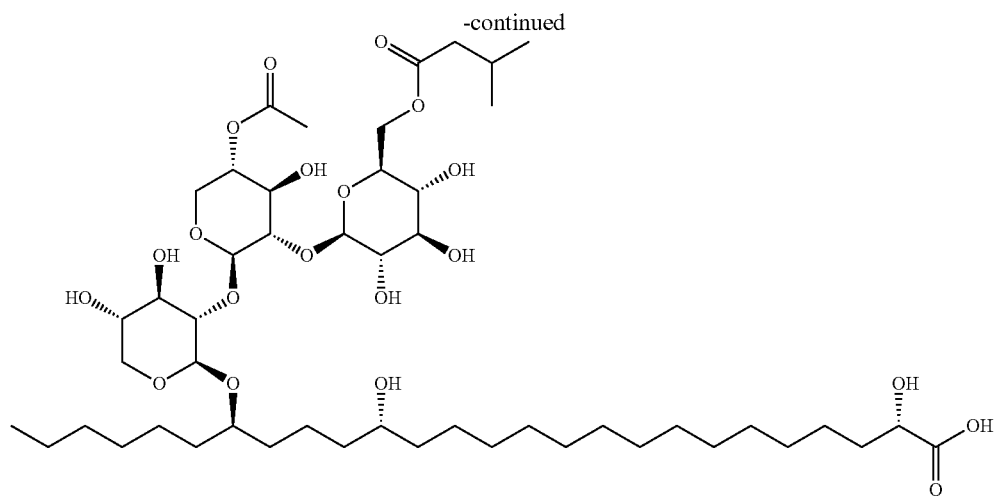
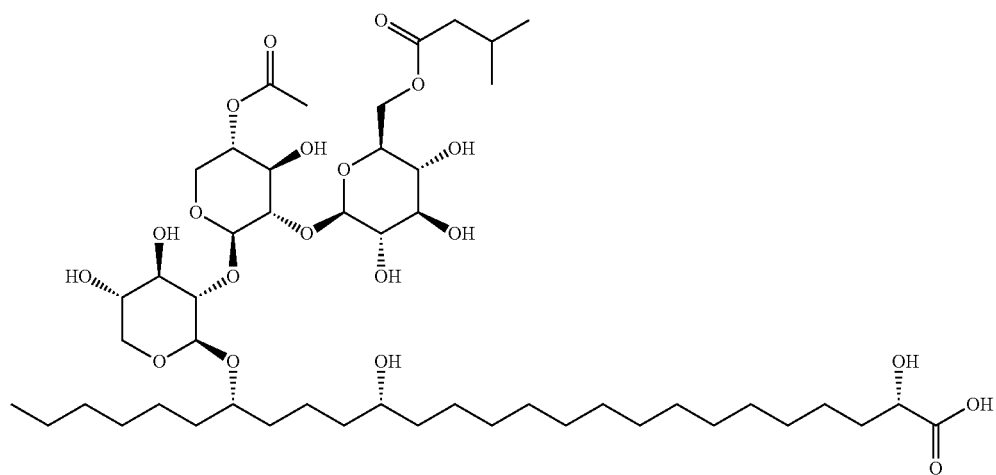
Particularly preferred are the following compounds of formulae [1c], [12c], [13c] and [18c], mixtures thereof, and the physiologically acceptable salts thereof
[1c]
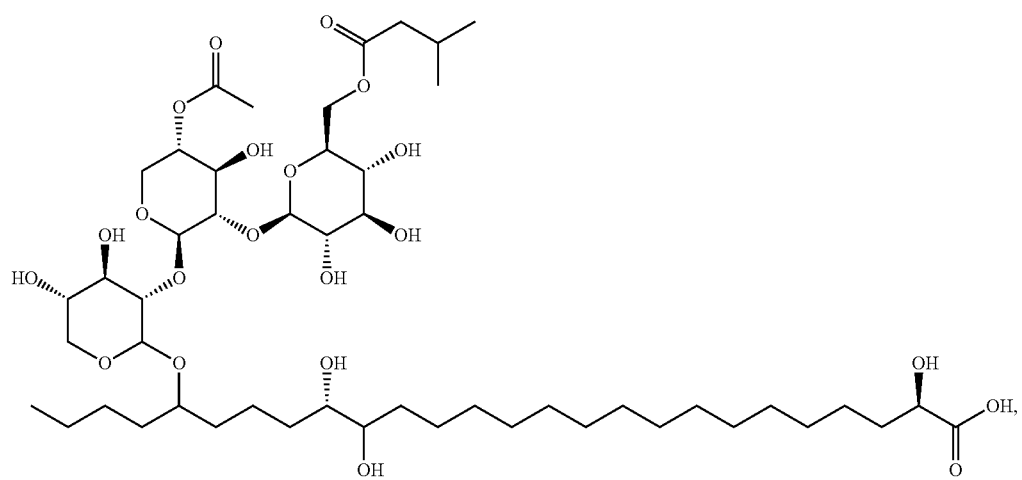

more preferably
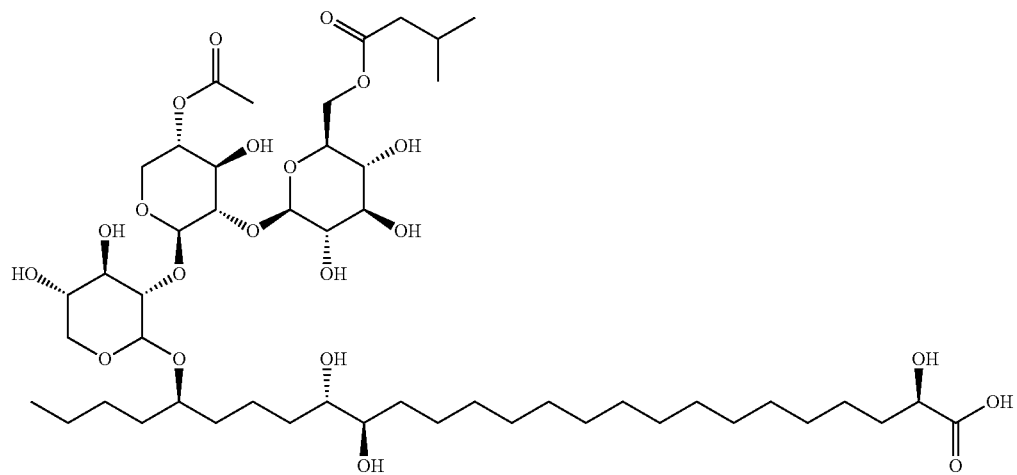
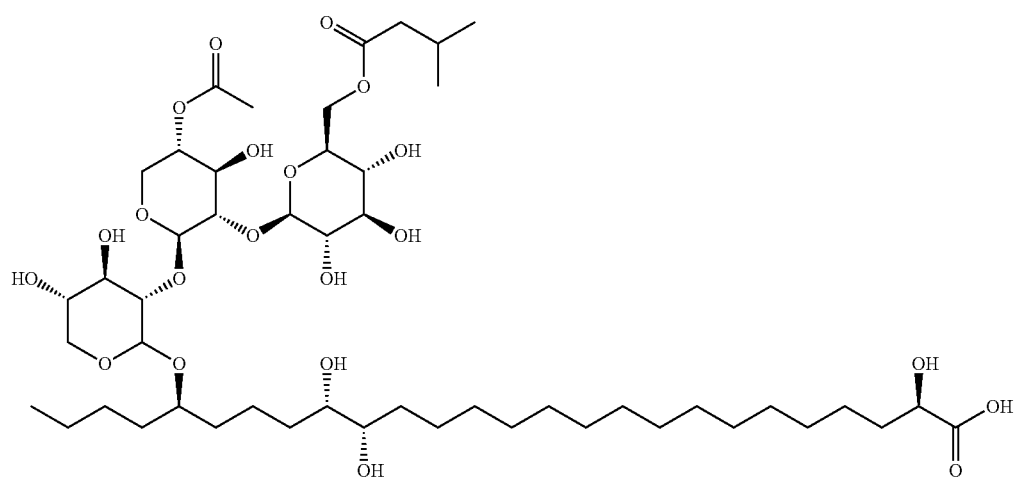
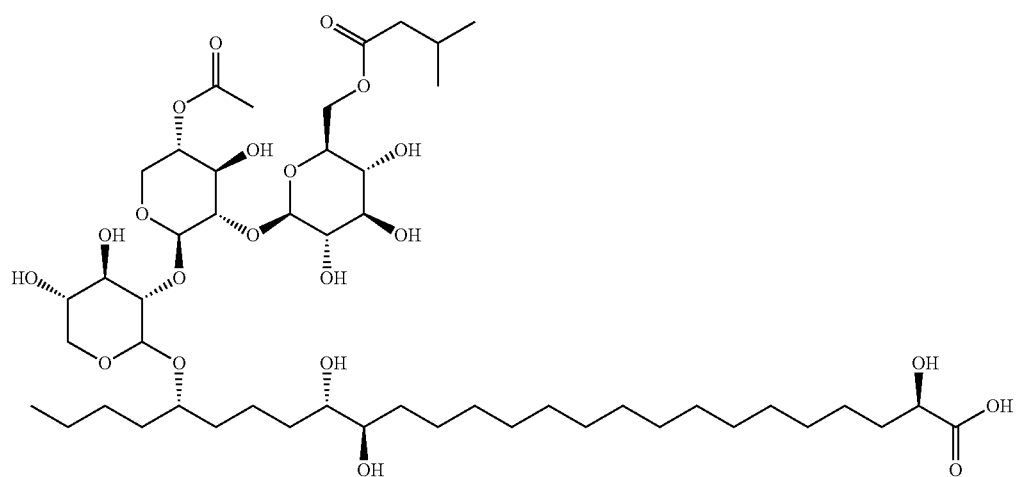 [SMILES: CCCC[C@@H](CCC[C@H](O)[C@@H](O)CCCCCCCCCCCCCC[C@@H](O)C(=O)O)OC1OC[C@H](O)[C@@H](O)[C@@H]1O[C@H]1OC[C@H](OC(C)=O)[C@@H](O)[C@@H]1O[C@H]1O[C@@H](COC(=O)CC(C)C)[C@H](O)[C@@H](O)[C@@H]1O]

-continued
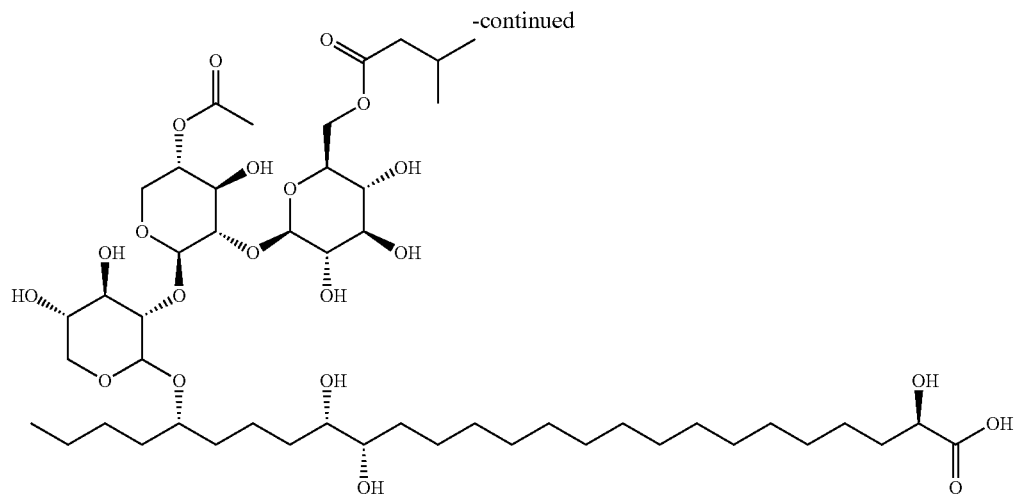
[12c]
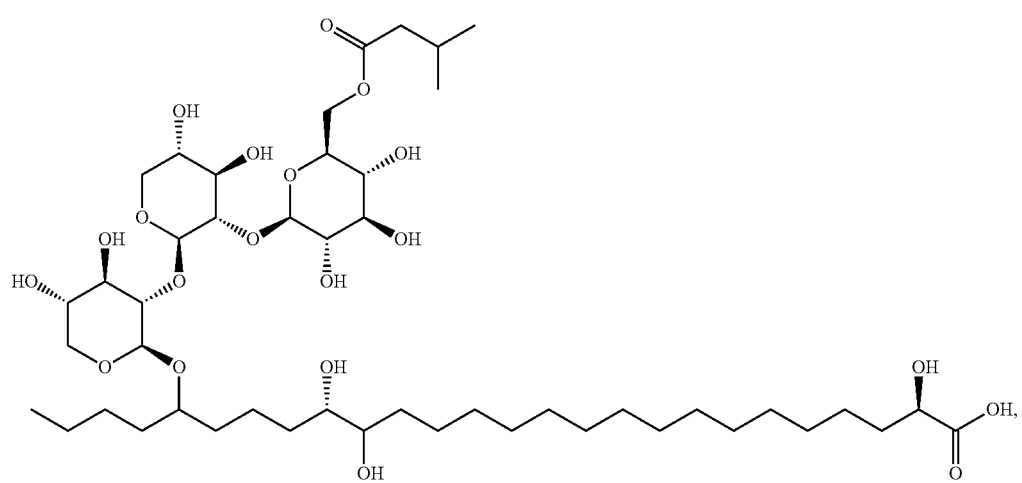
more preferably
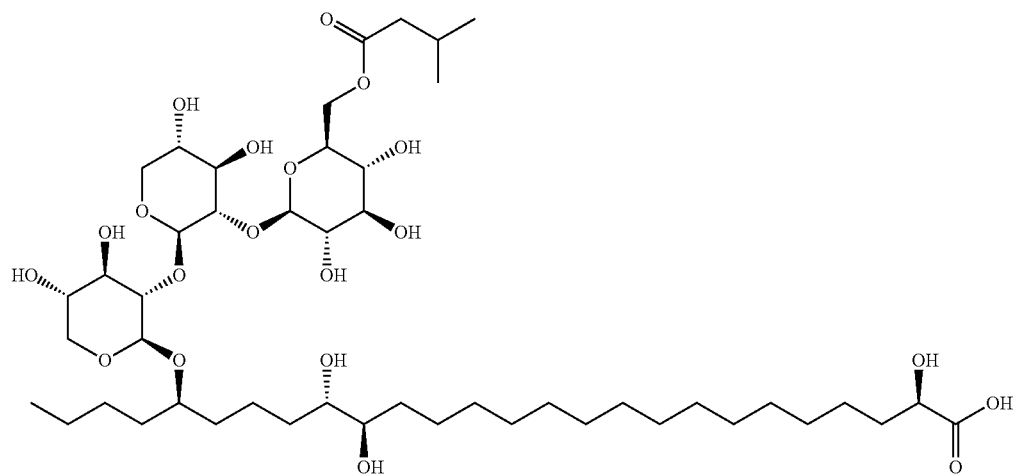

-continued
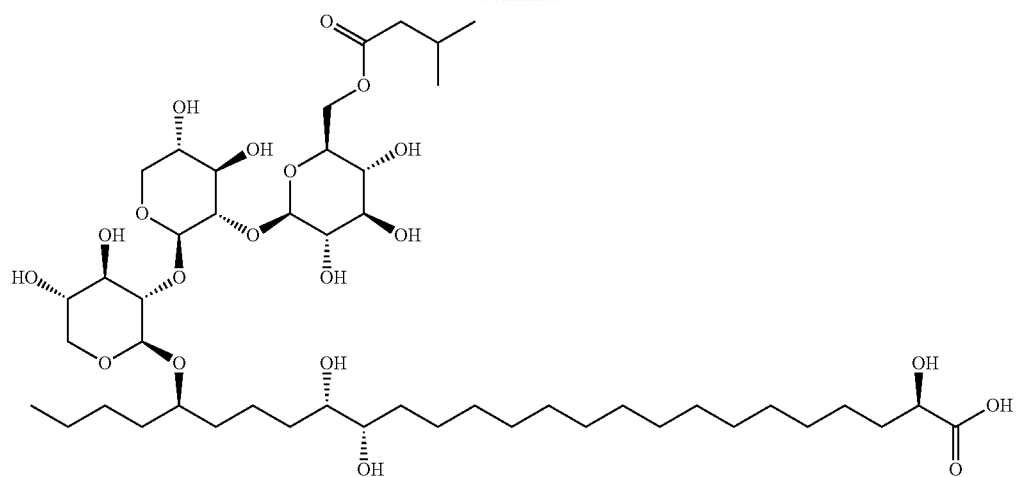
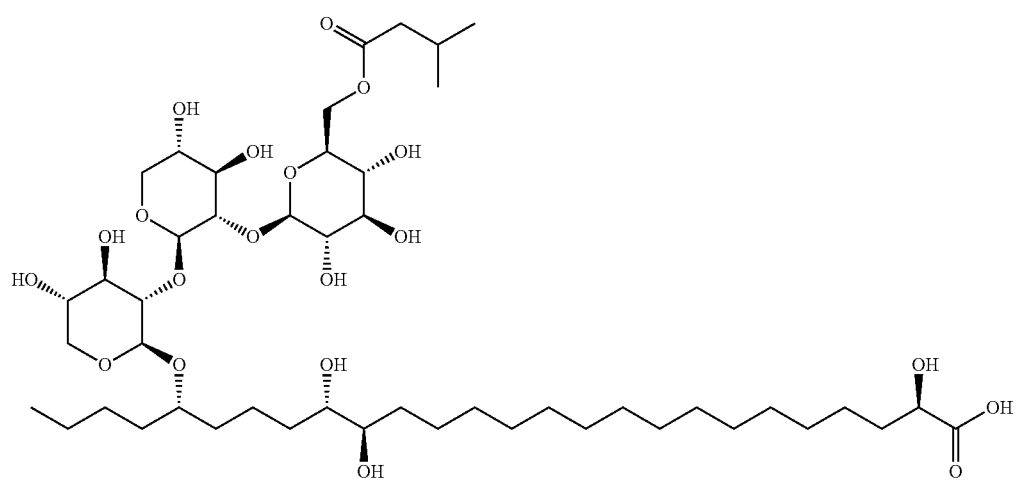
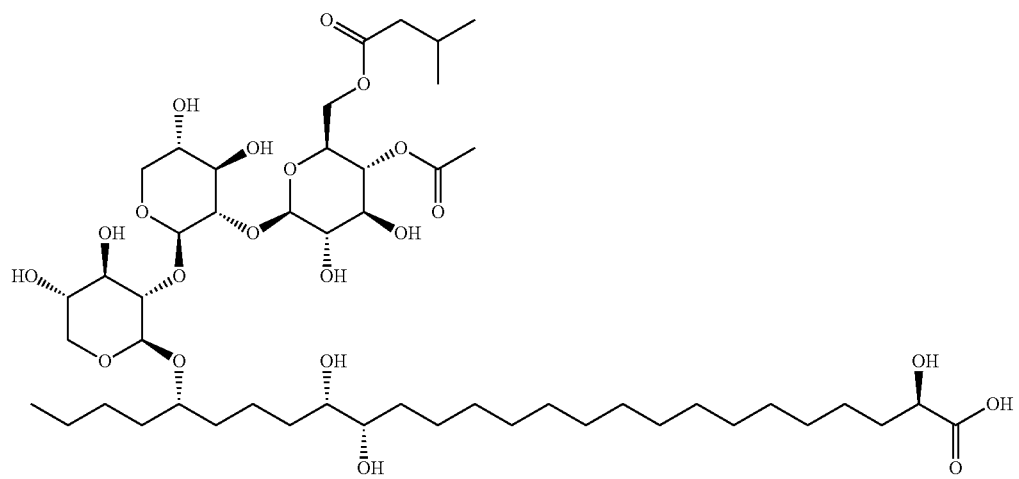 [SMILES: CCCC[C@@H](CCC[C@H](O)[C@@H](O)CCCCCCCCCCCCCC[C@@H](O)C(=O)O)O[C@H]1OC[C@H](O)[C@@H](O)[C@@H]1O[C@H]1OC[C@H](O)[C@@H](O)[C@@H]1O[C@H]1O[C@@H](COC(=O)CC(C)C)[C@H](OC(C)=O)[C@@H](O)[C@@H]1O]

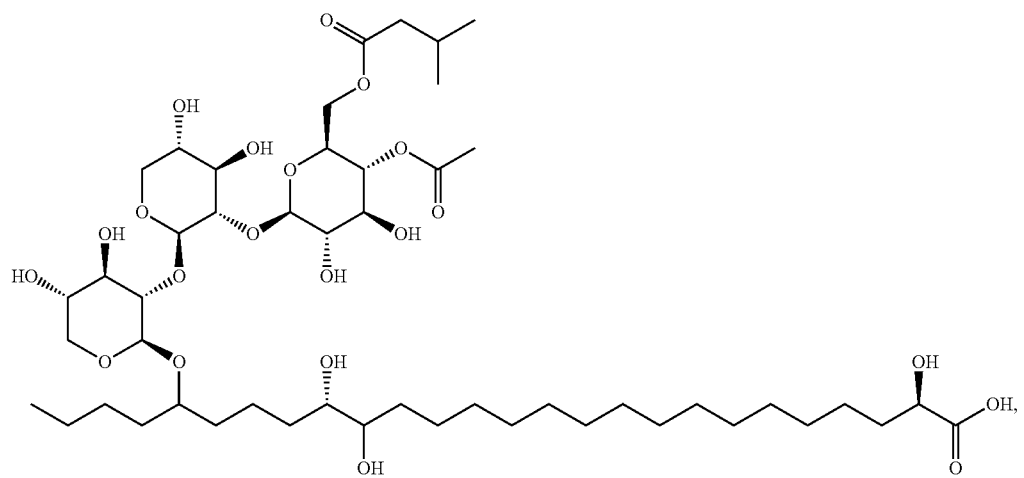
more preferably
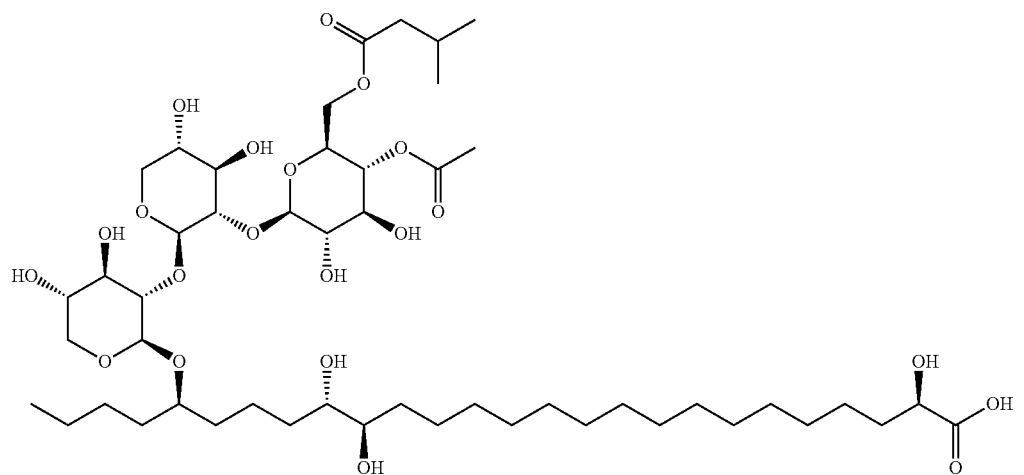
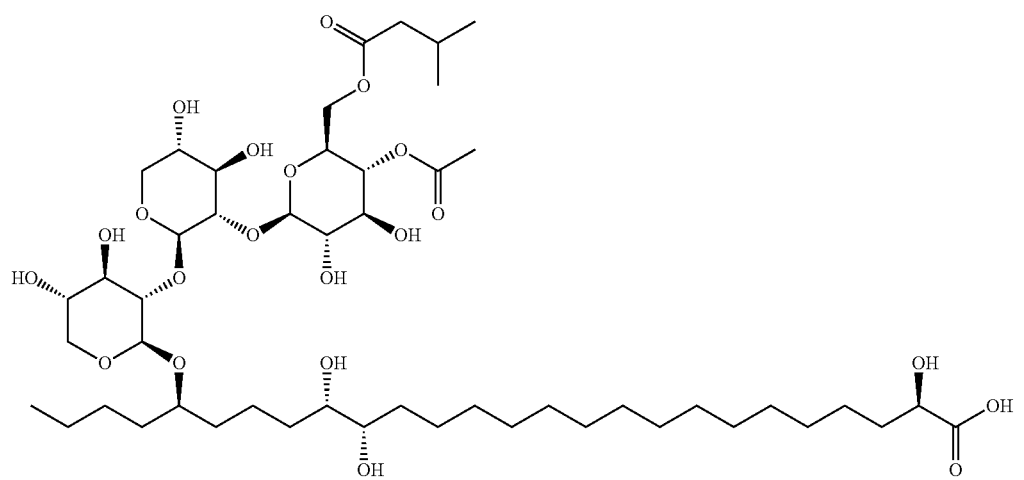

-continued
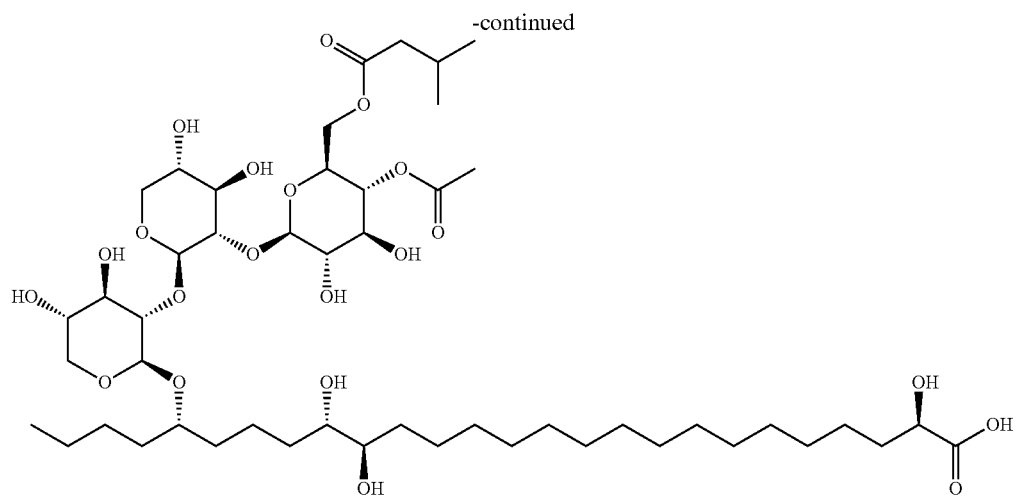
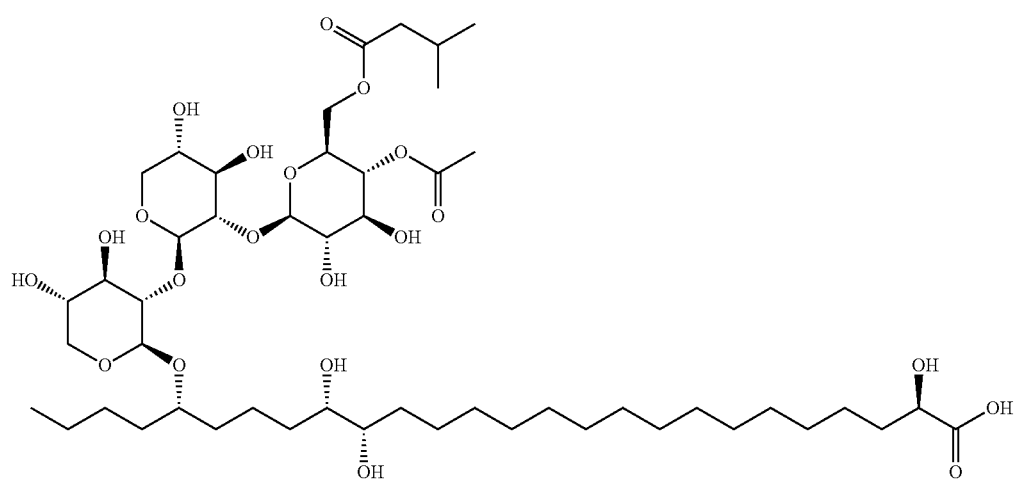 [SMILES: CCCC[C@@H](CCC[C@H](O)[C@@H](O)CCCCCCCCCCCCCC[C@@H](O)C(=O)O)O[C@H]1OC[C@H](O)[C@@H](O)[C@@H]1O[C@H]1OC[C@H](O)[C@@H](O)[C@@H]1O[C@H]1O[C@@H](COC(=O)CC(C)C)[C@H](OC(C)=O)[C@@H](O)[C@@H]1O]
[18c]
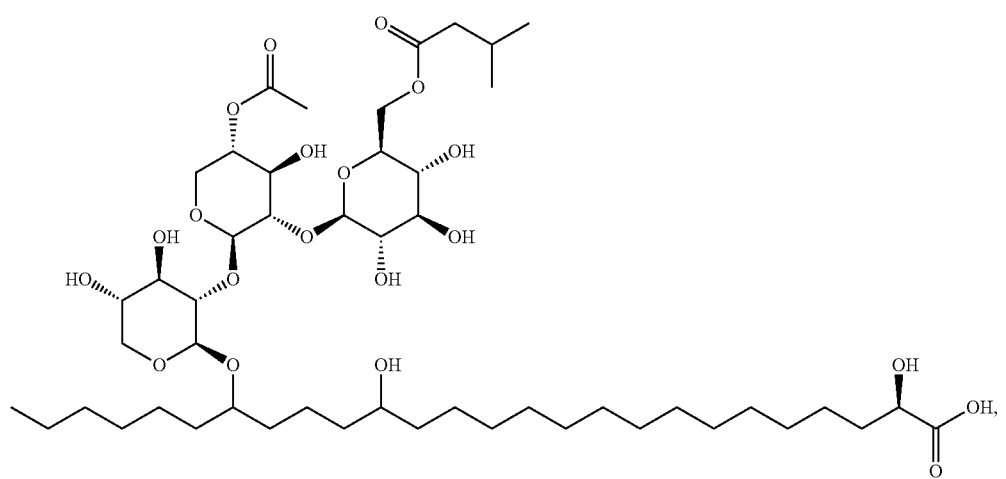

more preferably
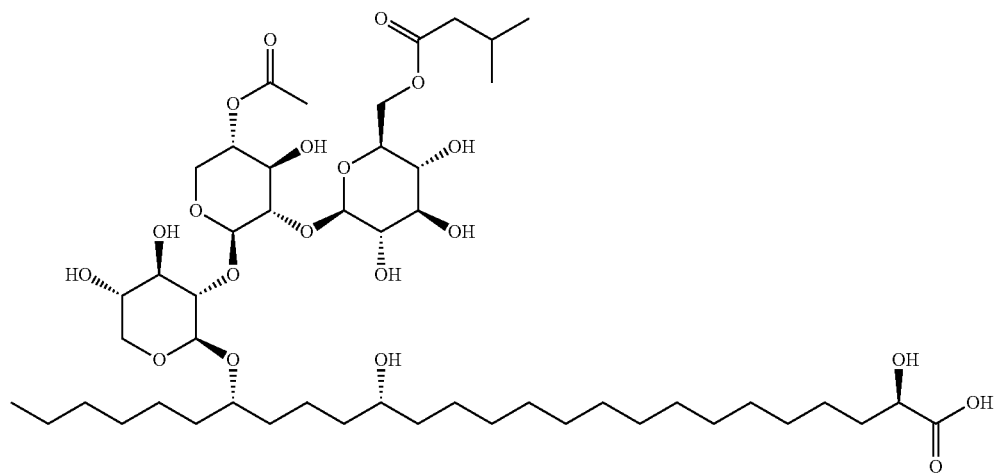
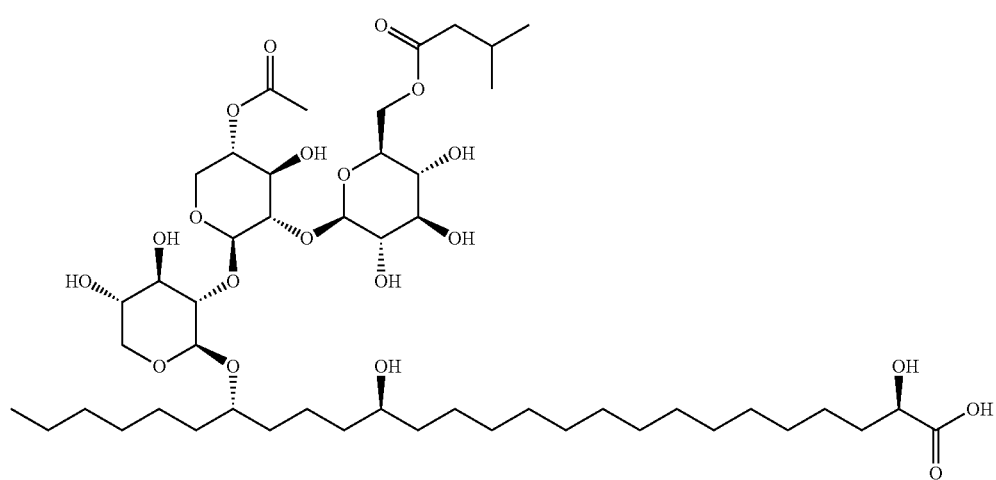
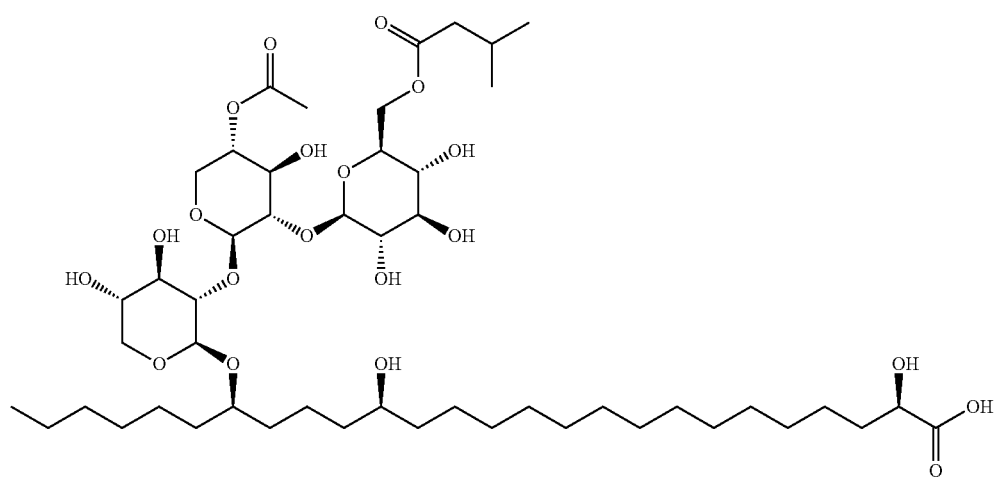

-continued

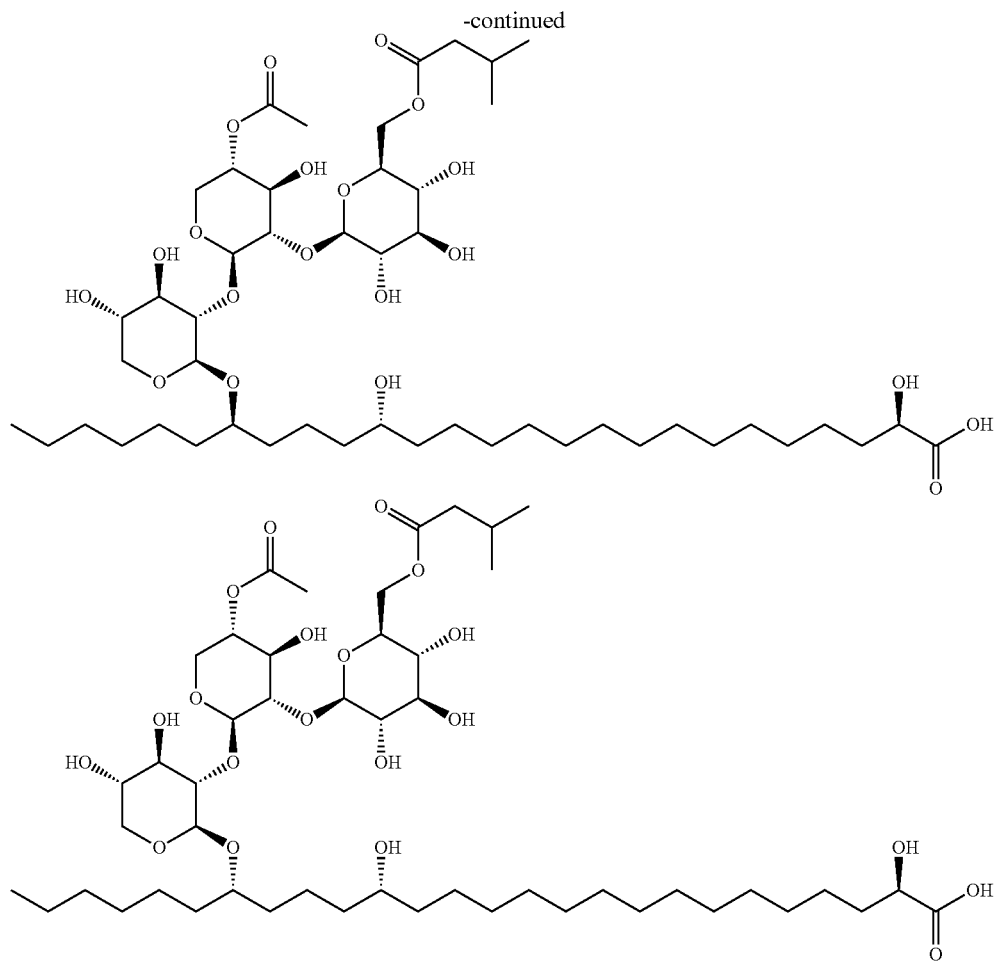

In a preferred embodiment, the present invention relates to a composition comprising or consisting of three, four, five, six, seven, eight, nine, ten, eleven, twelve or more compounds of formula I,
wherein the total amount of said compounds of formula I is greater than 75 wt. %, preferably greater than 80 wt. %, more preferably greater than 85 wt. %, particularly preferably greater than 90 wt. %, in each case based on the total weight the composition, and preferably
a total amount of 90 wt. % or less, more preferably of 75 wt. % or less, even more preferably of 50 wt. % or less, particularly preferably of 25 wt. % or less, especially preferably of 10 wt. % or less, and most preferably of 5 wt. % or less of liquid (at 25° C. and 1013 mbar) diluents, in particular water, in each case based on the total weight of the composition,
and/or
a total amount of 5 wt. % or less, more preferably of 2 wt. % or less, particularly preferably of 1.25 wt. % or less, and most preferably of 0.8 wt. % or less of proteins, in each case based on the total weight of the composition,
and/or
a total amount of 5 wt. % or less, more preferably of 3 wt. % or less, particularly preferably of 2 wt. % or less of sugar alcohols and mono- or disaccharides, in each case based on the total weight of the composition,
and/or
a total amount of 5 wt. % or less, more preferably of 4 wt. % or less, even more preferably of 3 wt. % or less, particularly preferably of 2 wt. % or less, most preferably of 1 wt. % or less of cells and cell material with a size in at least one dimension of greater than 3 micrometer (μm), preferably with a size in at least one dimension of greater than 2 μm, more preferably with a size in at least one dimension of greater than 1 μm, of fungi of the Dacrymycetaceae family, in each case based on the total weight of the composition.

In a particularly preferred embodiment, the present invention relates to a composition comprising or consisting of one or more, preferably two, three, four, five, six, seven, eight, nine, ten, eleven, twelve or more physiologically acceptable salts of one or more, preferably two, three, four, five, six, seven, eight, nine, ten, eleven, twelve or more compounds of formula I,
wherein the total amount of said physiologically acceptable salts of the compounds of formula I is greater than 70 wt. %, preferably greater than 80 wt. %, more preferably greater than 90 wt. %, particularly preferably greater than 95 wt. %, in each case based on the total amount of compounds of formula I and the physiologically acceptable salts thereof, and preferably
a total amount of 90 wt. % or less, more preferably of 75 wt. % or less, even more preferably of 50 wt. % or less, particularly preferably of 25 wt. % or less, especially preferably of 10 wt. % or less, and most preferably of 5 wt. % or less of liquid (at 25° C. and 1013 mbar) diluents, in particular water, in each case based on the total weight of the composition, and/or
- a total amount of 5 wt. % or less, more preferably of 3 wt. % or less, particularly preferably of 2 wt. % or less, and most preferably of 1 wt. % or less of proteins, in each case based on the total weight of the composition, and/or
- a total amount of 20 wt. % or less, more preferably of 15 wt. % or less, particularly preferably of 10 wt. % or less, most preferably of 5 wt. % or less of sugar alcohols and mono- or disaccharides, in each case based on the total weight of the composition, and/or
- a total amount of 5 wt. % or less, more preferably of 4 wt. % or less, even more preferably of 3 wt. % or less, particularly preferably of 2 wt. % or less, most preferably of 1 wt. % or less of cells and cell material with a size in at least one dimension of greater than 10 micrometer (μm), preferably with a size in at least one dimension of greater than 5 μm, more preferably with a size in at least one dimension of greater than 3 μm, most preferably with a size in at least one dimension of greater than 2 μm, of fungi of the Dacrymycetaceae family, in each case based on the total weight of the composition.

In a especially preferred embodiment, the present invention relates to a composition comprising or consisting of three, four, five, six, seven, eight, nine, ten, eleven, twelve or more physiologically acceptable salts of one or more, preferably two, three, four, five, six, seven, eight, nine, ten, eleven, twelve or more compounds of formula I,
wherein the total amount of said physiologically acceptable salts of the compounds of formula I is greater than 85 wt. %, more preferably greater than 90 wt. %, particularly preferably greater than 95 wt. %, in each case based on the total amount of compounds of formula I and the physiologically acceptable salts thereof,
and additionally
- a total amount of 25 wt. % or less, preferably of 10 wt. % or less, and particularly preferably of 5 wt. % or less of water, in each case based on the total weight of the composition,
- a total amount of 2 wt. % or less, preferably of 1 wt. % or less of proteins, in each case based on the total weight of the composition,
- a total amount of 10 wt. % or less, most preferably of 5 wt. % or less of sugar alcohols and mono- or disaccharides, in each case based on the total weight of the composition,
and
- a total amount of 2 wt. % or less, most preferably of 1 wt. % or less of cells and cell material with a size in at least one dimension greater than 2 μm, more preferably with a size in at least one dimension of greater than 1 μm, most preferably with a size in at least one dimension of greater than 0.7 μm of fungi of the Dacrymycetaceae family, in each case based on the total weight of the composition.

Preferably, the determination of the total amount of nitrogen and the total protein content is performed according to the Kjeldahl method, preferably according to ISO 5549: 1978.

It was found in our own investigations that said preferred or particularly preferred compositions according to the present invention comprising one or more physiologically acceptable salts of one or more compounds of formula I show improved, in particular longer, storage stability in comparison to the corresponding compounds of formula I in free acid form. It was also found in our own investigations that such compositions have a superior, i.e. higher, solubility in aqueous-alcoholic solvents or water in comparison to the corresponding compounds of formula I in free acid form. For example, while it is not possible to obtain a stable 1 wt. % solution of a mixture of compounds of formula I in free acid form in water, it is easily possible to produce a 10 wt. % solution of a mixture of compounds of formula I in their salt form. Thus, the one or more physiologically acceptable salts of one or more compounds of formula I have excellent formulation properties, in particular regarding aqueous food, beverage and cosmetic materials, in particular with a water content of 50 wt. % or more, which are superior in comparison to the corresponding compounds of formula I in free acid form. Additionally, said compositions and solutions showed very good skin compatibility.

Particularly preferably, the trisaccharide carbohydrate moiety R in the compounds of formula I—without including any substituents resulting from acylation of hydroxyl groups of said trisaccharide carbohydrate moiety R—is a beta-D-glucopyranosyl-(1→2)-beta-D-xylopyranosyl-(1→2)-beta-D-xylopyranoside moiety. Further, of said trisaccharide carbohydrate moiety R preferably one, two, three or four hydroxyl groups are esterified by a $C_2$-$C_{10}$-alkanoic acid, i.e. said trisaccharide carbohydrate moiety R being in mono- or di- or tri- or tetra-acylated form (i.e. esterified with an $C_2$-$C_{10}$-alkanoic acid). It was found in our own investigations that compounds of formula I without any acyl substituents in the trisaccharide carbohydrate moiety R (such as compound [16]) showed significantly inferior antimicrobial activities, in particular regarding Gram-positive bacteria, but also to a noticeable extent regarding yeasts and molds.

Therefore, a mixture according to the present invention, an extract according to the present invention, a material according to the present invention, and/or a composition according to the present invention preferably comprises less than 15 wt. % of compounds of formula I without any acyl substituents in the trisaccharide carbohydrate moiety R (particularly compound [16]), more preferably less than 10 wt. %, particularly preferably less than 5 wt. %, in each case based on the total amount of compounds of formula I and the physiologically acceptable salts thereof.

In a particularly preferred embodiment relates to the compounds of the formula I carrying one, two, three or four acylated hydroxyl groups in the trisaccharide carbohydrate moiety R, said acyl moiety preferably being a $C_3$-$C_6$-alkanoic acid, more preferably an isovaleryl (3-methylbutanoyl) moiety. These compounds were found to exhibit superior antimicrobial activity regarding certain Gram-positive bacteria and regarding fungi, yeasts and molds.

Preferably, such a mixture comprises, essentially consists of or consists of alkali and/or alkaline earth salts of two or more compounds of formula I, more preferably of sodium and/or potassium and/or calcium and/or magnesium salts thereof, in particular the sodium and/or potassium and/or calcium and/or magnesium salts of one, two, three, four, five, six, seven, eight, nine or more of the compounds selected from the group consisting of compounds [1], [4], [5], [6], [7], [8], [9], [10], [12], [13], [14], and [18], wherein the total amount of water preferably is less than 5 wt. %, more preferably less than 3 wt. %, and particularly preferably less than 1 wt. %, in each case based on the total weight of the mixture.

Preferably such a mixture comprises the sodium and/or potassium and/or calcium and/or magnesium salts of one, two, three, four, five, six, seven, eight or more of the compounds selected from the group consisting of [1], [4],

[5], [6], [7], [8], [9], [10], [12], [13], [14], and [18], wherein the total amount of salts of the compounds of formula I is greater than 70 wt. %, preferably greater than 75 wt. %, more preferably greater than 80 wt. %, particularly preferably greater than 85 wt. %, in each case based on the total weight of the mixture.

Particularly preferably such a mixture comprises the sodium and/or potassium and/or calcium and/or magnesium salts of one, two, three, four or all of the compounds selected from the group consisting of compounds [1], [7], [12], [13], and [18], wherein the total amount of said salts of the compounds [1], [7], [12], [13], and [18] is greater than 10 wt. %, preferably greater than 15 wt. %, more preferably greater than 20 wt. %, in each case based on the total weight of the mixture.

Preferably, such a mixture according to the present invention is either in solid (at 25° C. and 1013 mbar) form, preferably in powder form with a total residual water content of 5 wt. % or less, preferably of 3 wt. % or less, more preferably of 1 wt. % or less, or is in the form of an aqueous or aqueous-alcoholic solution, wherein the total amount compounds of formula I and the physiologically acceptable salts thereof is in the range of 1 to 40 wt. %, more preferably in the range of 2 to 33 wt. %, even more preferably in the range of 3 to 25 wt. %, and most preferably in the range of 5 to 20 wt. %, in each case based on the total weight of the mixture.

Further purification of an extract according to the present invention, a mixture according to the present invention, and in particular of a composition comprising or consisting of one or more physiologically acceptable salts of one or more compounds of formula I (as defined above) may be further purified according to methods and materials described in U.S. Pat. No. 6,051,212, WO 96/38057 and/or JP 2006-176438 A, preferably centrifugation and/or filtration (including ultrafiltration and/or microfiltration), preferably using one or more sorbent (absorbent or adsorbent) materials selected from the group consisting of activated carbons, charcoal, ion exchange resins (preferably a weakly basic or weakly acidic ion exchange resin, macroporous ion exchange resins in turn being preferred), silica, alumina, kieselgur (diatomaceous earth, e.g. celite), glass particles, glass wool, glass fibers, zeolites (such as zeolite A, zeolite X, zeolite Y), silicates and aluminosilicates (preferably clays and clay minerals like bentonite, kaolinite, montmorillonite, smectite, illite, chlorite).

In a further aspect the present invention relates to a method of producing an extract comprising a compound of formula I or a mixture of two or more compounds of formula I (for use) according to the present invention, in particular a mixture comprising one or more compounds selected from the group consisting of compounds [1], [2], [3], [4], [5], [6], [7], [8], [9], [10], [11], [12], [13], [14], [18], [19], [20], and [21], comprising the following steps:

preferably providing a fungus of the family Dacrymycetaceae, preferably a fungus of the genera *Dacryopinax, Dacrymyces, Ditiola, Femsjonia* or *Guepiniopsis*, more preferably a fungus of the species *Dacryopinax spathularia*, carrying out a fermentation process such that one, two or more compounds of formula I are produced (preferably by said fungus of the family Dacrymycetaceae), setting the pH value of the fermentation broth to a value below 4, preferably to a pH value in the range of from 1 to 3.5, more preferably to a pH value in the range of from 1.5 to 3, keeping the resulting reaction mixture at a pH value below 4, preferably at a pH value in the range of from 1 to 3.5, more preferably to a pH value in the range of from 1.5 to 3, thereby partially or essentially precipitating one, two or more compounds of formula I, and washing the resulting precipitate comprising, essentially consisting of or consisting of one, two or more compounds of formula I, preferably with an aqueous diluent, more preferably with water, particularly preferably with demineralized water, optionally suspending the precipitate comprising, essentially consisting of or consisting of one, two or more compounds of formula I in an aqueous diluent, more preferably in water, particularly preferably in demineralized water, optionally removing water from the resulting product, preferably freeze-drying the resulting product, thereby preferably yielding an extract comprising, essentially consisting of or consisting of one, two or more compounds of formula I in solid (and preferably essentially water-free) form.

In a further aspect the present invention relates to a method of producing one or more physiologically acceptable salts of one or more compounds of formula I according to the present invention, in particular one or more physiologically acceptable salts of one, two or more compounds selected from the group consisting of compounds [1], [2], [3], [4], [5], [6], [7], [8], [9], [10], [11], [12], [13], [14], [18], [19], [20], and [21], comprising the following steps:

providing a fungus of the family Dacrymycetaceae, preferably a fungus of the genera *Dacryopinax, Dacrymyces, Ditiola, Femsjonia* or *Guepiniopsis*, more preferably a fungus of the species *Dacryopinax spathularia*, carrying out a fermentation process such that a compound of formula I or a mixture of two or more compounds of formula I is produced by said fungus, setting the pH value of the fermentation broth to a value below 4, preferably to a pH value in the range of from 1 to 3.5, more preferably to a pH value in the range of from 1.5 to 3, keeping the resulting reaction mixture at a pH value below 4, preferably at a pH value in the range of from 1 to 3.5, more preferably to a pH value in the range of from 1.5 to 3, thereby partially or essentially precipitating a compound of formula I or a mixture of two or more compounds of formula I, preferably washing the resulting precipitate (pellet) preferably with an aqueous diluent, more preferably with water, particularly preferably with demineralized water, suspending the resulting precipitate (pellet) in an aqueous diluent, more preferably in water, particularly preferably in demineralized water, setting the pH value of the suspension to a value in the range of 4.5 to 7.5, preferably in the range of 5 to 7, particularly preferably in the range of 5.5 to 6.5, by adding an inorganic base (solution or suspension), preferably sodium hydroxide, potassium hydroxide, calcium hydroxide, and/or magnesium hydroxide, and removing water from the resulting product, preferably drying, particularly freeze-drying the resulting product, thereby obtaining one or more physiologically acceptable salts of one or more compounds of formula I according to the present invention as a solid, preferably a powder, and preferably in essentially water-free form.

Preferably, the fermentation is carried out in the absence of an effective amount of visible light (i.e. light with a wavelength in the range 380 to 750 nm), more preferably in the absence of an effective amount of visible light and ultraviolet light, most preferably in the absence of an effective amount of light. Due to such measure the production of carotenoids, in particular beta-carotene, is minimized or avoided (in contrast to U.S. Pat. No. 2,974,044).

Preferably, the fermentation is carried out with one or more fungi selected from the group consisting of

*Dacryopinax aurantiaca, Dacryopinax crenata, Dacryopinax dennisii, Dacryopinax elegans, Dacryopinax felloi, Dacryopinax fissus, Dacryopinax foliacea, Dacryopinax formosus, Dacryopinax imazekiana, Dacryopinax indacocheae, Dacryopinax lowyi, Dacryopinax macrospora, Dacryopinax martinii, Dacryopinax maxidorii, Dacryopinax parmastoensis, Dacryopinax petaliformis, Dacryopinax spathularia, Dacryopinax sphenocarpa, Dacryopinax taibaishanensis, Dacryopinax xizangensis, Dacryopinax yungensis,*

*Dacrymyces ancyleus, Dacrymyces aureosporus, Dacrymyces australis, Dacrymyces capitatus, Dacrymyces chrysocomus, Dacrymyces chrysospermus, Dacrymyces cupularis, Dacrymyces dictyosporus, Dacrymyces enatus, Dacrymyces flabelliformis, Dacrymyces intermedius, Dacrymyces lacrymalis, Dacrymyces macnabbii, Dacrymyces minor, Dacrymyces novae-zelandiae, Dacrymyces ovisporus, Dacrymyces paraphysatus, Dacrymyces pinacearum, Dacrymyces punctiformis, Dacrymyces stillatus, Dacrymyces subarcticus, Dacrymyces tortus, Dacrymyces variisporus,*

*Ditiola abieticola, Ditiola brasiliensis, Ditiola coccinea, Ditiola nuda, Ditiola oblique, Ditiola orientalis, Ditiola pezizaeformis, Ditiola radicata,*

*Guepiniopsis alpina, Guepiniopsis buccina, Guepiniopsis estonica, Guepiniopsis oresbia, Guepiniopsis ovispora, Guepiniopsis pedunculata,* and *Guepiniopsis suecica.*

In a preferred embodiment, a material according to the present invention comprising an above defined (preferred or particularly preferred) total amount of water are selected from the group consisting of an O/W-emulsion, a hydrodispersion, a suspension, a solution, or a hydrogel.

Preferably, a material according to the present invention comprises a high proportion of water, preferably water in a total amount of 50 wt. % or more, more preferably of 60 wt. % or more, even more preferably 65 wt. % or more, particularly preferably 70 wt. % or more, and most preferably 75 wt. % or more, in each case based on the total weight of the material.

Preferably, the total amount of water is in the range of 70 to 99.5 wt. %, more preferably in the range of 75 to 99 wt. %, and most preferably in the range of 80 to 98 wt. %, in each case based on the total weight of the material.

The total amount of water of an orally consumable material according to the present invention, in particular of a ready-to-drink composition according to the present invention, is 60 wt. % or more, preferably 70 wt. % or more, more preferably 75 wt. % or more, even more preferably 80 wt. % or more, in each case based on the total weight of the orally consumable material.

Preferably, the total amount of water, preferably of nondeionized water, particularly of drinking water or mineral water, of an orally consumable material according to the present invention, in particular of a ready-to-drink composition according to the present invention, is in the range of from 82 wt. % to 98 wt. %, more preferably in the range of from 83 wt. % to 96 wt. %, even more preferably in the range of from 84 wt. % to 95 wt. %, and most preferably in the range of from 85 wt. % to 94 wt. %, in each case based on the total weight of the orally consumable material.

In a preferred embodiment, a material according to the present invention comprising an above defined (preferred or particularly preferred) total amount of water has a pH-value at 25° C. of 6.8 or less, preferably in the range of 1.5 to 6.5, more preferably in the range of 2.0 to 6.0, even more preferably in the range of 2.1 to 5.8, particularly preferably in the range of 2.2 to 5.0, and most preferably in the range of 2.3 to 4.5.

The pH-value of an orally consumable material according to the present invention, in particular of a ready-to-drink composition according to the present invention, when measured at 25° C. (and preferably at 1013 mbar) preferably is in the range of from 1.5 to 6.5, preferably in the range of from 1.8 to 6.0, more preferably in the range of from 2.0 to 5.5, even more preferably in the range of from 2.0 to 5.0, particularly preferably in the range of from 2.1 to 4.4, especially preferably in the range of from 2.2 to 4.2, and most preferably in the range of from 2.3 to 3.9.

It should be emphasized that the one or more compounds of the above formula I, one or more physiologically acceptable salts of a compound of the above formula I, or a mixture thereof are stable (preferably at temperatures of 40° C. or lower) for a long period of time (generally more than 16 weeks at 25° C.) in such aqueous materials at the acidic pH-values indicated hereinbefore, i.e. the compounds of the above formula I are not decomposed or degraded to an appreciable or significant extent.

In a preferred embodiment, a material according to the present invention (preferably comprising an above defined preferred or particularly preferred total amount of water and having a pH-value in a preferred or particularly preferred range indicated above) suitable for oral consumption, preferably a food or a beverage, comprises one or more organic food acids and/or the physiologically acceptable salt thereof, preferably selected from the group consisting of acetic acid, adipic acid, caffeotannic acid, citric acid, iso-citric acid, maleic acid, fumaric acid, galacturonic acid, glucuronic acid, glyceric acid, glycolic acid, lactic acid, malic acid, oxalic acid, pyruvic acid, quinic acid, succinic acid, tannic acid, tartaric acid, and the physiologically acceptable salts thereof, preferably the sodium and/or potassium and/or calcium and/or magnesium salts thereof thereof, and/or one or more edible inorganic acids and/or the physiologically acceptable salt thereof, preferably selected from the group consisting of phosphoric acid, pyrophosphoric acid, polyphosphoric acids, and bisphosphonic acids (in particular those explicitly mentioned in paragraph [0050] of US 2010/0151104 A1), and the physiologically acceptable salts thereof, and/or one or more high potency sweeteners, preferably selected from the group consisting of magap, sodium cyclamate, acesulfame K, neohesperidin dihydrochalcone, saccharin sodium salt, aspartame, superaspartame, neotame, alitame, sucralose, stevioside, rebaudiosides (preferably rebaudioside A), lugduname, carrelame, sucrononate, sucrooctate, monatin, phyllodulcin, hernandulcin, dihydrochalcone glycosides, glycyrrhizin, glycyrrhetinic acid and its sweet tasting physiologically acceptable salts, preferably glycyrrhetinic acid ammonium salt, mogrosides, liquorice extracts (*Glycyrrhizza glabra* ssp.), *Lippia dulcis* extracts, *Momordica* ssp. extracts (in particular *Momordica grosvenori* [Luo Han Guo]), *Hydrangea dulcis* extracts and *Stevia* ssp. (e.g. *Stevia rebaudiana*) extracts, preferably one or more high potency sweeteners in a total amount isosweet to or sweeter than a 1.0 wt. % solution of sucrose in water, more preferably in a total amount isosweet to or sweeter than a 2.0 wt. % solution of sucrose in water, even more preferably in a total amount isosweet to or sweeter than a 3.0 wt. % solution of sucrose in water, particularly preferably in a total amount isosweet to or sweeter than a 4.0 wt. % solution of sucrose in water, and/or one or more sweet tasting mono- or disaccharides, preferably selected from the group consisting of sucrose, lactose, maltose, glucose, and fructose, the total amount of said sweet tasting mono- or disaccharides being in the range of 1.5 to 19 wt. %, preferably in the range of 2.5 to 16 wt. %, more preferably in the range of 3.5 to 14 wt. %, particularly preferably in the range of 4.5 to 13 wt. %, and most preferably in the range of 5.5 to 12 wt. %, in each case based on the total weight of the material, and preferably one, two, three, four, five or more flavouring agents, preferably having a molecular weight in the range of 120 to 300 g/mol, more preferably in the range of 130 to 280 g/mol.

The one or more compounds of formula I and/or the physiologically acceptable salts thereof, especially as defined in one of the preferred or particularly preferred embodiments, and the mixtures as defined in one of the preferred or particularly preferred embodiments, allow the prevention of spoilage of materials with such a high proportion of water (and preferably a pH-value at 25° C. in the range of 2.2 to 4.6) by microorganisms, within a sealed container for a period of at least 12 weeks, preferably at least 16 weeks at 25° C. Thus, a reduction or substitution of conventional preservatives (that may pose health and/or environmental concerns) is possible.

The one or more compounds of formula I and/or the physiologically acceptable salts thereof, especially as defined in one of the preferred or particularly preferred embodiments, and the mixtures as defined in one of the preferred or particularly preferred embodiments, allow to be used together in other known beverage preserving agents in an additive or synergistic manner to reduce the amount of preservative required and so improve the inventive beverage's sensory impact over beverages having conventional preservatives. Such other known beverage preserving agents are preferably selected from the group consisting of ethyl-N-alpha-lauroyl-L-arginate (LAE) and its hydrochloride, dimethyl dicarbonate, trans-cinnamic acid, EDTA (ethylene diamine tetraacetic acid) and its physiologically acceptable salts, preferably the sodium and/or calcium salts thereof, EDDS (ethylene diamine-N,N'-disuccinic acid) and its physiologically acceptable salts, preferably the sodium and/or calcium salts thereof, polyphosphoric acid and its physiologically acceptable salts (preferably comprising or consisting of sodium hexametaphosphate), bisphosphonic acids and bis-phosphonates (in particular those explicitly mentioned in paragraph [0050] of US 2010/0151104 A1), and the mixtures thereof.

The total amount of ethyl-N-alpha-lauroyl-L-arginate and its hydrochloride preferably is in the range of 1 to 25 ppm, more preferably 2 to 12 ppm, based on the total weight of the beverage.

The total amount of dimethyl dicarbonate preferably is in the range of 20 to 500 ppm, more preferably 50 to 250 ppm, based on the total weight of the beverage.

The total amount of trans-cinnamic acid preferably is in the range of 1 to 40 ppm, more preferably 2 to 30 ppm, based on the total weight of the beverage.

The total amount of EDTA (ethylene diamine tetraacetic acid) and its physiologically acceptable salts is in the range of 0.5 to 50 ppm, more preferably 1 to 30 ppm, based on the total weight of the beverage.

The total amount of EDDS (ethylene diamine-N,N'-disuccinic acid) and its physiologically acceptable salts is in the range of 1 to 500 ppm, more preferably 20 to 450 ppm, based on the total weight of the beverage.

The total amount of polyphosphoric acid and its physiologically acceptable salts is in the range of 10 to 1500 ppm, based on the total weight of the beverage.

As already mentioned above, the compounds of formula I, preferably the compounds [1], [2], [3], [4], [5], [6], [7], [8], [9], [10], [11], [12], [13], [14], [18], [19], [20], [21], and the physiologically acceptable salts thereof do not exhibit a distinctive taste or unpleasant mouth feeling, in particular no off-flavours, in particular in the total amounts used in the ready-to-use product.

The total amount of the compounds of formula I, preferably of the compounds [1], [2], [3], [4], [5], [6], [7], [8], [9], [10], [11], [12], [13], [14], [18], [19], [20], [21] and the physiologically acceptable salts thereof, more preferably of the compounds [1], [4], [5], [6], [7], [8], [9], [10], [12], [13], [14], [18], and the physiologically acceptable salts thereof, preferably is in the range of 0.1 to 1000 ppm, more preferably of 0.5 to 500 ppm, particularly preferably of 1 to 250 ppm, and most preferably of 2 to 150 ppm, in each case based on the total weight of the orally consumable material according to the present invention, particularly a food or beverage according to the present invention.

Therefore, the compounds of formula I and the physiologically acceptable salts thereof are preferably used in orally consumable materials, particularly foods or beverages, according to the invention, in combination with one or more flavouring agents, preferably having a molecular weight in the range of 120 to 300 g/mol, more preferably in the range of 130 to 280 g/mol.

Preferably, one, two, three or more of said flavouring agents are fresh, sweet, fruity, spicy and/or herbal flavouring agents, preferably selected from the group consisting of menthol (preferably L-menthol, D-menthol, racemic menthol, isomenthol, neoisomenthol, neomenthol), isomenthone, menthone, peppermint oil, L-carvone, D-carvone, spearmint oil, cineol, *eucalyptus* oil, cinnamaldehyde (preferably trans-cinnamaldehyde), cinnamic alcohol, cinnamon bark oil, cinnamon leaf oil, methyl cinnamate, benzaldehyde, furfural, furfuryl alcohol, methyl salicylate, wintergreen oil, thyme oil, thymol, carvacrol, clove oil, camphene, p-cymene, alpha-terpinene, borneol, eugenol, anise oil, star anise oil, anethole (preferably trans-anethole), anisole, cis-3-hexenol, cis-3-hexenyl acetate, D-limonene, L-limonene, linalool, citral, geraniol, geranyl acetate, nerol, citronellol, citronellal, alpha-phellandrene, beta-phellandrene, alpha-pinene, beta-pinene, vanilla extract, vanillin, ethylvanillin, 2-hydroxy-4-methoxybenzaldehyde, 2,5-dimethyl-4-hydroxy-3(2H)-furanone, 2-ethyl-4-hydroxy-5-methyl-3(2H)-furanone, 2-ethyl-5-methyl-4-hydroxy-3(2H)-furanone, 5-ethyl-2-methyl-4-hydroxy-3(2H)-furanone, 3-hydroxy-4,5-dimethyl-2(5H)-furanone, maltol, ethylmaltol, coumarin, butyrolactone, gamma-undecalactone, gamma-nonalactone, 4-methyl-delta-lactone, *massoia* lactone, sotolon, delta-decalactone, tuberolactone, methyl sorbate, 2-hydroxy-3-methyl-2-cyclopentenones, n-butyl acetate, isoamyl acetate, ethyl butyrate, n-butyl butyrate, isoamyl butyrate, ethyl 3-methyl-butyrate, ethyl n-hexanoate, allyl n-hexanoate, n-butyl n-hexanoate, ethyl n-octanoate, ethyl-3-methyl-3-phenylglycidate, ethyl-2-trans-4-cis-decadienoate, 4-(p-hydroxyphenyl)-2-butanone, 1,1-dimethoxy-2,2,5-trimethyl-4-hexane, 2,6-dimethyl-5-hepten-1-al, and phenylacetaldehyde.

Preferably, one, two, three or more of said flavouring agents are sweet, fruity and/or spicy flavouring agents, preferably selected from the group consisting of trans-cinnamaldehyde, cinnamic alcohol, methyl cinnamate, benzaldehyde, furfural, furfuryl alcohol, camphene, p-cymene, alpha-terpinene, borneol, eugenol, trans-anethole, anisole, cis-3-hexenol, cis-3-hexenyl acetate, D-limonene, L-limonene, linalool, citral, geraniol, geranyl acetate, nerol, citronellol, citronellal, alpha-phellandrene, beta-phellandrene, alpha-pinene, beta-pinene, vanilla extract, vanillin, ethylvanillin, 2-hydroxy-4-methoxybenzaldehyde, 2,5-dimethyl-4-hydroxy-3(2H)-furanone, 2-ethyl-4-hydroxy-5-methyl-3(2H)-furanone, 2-ethyl-5-methyl-4-hydroxy-3(2H)-furanone, 5-ethyl-2-methyl-4-hydroxy-3(2H)-furanone, 3-hydroxy-4,5-dimethyl-2(5H)-furanone, maltol, ethylmaltol, coumarin, gamma-undecalactone, gamma-nonalactone, 4-methyl-delta-lactone, *massoia* lactone, sotolon, delta-decalactone, tuberolactone, methyl sorbate, n-butyl acetate, isoamyl acetate, ethyl butyrate, n-butyl butyrate, isoamyl butyrate, ethyl 3-methyl-butyrate, ethyl n-hexanoate, allyl n-hexanoate, n-butyl n-hexanoate, ethyl n-octanoate, ethyl-3-methyl-3-phenylglycidate, ethyl-2-trans-4-cis-decadienoate, 4-(p-hydroxyphenyl)-2-butanone, 2,6-dimethyl-5-hepten-1-al, and phenylacetaldehyde.

The present invention also relates to foods, such as meat, meat products, fish and seafood products, with an increased shelf life stability and an increased resistance against the growth of Gram-positive bacteria. The preparation process for manufacturing foodstuffs using the compounds of formula I and/or the physiologically acceptable salts thereof according to the invention comprises, for example, combining an uncooked meat, meat products, fish or seafood product with one or more phosphates, one or more lactates, lactic acid, and preferably further and/or a flavouring agent, followed by further processing such as packing or cooking. In this specific aspect, the present invention makes use of phosphates which are functional in protein activation of meat, meat products, fish or seafood and have also properties to absorb lactates and flavouring agents.

In this context the present invention relates to a foodstuff treatment composition, particularly for the treatment of meat, meat products, fish and seafood products, said composition comprising (i) one or more compounds of formula I and/or the physiologically acceptable salts thereof, (ii) lactic acid and/or lactates, and (iii) one or more phosphates.

In a preferred embodiment of the invention said foodstuff treatment composition comprises (i) one, two, three or more of compounds [1], [2], [3], [4], [5], [6], [7], [8], [9], [10], [11], [12], [13], [14], [18], [19], [20], [21] and/or the physiologically acceptable salts thereof, preferably in a total amount of 0.0001 to 1 wt. %, more preferably in a total amount of 0.0005 to 0.5 wt. %, even more preferably in a total amount of 0.001 to 0.1 wt. %, particularly preferably in a total amount of 25 to 500 ppm, (ii) sodium lactate and/or potassium lactate, preferably in a total amount of 0.5 to 25 wt. %, more preferably in a total amount of 1 to 20 wt. %, even more preferably in a total amount of 1.5 to 15 wt. %, (iii) one or more sodium and/or potassium phosphates selected from the group consisting of sodium and/or potassium orthophosphates, pyrophosphates (diphosphates), metaphosphates, and polyphosphates (hexametaphosphates), preferably in a total amount of 1 to 45 wt. %, more preferably in a total amount of 2 to 30 wt. %, even more preferably in a total amount of 3 to 25 wt. %, (iv) preferably water, more preferably water in a total amount of 50 wt. % or more, even more preferably in a total amount of 60 wt. % or more, and optionally (v) one or more further constituents selected from the group consisting of sodium chloride, sodium nitrite, potassium nitrite, sodium nitrate, potassium nitrate, calcium lactate, sodium diacetate, acetic acid, sodium acetate, sodium diacetate, potassium acetate, potassium diacetate citric acid, and sodium citrate, wherein the amounts in each case are based on the total weight of the foodstuff treatment composition.

In another preferred embodiment of the invention the one or more sodium and/or potassium phosphate salts of constituent (iii) are selected from trisodium phosphate ($Na_3PO_4$), tetrasodium pyrophosphate ($Na_4P_2O_7$), sodium tripolyphosphate ($Na_5P_3O_{10}$), tripotassium phosphate ($K_3PO_4$), tetrapotassium pyrophosphate ($K_4P_2O_7$), potassium tripolyphosphate ($K_5P_3O_{10}$), and sodium hexametaphosphate ($NaPO_3)_6$.

These foodstuff treatment compositions are particularly useful for the treatment of meat, meat products, fish and seafood products, to increase the resistance of the foodstuff against the growth of bacteria, in particular of the genera *Listeria* (particularly *Listeria monocytogenes*), *Lactobacillus, Clostridia, Micrococcus* (particularly *Micrococcus luteus*), and/or *Bacillus* (particularly *Bacillus cereus*), whereby the foodstuff treatment composition is applied to the food in an amount to achieve a total amount of 0.25 to 6 wt %, preferably of 0.5 to 4 wt. %, of constituents (ii) lactic acid and lactates and (iii) phosphates in the final treated foodstuff.

In a preferred embodiment, a material according to the present invention (preferably comprising an above defined preferred or particularly preferred total amount of water and having a pH-value in a preferred or particularly preferred range indicated above) is a cosmetic product suitable for topical application onto the mucous membrane (mucosa) and/or the epidermis of a mammal, preferably in the form of an O/W-lotion, a milk, a (hydro)gel, a body care and/or hair care product (such as preferably a shower gel and/or a shampoo, a hair conditioning product, or a deodorant), comprises one or more surfactants not corresponding to formula I as defined in the context of the present invention, preferably one or more surfactants selected from the group consisting of anionic tensides, cationic tensides, non-ionic tensides, amphoteric (zwitterionic) tensides, and biosurfactants, and/or one or more mono-, di- or triols having 2 to 14 carbon atoms, preferably one or more di- or triols having 3 to 12 carbon atoms, wherein preferably the total amount of mono-, di- and triols is 1 wt. % or more, more preferably in the range of 1.1 to 30 wt. %, and/or one or more fragrance substances, preferably a mixture of three, five, eight or more fragrance substances, more preferably a perfume, preferably fragrance substances in a total amount of 0.1 to 3 wt. %, more preferably in a total amount of 0.15 to 2 wt. %, even more preferably in a total amount of 0.2 to 1 wt. %, wherein the percentages in each case are based on the total weight of the cosmetic product.

Preferably one, several or all mono-, di- or triols having 2 to 14 carbon atoms are selected from the group consisting of ethanol, 1-propanol, 2-propanol, ethylene glycol, 1,2-propylene glycol, glycerol (glycerin), 1,3-propandiol, 2-methyl-1,3-propandiol, trimethylolpropane, 1,2-butandiol, 1,3-butandiol, 1,4-butandiol, 1,2,3-butantriol, 1,2,4-butantriol, 1-pentanol, 2-pentanol, 3-pentanol, 1,2-pentandiol, 1,3-pentandiol, 1,5-pentandiol, 1-hexanol, 2-hexanol, 3-hexanol, 1,2-hexandiol, 1,3-hexandiol, dipropylene glycol, 1-octanol, 2-octanol, 3-octanol, 1,2-octandiol (caprylyl glycol), 1,3-octandiol, 2-methyl-5-cyclohexylpentanol, 2-methyl-4-phenyl-2-butanol, 4-methyl-4-phenyl-2-pentanol (dimethyl phenyl 2-butanol), 1-decanol, 2-decanol, 1,2-decandiol, 3-(2-ethylhexyloxy)propane-1,2-diol (ethylhexylglycerin, octoxyglycerin), 1-dodecanol, 2-dodecanol, 1,2-dodecandiol, 1,12-dodecandiol, 1-tetradecanol, 2-tetradecanol, 1,2-tetradecandiol and 1,14-tetradecandiol, wherein preferably the total amount of mono-, di- and triols having 2 to 14 carbon atoms is 0.5 wt. % or more, more preferably 1.0 wt. % or more, even more preferably 1.25 wt. % or more, and preferably is in the range of 1.25 to 25 wt. %, particularly in the range of 1.5 to 20 wt. %, in each case based on the total weight of the cosmetic product.

Preferably one, several or all di- or triols having 3 to 12 carbon atoms are selected from the group consisting of 1,2-propylene glycol, glycerol (glycerin), 1,3-propandiol, 2-methyl-1,3-propandiol, trimethylolpropane (2-(hydroxymethyl)-2-ethylpropane-1,3-diol), 1,2-butandiol, 1,4-butandiol, 1-pentanol, 2-pentanol, 1,2-pentandiol, 1,5-pentandiol, 1-hexanol, 2-hexanol, 1,2-hexandiol, dipropylene glycol, 1-octanol, 2-octanol, 1,2-octandiol, 2-methyl-4-phenyl-2-butanol, 4-methyl-4-phenyl-2-pentanol, 1-decanol, 1,2-decandiol, 1-dodecanol, 1,2-dodecandiol, 1,12-dodecandiol, and 3-(2-ethylhexyloxy)propane-1,2-diol (ethylhexylglycerin), wherein preferably the total amount of di- and triols having 3 to 12 carbon atoms is 0.5 wt. % or more, more preferably 1.0 wt. % or more, even more preferably is in the range of 1.25 to 15 wt. %, particularly in the range of 1.5 to 10 wt. %, in each case based on the total weight of the cosmetic product.

The anionic tensides, cationic tensides non-ionic tensides, amphoteric (zwitterionic) tensides, and biosurfactants are preferably selected from
  anionic tensides based on permanent anions (sulfate, sulfonate, phosphate) or pH-dependent anions (carboxylate), preferably sulfates [alkyl sulfates, such as ammonium lauryl sulfate, sodium lauryl sulfate (SDS, sodium dodecyl sulfate), alkyl ether sulfates, such as sodium laureth sulfate, also known as sodium lauryl ether sulfate (SLES), sodium myreth sulfate], sulfonates [docusates, such as dioctyl sodium sulfosuccinate, sulfonate fluorosurfactants (perfluorooctanesulfonate (PFOS), perfluorobutanesulfonate), alkyl benzene sulfonates], phosphates [alkyl aryl ether phosphate, alkyl ether phosphate], carboxylates [alkyl carboxylates, fatty acid salts (soaps), such as sodium stearate, sodium lauroyl sarcosinate, carboxylate fluorosurfactants, such as perfluorononanoate, perfluorooctanoate (PFOA or PFO)],
  cationic tensides based on pH-dependent primary, secondary, or tertiary amines (such as octenidine dihydrochloride, quaternary ammonium cations, preferably alkyltrimethylammonium salts (such as cetyl trimethylammonium bromide (hexadecyl trimethyl ammonium bromide), cetyl trimethylammonium chloride, cetylpyridinium chloride, benzalkonium chloride, benzethonium chloride, dimethyldioctadecylammonium chloride and dioctadecyldimethylammonium bromide),
  zwitterionic (amphoteric) tensides based on primary, secondary, or tertiary amines or quaternary ammonium cation with sulfonates (such as (3-[(3-cholamidopropyl)dimethylammonio]-1-propanesulfonate) (CHAPS), sultaines (such as cocamidopropyl hydroxysultaine), carboxylates (e.g. from amino acids, imino acids), betaines (such as cocamidopropyl betaine), and phosphates (such as lecithins),
  nonionic tensides, preferably fatty alcohols (such as cetyl alcohol, stearyl alcohol, cetostearyl alcohol (essentially consisting of cetyl and stearyl alcohols), oleyl alcohol), polyoxyethylene glycol alkyl ethers $CH_3$—$(CH_2)_{10\text{-}16}$—$(O$—$C_2H_4)_{1\text{-}25}$—$OH$ (such as octaethylene glycol monododecyl ether, pentaethylene glycol monododecyl ether), polyoxypropylene glycol alkyl ethers $CH_3$—$(CH_2)_{10\text{-}16}$—$(O$—$C_3H_6)_{1\text{-}25}$—$OH$, glucoside alkyl ethers $CH_3$—$(CH_2)_{10\text{-}16}$—$(O$-glucoside$)_{1\text{-}3}$-$OH$ (such as decyl glucoside, lauryl glucoside, octyl glucoside), polyoxyethylene glycol octylphenol ethers $C_8H_{17}$—$(C_6H_4)$—$(O$—$C_2H_4)_{1\text{-}25}$—$OH$ (such as Triton X-100), polyoxyethylene glycol alkylphenol ethers $C_9H_{19}$—$(C_6H_4)$—$(O$—$C_2H_4)_{1\text{-}25}$—$OH$ (such as nonoxynol-9), glycerol alkyl esters (such as glyceryl laurate), polyoxyethylene glycol sorbitan alkyl esters (such as polysorbates, preferably polysorbate 20, polysorbate 40, polysorbate 60, polysorbate 65, polysorbate 80, polysorbate 85 and/or polysorbate 120; these are all commercially available, e.g. under the brand names Canarcel® or Tween®), sorbitan alkyl esters, cocamide MEA, cocamide DEA, dodecyldimethylamine oxide, block copolymers of polyethylene glycol and polypropylene glycol (such as poloxamers (commercially available, e.g. under the brand name Pluronic®)), and polyethoxylated tallow amine (POEA),
  biosurfactants, preferably sophoroplipids, rhamnolipids, mannosyl-erythritol lipids, and lipopeptides (preferred lipopeptides are chlamydocin, surfactin, lichenysin G, and fengycin-like lipopeptides).

Preferably, one, two, three, four, five or more fragrance substances with one or more notes selected from the group fresh, floral (flowery), aldehydic, watery, fruity, sweet, woody, musky, green and herbal, more preferably with one or more notes selected from the group floral (preferably rose and/or lily-of-the-valley (muguet)), aldehydic, vanilla, citrus, sandalwood, and musk.

The epidermis refers to the outermost layers of cells in the skin of a mammal, in particular certain parts of the body of a human being, namely hand, arm, foot, head and axillary region (particularly the armpit). The mucous membrane (mucosa) lines cavities that are exposed to the external environment and internal organs, particularly at the nostrils, the mouth (oral cavity), the lips, the eyelids, and the genital area.

A cosmetic deodorant composition according to the present invention preferably comprises
  an antimicrobial effective amount of one or more compounds of formula I and/or the physiologically acceptable salts thereof, preferably 2 ppm or more, more preferably 5 ppm or more, even more preferably 10 ppm or more,
  water, preferably in a total amount of 10 wt. % or more, more preferably in a total amount of 50 wt. % or more, particularly preferably in a total amount of 60 wt. % or more, one or more alcohols selected from the group consisting of ethanol, 1,2-propylene glycol, glycerol (glycerin), 2-methyl-1,3-propandiol, 1,2-butandiol, 1,3-butandiol 1,4-butandiol, 1,2,4-butantriol, 1-pentanol, 1,2-pentandiol, 1,5-pentandiol, 1,2-hexandiol, 1-octanol, 1,2-octandiol, and 3-(2-ethylhexyloxy)propane-1,2-diol (ethylhexylglycerin, octoxyglycerin), preferably in a total amount of 1.5 wt. % or more, more preferably in a total amount of 2.5 wt. % or more, wherein the amounts indicated in each case relate to the total weight of the cosmetic deodorant composition.

Such a cosmetic deodorant composition according to the present invention preferably additionally comprises one or more constituents selected from the group consisting of antiperspirants, fragrance substances, and further surfactants.

Antiperspirants inhibit the secretion of sweat. As antiperspirants astringent metal salts are generally used, in particular inorganic and organic metal salts of the elements aluminum, zinc, magnesium, tin and zirconium as well as mixtures thereof are used. Frequently, aluminum and zirconium salts and their mixtures are also used in complex form, with propylene glycol, polyethylene glycol or glycerin being used as complexing agents. One ore more antiperspirants are preferably selected from the group consisting of aluminium chlorohydrate; aluminium sesquichlorohydrate, aluminium chlorohydrex propylene glycol, aluminium dichlorohydrex propylene glycol, aluminium sesquichlorohydrex propylene glycol, aluminium chlorohydrex polyethylene glycol, aluminium dichlorohydrex polyethylene glycol, aluminium sesquichlorohydrex polyethylene glycol, aluminium chloride, aluminium zirconium chlorohydrate, aluminium zirconium trichlorohydrate, aluminium zirconium tetrachlorohydrate, aluminium zirconium pentachlorohydrate, aluminium zirconium octachlorohydrate, aluminium zirconium trichlorohydrex-glycerin, aluminium zirconium tetrachlorohydrex-glycerin, aluminium zirconium pentachlorohydrex-glycerin, aluminium zirconium octachlorohydrex-glycerin, basic aluminium chloride, zirconium hydroxychloride, zirconium chloride.

Preferably one or more of the further surfactants are selected from the group consisting of anionic tensides, cationic tensides, non-ionic tensides, or amphoteric tensides explicitly mentioned above.

Examples of preferred materials according to the present invention, particularly orally consumable materials, are fruit or vegetable containing products (preferably products containing juice, extract, puree, mash, pulp, concentrate, dried parts of lemon, lime, grapefruit, orange, sweet orange, bitter orange, bergamot, mandarin, apple, pear, prickly pear, peach, apricot, fig, pineapple, prune, mango, melon, plum, kiwi, lychee, banana, cherry, sweet cherry, strawberry, raspberry, red currant, black currant, blackberry, blueberry, marionberry, passion fruit, grapes (white grape, red grape, green grape, purple grape), pomegranate, acerola, tomato, carrot, parsnip, pumpkin, lettuce, cabbage, fermeted cabbage, bean, pea, potato, bell pepper, red chilli, green chilli, onion, celery, cucumber, leek, broccoli, cauliflower, radish, aubergine, zucchini), soy based products (preferably soy milk, soy drinks, soy yoghurts), non-alcoholic beverages and syrups (preferably lemonades, beverage concentrates (syrups), non-carbonated soft drinks, and carbonated soft drinks), alcoholic beverages, products containing 50 wt. % or more of water and one or more other extracts from herbs and/or spices (preferably selected from the group consisting of vanilla, cinnamon, anise, fennel, clove, cardamom, tamarind, nutmeg, allspice, black pepper, licorice, ginger, rose hip, green tea, red tea, rooibos tea, mate tea, honeybush tea, pu-erh tea, oolong tea, black tea, coffee bean, cocoa bean, peppermint, spearmint, and wintergreen), non-frozen fermented or non-fermented dairy or dairy-based products (preferably milk, quark, cream cheese, cheese, custards, puddings, mousses, milk based drinks, drink yoghurts, and yoghurts), frozen products (preferably ice-cream, frozen yoghurt, sorbet, ice milk, frozen custard, water-ices, granitas, sherbets, and frozen fruit purees), doughs and batters (preferably pancake batter, wafle dough, cake doughs, bread dough, bun dough, pasta doughs), O/W-emulsions (spreads, sauces, and (salad) dressings).

In a preferred embodiment, the one or more compounds of formula I and/or the physiologically acceptable salts thereof (for use) according to the present invention, the extracts according to the present invention are combined with one or more ingredients selected from the group consisting of lactic acid, lactose, sucrose, calcium salts (preferably calcium phosphate, calcium gluconate, calcium lactate, and calcium chloride), calcium oxide, magnesium salts, magnesium oxide, iron salts (preferably ferrous fumarate, ferrous succinate, iron sucrate-malate, iron fructate-malate, iron sucrate-citrate, iron fructatecitrate, iron sucrate-ascorbate, iron fructate-ascorbate, and mixtures thereof), vitamin A (particularly retinol (vitamin A1)), vitamin B6, vitamin B12, vitamin C, vitamin D, vitamin E, thiamine, niacin, biotin, riboflavin, pantothenic acid, phytic acid, daidzein, genistein, proteins (preferably casein, caseinates (preferably sodium caseinate), milk protein, milk protein hydrolyzate, milk protein isolate, whey protein, whey protein hydrolyzate, whey protein isolate, soy protein, soy protein hydrolyzate, soybean protein isolate), milk powder, soy powder, polyunsaturated fatty acids [preferably omega-3-, omega-6- and/or omega-9-fatty acids, preferably selected from the group consisting of docosahexaenoic acid (DHA, all-cis-docosa-4,7,10,13,16,19-hexaenoic acid), eicosatetraenoic acid (ETA, all-cis-8,11,14,17-eicosatetraenoic acid), eicosatetraenoic acid (ETA, all-cis-8,11,14,17-eicosatetraenoic acid), stearidonic acid (SDA, all-cis-6,9,12,15-octadecatetraenoic acid), docosapentaenoic acid (DPA; clupanodonic acid, all-cis-7,10,13,16,19-docosapentaenoic acid), linoleic acid, α-linolenic acid (all-cis-9,12,15-octadecatrienoic acid), and γ-linolenic acid], soy oil, butterfat, (refined) fish oil, algal oil, squid oil, flaxseed oil, grape seed oil, and triglycerides derived from the fatty acids myristic acid, palmitic acid and/or oleic acid, thereby forming preferred materials according to the present invention, particularly materials suitable for oral consumption.

Preferably, a material according to the present invention (preferably comprising an above defined preferred or particularly preferred total amount of water and having a pH-value in a preferred or particularly preferred range indicated above) suitable for oral consumption comprises a total amount of glutamic acid and sodium glutamate of less than 0.2 wt. %, preferably of less than 0.15 wt. %, more preferably of less than 0.1 wt. %, particularly preferably of less than 0.05 wt. %, and most preferably is free of glutamic acid and sodium glutamate.

Examples of stabilizers and/or thickeners which may be part of a (preferably orally consumable) material according to the present invention are preferably selected from the group consisting of carbohydrate polymers (polysaccharides, preferably starches, polydextrose (E-number E1200), physically modified starches, chemically modified starches (preferably oxidized starch (E-number E1404), monostarch phosphate (E-number E1410), distarch phosphate (E-number E1412), phosphated distarch phosphate (E-number E1413), acetylated distarch phosphate (E-number E1414), acetylated starch (starch acetate esterified with acetic anhydride; E-number E1420), acetylated distarch adipate (E-number E1422), hydroxy propyl starch (E-number E1440), hydroxy propyl distarch phosphate (E-number E1442) starch sodium octenyl succinate (E-number E1450), and acetylated oxidized starch (E-number E1451)), cyclodextrins, celluloses, modified celluloses (preferably methylcellulose, ethylcellulose, hydroxymethyl cellulose, hydroxyethyl cellulose, hydroxypropyl cellulose, hydroxyethyl methylcellulose, hydroxypropyl methylcellulose), gum Arabic (gum acacia), gum ghatti, gum tragacanth, gum karaya, carrageenan, guar gum, carob gum (carob flour, locust bean gum, E-number E410), alginates, pectins, inulin and xanthan gum.

In a further preferred embodiment the total amount of compounds of formula I and the physiologically acceptable salts thereof in an orally consumable material according to the present invention, in particular of a ready-to-drink composition according to the present invention, is in the range of from 1 to 200 ppm, more preferably in the range of from 2 to 150 ppm, even more preferably in the range of from 5 to 100 ppm, in each case based on the total weight of the orally consumable material.

Preferably, the total amount of glucose, fructose and sucrose of an orally consumable material according to the present invention, in particular of a ready-to-drink composition according to the present invention, is in the range of from 1.5 to 15.0 wt. %, more preferably in the range of from 2.0 to 12.0 wt. %, even more preferably in the range of from 2.5 to 10.5 wt. %, particularly preferably in the range of from 3.0 to 9.5 wt. %, in each case based on the total weight of the orally consumable material.

Glucose, fructose and sucrose are commercially readily available from various sources and in various forms, and may be obtained from suitable plant sources, for example from sugar beet (*Beta vulgaris* ssp., sugar fractions, sugar syrup, molasses), from sugar cane (*Saccharum officinarum* ssp., e.g. molasses, sugar syrups), from sugar maple (*Acer* ssp.), from agave (agave thick juice), sorghum, certain palm trees, invert sugar syrup, high fructose corn syrup (HFCS, also called glucose-fructose syrup, e.g. made from wheat or corn starch), or fruit concentrates (e.g. from apples or pears, apple syrup, pear syrup).

In a preferred embodiment, an orally consumable material according to the present invention, in particular a ready-to-drink composition according to the present invention, preferably comprises one, two, three or more fruity flavouring agents having a molecular weight in the range of 135 to 190 g/mol, more preferably a molecular weight in the range of 135 to 180 g/mol, said fruity flavouring agents preferably imparting a flavour note selected from the group consisting of lemon, lime, grapefruit, orange, sweet orange, bitter orange, bergamot, mandarin, apple, pear, prickly pear, peach, apricot, pineapple, prune, mango, melon, plum, kiwi, lychee, banana, cherry, sweet cherry, strawberry, raspberry, red currant, black currant, blackberry, blueberry, passion fruit, grape, pomegranate, acerola, coconut, vanilla and mixtures thereof.

Preferably, an orally consumable material according to the present invention, in particular of a ready-to-drink composition according to the present invention, comprises one or more organic food acids (i.e. organic acids suitable for oral consumption), preferably selected from the group consisting of acetic acid, adipic acid, caffeotannic acid, citric acid, iso-citric acid, maleic acid, fumaric acid, galacturonic acid, glucuronic acid, glyceric acid, glycolic acid, lactic acid, malic acid, oxalic acid, pyruvic acid, quinic acid, succinic acid, tannic acid, tartaric acid, and the physiologically acceptable salts thereof, preferably the sodium and/or potassium and/or calcium and/or magnesium salts thereof.

Preferred physiologically acceptable salts of phosphoric acid are for example sodium acetate, monosodium phosphate, disodium phosphate, monopotassium phosphate, dipotassium phosphate, sodium hexametaphosphate, and sodium bis-phosphonates.

Preferably, an orally consumable material according to the present invention, in particular a ready-to-drink composition according to the present invention, comprises one or more acids selected from the group consisting of citric acid, tartaric acid, lactic acid, malic acid, maleic acid, fumaric acid, phosphoric acid, pyrophosphoric acids, polyphosphoric acids, bisphosphonic acids and the physiologically acceptable salts thereof.

A more preferred orally consumable material according to the present invention, in particular a ready-to-drink composition according to the present invention, comprises
  sucrose, and/or
  a mixture of glucose and fructose, wherein the amount of fructose is in the range of from 30 to 95 wt. %, preferably 40 to 92 wt. %, based on the total amount of glucose and fructose in the orally consumable material.

Another preferred orally consumable material according to the present invention, in particular a ready-to-drink composition according to the present invention, comprises one or more further constituents suitable for consumption selected from:
  one or more emulsifiers, and/or
  one or more antioxidants and optionally one or more substances for intensifying the antioxidative effect of said antioxidants, and/or
  one or more preservatives, and/or
  one or more vitamins and the physiologically acceptable salts or esters thereof, and/or
  one or more coloring agents, and/or
  one or more weighting agents, and/or
  one or more sugar alcohols, and/or
  one or more high potency sweeteners, preferably one or more naturally occurring high potency sweeteners, and/or
  one or more stabilizers and/or thickeners.

Preferably, an orally consumable material according to the present invention, in particular a ready-to-drink composition according to the present invention, comprises one or more further constituents suitable for oral consumption, particularly
  one or more emulsifiers, preferably selected from the group consisting of lecithins (preferably naturally occurring lecithins, particularly lecithin from egg or soy), phospholipids (preferably phosphatidylcholines), monoacylglycerols, and diacylglycerols, and/or
one or more antioxidants and optionally one or more substances for intensifying the antioxidative effect of said antioxidants,
and/or
one or more preservatives (preferably selected from the group consisting of benzoic acid, sodium benzoate, potassium benzoate, sorbic acid, sodium sorbate, sodium sorbate, butylated hydroxyanisole (BHA), and butylated hydroxytoluene (BHT)), preferably in a total amount of from 0.05 to 0.5 wt. %, more preferably of from 0.1 to 0.3 wt. %, based on the total weight of the composition,
and/or
one or more vitamins and the physiologically acceptable salts or esters thereof, preferably selected from the group consisting of vitamin A, vitamin A palmitate, vitamin B1, vitamin B2 (riboflavin), vitamin B3 (niacin), vitamin B6, vitamin B9 (folic acid) vitamin B12, vitamin C (ascorbic acid), monosodium ascorbate, monopotassium ascorbate, calcium diascorbate, magnesium diascorbate, ascorbyl palmitate, ascorbyl stearate, vitamin D, and vitamin E, vitamin E acetate, vitamin E palmitate, vitamin H (biotin), vitamin K,
and/or
one or more coloring agents, preferably selected form the group consisting of carotenes (E-number E160a, preferably beta-carotene), paprika extract (E-number E160c), red beet juice powder (comprising betanine, beetroot red, E-number E162), annatto (E-number E160b), anthocyanins (E-number E163), chlorophylls (E-number E140), turmeric (E-number E100, comprising curcumin), tartrazine (FD&C Yellow No. 5, E-number E102), amaranth (E-number E123), titanium dioxide (E-number E171), iron oxides and iron hydroxides (E-number E172), erythrosine (E-number E127), caramel color (E-number E150, preferably E150d), FD&C yellow No. 6 (E-number E110), allura red (FD&C red No. 40, E-number E129), FD&C green No. 3 (fast green, E-number E143), FD&C blue No. 1 (brilliant blue, E-number E133) and FD&C blue No. 2 (indigotine, E-number E132),
and/or
one or more bitter tasting substances selected from the group consisting of quinine, neohesperidin, hesperidin, naringin, quercitrin, phloridzin, phloretin-2-O'-xyloglucoside, caffeic acid, chlorogenic acid, neochlorogenic acid, cryptochlorogenic acid, limonoids (preferably limonin or nomilin from citrus fruits), lupolones from hops, humulones from hops, gallic and ellagic acid esters of carbohydrates (preferably pentagalloylglucose), catechins and epicatechins (preferably selected from the group consisting of galloylated catechins, galloylated epicatechins, gallocatechins or epigallocatechins, galloylated gallocatechins or galloylated epigallocatechins), theaflavins (in particular theaflavin, isotheaflavin, neotheaflavin), galloylated theaflavins, and procyanidines (=proanthocyanidines) (in particular Procyanidin B1, Procyanidin B2, Procyanidin A2, Procyanidin B5, and Procyanidin C1),
and/or
one or more stabilizers and/or thickeners, preferably selected from the group consisting of sodium octenyl succinate, carboxymethyl cellulose, maltodextrin, gum Arabic, guar gum, carob gum, alginates, pectin, and xanthan gum.

Examples of stabilizers and/or thickeners which may be part of an orally consumable material according to the present invention, in particular of a ready-to-drink composition according to the invention, are preferably selected from the group consisting of carbohydrate polymers (polysaccharides), cyclodextrins, starches, degraded starches (starch hydrolysates), chemically or physically modified starches (preferably starch sodium octenyl succinate, E1450), modified celluloses (preferably carboxymethyl cellulose), gum Arabic (gum acacia), gum ghatti, gum tragacanth, gum karaya, carrageenan, guar gum, carob gum (carob flour), alginates, pectin, inulin and xanthan gum.

If an orally consumable material according to the present invention, in particular a ready-to-drink composition according to the present invention, comprises one or more thickeners, then the total amount of thickeners preferably is in the range of from 0.0025 to 1 wt. %, more preferably in the range of from 0.01 to 0.4.%, even more preferably in the range of from 0.015 to 0.2.%, in each case based on the total weight of the composition.

An orally consumable material according to the present invention, in particular a ready-to-drink composition according to the present invention, preferably comprises 200 ppm or more hydrogen carbonate ($HCO_3^-$), more preferably 250 ppm or more hydrogen carbonate, even more preferably 300 ppm or more hydrogen carbonate, and particularly preferably 400 ppm or more hydrogen carbonate, in each case based on the total weight of the orally consumable material.

If an orally consumable material according to the present invention, in particular a ready-to-drink composition according to the present invention, is carbonated, the total amount of carbon dioxide ($CO_2$) preferably is in the range of from 0.02 to 5.0 wt. %, more preferably in the range of from 0.05 to 3 wt. %, even more preferably in the range of from 0.1 to 2.5 wt. %, particularly preferably in the range of from 0.2 to 2.0 wt. %, most preferably in the range of from 0.25 to 1.5 wt. %, in each case based on the total weight of the orally consumable material.

An orally consumable material according to the present invention, in particular a ready-to-drink composition according to the present invention, may additionally comprise lactose and/or maltose, and/or one or more sugar alcohols such as dulicitol, fucitol, maltitol, erythritol, isomaltitol (E 953), lactitol (E 966), maltitol, mannitol (E421), sorbitol (E420), xylitol (E967), and mixtures thereof.

An orally consumable material according to the present invention, in particular a ready-to-drink composition according to the present invention, may additionally comprise one or more high potency sweeteners are preferably selected from the group consisting of sodium cyclamate, acesulfame K, neohesperidin dihydrochalcone, saccharin, saccharin sodium salt, aspartame, superaspartame, neotame, alitame, sucralose, magap, lugduname, carrelame, sucrononate, sucrooctate, miraculin, curculin, monellin, mabinlin, thaumatin, curculin, brazzein, pentadin, or extracts or fractions thereof obtained from natural sources containing said amino acids and/or proteins, neohesperidin dihydrochalcone, steviolgylcoside, stevioside, steviolbioside, rebaudiosides (preferably rebaudioside A, rebaudioside B, rebaudioside C, rebaudioside D, rebaudioside E, rebaudioside F, rebaudioside G, rebaudioside H, dulcoside, rubusoside), suavioside A, suavioside B, suavioside G, suavioside H, suavioside I, suavioside J, baiyunoside 1, baiyunoside 2, phlomisoside 1, phlomisoside 2, phlomisoside 3, phlomisoside 4, abrusoside A, abrusoside B, abrusoside C, abrusoside D, cyclocaryoside A and cyclocaryoside I, oslandin, polypodoside A, strogin 1, strogin 2, strogin 4, selligueanin A, dihydroquercetin-3- acetate, perillartine, telosmoside $A_{15}$, periandrin I-V, pterocaryoside, cyclocaryoside, mukurozioside, bryoside, bryonoside, bryonodulcoside, carnosifloside, scandenoside, gypenoside, trilobatin, phloridzin, dihydroflavanol, hematoxylin, cyanin, chlorogenic acid, albiziasaponin, telosmoside, gaudichaudioside, mogroside, hernandulcine, monatin, glycyrrhetin acid, glycyrrhizin, phyllodulcin, or the physiologically acceptable salts thereof, preferably the respective potassium, sodium, calcium or ammonium salts thereof, liquorice extracts (Glycyrrhizza glabra ssp.), Lippia dulcis extracts, Momordica ssp. extracts or individual substances (in particular Momordica grosvenori [Luo Han Guo] and the mogrosides obtained therefrom), Hydrangea dulcis or Stevia ssp. (e.g. Stevia rebaudiana) extracts or individual substances.

An orally consumable material according to the present invention, in particular a ready-to-drink composition according to the present invention, preferably comprises one or more high potency sweeteners, preferably selected from the group indicated above, more preferably selected from the group consisting of aspartame, neotame, superaspartame, advantame, saccharin, sucralose, cyclamate, acesulfam, tagatose, monellin, stevioside, rebaudioside A, rebaudioside C, rebaudioside D, rubusosid, phyllodulcin, hernandulcin, thaumatin, brazzein, miraculin, glycyrrhizin, glycyrrhetinic acid, the physiologically acceptable salts (preferably the sodium, potassium or calcium salts) of the these compounds.

An orally consumable material according to the present invention, in particular a ready-to-drink composition according to the present invention, preferably comprises a total amount of less than 4.5 wt. % fats and fatty oils (i.e. triglycerides), more preferably less than 3.5 wt. % fats and fatty oils, even more preferably less than 2.0 wt. % fats and fatty oils, particularly preferably less than 1.0 wt. % fats and fatty oils, and most preferably less than 0.5 wt. % fats and fatty oils, in each case based on the total weight of the orally consumable material.

An orally consumable material according to the present invention, in particular a ready-to-drink composition according to the present invention, preferably comprises a total amount of less than 5.0 wt. % proteins, more preferably less than 4.0 wt. % proteins, even more preferably less than 3.0 wt. % proteins, particularly preferably less than 1.0 wt. % proteins, and most preferably less than 0.5 wt. % proteins, in each case based on the total weight of the orally consumable material.

Preferred orally consumable materials according to the present invention are alcoholic or non-alcoholic beverages (preferably coffee-containing beverages, tea-containing beverages, cocoa-containing beverages, wine-containing drinks, beer-containing drinks, fruit-containing soft drinks, isotonic drinks, soft drinks, energy drinks, nectars, fruit and vegetable juices, instant beverage powders after dilution in water, beverage concentrates, beverage syrups, fountain syrups, smoothies), dairy products (preferably flavoured milk, yoghurts, yoghurt drinks, kefir, buttermilk drinks, milk shakes, milk mix beverages), ice products (water ice, ice cream), fruit preparations (preferably sorbets, fruit sauces, fruit fillings, fruit ice creams), vegetable products (preferably soy milk products, ketchup, sauces), emulsions (preferably mayonnaise, remoulade, dressings, bakery flavour emulsions), jams, jellies, bakery fillings, pickle brine, frozen juice compositions, sour confections, fruit pie fillings, desserts, marinades, and soups.

A (preferably acidic) beverage of this invention may be prepared, for example, from a corresponding (preferably acidic) syrup composition based on a dilution or a throw of the (preferably acidic) syrup. Those skilled in the art recognize that a common throw for a soft drink, e.g. a cola-flavoured carbonated soft drink, is 1+5 so that a preparer uses one part of cola syrup and five parts water to prepare the (preferably acidic) beverage from the (preferably acidic) syrup. The amount of (preferably acidic) syrup employed to prepare the (preferably acidic) beverage of this invention will of course vary depending on the concentration of the syrup and the desired end product. Such amount can be readily determined by those of ordinary skill in the art.

In a preferred embodiment, an orally consumable material according to the present invention, in particular a ready-to-drink composition according to the present invention, is clear. The term "clear" in the context of the present invention refers to a composition of matter having a turbidity of less than 25 FNU (Formazin Nephelometric Units) as measured according to DIN EN ISO 7027—Water quality—Determination of turbidity (ISO 7027:1999).

Preferably, an orally consumable material according to the present invention, in particular a ready-to-drink composition according to the present invention, has a turbidity of less than 12 FNU, more preferably of less than 6 FNU, preferably measured with a Hach Turbidimeter 2100N IS.

Preferred orally consumable materials according to the present invention are in particular clear or turbid (carbonated or non-carbonated) beverages, preferably selected from the group consisting of lemonade, carbonated soft drinks, tea, ice-tea, beer-lemonade mixes, cola, beer-cola mixes, whey drink lemonade, tea, beer-lemonade mixtures, cola drinks, beer-cola mixes, and whey drinks, and the concentrates for producing said beverages.

An orally consumable material according to the present invention (as defined above) at 20° C. and 1013 mbar preferably is pourable, and more preferably liquid.

An orally consumable material according to the present invention, in particular a ready-to-drink composition according to the invention, preferably has dynamic viscosity value of smaller than 1250 mPa s (mPa s=milli Pascal seconds; equal to cP=centiPoise), preferably of smaller than 600 mPa s, more preferably of smaller than 250 mPa s, particularly preferably of smaller than 100 mPa s, especially preferably of smaller than 50 mPa s, and most preferably of smaller than 25 mPa s, in each case measured at 20° C. and at a shear rate of $D=10\ s^{-1}$, e.g. as determined with a Brookfield® viscometer according to DIN 53018.

An orally consumable material according to the present invention, in particular a ready-to-drink composition according to the invention, preferably has dynamic viscosity value in the range of from 1 to 1000 mPa s (mPa s=milli Pascal seconds; equal to cP=centiPoise), preferably in the range of 2 to 500 mPa s, more preferably in the range of 2 to 125 mPa s, particularly preferably in the range of 3 to 50 mPa s, especially preferably in the range of 3 to 25 mPa s, in each case measured at 20° C. according to DIN 53018.

The flavour of an orally consumable material according to the present invention, in particular of a ready-to-drink composition according to the present invention, preferably is selected from the group consisting of berries, citrus fruits, pomaceous fruit, spices, herbs, mints, teas, coffees, milk and/or milk products, and more particularly preferably selected from the group consisting of cola, lemon, lime, lemon-lime, grapefruit, orange, sweet orange, bitter orange, bergamot, mandarin, apple, pear, prickly pear, peach, apricot, pineapple, prune, mango, melon, plum, kiwi, lychee, banana, cherry, sweet cherry, strawberry, raspberry, red currant, black currant, blackberry, blueberry, passion fruit, grape, pomegranate, acerola, vanilla, cinnamon, anise, fennel, clove, cardamom, tamarind, nutmeg, allspice, black pepper, honey, licorice, ginger ale, ginger, root beer, rose hip, green tea, red tea, rooibos tea, mate tea, honeybush tea, pu-erh tea, oolong tea, black tea, kombucha, milk, coffee, espresso, cocoa, chocolate, hazelnut, walnut, almond, peppermint, spearmint, wintergreen and mixtures thereof.

In a preferred embodiment, an orally consumable material according to the present invention, in particular a ready-to-drink composition according to the present invention, comprises one or more amino carboxylic acids and/or one or more amino sulfonic acids, preferably gamma-amino butyric acid and/or taurine (2-aminoethanesulfonic acid).

An orally consumable material according to the present invention, in particular a ready-to-drink composition according to the present invention, may preferably comprise one or more fruit derived ingredients, in particular fruity flavours, fruit juices, fruit purees and fruit juice concentrates.

Fruit juices or fruit juice concentrates that can be used are preferably derived from citrus fruits such as orange, lemon, grapefruit and tangerine, and other fruits such as apple, pear, grape, apricot and pineapple. Furthermore, fruit juices and fruit juice concentrates may be derived from soft fruits like blackberry, gooseberry, currant, blueberry, elderberry, strawberry and raspberry.

Preferably, an orally consumable material according to the present invention, in particular a ready-to-drink composition according to the present invention, is an emulsion. Densities of the disperse phase, which are preferred for an adequate stabilization and avoidance of ringing, preferably lie in the range of from 0.92 to 1.06 g/ml, more preferably in the range of from 0.94 to 1.03 g/ml. "Ringing" is the formation of a ring around the neck of a (beverage) container which is sought to be avoided.

If an orally consumable material according to the present invention, in particular a ready-to-drink composition according to the present invention, comprises one or more weighting agents, these are preferably selected from the group consisting of sucrose acetate isobutyrate (SAIB, E 444), estergum (E 445), dammar gum, and brominated vegetable oils in an amount not exceeding the respective legally authorized concentrations.

In a preferred embodiment, an orally consumable material according to the present invention, in particular a ready-to-drink composition according to the present invention, is a cloudy (turbid) emulsion, preferably comprising one or more clouding agents, such as titanium dioxide, palm oil, or terpene oils like limonene.

If an orally consumable material according to the present invention, in particular a ready-to-drink composition according to the present invention, is an emulsion, e.g. prepared as described in U.S. Pat. No. 5,616,358, EP 2 025 250 or EP 1 151 677.

If an orally consumable material according to the present invention, in particular a ready-to-drink composition according to the present invention, is a cloudy (turbid) emulsion, the D90 particle (droplet) size of the disperse phase (as measured by laser diffraction) is in the range of from 0.15 to 1.0 μm (microns), in some preferred embodiments in the range of from 0.35 to 0.5 μm, in some other preferred embodiments in the range of from 0.6 to 0.75 μm.

In a preferred embodiment, a beverage according to the present invention comprises a terpene oil, more preferably a terpene citrus oil. Preferred terpene oils in the context of the present invention comprise or consist of orange, lemon and/or grapefruit oils and fractions thereof, preferably limonene (especially D-limonene) and/or orange oil terpenes.

A material according to the present invention, preferably a food or cosmetic product according to the present invention, may additionally comprise one or more physiological cooling agents, preferably selected from the group consisting of menthone derivatives (preferably L-menthone glycerol ketal), p-menthane-3,8-diol, cubebol, isopulegol and its esters (preferably L-(−)-isopulegol, L-(−)-isopulegol acetate), menthyl ethers (preferably (L-menthoxy)-1,2-propanediol, (L-menthoxy)-2-methyl-1,2-propanediol, L-menthyl-methyl ether), menthyl esters (preferably menthyl formate, menthyl acetate, menthyl isobutyrate, menthyl lactate, L-menthyl-L-lactate, L-menthyl-D-lactate, L-menthyl-(2-methoxy)acetate, L-menthyl-(2-methoxyethoxy)acetate, L-menthyl pyroglutamate), menthyl carbonates (preferably L-menthyl propylene glycol carbonate, L-menthyl ethylene glycol carbonate, L-menthyl glycerol carbonate or mixtures thereof), semi-esters of menthols with a dicarboxylic acid or derivatives thereof (preferably menthyl oxamate, menthyl-N-methyloxamate, menthyl-N-ethyloxamate, mono-L-menthyl succinate, mono-L-menthyl glutarate, mono-L-menthyl malonate, O-L-menthyl succinic acid ester-N,N-(dimethyl) amide, O-L-menthyl succinic acid ester amide), 2,3-dimethyl-2-(2-propyl)-butanoic acid derivatives (preferably 2,3-dimethyl-2-(2-propyl)-butanoic acid-N-methyl amide [WS-23]), menthane carboxylic acid amides (preferably L-menthane carboxylic acid-N-ethyl amide [WS-3], $N^\alpha$-(L-menthanecarbonyl)glycine ethyl ester [WS-5], menthane carboxylic acid-N-(4-methoxyphenyl)-amide [WS-12], L-menthane carboxylic acid-N-tert-butyl amide [WS-14], L-menthane carboxylic acid-N-(4-cyanophenyl)amide, N-(4-cyanomethylphenyl) p-menthanecarboxamide), L-menthane carboxylic acid-N-(alkoxyalkyl)amides, L-menthane carboxylic acid-N-(alkylthioalkyl)amides, and pyrrolidone derivatives of cycloalkyldione derivatives (preferably 3-methyl-2(1-pyrrolidinyl)-2-cyclopenten-1-one).

In one aspect of the present invention, preferred cosmetic products of the invention are oral hygiene products (oral care products). Preferred oral hygiene products are creams, gels, pastes, foams, emulsions, suspensions, aerosols, sprays or chewing gums. Such formulations serve to clean and care for the tooth substance and oral cavity and to freshen the breath. More preferred oral hygiene products are toothpastes, tooth gels, 2-in-1 tooth gels, mouthwashes, mouth rinses, gargles and mouth or breath sprays.

A cosmetic, in particular an oral hygiene oral product according to the invention can contain further auxiliary substances such as are conventionally used in such preparations, for example further preservatives, abrasives, antibacterial agents, anti-inflammatory agents, irritation-preventing agents, irritation-inhibiting agents, further antimicrobial agents, antioxidants, astringents, antiseptic agents, antistatics, binders, buffers, support materials, chelating agents, cell stimulants, cleansing agents, conditioning agents, further surface-active substances, deodorising agents, softeners, emulsifiers, enzymes, essential oils, film formers, foaming agents, foam stabilisers, substances to prevent foaming, gelling agents, moisturizing substances, moisture-retaining substances, bleaching agents, optical brighteners, dirt-repelling agents, lubricants, opacifiers, brighteners, polymers, powders, proteins, silicones, skin-calming agents, skin-cleansing agents, skin care agents, skin-healing agents, skin-cooling agents, skin-warming agents, stabilisers, thickeners, vitamins, oils, waxes, fats, phospholipids, saturated fatty acids, mono- or polyunsaturated fatty acids, alpha-hydroxy acids, polyhydroxy fatty acids, dyes, colour-protecting agents, pigments, aroma substances, perfumes, and other conventional constituents, such as alcohols, polyols, electrolytes, organic solvents, sweeteners, sugar substitutes, silicas, calcium carbonate, calcium hydrogen phosphate, aluminium oxide, fluorides, zinc, tin, potassium, sodium and strontium salts, pyrophosphates, hydrogen peroxide, and hydroxyapatites.

Examples of aroma substances which can preferably be part of an oral hygiene product according to the invention are: anethole, menthol, menthone, isomenthone, menthyl acetate, menthyl propionate, menthofuran, mintlactone, eucalyptol (1,8-cineol), limonene, eugenol, eugenol acetate, isoeugenol methyl ether, thymol, pinene, sabinene hydrate, 3-octanol, carvone, gamma-octalactone, gamma-nonalactone, germacrene-D, viridiflorol, 1,3E,5Z-undecatriene, isopulegol, piperitone, 2-butanone, ethyl formate, 3-octyl acetate, isoamyl isovalerianate, hexanol, hexanal, cis-3-hexenol, linalool, alpha-terpineol, cis- and trans-carvyl acetate, p-cymol, damascenone, damascone, rose oxide, fenchol, acetaldehyde diethylacetal, 1-ethoxyethyl acetate, cis-4-heptenal, isobutyraldehyde, isovaleraldehyde, cis-jasmone, methyl dihydrojasmonate, anisaldehyde, methyl salicylate, 2'-hydroxypropiophenone, menthyl methyl ether, myrtenyl acetate, 2-phenylethyl alcohol, 2-phenylethyl isobutyrate, 2-phenylethyl isovalerate, cinnamaldehyde, geraniol, nerol. In the case of chiral compounds the aroma substances can be used as a single enantiomer or a mixture of enantiomers, e.g. in the form of a racemate.

Aroma substances which preferably are part of an oral hygiene product according to the invention are preferably selected from the group consisting of aniseed oil, basil oil, bitter almond oil, camphor oil, citronella oil, citrus oils, *eucalyptus citriodora* oil, *eucalyptus* oil, camomile oil, spearmint oil, limette oil, mandarin oil, clove oil, orange oil, peppermint oil, sage oil, thyme oil, wintergreen oil, cinnamon oil, cinnamon bark oil, I-menthol, menthone, isomenthone, 1,8-cineol (eucalyptol), carvone, alpha-terpineol, methyl salicylate, 2'-hydroxypropiophenone, and menthyl methyl ether.

Another group of preferred cosmetic products of the invention are sanitary articles, preferably selected from the group consisting of wet wipes, sanitary towels, diapers, tampons, handkerchiefs and refreshing tissues containing one or more compounds of formula I (to be used) according to the invention and/or one or more physiologically acceptable salts thereof. Said sanitary articles according to the invention preferably contain a material according to the present invention, in particular in one of the preferred variants described herein.

In a non-woven system, preferably at least one layer comprises an absorbent non-woven fabric or a porous polymer which is impregnated with a solution or suspension comprising one or more compounds of formula I (to be used) according to the invention and/or one or more physiologically acceptable salts thereof, and preferably comprises one or more additional other active substances (such as skin-soothing and/or skin-moisturizing agents).

The following Examples illustrate the invention without limiting its scope.

EXAMPLES

| Abbreviation | Definition |
| --- | --- |
| ppm = µg/mL | Part per million identical with micro gram per millilitre |
| ACN | Acetonitrile |
| CFU | Colony forming units |
| ELSD | Evaporative Light Scattering Detection |

-continued

| Abbreviation | Definition |
| --- | --- |
| HPGPC | High Performance Gel Permeation Chromatography |
| HPLC | High Performance Liquid Chromatography |
| HR-ESIMS | High Resolution Electrospray Ionisation Mass Spectrometry |
| LCT | Liquid Chromatography Time of Flight |
| MS | Mass Spectrometry |
| TFA | Trifluoroacetic acid |
| UV/Vis | Ultraviolet/visible light |

Example 1: Cultivation

A) Media:
1) SDB (Sabouraud Dextrose Broth, Ref. 238230, Difco™ Lawrence, Kans., USA, containing 0.5% Peptic Digest of Animal Tissue, 0.5% Pancreatic Digest of Casein, 2.0% Dextrose, pH 5.6.
2) YMG (Yeast-Malt-Glucose) medium: D-glucose 0.4% (Merck, Darmstadt, Germany, Ref. K25252846 831), malt extract 1% (Carl Roth, Karlsruhe, Germany, Ref. X976.2), yeast extract 0.4% (Merck, Darmstadt, Germany, Ref. 1.11926.1000), pH 6.3.
3) PDB (Potato Dextrose Broth): 2.0% D-glucose, 0.4% mashed potatoes (Pfanni, Hamburg, Germany).
4) Cornmeal medium (CM): 2.0% corn meal (Neuform, Zarrentin, Germany), 1.0% D-glucose.
5) GM1 (Glucose-Yeast medium 1): 2.0% D-glucose, 0.5% yeast extract.
6) GM2 (Glucose-Yeast medium 2): 2.0% D-glucose, 0.1% yeast extract.
7) Malt medium 1: 2.0% malt extract, 0.5% yeast extract.
8) Malt medium 2: 2.0% malt extract without yeast extract.
9) Apple juice medium: 10% apple juice (common commercial product: clear juice, EAN 20009717, Fruchtstern®, trademark by Netto Marken-Discount AG & Co.KG, MaxhOtte-Haidhof, Germany), 4.83% glucose, 5.94% fructose, 0.23% sucrose, 0.1% (v/v) hardness solution (prepared from 4.4 g $CaCl_2*2H_2O$+ 3.04 g $MgCl_2*6H_2O$ dissolved in 100 ml water), 0.2% (v/v) 1M sodium malate, 0.2% (v/v) 1M maleic acid; adjusted to pH 3.2-3.4 with 1M maleic acid.
10) Trypticase Soy Yeast Extract medium: 3% Trypticase soy broth (Difco, Lawrence USA, Ref. 211825), 0.3% Yeast extract (Merck, Darmstadt Germany, Ref. 111926).

B) Fermentation (Exemplarily Presented Using the Strain FU50088)

a) Seed Cultures (Shake Flask Cultures)

One ml of a cryo vial containing a mycelial suspension of FU50088 in 10% glycerol was retrieved from liquid nitrogen and, after thawing, used to inoculate 200 ml Erlenmeyer flasks containing 50 ml of sterile YMG medium and propagated on a rotary shaker at 240 rpm and 23° C. for 72 h. Thereafter, each two ml of the primary seed culture were transferred into batches of two 500 ml Erlenmeyer flasks containing 200 ml of the same medium and propagated on a rotary shaker at 140 rpm and 23° C. for 120 h. These flasks served as secondary seed cultures.

b) Fermentation in 30l Scale

A 40 l Biostat LP42 fermentor (Bioengeneering, Wald, Switzerland) containing 30 l of medium was sterilized in situ (1 h at 121° C. and 1.1 bar) and inoculated with 400 ml of the secondary seed culture. The production culture was grown under stirring (240 rpm) and aeration (0.2 vvm (volumes of air per minute per volume of batch)) at 30° C.

Furthermore at each point of incubation time listed above, HPLC analysis of crude extracts prepared from 20 ml samples taken under sterile conditions and extracted with equal amounts of ethyl acetate served as a means of detection and estimation of glycolipids. For this purpose, the ethyl acetate extracts are dried over anhydrous sodium sulfate, evaporated to dryness, re-dissolved in 2-propanol and analyzed using the HPLC systems described below in HPLC-MS methods "fermentation control".

TABLE A

Dependency of yield on nutrient composition

| Culture medium | Production maximum [h fermentation] | pH value | Mycelial dry weigth [g/l] | Extractable material [g/l] | Diameter of inhibition zone (mm)** | |
|---|---|---|---|---|---|---|
| | | | | | B. subtilis | S. cerevisiae |
| SDB | 192 | 4.6 | 6.2 | 0.26 | 18 | 10 |
| YMG | 216 | 6.0 | 4.8 | 0.13 | 12 | 0 |
| PDB | 312 | 4.7 | 1.7 | 0.76 | 18 | 9 |
| CM | 216 | 4.6 | * | 0.65 | 17 | 14 |
| GM1 | 312 | 4.7 | 4.3 | 0.69 | 20 | 13 |
| GM2 | 192 | 4.1 | 3.3 | 1.26 | 20 | 13 |
| MM1 | 192 | 5.2 | 12.8 | 0.24 | 18 | 11 |
| MM2 | 192 | 4.4 | 8.0 | 1.07 | 19 | 15 |

*Mycelial weight was not determined (medium contaning solid constitutents)
**Inhibition zones caused after 24 h by 50 µg of ethyl acetate extract dissolved in methanol on a paper disk (6 mm diameter)

For optimisation of culture media, *Dacryopinax spathularia* was propagated in a series of 500 ml shake flask batches containing each 200 ml of culture media as described above (Example 1 B) under "a) Shake flask cultures (including "Seed cultures). During fermentation, samples were taken, and pH, mycelial dry weight, amount of extractable material and biological activities of crude ethyl acetate extracts of the culture broth against *Bacillus subtilis* and *Zygosaccharomyces bailii* in the agar diffusion assay were determined. The results (Table A) show that, even though the glycolipids are produced in a variety of different culture media, GM2 medium showed the highest specific biological activity with respect to the mycelial dry weight and the fermentation time. As it could even be observed during fermentation by microscopic control that the glycolipids sticked to the mycelial hyphae during the production phase, it was deemed favorable to use GM2 medium for large scale fermentation, in order to direct the majority of the products to be located in the culture broth, especially in view of the precipitation experiments that were finally found the most effective and ecologically friendly way of obtaining the desired compounds. In addition, the maximum of production was obtained earlier than in most other fermentation media.

c) Fermentation in 200l Scale

The fermentation was performed in a 300 l fermentor (Bioengineering Type P, equipped with four Ekato Intermig® impellers) containing 200 l of GM2 medium, sterilized under steam for 45 min at 121° C., inoculated with the above described 20 l seed culture. To prevent foaming, 0.03 ml/l of Clarol FBA 3003K (Cognis, Monheim, Germany) as anti-foam agent were added; no additional supply of anti-foam was necessary during fermentation. The fermentation was performed at ca. 33° C., under agitation (75 rpm) and aeration (0.2 vvm). The fermentation was stopped after 300 h when the free glucose had almost been consumed and the oxygen partial pressure had dropped to 20%.

C) Preparation of Extracts a) Preparation of Mycelial Extract:

The cultures from 10 shake flasks were harvested. The culture fluid was separated by filtration from the mycelia. The wet mycelia were extracted two times with equal volumes of acetone for each 30 min in an ultrasonic bath. This acetone was evaporated in vacuo at 40° C. and the remaining aqueous phase was diluted to 700 ml with water. This phase was extracted three times with equal volumes of ethyl acetate (EtOAc). The combined organic phases were dried over anhydrous $Na_2SO_4$ and evaporated in vacuo to yield 329 mg of a crude extract.

b) Preparation of the Culture Fluid Extract:

1000 g Amberlite® XAD16 (Sigma-Aldrich, St. Louis, Mo. 63103, CAS 90003-69-4, Batch-No. 099K0079) were added to 30 l culture filtrate (from a 30 l fermenter, GM2 medium) and incubated over night under stirring (60 rpm). The resin was harvested by filtration and the dry resin was incubated with two liters of methanol and incubated for 30 min in an ultrasonic bath. Thereafter, the methanol eluate was removed by filtration. This methanol elution process was repeated twice. The methanol eluates (ca. 6 l) were combined evaporated in vacuo and the resulting oily residue redissolved in 500 ml distilled water. The pH was adjusted with 2 M HCl to pH 2.9, and the resulting suspension was extracted three times each with equal amounts of ethyl acetate. The combined organic phases were dried over sodium sulfate, evaporated in vacuo (40° C.) to yield 25 g of an amorphous, light brown crude extract.

c) Preparation of a Sedimentation (Precipitation) (Downstream Processing) Product The culture broth resulting from a 200 l fermentation was alkalized from an initial pH value of 4.5 to pH 8 with 1 N sodium hydroxide solution to allow the glycolipids that partially stick to the cells under acidic conditions to become largely released from the mycelia. After 1 h the mycelia were separated using a Westfalia KA1-06-525 separator, and in addition the culture broth was filtrated through a Pall (Dreieich Germany) 0.1 µm polysulfone membrane filter cassettes, diameter of fibers 1.4 mm, total area 24 m²) microfiltration system to completely retain the mycelia. The product was sedimented (precipitated) by acidifying the filtrate with 2 N hydrochloric acid to pH 3 and incubating for 16 h under cooling to 11° C. The fluid was removed by decantation and subsequent centrifugation (4500 rpm, 15 min, Typ Jouan SA LR 5.22 (Jouan, Paris France), resulting in a whitish-grey gel. This crude product was washed immediately with water (pH 7), centrifuged again at (4500 rpm for 15 min) and freeze-dried. This process yielded 380 g dry glycolipid which was further characterized by HPLC-MS (see e.g. HPLC chromatogram in FIG. 2).

D) Isolation of Compounds a) Flash Chromatography 10 g of the raw product were dissolved in 5 ml of methanol and bound onto 10 g of Chromabond XTR (Kieselguhr for liquid-liquid extraction Macherey-Nagel, Article No. 730 595.500, Düren, Germany) and the solvent was evaporated in vacuo. This dried material was applied onto a Biotage Isolera (Uppsala, Sweden) MPLC system, using a Chromabond® flash (120 Nucleodur 100-20 C18ec; 130×40 mm) (trademark by Macherey-Nagel) as stationary phase.

The column was equilibrated with ACN/water (1:5) and then eluted using the following conditions at a flow of 20 ml/min: 3:30 min, ACN/water (1:5) isocratic; 9 min, ACN/water (1:1) gradient; 19:00 min, ACN/water (1:1) isocratic; 29:00 min ACN/water (2:1) gradient; 49:00 min ACN/water (2:1) isocratic; 59:00 min pure ACN gradient.

Small aliquots of the fractions were taken, evaporated and dissolved in 2-propanol to concentrations of 5 mg/ml and analyzed by HPLC-MS using the "Adapted Method" as described in Example 3. The fractions were combined according to HPLC-MS results and concentrated in vacuo.

Fractions containing the compounds of the formula I elute according the following table.

TABLE 2

Flash chromatographic elution profile of compounds of the formula I

| Elution time [min] | Containing compound number | Yield [mg] |
|---|---|---|
| 17-26 | [16] | 686 |
| 27-29 | [14] | 791 |
| 32-33 | [12] | 505 |
| 34-35 | [13] | 542 |
| 36-38 | [1] | 1256 |
| 41-48 | [18] | 570 | b) Purification by HPLC

All these separation steps were performed with

CA: Waters SunFire C18 preparative HPLC column (7 μm, length 250 mm*diameter 19 mm)

CB: Kromasil C18 (7 μm, length 250 mm*diameter 40 mm)+pre column (Kromasil C18, 7 μm, length 50 mm*diameter 20 mm)

CC: Kromasil C8 (7 μm, length 250 mm*diameter 40 mm)

CD: Inertsil ODS-3 C18 (5 μm, length 250 mm*diameter 40 mm)

as stationary phase. The eluent was built up with ACN and water using a flow rate of 10 ml/min. The maximal capacity of this column is about 600 mg. Therefore it was necessary to perform several identical purifications in series in order to purify larger amounts.

The separations were monitored by a diode array detector at 200 and 210 nm. Five ml fractions were taken using an automatic fraction collector and finally combined according to UV absorption (200 and 210 nm), concentrated in vacuo and subjected to HPLC-MS, to assess their purity.

For those skilled in the art it is obvious to adapt the elution methodology to the retention necessities of each compound, e.g. less polar compounds will elute later, consequently it is possible to start with a higher content of ACN in the eluent. Sometimes it is better to use another slope of the gradient or it is necessary to use an isocratic system.

TABLE 3

HPLC purification elution profiles of compounds of the formula I

| Purified compound | Retention time [min] | Column code | Gradient flow | Purity (NMR) |
|---|---|---|---|---|
| [16] | 6.5-8.5 | CB | 10 min: ACN 50%<br>30 min: ACN 50% → 80%<br>45 min: ACN 80%<br>50 min: ACN 80% → 85%<br>70 min: ACN 85%<br>90 min: ACN 85% → 100%<br>20 ml/min | 85% (NMR) |
| [14] | 49.5-54 | CC | 15 min: MeOH 20% → 50%,<br>70 min: MeOH 50% → 100%,<br>100 min: MeOH 100%,<br>20 ml/min | |
| II | 26.5-28.5 | CD | 15 min: ACN 20% → 45%,<br>30 min: ACN 45%<br>35 min: ACN 45% → 50%,<br>50 min: ACN 50%<br>55 min: ACN 50% → 55%,<br>70 min: ACN 55%<br>90 min: ACN 55% → 100%,<br>100 min: ACN 100%<br>20 ml/min | 75% (NMR) |
| I | | CB | 10 min: ACN 50%<br>30 min: ACN 50% → 80% | |

TABLE 3-continued

HPLC purification elution profiles of compounds of the formula I

| Purified compound | Retention time [min] | Column code | Gradient flow | Purity (NMR) |
|---|---|---|---|---|
| [12] | 19.5-21 | | 45 min: ACN 80%<br>50 min: ACN 80% → 85%<br>70 min: ACN 85%<br>90 min: ACN 85% → 100%<br>20 ml/min | 95% (NMR) |
| [13] | I<br>55-56 | CC | 15 min: MeOH 20% → 50%,<br>70 min: MeOH 50% → 100%,<br>100 min: MeOH 100%,<br>20 ml/min | |
| | II<br>35-36 | CD | 15 min: ACN 20% → 50%,<br>30 min: ACN 50%<br>35 min: ACN 50% → 55%,<br>50 min: ACN 55%<br>55 min: ACN 55% → 60%,<br>70 min: ACN 60%<br>90 min: ACN 60% → 100%,<br>100 min: ACN 100%<br>20 ml/min | 85% (NMR) |
| [1] | I<br>35-36 min. | CB | 10 min: ACN 50%<br>30 min: ACN 50% → 80%<br>45 min: ACN 80%<br>50 min: ACN 80% → 85%<br>70 min: ACN 85%<br>90 min: ACN 85% → 100%<br>20 ml/min | 95% (NMR) |
| [18] | I<br>42 min | CA | 15 min: ACN 20% → 50%,<br>35 min: ACN 50%,<br>40 min: ACN 50% → 100%,<br>50 min: ACN 100%,<br>20 ml/min | |
| | II<br>17 min | CA | 40 min: ACN 40% → 100%,<br>45 min: ACN 100%,<br>20 ml/min | 93% (NMR) |

Exemplarily the purification of compound [1] is described herein in detail: The elution profile was running from: 10 min isocratic ACN 50%; 30 min gradient ACN 50% →80%; 45 min isocratic ACN 80%; 50 min gradient ACN 80% →85%; 70 min isocratic ACN 85%; 90 min gradient ACN 85% →100% with a flow of 20 ml/min using column CB (Kromasil C18). Within a retention time of 35-36 min compound [1] eluted from the above described system. The purity was determined as 95% by $^1$H-NMR.

E) Definition of Extracts

Extracts containing compounds of the formula I are defined with their preparation procedures, e.g. the use of the above explained processes.

TABLE 4

| Extract id | Strain | Fermentation process B | Preparation of extracts process C | Full process code |
|---|---|---|---|---|
| [X1] | MUCL53181 | example 1, B b) | example 1, C c) | MUCL53181 example 1, B b), C c) |
| [X2] | MUCL53181 | example 1, B c) | example 1, C c) | MUCL53181 example 1, B c), C c) |
| [X3] | MUCL53181 | example 1, B a) | example 1, C a) | MUCL53181 example 1, B a), C a) |
| [X4] | MUCL53182 | example 1, B a), | example 1, C b) | MUCL53182 example 1, B a), C b) |
| [X5] | MUCL53179 | example 1, B a), | example 1, C a) | MUCL53179 example 1, B a), C a) |
| [X6] | MUCL53500 | example 1, B b), | example 1, C c) | MUCL53500 example 1, B b), C c) |

Exemplarily the codation of [X1] is described herein in detail: The use of the strain FU50088 of the species *Dacryopinax spathularia* in a fermentation procedure as described above in the example 1 "Cultivation" with a process as described in this example under section B "fermentation" using a 30 l fermentor as described in this section under subsection b) "30 l fermentations" followed by a preparation procedure as described in the same example 1 with a process as described under section C "Preparation of extracts" using a precipitation process as described in this section under subsection c) "Preparation of a sedimentation product" is coded as "an extract of FU50088 according example 1 using a production process B b) and an extraction process C c)" or in short terms "extract FU50088 example 1, B b), C c)".

Example 2: Structural Characterisation

Compound No. [1]

The molecular structure was elucidated by thorough interpretation of high resolution mass spectrometric data and 1D and 2D NMR spectra. The structural characterisation follows the general methodology which is known to the person skilled in the art and described in more detail in the scientific literature (examples: Nishida et al., *J. Antibiot.* 1991, 44, 541; Nishida et al, *Chem. Pharm. Bull.* 1991, 39, 3044).

The numbering of the atoms is shown in FIG. 1.

Chemical Formula: $C_{49}H_{88}O_{21}$

Exact Mass: 1012.5818 Da

Molecular Weight: 1013.2104 Da

HR-ESIMS: found m/z 1013.5874; calculated m/z 1013.5891 for $[M+H]^+$

NMR spectra were obtained in $CD_3OD$ at 293 K on a Bruker DRX spectrometer operating at 500 MHz proton frequency. The residual solvent peak was used as internal reference ($\delta_H$=3.30; $\delta_C$=49.0). The assigned NMR data are summarized in Tables 5-14.

TABLE 5

NMR data for Compound No. [1]

| aglycon moiety | | | carbohydrate moiety | |
| --- | --- | --- | --- | --- |
| atom | $\delta_C$  $\delta_H$, mult. | atom | | $\delta_C$  $\delta_H$, mult. |
| 1 | 178.1 — | 1' | | 102.5 4.38, d (4.7) |
| 2 | 71.4 4.09, dd (7.6, 4.4) | 2' | | 84.5 3.25, m |
| 3 | 35.4 1.63, 1.74, m | 3' | | 77.1 3.52, m |
| 4 | 26.2 1.42, m | 4' | | 70.6 3.50, m |
| 5 | 30.7 1.33, m | 5' | | 66.6 3.16, 3.83, m |
| 6-14 | 30.8 1.30, m | 1" | | 104.2 4.61, d (7.1) |
| 15 | 26.9 1.33, 1.53, m | 2" | | 83.1 3.51, m |
| 16 | 33.5 1.33, 1.60, m | 3" | | 74.4 3.80, m |
| 17 | 76.0 3.36, m | 4" | | 72.9 4.69, m |
| 18 | 76.0 3.36, m | 5" | | 63.5 3.23, 3.96, m |
| 19 | 33.5 1.33, 1.60, m | 1''' | | 105.4 4.67, d (7.6) |
| 20 | 22.6 1.36, 1.62, m | 2''' | | 75.6 3.25, m |
| 21 | 35.9 1.54, m | 3''' | | 77.7 3.37, m |
| 22 | 80.1 3.62, m | 4''' | | 71.4 3.30, m |
| 23 | 35.4 1.43, 1.45, m | 5''' | | 76.0 3.53, m |
| 24 | 28.5 1.33, 1.38, m | 6''' | | 64.4 4.21, 4.49, m |
| 25 | 24.2 0.92, 1.32, m | 4"-O—$\underline{C}OCH_3$ | | 172.5 — |
| 26 | 14.6 0.92, t (6.8) | 4"-O—CO$\underline{CH_3}$ | | 20.8 2.06, s |
| | | 6'''-O—$\underline{C}OCH_2CH(CH_3)_2$ | | 174.8 — |
| | | 6'''-O—CO$\underline{CH_2}CH(CH_3)_2$ | | 44.2 2.29, d (7.1) |
| | | 6'''-O—COCH$_2\underline{CH}$(CH$_3$)$_2$ | | 26.9 2.10, m |
| | | 6'''-O—COCH$_2$CH($\underline{CH_3}$)$_2$ | | 23.0 0.98, d (6.8) |

TABLE 6

NMR data for Compound No. [13]

| aglycon moiety | | | carbohydrate moiety | |
| --- | --- | --- | --- | --- |
| atom | $\delta_C$  $\delta_H$, mult. | atom | | $\delta_C$  $\delta_H$, mult. |
| 1 | 178.3 — | 1' | | 102.3 4.40, d (6.8) |
| 2 | 71.5 4.08, m | 2' | | 84.0 3.27, m |
| 3 | 35.4 1.62, 1.74, m | 3' | | 77.2 3.51, m |
| 4 | 26.1 1.42, m | 4' | | 70.7 3.50, m |
| 5 | 30.6 1.33, m | 5' | | 66.5 3.17, 3.86, m |
| 6-14 | 30.2 1.29, m | 1" | | 104.1 4.60, d (6.8) |
| 15 | 26.9 1.33/1.52, m | 2" | | 83.4 3.44, t (7.9) |
| 16 | 33.4 1.32/1.60, m | 3" | | 77.2 3.55, m |
| 17 | 76.0 3.36, m | 4" | | 70.7 3.50, m |
| 18 | 76.0 3.36, m | 5" | | 66.5 3.17, 3.86, m |
| 19 | 33.4 1.32/1.60, m | 1''' | | 105.4 4.71, d (7.6) |
| 20 | 22.4 1.36/1.62, m | 2''' | | 75.8 3.36, m |
| 21 | 35.8 1.55, m | 3''' | | 75.5 3.57, m |

TABLE 6-continued

NMR data for Compound No. [13]

| aglycon moiety | | | carbohydrate moiety | | |
|---|---|---|---|---|---|
| atom | $\delta_C$ | $\delta_H$, mult. | atom | $\delta_C$ | $\delta_H$, mult. |
| 22 | 80.1 | 3.62, m | 4''' | 72.0 | 4.83, m |
| 23 | 35.2 | 1.45, m | 5''' | 73.6 | 3.72, m |
| 24 | 28.3 | 1.33, m | 6''' | 63.4 | 4.19, m |
| 25 | 24.0 | 1.31, m | 4'''-O—COCH$_3$ | 171.8 | — |
| 26 | 14.5 | 0.91, t (6.5) | 4'''-O—COCH$_3$ | 20.9 | 2.06, s |
| | | | 6'''-O—COCH$_2$CH(CH$_3$)$_2$ | 174.9 | — |
| | | | 6'''-O—COCH$_2$CH(CH$_3$)$_2$ | 44.0 | 2.26, d (7.1) |
| | | | 6'''-O—COCH$_2$CH(CH$_3$)$_2$ | 26.7 | 2.08, m |
| | | | 6'''-O—COCH$_2$CH(CH$_3$)$_2$ | 22.9 | 0.96, d (7.0) |

TABLE 7

NMR data for Compound No. [16]

| aglycon moiety | | | carbohydrate moiety | | |
|---|---|---|---|---|---|
| atom | $\delta_C$ | $\delta_H$, mult. | atom | $\delta_C$ | $\delta_H$, mult. |
| 1 | 178.3 | — | 1' | 102.3 | 4.43, d (6.5) |
| 2 | 71.0 | 4.09, dd (7.1, 4.1) | 2' | 83.6 | 3.31, m |
| 3 | 35.8 | 1.62, 1.74, m | 3' | 76.3 | 3.57, m |
| 4 | 26.1 | 1.42, m | 4' | 70.7 | 3.51, m |
| 5 | 30.5 | 1.33, m | 5' | 66.1 | 3.18, 3.86, m |
| 6-14 | 30.2 | 1.29, m | 1'' | 104.2 | 4.61, m |
| 15 | 27.0 | 1.33/1.52, m | 2'' | 84.0 | 3.44, m |
| 16 | 33.4 | 1.32/1.60, m | 3'' | 77.3 | 3.53, m |
| 17 | 75.7 | 3.36, m | 4'' | 70.8 | 3.51, m |
| 18 | 75.7 | 3.36, m | 5'' | 66.8 | 3.18, 3.86, m |
| 19 | 33.5 | 1.32/1.60, m | 1''' | 105.7 | 4.62, d (7.2) |
| 20 | 22.6 | 1.36/1.62, m | 2''' | 75.9 | 3.25, m |
| 21 | 35.8 | 1.55, m | 3''' | 77.3 | 3.35, m |
| 22 | 80.1 | 3.62, m | 4''' | 71.1 | 3.31, m |
| 23 | 35.4 | 1.45, m | 5''' | 78.8 | 3.31, m |
| 24 | 28.4 | 1.33, m | 6''' | 62.4 | 3.71, 3.90, m |
| 25 | 24.1 | 1.31, m | | | |
| 26 | 14.5 | 0.91, t (6.5) | | | |

TABLE 8

NMR data for Compound No. [17]

| aglycon moiety | | | carbohydrate moiety | | |
|---|---|---|---|---|---|
| atom | $\delta_C$ | $\delta_H$, mult. | atom | $\delta_C$ | $\delta_H$, mult. |
| 1 | 176.4 | — | 1' | 102.3 | 4.44, d (6.8) |
| 2 | 71.7 | 4.13, dd (7.6, 4.6) | 2' | 83.6 | 3.31, m |
| 3 | 35.3 | 1.64, 1.74, m | 3' | 76.4 | 3.57, m |
| 4 | 25.8 | 1.42, m | 4' | 70.6 | 3.51, m |
| 5 | 30.6 | 1.33, m | 5' | 66.2 | 3.19, 3.86, m |
| 6-14 | 30.2 | 1.29, m | 1'' | 104.2 | 4.61, d (6.5) |
| 15 | 26.9 | 1.33/1.52, m | 2'' | 84.0 | 3.43, t (7.8) |
| 16 | 33.4 | 1.32/1.60, m | 3'' | 77.3 | 3.53, m |
| 17 | 76.0 | 3.35, m | 4'' | 70.9 | 3.51, m |
| 18 | 76.0 | 3.35, m | 5'' | 66.7 | 3.17, 3.86, m |
| 19 | 33.4 | 1.33, m | 1''' | 105.9 | 4.62, d (7.4) |
| 20 | 22.4 | 1.35, m | 2''' | 75.9 | 3.25, m |
| 21 | 35.8 | 1.53, m | 3''' | 77.7 | 3.36, m |
| 22 | 80.2 | 3.63, m | 4''' | 70.9 | 3.31, m |
| 23 | 33.4 | 1.46, m | 5''' | 78.8 | 3.31, m |
| 24 | 28.5 | 1.34, m | 6''' | 62.5 | 3.71, 3.89, m |
| 25 | 23.8 | 1.33, m | | | |
| 26 | 14.5 | 0.91, t (7.0) | | | |
| OMe | 52.4 | 3.71, s | | | |

TABLE 9

NMR data for Compound No. [12]

| aglycon moiety | | | carbohydrate moiety | | |
|---|---|---|---|---|---|
| atom | $\delta_C$ | $\delta_H$, mult. | atom | $\delta_C$ | $\delta_H$, mult. |
| 1 | 178.0 | — | 1' | 102.5 | 4.39, d (6.8) |
| 2 | 71.5 | 4.09, dd (7.4, 4.4) | 2' | 84.4 | 3.26, m |
| 3 | 35.5 | 1.62, 1.73, m | 3' | 77.4 | 3.52, m |
| 4 | 26.1 | 1.42, m | 4' | 71.0 | 3.51, m |
| 5 | 30.6 | 1.32, m | 5' | 66.5 | 3.18, 3.86, m |
| 6-14 | 30.8 | 1.30, m | 1'' | 104.3 | 4.55, d (6.8) |
| 15 | 26.8 | 1.33, 1.52, m | 2'' | 83.4 | 3.43, m |
| 16 | 33.6 | 1.34, m | 3'' | 76.9 | 3.55, m |
| 17 | 76.0 | 3.36, m | 4'' | 71.0 | 3.51, m |
| 18 | 76.0 | 3.36, m | 5'' | 66.5 | 3.18, 3.86, m |
| 19 | 33.5 | 1.34, 1.49, m | 1''' | 105.4 | 4.65, d (6.8) |
| 20 | 22.6 | 1.36, 1.61, m | 2''' | 75.7 | 3.28, m |
| 21 | 35.8 | 1.53, m | 3''' | 77.7 | 3.38, m |
| 22 | 80.1 | 3.61, m | 4''' | 71.5 | 3.30, m |
| 23 | 35.4 | 1.47, 1.56, m | 5''' | 75.7 | 3.52, m |
| 24 | 28.4 | 1.33, m | 6''' | 64.4 | 4.21, 4.49, m |
| 25 | 24.1 | 1.32, m | 6'''-O—COCH$_2$CH(CH$_3$)$_2$ | 174.9 | — |
| 26 | 14.5 | 0.91, t (6.8) | 6'''-O—COCH$_2$CH(CH$_3$)$_2$ | 44.2 | 2.28, d (7.1) |
| | | | 6'''-O—COCH$_2$CH(CH$_3$)$_2$ | 26.8 | 2.10, m |
| | | | 6'''-O—COCH$_2$CH(CH$_3$)$_2$ | 22.9 | 0.97, d (6.6) |

TABLE 10

NMR data for Compound No. [14]

| | aglycon moiety | | carbohydrate moiety | | |
|---|---|---|---|---|---|
| atom | $\delta_C$ | $\delta_H$, mult. | atom | $\delta_C$ | $\delta_H$, mult. |
| 1 | 178.0 | — | 1' | 102.3 | 4.42, d (6.3) |
| 2 | 71.5 | 4.09, dd (7.4, 4.6) | 2' | 83.2 | 3.30, m |
| 3 | 35.8 | 1.62, 1.74, m | 3' | 76.8 | 3.57, m |
| 4 | 26.1 | 1.42, m | 4' | 70.7 | 3.50, m |
| 5 | 30.5 | 1.33, m | 5' | 66.3 | 3.17, 3.85, m |
| 6-14 | 30.2 | 1.29, m | 1" | 104.1 | 4.69, d (7.1) |
| 15 | 26.9 | 1.34, 1.55, m | 2" | 83.5 | 3.44, t (7.9) |
| 16 | 33.4 | 1.33, m | 3" | 74.2 | 3.55, m |
| 17 | 76.0 | 3.36, m | 4" | 72.9 | 3.50, m |
| 18 | 76.0 | 3.36, m | 5" | 63.4 | 3.17, 3.86, m |
| 19 | 33.4 | 1.33, 1.63, m | 1'" | 105.8 | 4.71, d (7.6) |
| 20 | 22.5 | 1.38, 1.63, m | 2'" | 75.66 | 3.36, m |
| 21 | 35.8 | 1.53, m | 3'" | 77.2 | 3.57, m |
| 22 | 80.2 | 3.63, m | 4'" | 71.1 | 4.83, m |
| 23 | 35.2 | 1.40, m | 5'" | 78.7 | 3.72, m |
| 24 | 28.4 | 1.32, m | 6'" | 62.5 | 4.19, m |
| 25 | 23.8 | 1.32, m | 4'"-O—$\underline{C}$OCH$_3$ | 172.2 | — |
| 26 | 14.5 | 0.91, t (6.5) | 4'"-O—CO$\underline{CH_3}$ | 20.8 | 2.06, s |

TABLE 11

NMR data for Compound No. [10]

| | aglycon moiety | | carbohydrate moiety | | |
|---|---|---|---|---|---|
| atom | $\delta_C$*[)] | $\delta_H$, mult. | atom | $\delta_C$*[)] | $\delta_H$, mult. |
| 1 | 179.1 | — | 1' | 102.0 | 4.39, d (6.8) |
| 2 | 72.2 | 3.97, dd (7.4, 4.4) | 2' | 84.0 | 3.25, m |
| 3 | 35.4 | 1.60, 1.73, m | 3' | 76.9 | 3.50, m |
| 4 | 26.1 | 1.42, m | 4' | 70.4 | 3.49, m |
| 5-13 | 30.3 | 1.28, m | 5' | 66.3 | 3.17, 3.84, m |
| 14 | 26.3 | 1.31, 1.42, m | 1" | 103.9 | 4.63, d (6.8) |
| 15 | 38.2 | 1.35, 1.42, m | 2" | 83.2 | 3.52, m |
| 16 | 72.1 | 3.50, m | 3" | 74.1 | 3.79, m |
| 17 | 38.2 | 1.35, 1.42, m | 4" | 72.6 | 4.68, m |
| 18 | 22.0 | 1.35, 1.51, m | 5" | 63.2 | 3.23, 3.97, m |
| 19 | 35.7 | 1.51, m | 1'" | 105.2 | 4.66, d (6.8) |
| 20 | 79.8 | 3.61, m | 2'" | 75.4 | 3.27, m |
| 21 | 34.6 | 1.44, 1.54, m | 3'" | 77.4 | 3.36, m |
| 22 | 30.3 | 1.28, m | 4'" | 71.0 | 3.33, m |
| 23 | 30.3 | 1.28, m | 5'" | 75.6 | 3.52, m |
| 24 | 32.8 | 1.28, m | 6'" | 64.1 | 4.22, dd (11.7, 5.2), 4.46, d (11.7) |
| 25 | 23.4 | 1.33, m | 4"-O—$\underline{C}$OCH$_3$ | 171.8 | — |
| 26 | 13.9 | 0.91, t (6.8) | 4"-O—CO$\underline{CH_3}$ | 20.5 | 2.06, s |
| | | | 6'"-O—$\underline{C}$OCH$_3$ | 172.6 | — |
| | | | 6'"-O—CO$\underline{CH_3}$ | 20.7 | 2.10, s |

*[)]carbon chemical shifts obtained from HSQC/HMBC experiments.

TABLE 12

NMR data for Compound No. [18]

| | aglycon moiety | | carbohydrate moiety | | |
|---|---|---|---|---|---|
| atom | $\delta_C$*[)] | $\delta_H$, mult. | atom | $\delta_C$*[)] | $\delta_H$, mult. |
| 1 | 178.1 | — | 1' | 102.5 | 4.38, d (6.8) |
| 2 | 71.5 | 4.07, m | 2' | 84.4 | 3.25, m |
| 3 | 35.5 | 1.63, 1.74, m | 3' | 77.1 | 3.52, m |
| 4 | 26.1 | 1.43, m | 4' | 70.6 | 3.51, m |
| 5-13 | 30.6 | 1.30, m | 5' | 66.5 | 3.11, 3.84, m |
| 14 | 26.0 | 1.35, 1.42, m | 1" | 104.3 | 4.62, d (6.5) |
| 15 | 38.4 | 1.34, m | 2" | 83.3 | 3.52, m |
| 16 | 72.4 | 3.50, m | 3" | 74.4 | 3.80, m |
| 17 | 38.4 | 1.34, m | 4" | 72.9 | 4.69, m |
| 18 | 22.3 | 1.35, 1.51, m | 5" | 63.5 | 3.23, 3.97, m |
| 19 | 35.8 | 1.51, m | 1'" | 105.4 | 4.66, d (7.6) |
| 20 | 80.2 | 3.61, m | 2'" | 75.6 | 3.26, m |
| 21 | 34.9 | 1.44, 1.54, m | 3'" | 77.7 | 3.36, m |
| 22 | 30.6 | 1.30, m | 4'" | 71.5 | 3.31, m |
| 23 | 30.6 | 1.30, m | 5'" | 75.9 | 3.53, m |
| 24 | 33.4 | 1.27, m | 6'" | 64.4 | 4.21, dd (11.7, 5.5), 4.56, d (11.7) |
| 25 | 23.8 | 1.32, m | 4"-O—$\underline{C}$OCH$_3$ | 172.2 | — |
| 26 | 14.5 | 0.91, t (6.8) | 4"-O—CO$\underline{CH_3}$ | 20.8 | 2.06, s |
| | | | 6'"-O—$\underline{C}$OCH$_3$ | 174.8 | — |
| | | | 6'"-O—CO$\underline{CH_2}$CH(CH$_3$)$_2$ | 44.2 | 2.29, d (7.1) |
| | | | 6'"-O—COCH$_2$$\underline{CH}$(CH$_3$)$_2$ | 26.8 | 2.10, m |
| | | | 6'"-O—COCH$_2$CH($\underline{CH_3}$)$_2$ | 22.9 | 0.98, d (6.5) |

TABLE 13

NMR data for Compound No. [7]

| aglycon moiety | | | carbohydrate moiety | | |
|---|---|---|---|---|---|
| atom | $\delta_C$ | $\delta_H$, mult. | atom | $\delta_C$ | $\delta_H$, mult. |
| 1 | 178.1 | — | 1' | 102.5 | 4.47, d (6.8) |
| 2 | 71.5 | 4.09, m | 2' | 85.3 | 3.33, m |
| 3 | 35.4 | 1.64, 1.75, m | 3' | 74.2 | 3.77, t (9.1) |
| 4 | 26.1 | 1.43, m | 4' | 73.0 | 4.71, m |
| 5 | 30.7 | 1.33, m | 5' | 63.5 | 3.25, 3.95, m |
| 6-14 | 30.7 | 1.30, m | 1" | 104.8 | 4.64, d (7.4) |
| 15 | 26.9 | 1.33, 1.53, m | 2" | 84.7 | 3.40, m |
| 16 | 33.4 | 1.34, 1.59, m | 3" | 77.6 | 3.53, m |
| 17 | 76.0 | 3.37, m | 4" | 70.9 | 3.51, m |
| 18 | 76.0 | 3.37, m | 5" | 66.9 | 3.17, 3.84, m |
| 19 | 33.4 | 1.34, 1.59, m | 1''' | 106.1 | 4.64, d (7.6) |
| 20 | 22.6 | 1.36, 1.61, m | 2''' | 76.0 | 3.27, m |
| 21 | 35.8 | 1.54, m | 3''' | 77.6 | 3.37, m |
| 22 | 80.1 | 3.63, m | 4''' | 71.1 | 3.33, m |
| 23 | 34.8 | 1.47, m | 5''' | 75.9 | 3.55, m |
| 24 | 28.4 | 1.34, m | 6''' | 64.6 | 4.18, dd (12.0, 5.7), 4.41, d (11.4) |
| 25 | 23.8 | 1.33, m | 4'-O—COCH$_3$ | 172.2 | — |
| 26 | 14.5 | 0.92, t (6.8) | 4'-O—COC$\underline{H}_3$ | 20.9 | 2.04, s |
| | | | 6'''-O—COCH$_3$ | 172.7 | — |
| | | | 6'''-O—COC$\underline{H}_3$ | 21.0 | 2.09, s |

TABLE 14

NMR data for Compound No. [6]

| aglycon moiety | | | carbohydrate moiety | | |
|---|---|---|---|---|---|
| atom | $\delta_C$ | $\delta_H$, mult. | atom | $\delta_C$ | $\delta_H$, mult. |
| 1 | 178.2 | — | 1' | 102.4 | 4.41, d (6.8) |
| 2 | 70.7 | 4.12, m | 2' | 84.2 | 3.30, m |
| 3 | 34.2 | 1.67, 1.78, m | 3' | 77.1 | 3.55, t (9.1) |
| 4 | 24.6 | 1.46, m | 4' | 70.9 | 3.51, m |
| 5 | 30.8 | 1.33, m | 5' | 66.4 | 3.21, 3.87, m |
| 6-14 | 30.8 | 1.30, m | 1" | 104.2 | 4.62, d (7.1) |
| 15 | 27.0 | 1.33, 1.53, m | 2" | 83.6 | 3.40, m |
| 16 | 34.5 | 1.34, 1.59, m | 3" | 77.3 | 3.53, m |
| 17 | 75.7 | 3.37, m | 4" | 70.6 | 3.51, m |
| 18 | 75.7 | 3.37, m | 5" | 66.7 | 3.17, 3.84, m |
| 19 | 34.0 | 1.59, m | 1''' | 105.5 | 4.73, d (7.6) |
| 20 | 22.5 | 1.48, 1.55, m | 2''' | 75.7 | 3.37, m |
| 21 | 35.7 | 1.56, m | 3''' | 75.2 | 3.59, m |
| 22 | 80.2 | 3.63, m | 4''' | 71.9 | 4.87, m |
| 23 | 34.5 | 1.52, m | 5''' | 73.5 | 3.73, m |
| 24 | 28.4 | 1.36, m | 6''' | 64.6 | 4.15, dd (11.0, 5.6), 4.22, d (11.7) |
| 25 | 24.1 | 1.35, m | 4'''-O—COCH$_3$ | 172.2 | — |
| 26 | 14.5 | 0.93, t (6.8) | 4'''-O—COC$\underline{H}_3$ | 20.9 | 2.09, s |
| | | | 6'''-O—COCH$_3$ | 172.7 | — |
| | | | 6'''-O—COC$\underline{H}_3$ | 20.9 | 2.09, s |

Example 3: HPLC-UV-MS-ELSD Analysis

A General Methods a) "Standard Method"

LC-MS/UVELSD analyses were performed using an Agilent HP1100 (Agilent, Waldbronn, Germany) liquid chromatograph coupled with a LCT mass spectrometer (Waters Corporation, Milford, Mass., USA) in the positive and negative electrospray ionization (ESI) mode and a Sedex 75 Evaporative Light Scattering Detector (Sedere, Alfortville Cedex, France). A Waters symmetry column (Waters Symmetry® (Trademark by Waters) C18, 3.5 µm, 2.1 mm×150 mm, Waters GmbH, Eschborn, Germany) was used as stationary phase with a flow rate of 0.4 ml/min at 40° C. Mobile phase A: 0.1% formic acid in water, mobile phase B: 0.1% formic acid in acetonitrile; gradient: 0-1 min. 98% A, from 1-21 min. to 100% B, from 21-27 min 100% B. The UV/Vis spectra were recorded between 200-500 nm, the LC-MS (Liquid Chromatography-Mass Spectrometry coupling) spectra were recorded in the range of molecular weights between 160 and 1.600 Da.

b) "Adapted Method"

LC-MS/UVELSD analyses were performed using an Agilent HP1100 (Agilent, Waldbronn, Germany) liquid chromatograph coupled with a LCT mass spectrometer (Waters Corporation, Milford, Mass., USA) in the positive and negative electrospray ionization (ESI) mode and a Sedex 75 Evaporative Light Scattering Detector (Sedere, Alfortville Cedex, France). A Waters symmetry column (Waters Symmetry® (Trademark by Waters) C18, 3.5 µm, 2.1 mm×150 mm, Waters GmbH, Eschborn, Germany) was used as stationary phase with a flow rate of 0.4 ml/min at 40° C. Mobile phase A: 0.1% formic acid in water, mobile phase B: 0.1% formic acid in acetonitrile; gradient: 0 min: 55% A, from 0-14 min. to 100% B, from 14-16 min 100% B. The UV/Vis spectra were recorded between 200-500 nm, the LC-MS (Liquid Chromatography-Mass Spectrometry coupling) spectra were recorded in the range of molecular weights between 160 and 1.600 Da.

c) "Fermentation Control"

HPLC system: Agilent 1100 analytical HPLC system including pumps and autosampler, DAD (200-500 nm) and ELSD detectors; column oven at 40° C.; column: Waters Symmetry® C18 3.5 µm (2.1×150 mm); solvents: deionised water (A) and acetonitrile (B) with 0.1% formic acid each. The flow was adjusted to 0.4 ml/min by using a temperature of 40° C. The gradient applied was optimized for separation and resolution of the glycolipid pattern: 0 to 14 min: from 45% to 100% (B); 14 to 16 min: 100% (B); 16 to 16.1 min: from 100% to 45% (B); 16.1 to 20 min: 45% (B). For HPLC analysis, samples were dissolved in 2-propanol.

B HPLC-MS of Pure Compounds

TABLE 15

Retention times and MS signals for compounds of the formula I, HPLC prepared according to the methods specified in Section A of this Example..

| Compound No. | HPLC "Standard method" | HPLC "Adapted method" | m/z |
|---|---|---|---|
| [16] | 14.09 | 2.94 | [M + H]$^+$ 887; [M acid]$^-$ 459 |
| [14] | 14.93 | 4.73 | [M + H]$^+$ 929; [M acid]$^-$ 459 |
| [6] | 15.15 | 4.99 | [M + H]$^+$ 971; [M acid]$^-$ 459 |
| [17] | 15.39 | 5.55 | [M + H]$^+$ 901; [M acid]$^-$ 473 |
| [7] | 15.44 | 5.68 | [M + H]$^+$ 971; [M acid]$^-$ 459 |
| [12] | 15.79 | 6.07 | [M + H]$^+$ 971; [M acid]$^-$ 459 |
| [3] | 16.32 | 6.84 | [M + H]$^+$ 1013; [M acid]$^-$ 459 |
| [13] | 16.52 | 7.06 | [M + H]$^+$ 1013; [M acid]$^-$ 459 |
| [1] | 17.00 | 7.48 | [M + H]$^+$ 1013; [M acid]$^-$ 459 |
| [4] | 17.50 | 8.38 | [M + H]$^+$ 1054; [M acid]$^-$ 459 |

TABLE 15-continued

Retention times and MS signals for compounds of the formula I, HPLC prepared according to the methods specified in Section A of this Example..

| Compound No. | HPLC "Standard method" | HPLC "Adapted method" | m/z |
|---|---|---|---|
| [10] | 17.67 | 8.50 | [M + H]+ 955; [M acid]− 443 |
| [18] | 19.36 | 10.43 | [M + H]+ 997; [M acid]− 443 |

C Characterization of Extracts
a) Extract of *Ditiola pezizaeformis* Strain ATCC13299

TABLE 16

Figure 3:
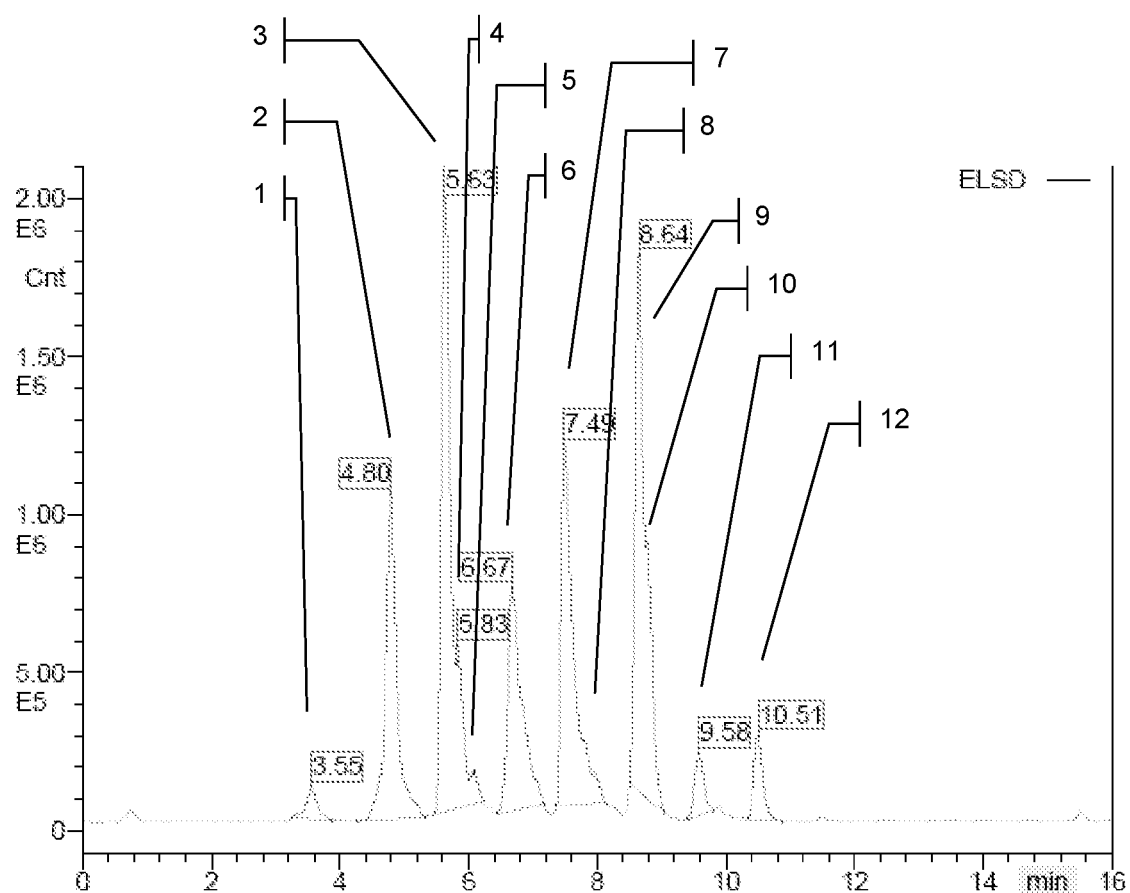
FIG. 3: Typical HPLC-ELSD chromatogram of an extract of *Ditiola pezizaeformis* strain ATCC13299 (MUCL 53500), peak annotation according to Table 16 below.

HPLC-MS analysis of an extract obtained from *Ditiola pezizaeformis* strain ATCC13299 (HPLC-ELSD chromatogram presented in FIG. 3)

| Peak | Compound No. | HPLC "Adapted method" | m/z |
|---|---|---|---|
| 1 |  | 3.55 | [M + H]+ 943; [M acid]− 431 |
| 2 |  | 4.80 | [M + H]+ 985; [M acid]− 431 |
| 3 | [7] | 5.63 | [M + H]+ 971; [M acid]− 459 |
| 4 |  | 5.83 | [M + H]+ 985; [M acid]− 431 |
| 5 | [12] | 6.08 | [M + H]+ 971; [M acid]− 459 |
| 6 |  | 6.67 | [M + H]+ 927; [M acid]− 415 |
| 7 | [1] | 7.49 | [M + H]+ 1013; [M acid]− 459 |
| 8 |  | 7.90 | [M + H]+ 969; [M acid]− 415 |
| 9 |  | 8.64 | [M + H]+ 969; [M acid]− 415 |
| 10 |  | 8.86 | [M + H]+ 969; [M acid]− 415 |
| 11 |  | 9.58 | [M + H]+ 983; [M acid]− 429 |
| 12 | [18] | 10.51 | [M + H]+ 997; [M acid]− 443 |

All shown signals were unequivocally assigned to be glycolipids by HPLC-MS/UV.

b) Extracts of *Dacryopinax spathularia* strain MUCL53181

Extract [X1]: Glycolipid mixture prepared according to Example 1 from 30 l fermentation
Extract [X2]: Glycolipid mixture prepared according to Example 1 from 200 l fermentation

TABLE 17

Figure 2:
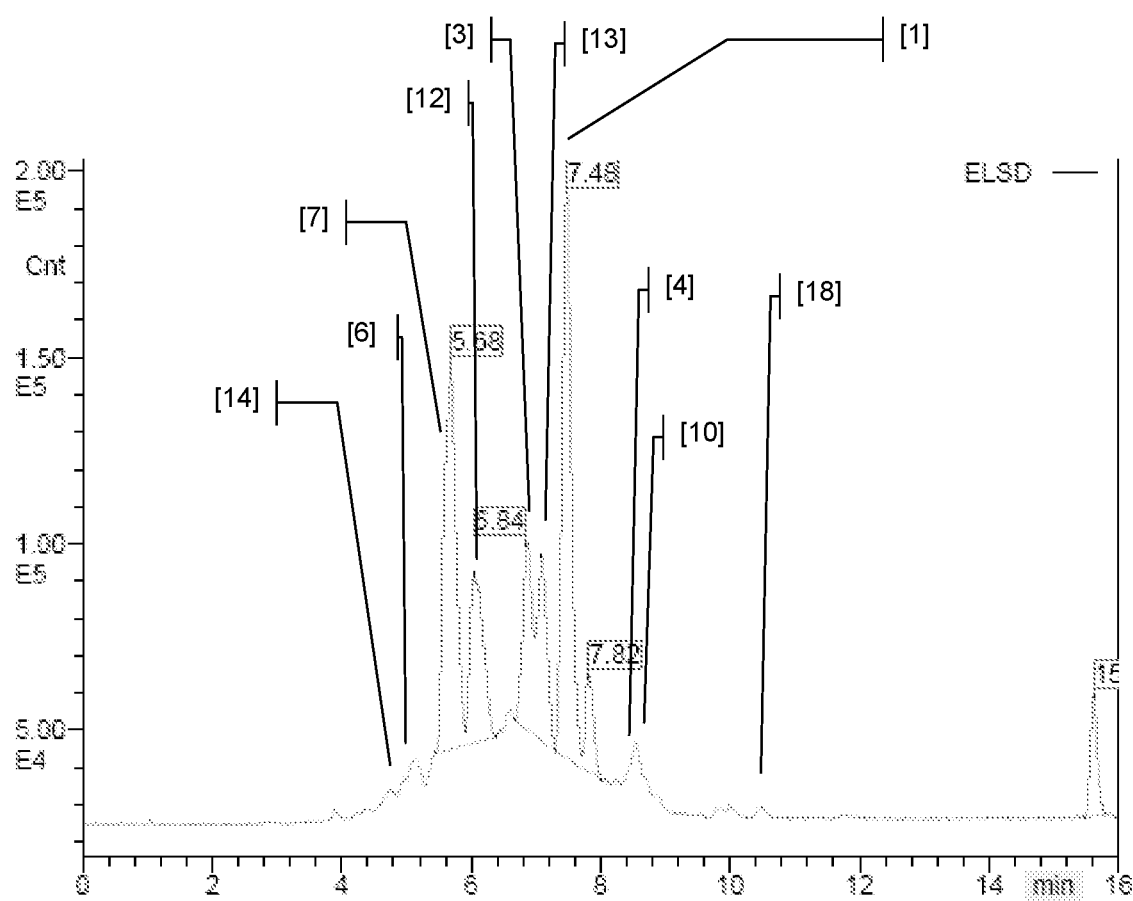
FIG. 2: Typical HPLC-MS of an extract of FU50088 (MUCL 53181) produced following the example 1 B Fermentation c) 200 l fermentation; C Preparation of extracts c) Preparation of a sedimentation product. Adjustment of signals according the "Adapted method" of Example 3. The numbers in brackets "[ . . . ]" represent the corresponding compound in Table 1.

HPLC-MS analysis (using the "Adapted method") of extracts obtained from *Dacryopinax spathularia* strain MUCL 53181 (HPLC-ELSD chromatogram for [X2] is presented in FIG. 2)

| Ret. time [min] | Nominal MW [Da] | Identified compound class | [X1] | [X2] |
|---|---|---|---|---|
| 3.8 | 942 | Glycolipid derivative | * | 0.4 |
| 4.3 | 928 | Glycolipid derivative | * | 0.3 |
| 4.6 | 928 | [14] | * | 0.4 |
| 4.9 | 984 | Glycolipid derivative | 0.3 |  |
| 5.1 | 970 | [6] | 0.9 | 1.3 |
| 5.6 | 970 | [7] | 72.5 | 25.1 |
| 6.1 | 970 | [12] | 8.3 | 12.3 |
| 6.5 | 998 | Glycolipid derivative | * | 0.7 |
| 6.6 | 1012 | Glycolipid derivative | 0.9 | * |
| 6.8 | 1012 | [3] | * | 10.8 |
| 7.0 | 998 | Glycolipid derivative | * | * |
| 7.1 | 1012 | [13] | 2.6 | 10.7 |
| 7.5 | 1012 | [1] | 7.8 | 29.8 |
| 7.8 | 1012 | Glycolipid derivative | 1.3 | 4.3 |
| 8.4 | 1054 | [4] |  | * |
| 8.5 | 954 | [10] | 5.2 | 2.2 |
| 8.8 | 954 + 1054 | Glycolipid derivatives | * | 0.3 |
| 8.9 | 954 | Glycolipid derivative | * | * |
| 9.8 | 982 | Glycolipid derivative | * | 0.4 |
| 10.0 | 996 | Glycolipid derivative | * | 0.5 |
| 10.4 | 996 | [18] | 0.4 | 0.6 |
| 11.3 | 1038 | Glycolipid derivative |  | * |

* Peak area below detection limit of ELSD, but compound was detected by ESI MS signals.

Example 4: Biological Activities

A. Determination of Minimal Inhibition Concentration
a) Non-Pathogenic Microorganisms Various nonpathogenic bacteria, yeasts, and filamentous fungi were obtained from public culture collections and maintained as recommended in the catalogues and protocols of the respective institutions. *Saccharomyces cerevisiae* strain HT10 and *Mucor plumbeus* were originally taken from the culture collection of InterMed Discovery GmbH but deposited with MUCL as reference strains for antimicrobial susceptibility testing. These strains were maintained under liquid nitrogen and, prior to the screening, on YMG agar.

Prior to the screening the yeast and bacterial strains were grown over night on SDB (medium 1), except for *Bacillus subtilis*, which was grown on YMG agar (medium 2) for 1 week to prepare spore suspensions. Likewise, the filamentous fungi were pre-incubated on YMG agar for 2-3 weeks to create inoculum for spore suspensions. The spores were then rinsed from the surface of the flasks using 0.9% saline, checked for viability by microscopic control and by plating on agar plates, and diluted to the desired concentration of spores. For all experiments, freshly prepared spore suspensions were used. The initial concentrations for the bioassays were adjusted to $1\times10^5$ CFU (i.e. cells or spores, respectively) per ml. Standards (preservative agents benzoic acid and sorbic acid; antibiotics: penicillin G, streptomycin sulphate, amphopthericin B) served as positive controls.

To adjust the initial titer prior to the bioassays, the CFU per ml was determined under the microscope using a counting chamber type "Brand Neubauer improved"; BRAND GmbH & Co KG, Wertheim, Germany). This microscopic control also served as means for assessment of the viability of the cells.

The actual assays were carried out in Greiner type Bio-one suspension culture plates (96 Well flat-bottom sterile, No 655185).

The compounds or extracts to be tested from stock material, including standards, were dissolved in appropriate volumes of DMSO prior to the test and diluted into the microtiter plates, using a final concentration of 1.5%. Aside from regular incubation time for determination of MIC (18-24 h), the stability of the inhibitory effects was also studied at prolonged incubation times. For this purpose, each microtiter plate vial was filled with 200 μl of the cell suspensions and the test plates were incubated in an incubator (Heraeus HERA cell) at 28° C. an absolute humidity of 95%, to prevent evaporation of the solvent. Under such conditions, no notable evaporation of the microtiter plates was observed for up to several weeks. MICs were generally determined in a traditional manner, by checking the MTP optically and determining the dilution of each individual compound where no visible growth had occurred. However, the $OD_{630}$ was also determined using a plate reader, in those cases where it appeared difficult to observe the MIC with the naked eye. In some instances, the $OD_{630}$ of the plates could be monitored and determined using the plate reader for up to four weeks. However, in general, the long term experiments were run for at least 168 hours. For determination of $OD_{630}$, the microtiter plates were scanned using a SPECTROstar Omega (BMG LABTECH, Offenburg, Germany) plate reader, except for the filamentous fungi, where a PHERAstar plus (BMG LABTECH, Offenburg, Germany) was used in "Wellscan" mode (orbital averaging at 4 mm), since this instrument provided more reliable data if mycelial colonies had arisen from the initial spore suspensions. MIC in the optical readout was determined using the following formula:

$$\text{Inhibition [\%]} = 100 - \left( \frac{(\bar{x}OD_{630}[\text{sample}]) \times 100}{(\bar{x}OD_{630}[\text{control}])} \right)$$

The MIC values reported relate to the concentration causing at least 80% inhibition as compared to the positive control.

Results:

TABLE 18

MIC values of standards in different media: sorbic acid [SA] and benzoic acid [BA]

| | day | [SA] SDB | [SA] apple-juice | [BA] SDB | [BA] apple-juice |
|---|---|---|---|---|---|
| Bacteria | | | | | |
| B. subtilis | 2 | 250 | | 250 | |
| (ATCC6633) | 7 | 250 | | 250 | |
| | 16 | 250 | | 250 | |
| | 28 | 500 | | 250 | |
| L. plantarum | 2 | >1000 | 31.3 | >1000 | 250 |
| (DSM12028) | 7 | >1000 | 500 | >1000 | >1000 |
| | 16 | >1000 | | >1000 | |
| | 28 | >1000 | | >1000 | |
| L welshimeri | 2 | 500 | | 500 | |
| | 7 | 500 | | 500 | |
| | 16 | 250 | | 250 | |
| | 28 | 500 | | 250 | |
| Filamentous fungi | | | | | |
| A. niger | 2 | 250 | | 500 | |
| (ATCC16404) | 7 | 1000 | | >1000 | |
| | 16 | 1000 | | >1000 | |
| | 28 | 1000 | | >1000 | |
| M. plumbeus | 2 | 250 | | 1000 | |
| (MUCL49355) | 7 | 500 | | 1000 | |
| | 16 | 1000 | | >1000 | |
| | 28 | 1000 | | >1000 | |
| Yeast | | | | | |
| D. bruxellensis | 2 | 500 | 250 | 500 | 125 |
| (DSM70726) | 7 | 500 | 500 | 1000 | 125 |
| | 16 | >1000 | 500 | >1000 | 250 |
| | 28 | >1000 | | >1000 | |
| D. naardenensis | 2 | 250 | | 500 | |
| (DSM70743) | 7 | 500 | | 500 | |
| | 16 | 500 | | 500 | |
| | 28 | 500 | | 500 | |
| B. fulva | 2 | 62.5 | | 62.5 | |
| (DSM62097) | 7 | 500 | | 500 | |
| | 16 | 500 | | 500 | |
| | 28 | 500 | | 500 | |
| Z. bailii | 2 | 500 | | >1000 | |
| (DSM70492) | 7 | 1000 | | >1000 | |
| | 16 | >1000 | | >1000 | |
| | 28 | >1000 | | >1000 | |

TABLE 19

SDB medium: pure compounds

| | day | [1] | [12] | [13] | [6] | [16] | [18] | [10] | [14] |
|---|---|---|---|---|---|---|---|---|---|
| Bacteria | | | | | | | | | |
| B. subtilis | 2 | 3.1 | 3.1 | 3.1 | 1.6 | 3.1 | 3.1 | <0.8 | |
| (ATCC6633) | 7 | 3.1 | 3.1 | 3.1 | 1.6 | 3.1 | 3.1 | <0.8 | |
| | 16 | 6.3 | 6.3 | 3.1 | 6.3 | 3.1 | 3.1 | <0.8 | |
| | 28 | 6.3 | 6.3 | 3.1 | 6.3 | 6.3 | 3.1 | <0.8 | |
| Filamentous fungi | | | | | | | | | |
| A. niger | 2 | 6.3 | | 6.3 | 6.3 | 12.5 | 3.1 | 3.1 | 50 |
| (ATCC16404) | 7 | 12.5 | | 12.5 | 12.5 | 25 | >100 | 6.3 | 50 |

TABLE 19-continued

SDB medium: pure compounds

|  | day | [1] | [12] | [13] | [6] | [16] | [18] | [10] | [14] |
|---|---|---|---|---|---|---|---|---|---|
|  | 16 | 12.5 |  | 12.5 | 62.5 | 25 | >100 | 6.3 |  |
|  | 28 | 12.5 | >100 | 25 | 12.5 | 50 | >100 | 6.3 |  |
| M. plumbeus |  | 25 | 50 | 12.5 | 25 | >100 | 25 | 12.5 | 50 |
| (MUCL49355) |  | 50 | 100 | 25 | 25 | >100 | >100 | 50 | >100 |
| Yeast |  |  |  |  |  |  |  |  |  |
| D. bruxellensis | 2 | 12.5 | 12.5 | 6.3 | 25 | >100 | 3.1 | 3.1 |  |
| (DSM70726) | 7 | 25 | 25 | 12.5 | 25 | >100 | 12.5 | 6.3 |  |
|  | 16 | 25 | 25 | 12.5 | 50 | >100 | 100 | 6.3 |  |
|  | 28 | 25 | 25 | 25 | 50 | >100 | 100 | 6.3 |  |
| D. naardenensis | 2 |  |  |  |  |  |  |  |  |
| (DSM70743) |  | 12.5 | 100 | 12.5 | 25 | 50 | 3.1 | 3.1 | 25 |
|  | 7 | 25 |  | 12.5 | 25 | >100 | 50 | 6.3 | 100 |
|  | 1 | 25 | 50 | 12.5 | 25 | >100 | >100 | 6.3 |  |
|  | 28 | 25 | >100 | 12.5 | 25 | >100 | >100 | 6.3 |  |
| B. fulva | 2 | 3.1 | 6.3 | 3.1 | 3.1 | 6.3 | 1.6 | 1.6 |  |
| (DSM62097) | 7 | 6.3 | 12.5 | 3.1 | 6.3 | 6.3 | 1.6 | 1.6 |  |
|  | 16 | 6.3 | 12.5 | 3.1 | 6.3 | 6.3 | 1.6 | 1.6 |  |
|  | 28 | 31.3 | 12.5 | 15.6 | 6.3 | 31.3 | 7.8 | 1.6 |  |
| Z. bailii | 2 | 25 | >100 | 12.5 | 25 | >100 | >100 | 6.3 |  |
| (DSM70492) | 7 | 25 | >100 | 12.5 | 25 | >100 | >100 | 12.5 |  |
|  | 16 | 12.5 | >100 | 12.5 | 25 | >100 | >100 | 12.5 |  |
|  | 28 | 25 | >100 | 12.5 | 25 | >100 | >100 | 12.5 |  |

TABLE 20

SDB medium: extracts

|  | day | [X1] | [X2] | [X3] | [X4] | [X5] | [X6] |
|---|---|---|---|---|---|---|---|
| Bacteria |  |  |  |  |  |  |  |
| B. subtilis | 2 | <3.9 | <3.9 | <3.9 | >500 | 7.8 | <3.9 |
| (ATCC6633) | 7 | <3.9 | <3.9 | <3.9 | >500 | 7.8 | <3.9 |
|  | 16 | <3.9 | <3.9 | <3.9 | <3.9 | 15.6 | <3.9 |
|  | 28 | <3.9 | <3.9 | <3.9 | <3.9 | 31.3 | 7.8 |
| Filamentous fungi |  |  |  |  |  |  |  |
| A. niger | 2 | <3.9 | <3.9 | <3.9 | <3.9 | 125 | <3.9 |
| (ATCC16404) | 7 | 7.8 | 7.8 | 7.8 | 15.6 | 500 | 7.8 |
|  | 16 | 7.8 | 7.8 | 7.8 | 7.8 | >500 | 7.8 |
|  | 28 | 7.8 | 7.8 | 7.8 | 15.6 | >500 | 7.8 |
| M. plumbeus | 2 | 7.8 | 7.8 | 7.8 | 15.6 | 62.5 | 7.8 |
| (MUCL49355) | 7 | 15.6 | 15.6 | 15.6 | 31.3 | 125 | 15.6 |
|  | 16 | 15.6 | 31.3 | 31.3 | 31.3 | >500 | 31.3 |
|  | 28 | 62.5 | 31.3 | 62.5 | 125 | >500 | 250 |
| Yeast |  |  |  |  |  |  |  |
| D. naardenensis | 2 |  |  |  |  |  |  |
| (DSM70743) |  | 7.8 | <3.9 | 7.8 | 7.8 | 125 | 7.8 |
|  | 7 | 7.8 | 7.8 | 15.6 | 15.6 | 500 | 15.6 |
|  | 16 | 7.8 | 7.8 | 15.6 | 15.6 | >500 | 31.3 |
|  | 28 | 7.8 | 15.6 | 15.6 | 15.6 | >500 | 15.6 |
| B. fulva | 2 | <3.9 | <3.9 | <3.9 | <3.9 | 15.6 | <3.9 |
| (DSM62097) | 7 | <3.9 | <3.9 | <3.9 | <3.9 | 62.5 | <3.9 |
|  | 16 | <3.9 | <3.9 | <3.9 | <3.9 | 62.5 | <3.9 |
|  | 28 | <3.9 | <3.9 | <3.9 | <3.9 | 62.5 | <3.9 |

TABLE 21

SDB vs apple juice medium: pure compounds and extracts

|  | day | [1] | [13] | [6] | [10] | [X1] | [X2] | [X3] | [X4] | [X5] | [X6] |
|---|---|---|---|---|---|---|---|---|---|---|---|
| Bacteria |  |  |  |  |  |  |  |  |  |  |  |
| L. plantarum | 2 |  |  |  |  |  |  |  |  |  |  |
| (DSM12028) |  | 12.5 | 6.3 | 25 | 3.1 | >100 | <3.9 | 7.8 | <3.9 | 250 | >500 |
| SDB | 7 | 25 | 12.5 | 25 | 6.3 | >100 | <3.9 | 15.6 |  | 500 | 7.8 |
|  | 16 | 25 | 12.5 | 50 | 6.3 | 15.5 | <3.9 | 31.3 | <3.9 | >500 | 7.8 |
|  | 28 | 25 | 6.3 | 25 | 6.3 | 15.6 | 31.3 | 31.3 | <3.9 | >500 | 7.8 |
| L. plantarum | 2 |  |  |  |  |  |  |  |  |  |  |
| (DSM12028) |  | 6.3 | <0.8 | 6.3 | <0.8 | <3.9 | <3.9 | <3.9 | <3.9 | 62.5 | <3.9 |
| apple juice | 7 | >100 | <0.8 | 50 | <0.8 | 62.5 | >500 | <3.9 | >500 | 259 | 125 |
| Yeast |  |  |  |  |  |  |  |  |  |  |  |
| Z. bailii | 2 | 25 | 12.5 | 25 | 6.3 | 7.8 | 7.8 | 7.8 | 15.6 | 125 | >500 |
| (DSM70492) | 7 | 25 | 12.5 | 25 | 12.5 | 7.8 | 7.8 | 7.8 | 15.6 | 125 | >500 |
| SDB | 16 | 12.5 | 12.5 | 25 | 12.5 | 7.8 | 7.8 | 7.8 | 15.6 | 250 | 15.6 |
|  | 28 | 25 | 12.5 | 25 | 12.5 | 15.6 | 15.6 | 7.8 | 15.6 | 250 | 15.6 |

TABLE 21-continued

SDB vs apple juice medium: pure compounds and extracts

| | day | [1] | [13] | [6] | [10] | [X1] | [X2] | [X3] | [X4] | [X5] | [X6] |
|---|---|---|---|---|---|---|---|---|---|---|---|
| Z. bailii | 2 | 6.3 | 3.1 | 3.1 | 3.1 | <3.9 | <3.9 | >500 | <3.9 | 31.3 | <3.9 |
| (DSM70492) | 7 | 6.3 | | 3.1 | 6.3 | <3.9 | <3.9 | >500 | <3.9 | 31.3 | <3.9 |
| apple juice | 16 | 6.3 | 3.1 | 3.1 | 3.1 | <3.9 | <3.9 | <3.9 | <3.9 | 31.3 | <3.9 |
| | 28 | 6.3 | 3.1 | 3.1 | 3.1 | <3.9 | <3.9 | <3.9 | <3.9 | 31.3 | <3.9 |
| D. bruxellensis | 2 | | | | | | | | | | |
| (DSM70726) | | 12.5 | 6.3 | 25 | 3.1 | 7.8 | <3.9 | 7.8 | 7.8 | 250 | 7.8 |
| SDB | 7 | 25 | 12.5 | 25 | 6.3 | 15.6 | 7.8 | 15.6 | 31.3 | >500 | 15.6 |
| | 16 | 25 | 12.5 | 50 | 6.3 | 15.6 | 7.8 | 15.6 | 15.6 | >500 | 31.3 |
| | 28 | 25 | 12.5 | 25 | 6.3 | 15.6 | 15.6 | 15.6 | 31.3 | >500 | 31.3 |
| D. bruxellensis | 2 | | | | | | | | | | |
| (DSM70726) | | 6.3 | 3.1 | 3.1 | 3.1 | <3.9 | <3.9 | <3.9 | <3.9 | 15.6 | <3.9 |
| apple juice | 7 | 25 | 6.3 | 3.1 | 3.1 | <3.9 | <3.9 | <3.9 | <3.9 | 31.3 | <3.9 |
| | 16 | 6.3 | 6.3 | 3.1 | 3.1 | <3.9 | <3.9 | <3.9 | <3.9 | 31.3 | <3.9 |
| | 28 | 6.3 | 3.1 | 3.1 | 3.1 | <3.9 | <3.9 | <3.9 | <3.9 | 31.3 | <3.9 |

Note:
Apple juice medium per se shows already limited growth which is based mainly on the low concentration of nitrogen compounds available and needed for growth.

It is evident and remarkable that independently of the extraction method (e.g. X1-X3) comparable results are achieved.

Bacteria
Bacillus subtilis (ATCC6633)
Clostridium perfringens (ATCC13124)
Corynebacterium variabile (DSM20132)
Corynebacterium variabile (ATCC15753)
Escherichia coli (ATCC9637)
Lactobacillus plantarum (DSM 12028)
Pseudomonas putida (ATCC 17484)
Staphylococcus aureus (ATCC 6538P)
Filamentous fungi («molds»)
Aspergillus fumigatus (ATCC 1028)
Aspergillus niger (ATCC 16404)
Byssochlamys fulva (DSM62097)
Mucor plumbeus (MUCL49355)
Yeasts
Dekkera bruxellensis (DSM70726)
Dekkera naardenensis (DSM70743)
Saccharomyces cerevisiae (HT10)
Zygosaccharomyces bailii (DSM70492)
Zygosaccharomyces bailii (ATCC60484)
Zygosaccharomyces bisporus (DSM70415)
Zygosaccharomyces florentinus (DSM70506)
Zygosaccharomyces rouxii (NCYC381)
b) Pathogenic Microorganisms Several samples of extracts and pure compounds were tested against Staphylococcus aureus (ATCC 6538P), Clostridium perfringens (ATCC 13124) or Aspergillus fumigatus (ATCC 1028). The test was performed by Ricerca Biosciences, LLC (Taiwan): S. aureus (cat no 604000) with Mueller-Hinton Broth medium using 1% DMSO as vehicle for an incubation time of 20 hours at 36° C. (di Modugno, Antimicrob Agents Chemother (1994) 38: 2362-8); C. perfringens (cat no 620700) with Reinforced Clostridial Medium using 1% DMSO as vehicle for an incubation time of 2 days at 36° C. (di Modugno, ibid); A. fumigatus (cat no 640010) with Potato Dextrose Broth medium using 1% DMSO as vehicle for an incubation time of 3 days at 28° C. (Turner, Antimicrob Agents Chemother (1989) 33(2): 215-22). MICs were detected via turbidity measurements in all cases.

The average mol weight was set to 1000 g/mol, the presented data in the following table 22 are given in mg/ml (ppm).

TABLE 22

MICs [ppm] of extracts and pure compounds against human pathogenic microorganisms.

| | S. aureus | C. perfringens | A. fumigatus |
|---|---|---|---|
| D. spathularia MUCL 53181 extract | | 60 | 20 |
| D. spathularia MUCL 53182 extract | | 60 | 60 |
| [1] | 200 | 60 | 20 |
| [12] | 200 | 60 | 20 |

Example 5: Sensory Evaluation

The extract [X2] was dissolved in water to final concentrations of 10 ppm and 100 ppm. These two test samples were presented together with a pure water sample (as negative control) to two test persons. The three samples were blinded prior to the taste evaluation.

None of the test persons were able to discriminate between pure water and the sample containing 10 ppm of the test compound. The sample containing 100 ppm of the test compound was described with a diffuse taste comparable with water which was stored for a longer time in an open PET bottle. No bitter, spicy or otherwise unpleasant taste was observed.

In a second trial one test person tried the pure dry powder of the above test compound. Even after this application no further adverse or unpleasant taste was named.

Example 6: Optical Rotation Values

Optical rotation values were determined in methanolic solutions using a Schmidt-Haensch, Unipol L 1000 polarimeter equipped with a silica glass micro cuvette (100 mm length; 1 ml sample volume).

TABLE 23

Specific optical rotation values in methanol

| Compound/extract | alpha$^D_{20}$ | c [g/100 mL] |
|---|---|---|
| [1] | −20.0 | 0.34 |
| [13] | −22.3 | 0.36 |

TABLE 23-continued

Specific optical rotation values in methanol

| Compound/extract | alpha$^D_{20}$ | c [g/100 mL] |
|---|---|---|
| [16] | +23.5 | 0.22 |
| [17] | n.d. | |
| [12] | −19.1 | 0.93 |
| [14] | n.d. | |
| [10] | −18.8 | 0.52 |
| [18] | −23.0 | 0.95 |
| [7] | n.d. | |
| [6] | −29.4 | 0.64 |
| [X2] | −25.5 | 0.68 |

Example 6: Apple Juice Based Beverage (cf. WO 2010/148045)

A 2% fruit juice based non-carbonated beverage of pH 3.4 and about 12 Brix is formed by combining the following ingredients.

| Ingredient | % Composition |
|---|---|
| Water | ca. 84 (added to final 100%) |
| Apple juice concentrate | 0.372 of concentrate to provide single strength concentration of about 2% |
| Sucrose | 6.8 |
| Glucose | 5.2 |
| Fructose | 0.2 |
| Compound extract [X2] | 0.000001–0.5% |
| Malic acid | 0.134 |
| Sodium malate | 0.013 |
| CaCl2—2H2O | 0.011 |
| MgCl2—6 H2O | 0.003 |
| EDTA | 0.003 |

A pH of 3.4 is achieved through combinations of malic acid and sodium malate. The total combined quantity of sodium malate and malic acid is near constant, but the ratio of malic acid and malate varied slightly depending on the content of compound extract [X2].

The above mixture is inoculated with test organisms and incubated for weeks at ambient temperature.

Example 7: Semifinished Products

A) The following mixtures can be used as concentrates for preservative efforts in different foods or beverages.

| Compound | Concentration in % | | |
|---|---|---|---|
| Variation | A | B | C |
| Water | ca. 70 | ca. 84 | ca. 50 |
| Sucrose, acetate isobutyrate | | 2 | 5 |
| Xanthan gum | | 0.16 | |
| Gum arab | 6 | | 4 |
| Beeswax | | 1 | |
| TWEEN 20 | 5 | | |
| Ethanol | | | 10 |
| Glycerol | | 5 | |
| Citric acid | | | 5 |
| Orange oil | | | 5 |
| Compound [X2] | 0.1 | 0.1 | 0.1 |

Compound extract [X2] is used as concentrated solution (concentrate) in DMSO which will be diluted to a final DMSO content of (concentrate) in the semi finished products. The compound extract [X2] solution is premixed with the appropriate alcohol, in variation C together with the orange oil, in variation B together with the beeswax, whereas the thickeners are mixed with an appropriate volume of water. The two mixtures are vigorously stirred, combined by continuing the stirring and filled up with water to the final volume (100%).

B) The following mixture is to be used as concentrate for an apple juice beverage (9 liter)

| Ingredients | Amount |
|---|---|
| Sucrose | 10% |
| Clear juice (apple) | 10% |
| Flavor emulsion (variant C of the above table) | 0.2% |
| Citric acid | 0.15% |
| Water | ca. 7.2 l |

The semifinished products are tested against microorganisms e.g. mold, yeasts and/or bacteria.

Example 8: Production and Isolation of a Mixture of Compounds of Formula I and a Mixture of Sodium Salts of Compounds of Formula I A) Fermentation Using the Strain FU50088 (*Dacryopinax spathularia* Strain MUCL 53181)

a) Seed Cultures (Shake Flask Cultures)

One ml of a cryo vial containing a mycelial suspension of strain MUCL 53181 in 10% glycerol was retrieved from liquid nitrogen and, after thawing, used to inoculate 200 ml Erlenmeyer flasks containing 50 ml of sterile YMG medium and propagated on a rotary shaker at 240 rpm and 23° C. for 72 h. Thereafter, each two ml of the primary seed culture were transferred into batches of two 500 ml Erlenmeyer flasks containing 200 ml of the same medium and propagated on a rotary shaker at 140 rpm and 28° C. for 90 h. These flasks served as secondary seed cultures.

b) Fermentation in 30 l Scale

A 40 l Biostat LP42 fermentor (Bioengineering, Wald, Switzerland) containing 30 l of GM2 medium was sterilized in situ (1 h at 121° C. and 1.1 bar) and inoculated with 1500 ml of the secondary seed culture. The production culture was grown under stirring (240 rpm) and aeration (0.2 vvm (volumes of air per minute per volume of batch) at 30° C. for 200 h.

B) Downstream Processing and Isolation

B-1) Isolation of a Mixture of Compounds of Formula I

The culture broth resulting from the 30 l fermentation of Example 8 A) b) was alkalized from an initial pH value of 4.5 to a pH value of 8 with 5 N sodium hydroxide solution to allow the glycolipids that partially stick to the cells under acidic conditions to become largely released from the mycelia. After 1 h the mycelia were separated from the culture broth by centrifugation, and then the culture broth was filtrated additionally through a Pall T1000 depth filter (Dreieich, Germany) to remove cell clusters and filamentous material. The product was sedimented (precipitated) by acidifying the filtrate with 6 N hydrochloric acid to pH 2.2 and subsequent storing for 20 h at 4° C. The fluid was removed by decantation, subsequent centrifugation (4500 rpm, 15 min, Type Jouan SA LR 5.22 (Jouan, Paris, France) and then discarded, resulting in a whitish-grey gel. This crude product was washed immediately with 1 l of slightly basic demineralized water (set to a pH-value of 8 with sodium hydroxide) and centrifuged at (4500 rpm for 15 min). The supernatant was removed and the remaining pellet suspended in 0.5 l demineralized water. After decantation the residue was freeze-dried to yield a slightly beige-grey powder (residual water content: 1.36% (according to the Karl Fischer method), the total protein content was below 1% (<1%) (Kjeldahl method according to ISO 5549: 1978). This process yielded a total of 87 g of glycolipids which subsequently were characterized by HPLC-MS (see [X7] in Table 24).

B-2) Isolation of a Mixture of Sodium Salts of Compounds of Formula I

The culture broth resulting from the 30 l fermentation of Example 8 A) b) was alkalized from an initial pH value of 4.5 to a pH value of 8 with 5 N sodium hydroxide solution to allow the glycolipids that partially stick to the cells under acidic conditions to become largely released from the mycelia. After 1 h the mycelia were separated from the culture broth in a separator, and then the culture broth was pumped through a combined filter assembly: first though a depth filter with a pore size of 0.65 μm and then through a membrane filter with a pore size of 0.45 μm to remove not only filamentous material and cell clusters but also cells. The product was sedimented (precipitated) by acidifying the filtrate with 6 N hydrochloric acid to pH 2 and then stored for 16 h at 4° C. The fluid was removed by decantation, subsequent centrifugation (4500 rpm, 15 min, Type Jouan SA LR 5.22 (Jouan, Paris, France) and then discarded, resulting in a whitish-grey gel. This crude product was washed immediately with 1 l demineralized water and centrifuged at (4500 rpm for 15 min). The supernatant was removed, the remainder suspended in 0.5 l demineralized water and the pH adjusted to a pH value of about 6 with 5 N sodium hydroxide solution. Finally, the resulting solution was freeze-dried to yield a total of 93 g of sodium salts of glycolipids in dry form as a slightly beige powder (residual water content: 1.2% (according to the Karl Fischer method), the total protein content was below 1% (<1%) (Kjeldahl method according to ISO 5549: 1978).

C) HPLC-MS Analysis—"Improved Method"

HPLC-MS analyses were performed using a Dionex Ultimate® 3000 RSLC (Thermo Fisher GmbH, Idstein; Germany) liquid chromatograph coupled with a amaZon SL ion trap mass spectrometer (Bruker Daltonik GmbH, Bremen, Germany) in the negative electrospray ionization (ESI) mode and a Sedex 85 ELSD (Sedere, Alfortville Cedex, France). A Nucleoshell RP18 column (2.7 μm, 2 mm×150 mm, Macherey-Nagel GmbH & Co. KG, Düren, Germany) was used as stationary phase with a flow rate of 0.4 ml/min at 40° C. Mobile phase A: 0.1% formic acid in water, mobile phase B: 0.1% formic acid in acetonitrile; gradient: 0 min: 70% A, from 0-40 min. to 40% A, from 40-42 min to 0% A, from 42-48 min. 0% A, from 48-49 min to 70% A, from 49-55 min 70% A. The LC-MS (Liquid Chromatography-Mass Spectrometry coupling) spectra were recorded in the range of molecular weights between 700 and 1.200 Da.

TABLE 24

HPLC-MS analysis (using the "Improved method") of the extract [X7] obtained from *Dacryopinax spathularia* strain MUCL 53181 according to Example 8 B-1)

| Ret. time [min] | Molecular weight [Da] | Identified compound (type) | [X7]* in wt. % |
|---|---|---|---|
| 13.49 | 886 | [16] | 0.1 |
| 14.20 | 886 | Glycolipid without acyl groups | 0.1 |
| 14.46 | 942 | Glycolipid | 1.6 |

TABLE 24-continued

HPLC-MS analysis (using the "Improved method") of the extract [X7] obtained from *Dacryopinax spathularia* strain MUCL 53181 according to Example 8 B-1)

| Ret. time [min] | Molecular weight [Da] | Identified compound (type) | [X7]* in wt. % |
|---|---|---|---|
| 15.46 | 928 | Glycolipid | 0.4 |
| 15.79 | 928 | Glycolipid | 1.2 |
| 16.27 | 928 | Glycolipid | 0.2 |
| 16.55 | 928 | Glycolipid | 1.2 |
| 16.98 | 928; 956 | Glycolipids | 1.1 |
| 17.38 | 928 | [14] | 0.8 |
| 17.49 | 970 | Glycolipid | 0.2 |
| 17.78 | 970 | Glycolipid | 0.9 |
| 18.26 | 970 | Glycolipid | 1.6 |
| 18.58 | 970 | Glycolipid | 0.5 |
| 19.00 | 970 | [6] | 2.3 |
| 19.73 | 970 | Glycolipid | 16.9 |
| 19.98 | 970 | [7] | 22.6 |
| 20.66 | 970; 984 | Glycolipids | 1.1 |
| 20.90 | 970 | Glycolipid | 3.4 |
| 21.44 | 970 | Glycolipid | 2.3 |
| 21.69 | 970 | [12] | 2.8 |
| 22.02 | 984 | Glycolipid | 0.3 |
| 22.57 | 970; 998 | Glycolipids | 1.3 |
| 22.86 | 926; 998 | Glycolipids | 1.2 |
| 23.09 | 1012 | Glycolipid | 1.0 |
| 23.91 | 1012 | [5] | 1.1 |
| 24.02 | 1012 | [9] | 2.4 |
| 24.19 | 1012 | Glycolipid | 0.4 |
| 24.73 | 1012 | [13] | 1.0 |
| 25.00 | 1012 | Glycolipid | 4.0 |
| 25.96 | 1012 | [8] | 1.9 |
| 26.22 | 1012 | [1] | 6.7 |
| 26.34 | 1012 | Glycolipid | 3.0 |
| 27.18 | 954; 1012 | Glycolipids | 0.7 |
| 27.33 | 1012 | Glycolipid | 0.4 |
| 27.89 | 968 | Glycolipid | 0.4 |
| 29.08 | 954 | [10] | 5.4 |
| 29.51 | 954; 968; 1054 | Glycolipids | 0.9 |
| 29.81 | 1054 | [4] | 1.6 |
| 30.52 | 954 | Glycolipid | 0.3 |
| 30.93 | 1054 | Glycolipid | 0.3 |
| 33.65 | 982 | Glycolipid | 0.5 |
| 34.46 | 996 | Glycolipid | 1.1 |
| 36.04 | 996 | [18] | 1.5 |
| 43.86 | | No Glycolipid | 1.1 |

*Some minor peaks of [X7] are not listed in Table 24.

D) Fermentation in 400 ml Scale

A 1 l Erlenmeyer flask containing 400 ml of sterilized medium (2.0% D-glucose, 0.5% malt extract) was inoculated with 2 ml of the secondary seed culture from Example 8 A a). The production culture was grown on a rotary shaker at (200 rpm) at 32° C. for 360 h.

Work-up after 360 h of fermentation yielded a total of 5.6 g/l of glycolipids of formula I which subsequently were characterized by HPLC-MS (see [X8] in Table 24A).

TABLE 24A

Figure 4:
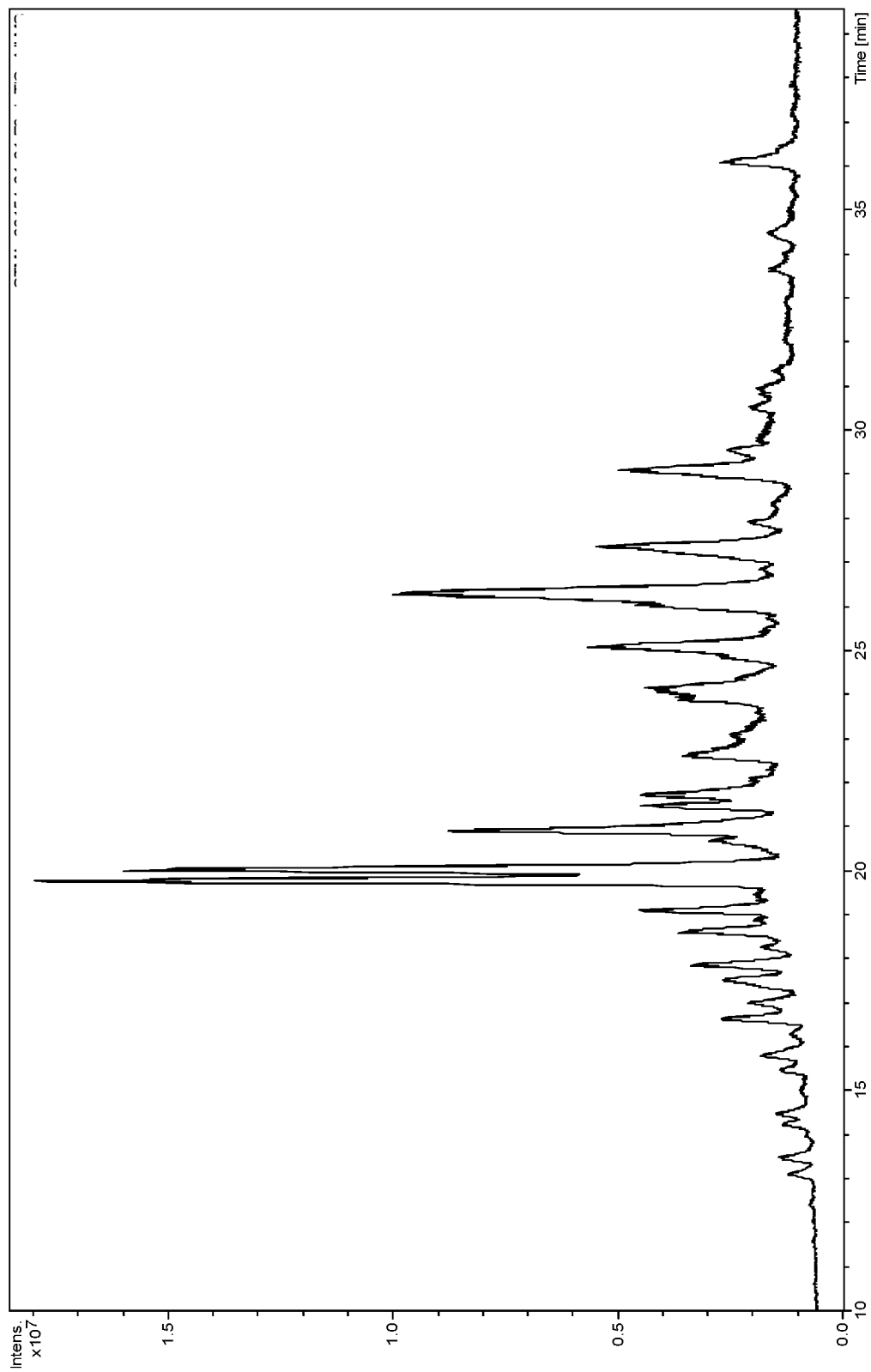
FIG. 4: Typical HPLC-MS of an extract [X8] obtained from *Dacryopinax spathularia* strain FU50088 (MUCL 53181) following example 8 D), annotation of signals according the "Improved method" of Example 8 C), for details see Table 24A below.

HPLC-MS analysis (using the "Improved method" of Example 8 C)) of the extract [X8] obtained from *Dacryopinax spathularia* strain MUCL 53181 according to Example 8 D) (the HPLC-ESI chromatogram for [X8] is presented in FIG. 4)

| Ret. time [min] | Molecular weight [Da] | Identified compound (type) | [X8]* in wt. % |
|---|---|---|---|
| 13.08 | 886 | Glycolipid without acyl groups | 0.4 |
| 13.49 | 886 | [16] | 0.5 |

TABLE 24A-continued

HPLC-MS analysis (using the "Improved method" of Example 8 C)) of the extract [X8] obtained from *Dacryopinax spathularia* strain MUCL 53181 according to Example 8 D) (the HPLC-ESI chromatogram for [X8] is presented in FIG. 4)

| Ret. time [min] | Molecular weight [Da] | Identified compound (type) | [X8]* in wt. % |
|---|---|---|---|
| 14.20 | 886 | Glycolipid without acyl groups | 0.4 |
| 14.46 | 942 | Glycolipid | 0.6 |
| 15.46 | 928 | Glycolipid | 0.5 |
| 15.79 | 928 | Glycolipid | 1.0 |
| 16.27 | 928 | Glycolipid | 0.2 |
| 16.55 | 928 | Glycolipid | 1.6 |
| 16.98 | 928; 956 | Glycolipids | 1.0 |
| 17.38 | 928 | [14] | 0.1 |
| 17.49 | 970 | Glycolipid | 1.4 |
| 17.78 | 970 | Glycolipid | 1.9 |
| 18.26 | 970 | Glycolipid | 0.3 |
| 18.58 | 970 | Glycolipid | 1.5 |
| 19.00 | 970 | [6] | 1.9 |
| 19.73 | 970 | Glycolipid | 12.7 |
| 19.98 | 970 | [7] | 12.4 |
| 20.66 | 970; 984 | Glycolipids | 1.4 |
| 20.90 | 970 | Glycolipid | 5.5 |
| 20.99 | 870 | Glycolipid without acyl groups | 1.5 |
| 21.44 | 970 | Glycolipid | 2.1 |
| 21.69 | 970 | [12] | 3.0 |
| 22.02 | 984 | Glycolipid | 0.4 |
| 22.57 | 970; 998 | Glycolipids | 2.9 |
| 23.09 | 1012 | Glycolipid | 0.9 |
| 23.91 | 1012 | [5] | 1.7 |
| 24.02 | 1012 | [9] | 2.8 |
| 24.19 | 1012 | Glycolipid | 0.8 |
| 24.73 | 1012 | [13] | 1.2 |
| 25.00 | 1012 | Glycolipid | 4.6 |
| 25.96 | 1012 | [8] | 2.1 |
| 26.22 | 1012 | [1] | 8.8 |
| 26.34 | 1012 | Glycolipid | 3.6 |
| 27.18 | 954; 1012 | Glycolipids | 1.3 |
| 27.33 | 1012 | Glycolipid | 4.4 |
| 27.89 | 968 | Glycolipid | 0.5 |
| 29.08 | 954 | [10] | 4.7 |
| 29.51 | 954; 968; 1054 | Glycolipids | 1.1 |
| 29.81 | 1054 | [4] | 0.2 |
| 30.52 | 954 | Glycolipid | 0.6 |
| 30.93 | 1054 | Glycolipid | 0.6 |
| 33.65 | 982 | Glycolipid | 0.6 |
| 34.46 | 996 | Glycolipid | 0.7 |
| 36.04 | 996 | [18] | 2.2 |
| 43.86 | | No Glycolipid | 1.0 |

*Some minor peaks of [X8] are not listed in Table 24A.

E) Fermentation in 400 ml Scale

A 1 l Erlenmeyer flask containing 400 ml of sterilized medium (4.0% D-glucose, 0.2% yeast extract) was inoculated with 6 ml of the secondary seed culture from Example 8 A a). The production culture was grown on a rotary shaker at (200 rpm) at 32° C. for 240 h.

Work-up after 240 h of fermentation yielded a total of 6.2 g/l of glycolipids of formula I.

Example 9: Biological Activities

In analogy to the methods described in Example 4 above, further biological activity MIC data were determined for several pure (purity >94 wt. %) compounds and for the mixture of compounds of formula I (extract [X8] as described in detail in Example 8 D).

The following Tables 25-27 represent the corresponding MIC values of several pure compounds after 48 h against various microorganisms.

In summary, Tables 25-27 demonstrate that individual compounds of formula I without any acyl substituents in the trisaccharide carbohydrate moiety R (such as the case for compound [16]) typically exhibit a significantly weaker antimicrobial activity, particularly against yeasts and molds, than the corresponding compounds being mono- or diacylated in the saccharide moiety.

Said Tables also demonstrate that individual compounds of formula I with an acyl substituent with more than 2 carbon atoms, such as an isovaleryl substituent, in the trisaccharide carbohydrate moiety R (such as the case for compounds [12], [13] and [1]) typically exhibit a stronger antimicrobial activity, particularly against yeasts and molds, and/or a broader activity spectrum than the corresponding compounds with one acetyl substituent in the trisaccharide carbohydrate moiety R (such as compound [14]).

TABLE 25

MIC values [ppm] after 48 h of pure compounds against Gram-positive bacteria

| Bacteria | [16] | [14] | [12] | [13] | [1] |
|---|---|---|---|---|---|
| *Bacillus subtilis* (ATCC6633) | 3.1 | 1.6 | 1.6 | 3.1 | 3.1 |
| *Propionibacterium acnes* (ATCC6919) | | | | | 100 |
| *Clostridium perfringens* (ATCC13124) | | | 60 | | 60 |
| *Corynebacterium variabile* (DSM20132) | 1.6 | 1.6 | <0.8 | 1.6 | 1.6 |
| *Lactobacillus plantarum* (DSM12028) | 50 | 25 | 25 | 25 | 25 |

TABLE 26

MIC values [ppm] after 48 h of pure compounds against filamentous fungi (molds)

| Filamentous fungi | [16] | [14] | [12] | [13] | [1] |
|---|---|---|---|---|---|
| *Aspergillus fumigatus* (ATCC1028) | | | 20 | | 20 |
| *Aspergillus niger* (ATCC16404) | 25 | 50 | 6.3 | 12.5 | 3.1 |
| *Byssochlamys fulva* (DSM62097) | 6.3 | | 6.3 | 3.1 | 3.1 |
| *Mucor plumbeus* (MUCL49355) | >100 | 50 | 6.3 | 12.5 | 6.3 |
| *Talaromyces luteus* (CBS348.51) | 50 | 50 | 25 | 25 | 12.5 |
| *Pyricularia oryzae* (DSM62938) | 25 | 25 | 25 | 6 | 6 |
| *Dekkera bruxellensis* (DSM70726) | >100 | 50 | 6.3 | 6.3 | 6.3 |
| *Dekkera naardenensis* (DSM70743) | 50 | 25 | 6.3 | 12.5 | 6.3 |

TABLE 27

MIC values [ppm] after 48 h of pure compounds against yeasts

| Yeasts | [16] | [14] | [12] | [13] | [1] |
|---|---|---|---|---|---|
| *Saccharomyces cerevisiae* (HT10) | >100 | 50 | 6.3 | 12.5 | 6.3 |
| *Zygosaccharomyces bailii* (DSM70492) | 25 | 25 | 6.3 | 6.3 | 6.3 |
| *Zygosaccharomyces bisporus* (DSM70415) | >100 | 50 | 12.5 | 25 | 12.5 |

TABLE 27-continued

MIC values [ppm] after 48 h of pure compounds against yeasts

| Yeasts | [16] | [14] | [12] | [13] | [1] |
|---|---|---|---|---|---|
| Zygosaccharomyces florentinus (DSM70506) | >100 | 50 | 6.3 | 12.5 | 6.3 |
| Zygosaccharomyces rouxii (NCYC381) | 100 | 25 | 6.3 | 12.5 | 6.3 |
| Candida albicans (ATCC10231) | | | | | 30 |

The following Table 28 represents the MIC values [ppm] of mixture [X8] and pure compound [12] after 48 h against various microorganisms.

TABLE 28

MIC values [ppm] of mixture [X8] and pure compound [12] after 48 h

| | [X8] | [12] |
|---|---|---|
| Bacteria | | |
| Bacillus cereus (ATCC11778) | 12.5 | 12.5 |
| Bacillus subtilis (ATCC6633) | 1.6 | |
| Propionibacterium acnes (ATCC6919) | 60 | |
| Clostridium perfringens (ATCC13124) | 60 | |
| Clostridium sporogenes (ATCC3584) | 50 | 50 |
| Enterococcus faecalis (ATCC19433) | 50 | 50 |
| Listeria welshimeri (DSM15452) | 25 | 25 |
| Listeria monocytogenes (ATCC19111) | 50 | 50 |
| Corynebacterium variabile (DSM20132) | <0.8 | |
| Lactobacillus plantarum (DSM12028) | 25 | |
| Staphylococcus aureus (ATCC6538) | 25 | |

TABLE 28-continued

MIC values [ppm] of mixture [X8] and pure compound [12] after 48 h

| | [X8] | [12] |
|---|---|---|
| Filamentous fungi | | |
| Aspergillus fumigatus (ATCC1028) | 20 | |
| Aspergillus niger (ATCC16404) | 6.3 | |
| Byssochlamys fulva (DSM62097) | 3.1 | |
| Mucor plumbeus (MUCL49355) | 6.3 | |
| Talaromyces luteus (CBS348.51) | <3.9 | |
| Pyricularia oryzae (DSM62938) | 6 | |
| Dekkera bruxellensis (DSM70726) | 6.3 | |
| Dekkera naardenensis (DSM70743) | 12.5 | |
| Yeasts | | |
| Saccharomyces cerevisiae (HT10) | 12.5 | |
| Zygosaccharomyces bailii (DSM70492) | 6.3 | |
| Zygosaccharomyces bisporus (DSM70415) | 12.5 | |
| Zygosaccharomyces florentinus (DSM70506) | 6.3 | |
| Zygosaccharomyces rouxii (NCYC381) | 6.3 | |
| Candida albicans (ATCC10231) | 12.5 | 25 |
| Candida glabrata (ATCC36583) | 20 | |

At a concentration of 25 ppm [X8], the observed inhibition of *Bacillus cereus* was 90%. At a concentration of 12.5 ppm [X8], the observed inhibition of *Candida albicans* was 90-100%. At a concentration of 50 ppm [X8], the observed inhibition of *Clostridium sporogenes* was 80-90%. At a concentration of 100 ppm [X8], the observed inhibition of *Staphylococcus aureus* was 90%.

The following Table 29 shows the results of several bacteria count tests performed with mixture [X8] for various microorganisms in comparison with an untreated control. Tests were performed at 37° C. at a pH of 7.4 in full medium. The respective bacteria count (Ba.C) is indicated in colony forming units/ml (CFU/ml).

TABLE 29

Bacteria count tests performed with mixture [X8]

| | | Initial Ba. C | Sample with [X8] Ba. C | | Untreated control Ba. C | |
|---|---|---|---|---|---|---|
| | [X8] | 0 h | after 2 h | after 6 h | after 2 h | after 6 h |
| Listeria monocytogenes (ATCC19111) | 100 ppm | $5 \times 10^5$ | $1 \times 10^4$ | $1 \times 10^4$ | $1.1 \times 10^6$ | $5 \times 10^7$ |
| Staphylococcus aureus (ATCC6538) | 100 ppm | $1 \times 10^5$ | $1 \times 10^4$ | $5 \times 10^3$ | $5 \times 10^5$ | $1 \times 10^8$ |
| Enterococcus faecalis (ATCC19433) | 200 ppm | $5 \times 10^4$ | $1 \times 10^4$ | $1 \times 10^4$ | $5 \times 10^5$ | $1 \times 10^8$ |
| Bacillus cereus (ATCC11778) | 50 ppm | $1 \times 10^5$ | $1 \times 10^2$ | <10 | $2 \times 10^6$ | $7 \times 10^8$ |
| Micrococcus luteus | 500 ppm | $1 \times 10^8$ | $2 \times 10^2$ | $2 \times 10^1$ | >1 × $10^8$ | >1 × $10^9$ |

Example 10: Sugar-Free Beverage Compositions

| Ingredient | A in wt. % | B in wt. % | C in wt. % | D in wt. % |
|---|---|---|---|---|
| Potassium sorbate | — | — | 0.03 | — |
| Sodium benzoate | 0.03 | — | 0.015 | — |
| Phosphoric acid | 0.048 | 0.06 | 0.025 | 0.16 |
| Citric acid | 0.016 | 0.012 | 0.025 | 0.02 |
| Caffeine | 0.013 | 0.009 | — | — |
| Sucralose | — | — | 0.008 | 0.0052 |
| Aspartame | 0.030 | 0.018 | — | — |
| Acesulfame K | 0.0095 | 0.0055 | 0.019 | — |
| Na cyclamate | — | 0.050 | 0.045 | 0.009 |
| Na Saccharin | — | 0.006 | 0.01 | — |
| Erythritol | 0.20 | — | — | 0.45 |
| Dimethylpolysiloxane | — | — | 0.00075 | 0.0008 |
| Lemon-orange flavor | — | — | 0.25 | 0.15 |
| Cola flavor | 0.35 | 0.42 | — | 0.20 |
| Caramel color (E150d) | 0.009 | 0.009 | — | 0.008 |
| Extract [X7] of Example 8 B-1) | 0.0003 | — | — | 0.0001 |
| Extract [X8] of Example 8 D) | — | 0.0005 | 0.0004 | — |
| Pure compound [1] | — | — | — | 0.0003 |
| Drinking water | Ad 100 | Ad 100 | Ad 100 | Ad 100 |

The beverage compositions A and C each were carbonated with 3.8 volumes of carbon dioxide after filling into bottles. The beverage compositions B and D each were carbonated with 3.0 volumes of carbon dioxide after filling into bottles.

Example 11: Tea Beverage Compositions

| Ingredient | A in wt. % | B in wt. % | C in wt. % | D in wt. % |
|---|---|---|---|---|
| Sucrose | 3.30 | — | — | — |
| Trisodium citrate | 0.50 | 0.50 | 0.25 | — |
| Citric acid | 0.40 | 0.60 | 0.50 | 0.80 |
| Malic acid | — | 0.20 | 0.30 | 0.50 |
| Ascorbic acid | 0.20 | 0.10 | 0.15 | 0.20 |
| Water soluble green tea powder | 2.50 | 2.25 | — | — |
| Water soluble Ceylon black tea powder | — | — | 2.75 | 2.40 |
| Sucralose | — | 0.08 | 0.05 | — |
| Acesulfame K | 0.0035 | 0.0035 | 0.0045 | 0.0055 |
| Aspartame | — | — | — | 0.025 |
| Rebaudioside A | 0.01 | — | 0.005 | — |
| Peach flavor | — | — | 0.40 | — |
| Lemon flavor | — | — | — | 0.70 |
| Jasmine tea flavor | — | 0.45 | — | — |
| Colorant | 0.007 | 0.009 | 0.009 | 0.008 |
| Extract [X7] of Example 8 B-1) | 0.0003 | — | — | 0.0002 |
| Extract [X8] of Example 8 D) | — | 0.0005 | 0.0004 | 0.0003 |
| Drinking water | Ad 100 | Ad 100 | Ad 100 | Ad 100 |

Example 12: Beverage Compositions

| Ingredient | A in wt. % | B in wt. % | C in wt. % | D in wt. % |
|---|---|---|---|---|
| Sucrose | 7.70 | 10.40 | 6.00 | 4.00 |
| Erythritol | 0.22 | — | — | 0.40 |
| Tagatose | 0.44 | — | — | 0.30 |
| Trehalose | — | — | 3.00 | — |
| Fructose | — | — | 1.00 | 1.00 |
| Citric acid, anhydrous | 0.30 | 0.235 | 0.21 | 0.21 |
| Sodium benzoate | — | — | 0.04 | 0.05 |
| Potassium sorbate | — | — | 0.02 | 0.03 |
| Ascorbic acid | 0.10 | 0.15 | 0.10 | 0.125 |
| Lemon oil, cold pressed | 0.08 | — | — | — |
| Orange oil, cold pressed | 0.02 | 0.09 | 0.09 | 0.09 |
| FD&C Yellow 5 | 0.003 | 0.007 | 0.007 | 0.007 |
| FD&C blue No. 1 | 0.006 | — | 0.002 | 0.002 |
| Rebaudioside A | — | 0.008 | — | 0.02 |
| Titanium dioxide | — | 0.08 | — | — |
| Extract [X7] of Example 8 B-1) | 0.0003 | — | — | — |
| Extract [X8] of Example 8 D) | — | 0.0005 | 0.0001 | 0.0003 |
| Pure compound [1] | — | — | 0.0002 | — |
| Tap water | Ad 100 | Ad 100 | Ad 100 | Ad 100 |

The beverage compositions A and C each were carbonated with 4 volumes of carbon dioxide after filling into bottles. The beverage composition B was carbonated with 2 volumes of carbon dioxide after filling into bottles.

Example 13: Yogurt Drink Compositions

Skimmed milk and whole milk were mixed in proportions to give milk with 1.1% fat, then 5 wt. % of sucrose were added thereto, and heated to 82° C. for 30 minutes. After cooling to 42° C., 0.7% of a commercially available starter culture of *Bifidobacterium bifidum* and 0.5% of a starter culture of *Streptococcus thermophilus* culture were added, and the mixture cultured at 39° C. until the pH-value of the mixture reached 4.4. The resulting firm yoghurt curd was then broken by stirring, and split in two portions (portion A and portion B).

Preparation of LiqYog A: To stirred portion A were added 0.4 wt. % (based on the mass of firm yoghurt) of high methoxyl citrus pectin as 5 wt. % solution in water and the mixture cooled with stirring to 5° C. This product was then passed through a sterilized homogenizer at 40 bar to give a liquid yoghurt having a dynamic viscosity of 380 mPas at 10° C. Thereto were first added with stirring 45 ppm of the extract [X7] of Example 8 B-1), and then 9.0 wt. % of a pasteurized peach pulp, in both cases based on the total weight of the liquid yoghurt. The resulting mixture was homogenized giving LiqYog A which was transferred into a glass container, and stored at 7° C. for 10 days.

Preparation of LiqYog B: To stirred portion B were added 0.6 wt. % (based on the mass of firm yoghurt) of high methoxyl apple pectin as 5 wt. % solution in water and the mixture cooled with stirring to 5° C. This product was then passed through a sterilized homogenizer at 15 bar to give a liquid yoghurt having a dynamic viscosity of 600 mPas at 10° C. Thereto were first added with stirring 95 ppm of the extract [X8] of Example 8 D), and then 7.5 wt. % of a pasteurized strawberry-blueberry puree, in both cases based on the total weight of the liquid yoghurt. The resulting mixture was homogenized giving LiqYog B which was stored at 8° C. before further processing.

Example 14: Mouthwashes

| Ingredient | A in wt. % | B in wt. % | C in wt. % |
|---|---|---|---|
| Ethanol (96% in water) | 8.00 | 5.00 | — |
| Glycerin | 8.00 | 10.00 | 12.00 |
| 1,2-Propylene Glycol | — | — | 2.00 |
| Sodium Fluoride | 0.05 | 0.13 | 0.10 |
| Poloxamer 407 (Pluronic F-127 ®, BASF) | 1.40 | — | 0.60 |
| PEG-40 hydrogenated castor oil and propylene glycol (Cremophor ® CO 40, BASF) | — | 1.00 | 0.50 |
| Sodium Phosphate buffer (pH 7.0) | 1.10 | — | 1.00 |
| Blue colorant (1% in water) | 0.10 | 0.05 | — |
| Red colorant (1% in water) | — | 0.05 | 0.08 |
| Sorbic acid | 0.025 | — | — |
| Benzoic acid | 0.025 | — | — |
| 4-Hydroxybenzoic acid methylester Na Salt | — | — | 0.06 |
| Sodium Saccharinate | 0.10 | — | 0.12 |
| Sorbitol (70% in water) | — | 3.00 | — |
| Eucalyptus oil-menthol-wintergreen flavour | 0.15 | 0.10 | — |
| Peppermint-spearmint flavour (menthol content: 58%) | — | 0.10 | 0.20 |
| Cetylpyridinium Chloride | 0.05 | — | 0.07 |
| Hydrogen Peroxide (30% in water) | — | — | 3.00 |
| Extract [X7] of Example 8 B-1) | 0.0005 | — | — |
| Extract [X8] of Example 8 D) | — | 0.001 | 0.0003 |
| Pure compound [1] | — | — | 0.0001 |
| Deionized water | Ad 100 | Ad 100 | Ad 100 |

Example 15: Perfume Oils for Use in Cosmetic Compositions

| Ingredient | Perfume oil P1 parts by weight | Perfume oil P2 parts by weight |
|---|---|---|
| Acetophenone, 10% in DPG | 10.00 | — |
| n-Undecanal | 15.00 | 5.00 |
| Allylamylglycolate, 10% in DPG | 20.00 | — |
| Amylsalicylate | 25.00 | 15.00 |
| Benzyl acetate | 60.00 | 40.00 |
| Citronellol | 80.00 | 50.00 |
| D-Limonen | 60.00 | 10.00 |
| Dihydromyrcenol | 60.00 | 15.00 |
| Eucalyptus oil | 10.00 | — |
| Geraniol | 40.00 | 60.00 |
| Nerol | 20.00 | 20.00 |
| Geranium oil | 15.00 | 15.00 |
| Hexenol cis-3, 10% in DPG | 5.00 | 15.00 |
| Hexenyl salicylate cis-3 | 20.00 | — |
| Indole, 10% in DPG | 10.00 | — |
| Alpha-Ionone | 15.00 | 15.00 |
| Vanillin | 5.00 | — |
| Lilial (2-methyl-3-(4-tert-butyl-phenyl)propanal) | 60.00 | — |
| Linalool | 40.00 | 60.00 |
| Methylphenyl acetate | 10.00 | — |
| Phenylethyl alcohol | 255.00 | 30.00 |
| Styrene acetate | 20.00 | 20.00 |
| Terpineol | 30.00 | — |
| Tetrahydrolinalool | 50.00 | 50.00 |
| Cinnamon alcohol | 10.00 | — |
| Ambrettolide | — | 25.00 |
| p-tert-Butyl cyclohexyl acetate | 20.00 | 80.00 |
| Exaltolide | — | 50.00 |
| Galaxolide, 50% in IPM | 30.00 | 120.00 |
| Hexadecanolide | — | 10.00 |
| Iso E Super | 20.00 | 75.00 |
| Musk indanone | — | 70.00 |
| Coumarine | — | 20.00 |
| Patchouli oil | — | 70.00 |
| Vetiveryl acetate | — | 50.00 |
| Methyl dihydrojasmonate | 20.00 | 90.00 |

DPG = Dipropylene glycol;

IPM = Isopropyl myristate

Example 16: Roll-on Deodorant Emulsions

| Ingredient | A in wt. % | B in wt. % | C in wt. % |
|---|---|---|---|
| PEG-40 Stearate | 5.00 | 4.00 | 5.50 |
| Ethylhexylglycerin (Octoxyglycerin) | 1.00 | 1.20 | — |
| Cetyl Alcohol | 2.00 | 1.00 | 1.70 |
| Stearyl Alcohol | — | 1.00 | 0.50 |
| Mineral oil | 2.00 | 2.00 | 2.00 |
| Aluminum Hydrochlorate powder | — | 8.00 | 15.00 |
| Polysorbate 80 | 0.80 | 1.00 | 1.20 |
| Glycerin | 2.50 | 1.50 | 1.50 |
| Mg-Aluminium Silicate | 0.80 | 0.80 | 0.80 |
| Talc | 1.50 | — | — |
| 1,2-Pentandiol | — | — | 0.60 |
| 1,2-Octandiol | — | 0.75 | 0.20 |
| 2-Benzyl heptanol | — | 0.10 | — |
| 2-Methyl-4-phenyl-2-butanol | — | 0.10 | 0.30 |
| 4-Methoxybenzyl alcohol | 0.10 | — | — |
| 4-Methyl-4-phenyl-2-pentanol | 0.05 | — | 0.10 |
| Extract [X7] of Example 8 B-1) | 0.001 | — | 0.0004 |
| Extract [X8] of Example 8 D) | — | 0.0005 | 0.0004 |
| Perfume oil P1 according to Example 14 | 0.70 | — | 0.65 |
| Perfume oil P2 according to Example 14 | 0.10 | 0.60 | — |
| Water | Ad 100 | Ad 100 | Ad 100 |

Example 17: Deodorant Microemulsions

| Ingredient | A in wt. % | B in wt. % | C in wt. % |
|---|---|---|---|
| Glycerin Isostearate | 1.80 | 2.00 | 1.80 |
| Octoxyglycerin | — | 0.80 | 0.90 |
| Ceteareth-15 | 5.25 | 5.50 | 5.00 |
| Isotridecyl Isononanoate | 3.30 | 3.50 | 3.80 |
| Cyclomethicon | 6.80 | 6.40 | 6.00 |
| L-Menthyl-L-Lactate | — | 0.20 | 0.10 |
| Octyldodecanol | — | 0.40 | — |
| Aluminium Chlorohydrate | — | 5.00 | 9.00 |
| Triclosan ® | — | — | 0.25 |
| Extract [X7] of Example 8 B-1) | 0.0012 | — | 0.0004 |
| Extract [X8] of Example 8 D) | — | 0.0005 | 0.0006 |
| Perfume oil P1 according to Example 14 | 0.65 | 0.10 | 0.45 |
| Perfume oil P2 according to Example 14 | — | 0.40 | 0.25 |
| Water | Ad 100 | Ad 100 | Ad 100 |

Example 18: Shampoo Compositions

| Ingredient | A in wt. % | B in wt. % | C in wt. % |
|---|---|---|---|
| $C_{10-30}$ Alkyl acrylate crosspolymer | 0.60 | 0.60 | 0.60 |
| Sodium Hydroxide, 15% in water | 0.10 | 0.12 | 0.10 |
| Disodium EDTA | 0.10 | 0.10 | 0.10 |
| 1,2-Decandiol | 1.00 | 0.50 | 1.00 |
| 1,2-Dodecandiol | — | 0.70 | — |
| 1-Tetradecanol | — | — | 0.50 |
| Glycol Distearate, Laureth-4, Cocamidopropyl Betaine | 3.00 | 3.00 | 3.00 |
| Sodium Laureth Sulfate (SLES), 53% in water | 12.00 | 14.00 | 10.00 |
| Sodium Cocamphoacetate | 5.00 | 5.00 | 7.00 |
| Ammonium Cocoyl Isethionate | 10.00 | 8.00 | 9.00 |
| Acetamide MEA | 1.00 | 1.50 | 0.50 |
| Palmitamide MEA | 0.50 | — | 0.50 |
| Phenoxyethanol | — | 0.70 | 0.30 |
| Extract [X7] of Example 8 B-1) | 0.0015 | — | 0.0003 |
| Extract [X8] of Example 8 D) | — | 0.0010 | 0.0006 |
| 2-Methyl-4-phenyl-2-butanol | 0.08 | — | — |
| Perfume oil P1 according to Example 14 | 0.20 | 0.40 | 0.25 |
| Perfume oil P2 according to Example 14 | — | — | 0.15 |
| Water | Ad 100 | Ad 100 | Ad 100 |

Example 19: Clear Shampoo Compositions with UV-Protection

| Ingredient | A in wt. % | B in wt. % | C in wt. % |
|---|---|---|---|
| Polyquaternium-7 | 0.50 | 0.50 | 0.65 |
| Disodium Phenyl Dibenzimidazole Tetrasulfonate | 0.50 | — | — |
| Butyl Methoxydibenzoylmethane (Avobenzone) | 0.25 | — | 0.80 |
| Phenylbenzimidazole Sulfonic Acid, Sodium Salt | 0.80 | 1.00 | 1.20 |
| Amino Methyl Propanol | 0.50 | 0.60 | 0.40 |
| Sodium Laureth Sulfate (SLES), 28% in water | 30.00 | 25.00 | 20.00 |
| Cocoamidopropyl Betaine | 5.00 | 6.00 | 7.50 |
| Propylene Glycol, PEG-55 Propylene Glycol Dioleate | 0.80 | 0.80 | 0.80 |
| Panthenol | 1.00 | 0.40 | — |
| Allantoin | — | 0.25 | 0.50 |
| Methylparaben, Ethylparaben, Butylparaben, Propylparaben, Isopropylparaben, Isobutylparaben, Benzylparaben | — | 0.30 | 0.55 |
| Phenoxyethanol | — | 0.25 | — |
| 1,2-Propylene Glycol | 1.00 | — | 0.30 |
| Glycerin | — | 1.00 | 0.60 |
| Sodium Chloride | 0.70 | 0.60 | 0.70 |
| Extract [X7] of Example 8 B-1) | 0.0025 | — | 0.0004 |
| Extract [X8] of Example 8 D) | — | 0.0010 | 0.0005 |
| Perfume oil P1 according to Example 14 | 0.40 | 0.35 | 0.25 |
| Perfume oil P2 according to Example 14 | — | 0.10 | 0.15 |
| Water | Ad 100 | Ad 100 | Ad 100 |

Example 20: Wetting Compositions for Wet Wipes

| Ingredient | A in wt. % | B in wt. % | C in wt. % | D in wt. % |
|---|---|---|---|---|
| Ceterayl isononanoate, Ceterareth-20, Stearyl alcohol, Glyceryl stearate, Glycerin, Ceterareth-21, Cetyl palmitate | 3.00 | — | — | 2.50 |
| Mineral oil | 3.00 | — | 3.00 | — |
| Paraffinum liquidum | — | — | 4.00 | — |
| Ethylhexyl ethylhexanoate | — | — | 5.00 | — |
| Cetearyl ethylhexanoate | — | — | 3.50 | — |
| PEG-40 Hydrogenated castor oil, Trideceth-9, Propylene glycol, water | — | 2.00 | — | — |
| Citric acid, anhydrous | — | 0.01 | — | — |
| Vitamin E Acetate (Tocopheryl Acetate) | 0.10 | — | — | 0.08 |
| Phenoxyethanol | 0.40 | — | — | 0.10 |
| Imidazolinyl urea | — | 0.10 | — | — |
| Diazolidinyl urea | — | — | 0.15 | 0.05 |
| Benzethonium chloride | — | 0.05 | — | 0.05 |
| (−)-Alpha-Bisabolol, natural | — | — | 0.09 | 0.10 |
| Chamomile extract | — | 0.35 | — | — |
| Allantoin | 0.10 | — | 0.08 | — |
| Acrylates/C10-30 Acrylates Copolymer | — | — | 0.20 | — |
| Glycerin | 0.50 | — | — | — |
| 1,2-Pentandiol | 2.00 | — | — | 0.50 |
| 1,2-Hexandiol | 1.00 | — | — | 1.50 |
| 1,2-Propylene glycol | — | 8.00 | — | 2.00 |
| Extract [X7] of Example 8 B-1) | 0.0012 | — | 0.0004 | 0.0001 |
| Extract [X8] of Example 8 D) | — | 0.0010 | 0.0004 | 0.0003 |
| Lavender oil | — | — | — | 0.05 |
| Perfume oil P1 according to Example 14 | — | 0.10 | 0.25 | — |
| Perfume oil P2 according to Example 14 | — | 0.01 | — | — |
| Water | Ad 100 | Ad 100 | Ad 100 | Ad 100 |

The emulsions/lotions A, C and D were each applied separately to a nonwoven fabric to produce wet wipes (premoistened wipes). Solution B was applied to woven fabric sheets.

Example 21: Wetting Compositions for Wet Wipes

| Ingredient | A in wt. % | B in wt. % | C in wt. % | D in wt. % |
| --- | --- | --- | --- | --- |
| Sodium chloride | 1.25 | 2.10 | 2.60 | 1.50 |
| Zinc chloride | 0.50 | 0.50 | — | 0.25 |
| Glycerin | 1.00 | 1.30 | 0.50 | 1.50 |
| 1,2-Butylene glycol | — | 0.40 | 0.80 | — |
| DMDM Hydantoin | — | 0.10 | — | 0.10 |
| Phenoxyethanol | — | — | 0.40 | — |
| Imidazolinyl urea | 0.10 | — | — | 0.05 |
| Cyclodextrins | — | 0.15 | — | 0.20 |
| Acyl Glutamate (surfactant) | 1.00 | — | 0.90 | 1.10 |
| Dimethiconol and TEA Dodecylbenzene sulfonate | 0.70 | 0.50 | 0.60 | 0.80 |
| PEG-75 Lanolin | 0.25 | 0.75 | 0.50 | 0.60 |
| Polysorbate 20 | 0.22 | 0.40 | 0.30 | 0.50 |
| Malic acid | 0.05 | 0.07 | 0.10 | 0.10 |
| Extract [X7] of Example 8 B-1) | 0.0008 | — | 0.0002 | 0.0003 |
| Extract [X8] of Example 8 D) | — | 0.0006 | 0.0002 | 0.0004 |
| Chamomile extract | — | — | — | 0.10 |
| Rose and lavender perfume oil | — | — | — | 0.05 |
| Perfume oil P1 according to Example 14 | 0.08 | 0.15 | — | — |
| Water | Ad 100 | Ad 100 | Ad 100 | Ad 100 |

The compositions A-D were each applied separately to a nonwoven fabric to produce wet wipes.

Example 22: Cosmetic O/W—Lotions

| Ingredient | A in wt. % | B in wt. % | C in wt. % | D in wt. % |
| --- | --- | --- | --- | --- |
| Paraffin oil | 5.00 | 5.00 | 5.00 | 5.00 |
| Isopropyl palmitate | 5.00 | 5.00 | 5.00 | 5.00 |
| Cetyl alcohol | 2.00 | — | 1.00 | 2.00 |
| Stearyl alcohol | — | 2.00 | 1.00 | — |
| Beeswax | 2.00 | 2.00 | 1.00 | 2.00 |
| Ceteareth-20 | 2.00 | 2.00 | 2.00 | 2.00 |
| PEG-20-glyceryl stearate | 1.50 | 1.50 | 1.50 | 1.50 |
| Glycerine | 3.00 | 3.00 | 4.00 | 2.00 |
| 1,2-Butylene glycol/1,2-Propylene glycol (1:1) | — | 0.50 | — | 1.50 |
| Phenoxyethanol | — | 0.25 | — | 0.15 |
| Extract [X7] of Example 8 B-1) | 0.001 | — | 0.0004 | 0.0007 |
| Extract [X8] of Example 8 D) | — | 0.0005 | 0.0006 | — |
| Perfume oil P1 according to Example 14 | 0.75 | 0.10 | 0.45 | — |
| Perfume oil P2 according to Example 14 | — | 0.40 | 0.25 | 0.70 |
| Water | Ad 100 | Ad 100 | Ad 100 | Ad 100 |

Example 23: Cosmetic O/W Sunprotection Compositions

| Ingredient | A in wt. % | B in wt. % | C in wt. % |
| --- | --- | --- | --- |
| Glyceryl Oleate Citrate, Caprylic/Capric Triglyceride | 2.00 | — | 2.00 |
| Potassium Cetyl Phosphate | — | 1.50 | — |
| Cetearyl alcohol | — | 1.00 | — |
| C12-15 - Alkyl Benzoate | — | 2.50 | — |
| Homosalate | 5.00 | 2.00 | 5.00 |
| Butyl Methoxydibenzoylmethane (Avobenzone) | 3.00 | 3.00 | 3.00 |
| Ethylhexyl Salicylate | 3.00 | 4.00 | 3.00 |
| Octocrylene | — | 5.50 | — |
| Isoamyl p-Methoxycinnamate | — | 3.00 | — |

-continued

| Ingredient | A in wt. % | B in wt. % | C in wt. % |
|---|---|---|---|
| Diisopropyl Adipate | 6.00 | — | 6.00 |
| Ethylhexyl Isononanoate | — | 2.00 | — |
| Diethylhexyl 2,6 Naphthalate | 1.50 | — | 2.00 |
| Disodium EDTA | 0.10 | 0.10 | 0.10 |
| Vitamin E Acetate (Tocopheryl Acetate) | 0.50 | 0.50 | 0.50 |
| Micronized rutile ($TiO_2$), Alumina (9.5%) and Simethicone (2%) | — | 3.00 | 0.80 |
| Dimethicone | 1.00 | 2.00 | 1.30 |
| (−)-Alpha-Bisabolol, natural | 0.10 | 0.10 | 0.15 |
| Allantoin | 0.10 | — | 0.15 |
| Acrylates/C10-30 Acrylates Copolymer | 0.25 | — | 0.25 |
| Carbomer | — | 0.20 | — |
| Xanthan Gum | — | 0.20 | — |
| Sodium Cetearyl Sulfate | — | 0.60 | — |
| Phenylbenzimidazole Sulfonic Acid, Sodium Salt, 35% solution in water, neutralized with triethanolamine | 2.50 | 3.00 | 2.00 |
| Disodium Phenyl Dibenzimidazole Tetrasulfonate, 30% solution in water, neutralized with triethanolamine | — | 2.00 | — |
| Tris-Hydroxyaminomethane | 0.45 | — | 0.50 |
| Glycerin | 4.00 | 1.00 | 3.00 |
| 1,2-Butylene glycol and 1,3-Butylene glycol (1:1) | 3.00 | — | 2.00 |
| Extract [X7] of Example 8 B-1) | 0.0016 | — | 0.0004 |
| Extract [X8] of Example 8 D) | — | 0.0004 | 0.0004 |
| Perfume oil P1 according to Example 14 | 0.25 | 0.20 | 0.15 |
| Perfume oil P2 according to Example 14 | — | 0.10 | 0.25 |
| Water | Ad 100 | Ad 100 | Ad 100 |

Compositions A and C are sunsprays, composition B is a sunscreen softcream.

Example 24: Hand Sanitizing Composition

A clear liquid composition having a pH-value of 5.6 was prepared consisting of 2-propanol (45 wt. %), 1-propanol (30 wt. %), lactic acid (0.3 wt. %), 1-tetradecanol, medium chain triglycerides, glycerol, sodium lactate, extract [X7] of Example 8 B-1) (25 ppm), and water.

Example 25: Hand Sanitizing Composition

A clear liquid composition having a pH-value of 5.3 was prepared consisting of 1-propanol (40 wt. %), 2-propanol (28 wt. %), citric acid (0.2 wt. %), lactic acid (0.15 wt. %), 1-dodecanol, medium chain triglycerides, glycerol, 1,2-propylene glycol, extract [X8] of Example 8 D) (45 ppm), and water.

Example 26: Hand Sanitizing Composition

A composition was prepared consisting of ethanol (55 wt. %), 1-propanol (10 wt. %), 1,2-propylene glycol (6 wt. %), 1,3-butylene glycol, lactic acid, extract [X8] of Example 8 D) (15 ppm), and water.

Example 27: Medical Sanitizing/Disinfecting Compositions

| Ingredient | A in wt. % | B in wt. % | C in wt. % | D in wt. % |
|---|---|---|---|---|
| Benzalkonium chloride | 2.00 | 2.50 | 0.10 | 0.15 |
| Cocopropylenediamine guanidinium acetate | 14.00 | 14.00 | 0.25 | — |
| Phenoxypropanol | 35.00 | 30.00 | 0.50 | — |
| Tetrakis-(2-hydroxypropyl)-N,N,N',N'-ethylenediamine | 5.00 | — | 0.08 | — |
| Disodium EDTA | — | 1.00 | 0.10 | 0.05 |
| Laurylpropylenediamine | — | 4.50 | — | 0.10 |
| Maleic acid | 0.45 | 0.15 | 0.02 | 0.01 |
| Citric acid | — | 0.25 | — | 0.01 |
| Tridecyl ethoxylate-12EO | 15.00 | — | 0.15 | 0.05 |
| Tridecyl ethoxylate-5EO | — | 10.00 | 0.10 | 0.20 |
| Ethanol | 8.00 | 10.00 | 0.25 | 0.20 |
| 1-Propanol | 1.00 | — | — | 0.10 |
| Extract [X7] of Example 8 B-1) | 0.10 | — | 0.0004 | 0.0007 |
| Extract [X8] of Example 8 D) | — | 0.08 | 0.0006 | — |
| Perfume oil P1 according to Example 14 | 1.55 | 0.90 | 0.05 | — |
| Perfume oil P2 according to Example 14 | — | 0.40 | — | — |
| Water | Ad 100 | Ad 100 | Ad 100 | Ad 100 |

Compositions A and B are concentrates which are diluted with water in a ratio (concentrate:water) in the range of 1:80 to 1:20 to give a ready-to-use solution.

Compositions C and D are ready-to-use solutions.

Example 28: Ready-to-Use Sanitizing/Disinfecting Compositions

| Ingredient | A in wt. % | B in wt. % | C in wt. % | D in wt. % |
|---|---|---|---|---|
| Benzalkonium chloride | 0.20 | 0.05 | — | — |
| Ethylhexylglycerin (Octoxyglycerin) | 0.25 | 0.20 | 0.25 | — |
| Octenidine dihydrochloride | — | 0.07 | — | 0.10 |
| Laureth-35 | 0.02 | — | 0.01 | — |
| Sodium gluconate | — | 0.40 | — | 0.30 |
| Glycerol | 2.10 | 2.50 | 1.50 | 3.00 |
| Mecetroniumetilsulfate | — | — | 0.15 | — |
| Phenoxypropanol | — | — | — | 1.00 |
| Cocoamidopropyl betaine | — | 0.30 | 0.25 | — |
| 2-Propanol | 0.50 | — | — | 0.45 |
| Extract [X7] of Example 8 B-1) | 0.002 | — | 0.0006 | 0.0007 |
| Extract [X8] of Example 8 D) | — | 0.001 | 0.0003 | — |
| Lemon perfume oil | — | 0.10 | 0.05 | — |
| Water | Ad 100 | Ad 100 | Ad 100 | Ad 100 |

The invention claimed is:

1. A beverage comprising an additive to the beverage, said additive being in the form of one or more compounds, said beverage being selected from the group consisting of wine containing alcohol, a 100% fruit juice, other fruit containing beverages which provide the flavor of fruit juices and contain greater than 0% fruit juice but less than 100% fruit juice, artificial fruit-flavor beverages, malt beverages, green tea, red tea, rooibos tea, mate tea, honeybush tea, pu-erh tea, oolong tea, black tea, ice-tea, ready-to-drink tea, beer-lemonade mixes, and beer-cola mixes, and wherein each one of said one or more compounds is a compound of the formula I:

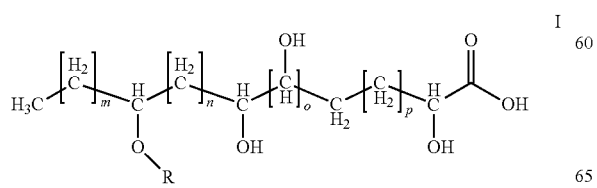

wherein m is 3 to 5, n is 2 to 5, o is 0 or 1 and p is 3 to 17, with the proviso that the sum m+n+o+p is not less than 14; and R is a carbohydrate moiety bound via one of its carbon atoms to the O atom to which R is attached in formula I, where the moiety R carries at least one hydroxyl group esterified with isovaleric acid, where the compound is present in an open chain form or in the form of a lactone formed between

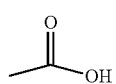

in formula I and any free OH depicted in formula I or on R, or a physiologically acceptable salt of said compound, and/or an ester of said compound with a $C_{1-10}$-alcohol.

2. The beverage according to claim 1, wherein the compound of formula (I) is selected from the group consisting of compounds represented in the following table:

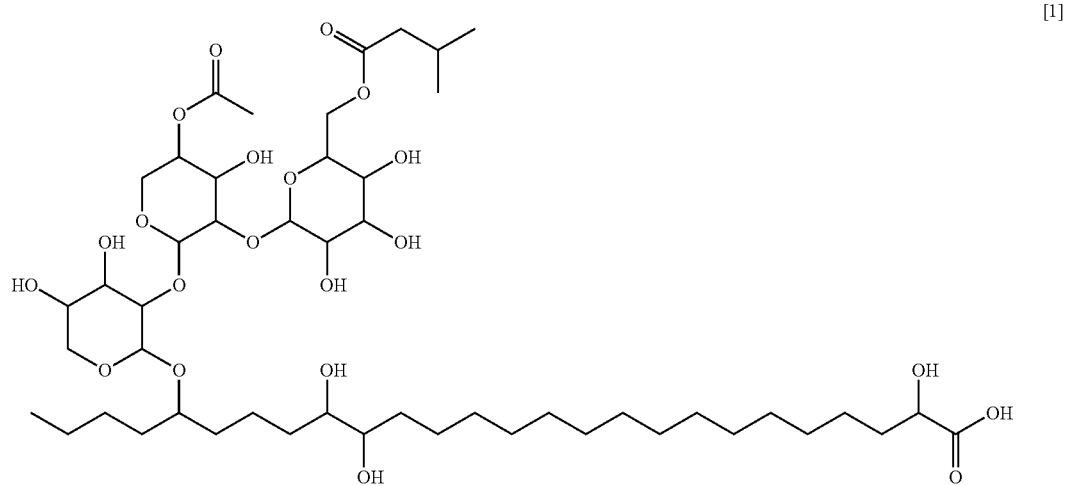
[1]
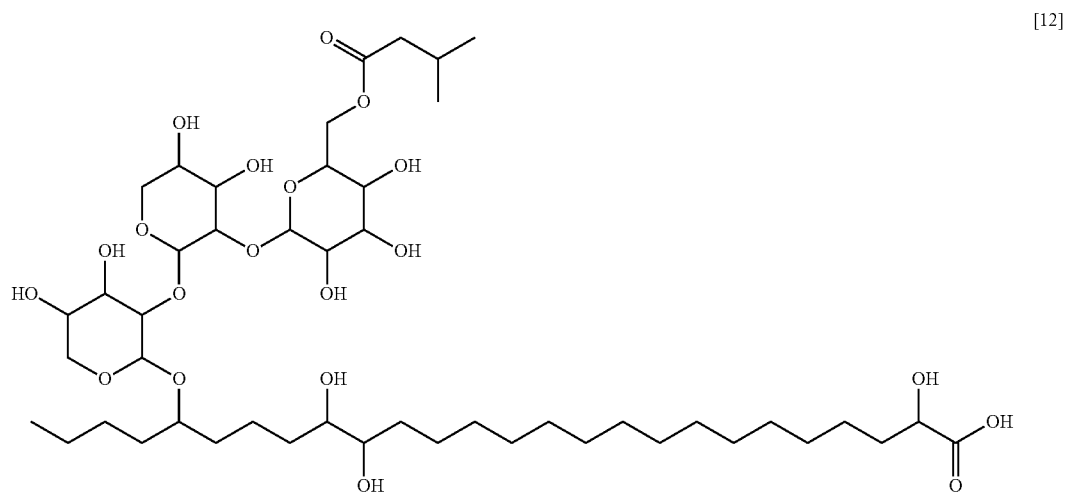
[12]
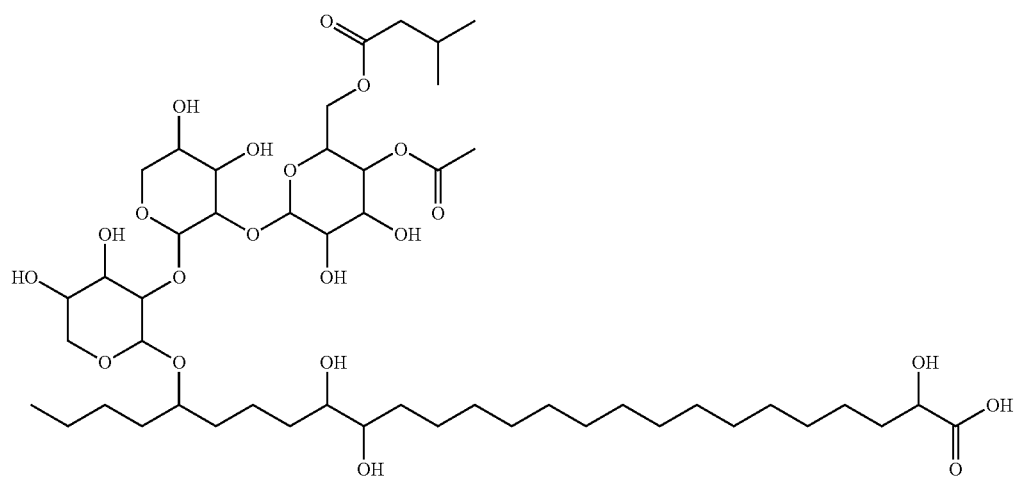
[13]

-continued
[18]
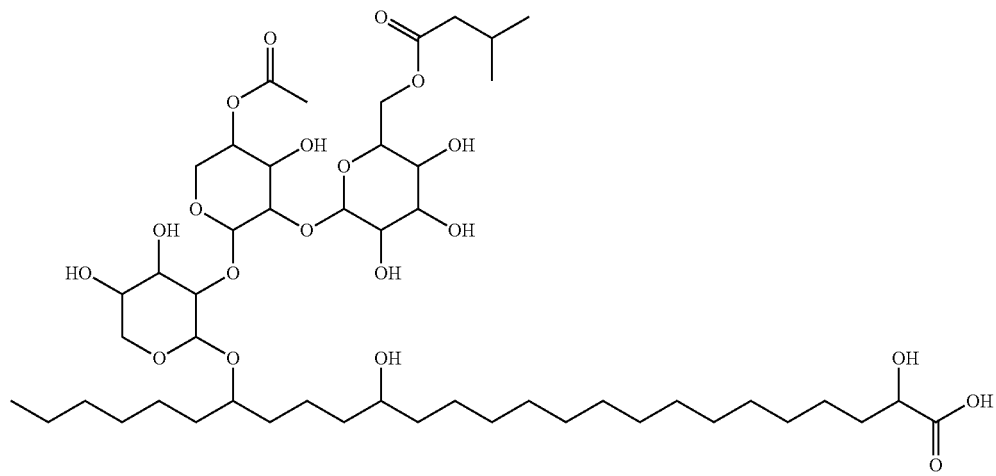
and physiologically acceptable salts and esters thereof.
3. The beverage according to claim 2, wherein the compound of formula (I) is selected from the group consisting of compounds represented in the following table:
[1]
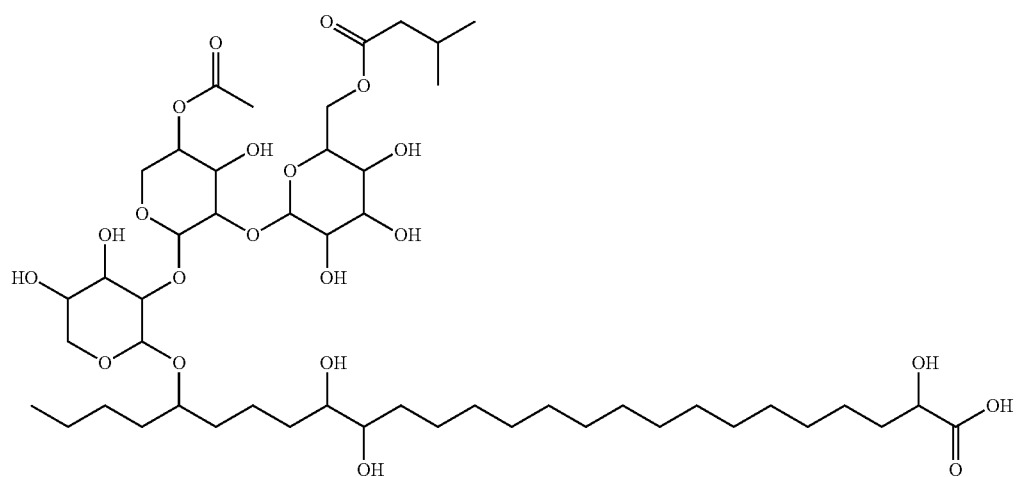
[13]
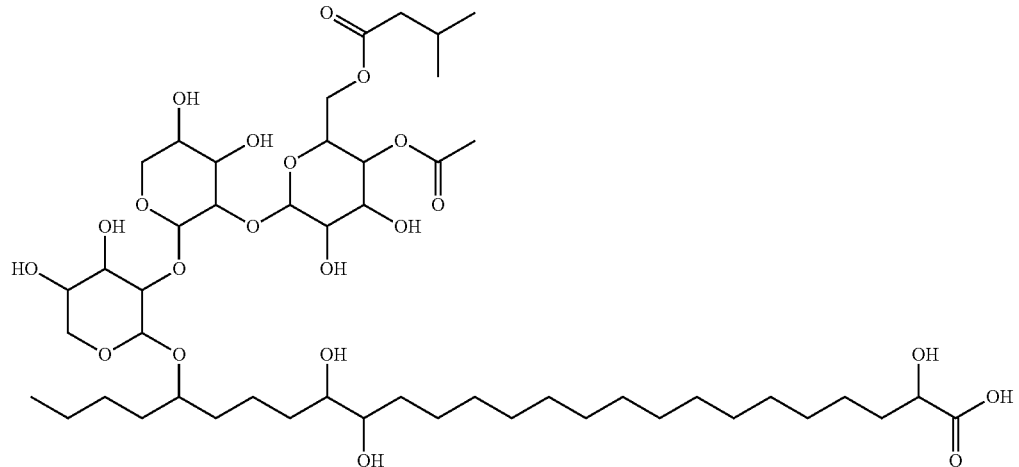
and physiologically acceptable salts and esters thereof.

4. The beverage according to claim 3, which is selected from the group consisting of (A) a 100% fruit juice, and (B) other fruit containing beverages which provide the flavor of fruit juices and contain greater than 0% fruit juice but less than 100% fruit juice.

5. The beverage according to claim 2, which is selected from the group consisting of (A) a 100% fruit juice, and (B) other fruit containing beverages which provide the flavor of fruit juices and contain greater than 0% fruit juice but less than 100% fruit juice.

6. The beverage according to claim 1, which is selected from the group consisting of (A) a 100% fruit juice, and (B) other fruit containing beverages which provide the flavor of fruit juices and contain greater than 0% fruit juice but less than 100% fruit juice.

7. A method of enhancing microbial stability of a beverage comprising adding an additive to the beverage, said additive being in the form of one or more compounds, said beverage being selected from the group consisting of wine containing alcohol, a 100% fruit juice, other fruit containing beverages which provide the flavor of fruit juices and contain greater than 0% fruit juice but less than 100% fruit juice, fruit-flavor beverages, malt beverages, green tea, red tea, rooibos tea, mate tea, honeybush tea, pu-erh tea, oolong tea, black tea, ice-tea, ready-to-drink tea, beer-lemonade mixes, and beer-cola mixes, and wherein the one or more compounds are selected from compounds or a mixture of compounds of the formula I:

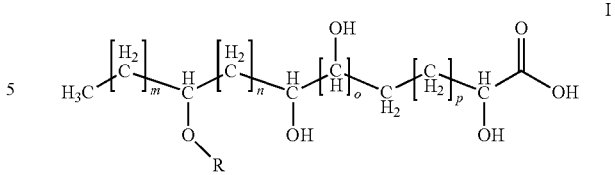

wherein m is 3 to 5, n is 2 to 5, o is 0 or 1 and p is 3 to 17, with the proviso that the sum m+n+o+p is not less than 14; and R is a carbohydrate moiety bound via one of its carbon atoms to the binding oxygen, and/or a physiologically acceptable salt thereof, or an ester thereof, where the moiety R carries at least one hydroxyl group esterified with isovaleric acid, where the compound may be present in open chain form and/or in the form of a lactone, or a physiologically acceptable salt, and/or an ester thereof.

8. The method according to claim 7, wherein the beverage is selected from the group consisting of (A) a 100% fruit juice, and (B) other fruit containing beverages which provide the flavor of fruit juices and contain greater than 0% fruit juice but less than 100% fruit juice.

* * * * *

SEQUENCE LISTING

<160> NUMBER OF SEQ ID NOS: 5

<210> SEQ ID NO 1
<211> LENGTH: 256
<212> TYPE: DNA
<213> ORGANISM: Dacryopinax spathularia FU50088, MUCL 53181

<400> SEQUENCE: 1

```
cccctagtaa ctgcgagtga agcgggaaaa gctcaaattt aaaatccctt cggggagttg      60
taatctagag acgtgttttc ggtcgttgcc tcggacaagt cccttggaac agggcgtcat     120
agagggtgag aatcccgtac ttgccgagct cccaatgact atgtgataca cgttcgaaga    180
gtcgagttgt ttgggaatcg agctcaaaat gggtgtgaaa ctccatctaa agctaaatat    240
tggcgagaga ccgata                                                     256
```

<210> SEQ ID NO 2
<211> LENGTH: 256
<212> TYPE: DNA
<213> ORGANISM: Dacryopinax spathularia CBS197.83, MUCL 53182

<400> SEQUENCE: 2

```
cccctagtaa ctgcgagtga agcgggaaaa gctcaaattt aaaatccctt ccgggagttg      60
taatctagag acgtgttttc ggtcgttgcc tcggacaagt cccttggaat agggcgtcat     120
agagggtgag aatcccgtac ttgccgagct cccaatgact atgtgataca cgttcgaaga    180
gtcgagttgt ttgggaatgc agctcaaaat gggtggtaaa ctccatctaa agctaaatat    240
tggcgagaga ccgata                                                     256
```

<210> SEQ ID NO 3
<211> LENGTH: 254
<212> TYPE: DNA
<213> ORGANISM: Ditiola nuda CBS173.60, MUCL 53179

<400> SEQUENCE: 3

```
cccctagtaa ctgcgagtga agcgggaaaa gctcaaattt gaaatccttc gggagttgta      60
```

```
atctagagaa gtgttttcgg tcgttgcctc ggacaagtcc cttggaacag ggcgtcatag    120
agggtgagaa tcccgtcctt gccgagctac caacgtctat gtgatgcgct ctcgaagagt    180
cgagttgttt gggaatgcag ctcaaaatgg gtggtaaact ccatctaaag ctaaatattg    240
gcgagagacc gata                                                      254

<210> SEQ ID NO 4
<211> LENGTH: 254
<212> TYPE: DNA
<213> ORGANISM: Ditiola radicata CBS126.84, MUCL 53180

<400> SEQUENCE: 4
cccctagtaa ctgcgagtga agcgggaaaa gctcaaattt agaacccttc gggaattgta     60
atctagagaa gtgttttcgg tcgttgcctc ggacaagtcc cttggaacag ggcgtcatag    120
agggtgagaa tcccgtcctt gccgagctac caacgtctat gtgatgcgct ctcgaagagt    180
cgagttgttt gggaatgcag ctcaaaatgg gtggtaaact ccatctaaag ctaaatattg    240
gcgagagacc gata                                                      254

<210> SEQ ID NO 5
<211> LENGTH: 272
<212> TYPE: DNA
<213> ORGANISM: Ditiola pezizaeformis ATCC13299, MUCL
<220> FEATURE:
<221> NAME/KEY: misc_feature
<222> LOCATION: (52)..(53)
<223> OTHER INFORMATION: n is a, c, g, or t

<400> SEQUENCE: 5
gcggaggaaa agaaactaac aaggattccc ctagtaactg cgagtgaagc gnngaaaagc     60
tcaaatttaa aagccttcgg gcgttgtaat ctatagaagt gttttcggtc gttgcctcgg    120
ataagtctct tggaacagag tgtaaagagg gtgagaatcc cgttcttgcc gagctaccaa    180
cgtctatgcg atacatttca aagagtcgag ttgtttggga atgcagctca aaatcgggtg    240
gtaaactcca tctaaagcta aatattcggc cg                                  272
```